US008623895B2

(12) United States Patent
Hans et al.

(10) Patent No.: US 8,623,895 B2
(45) Date of Patent: Jan. 7, 2014

(54) MITOTIC KINESIN INHIBITORS AND METHODS OF USE THEREOF

(75) Inventors: Jeremy Hans, Boulder, CO (US); Eli M. Wallace, Lyons, CO (US); Qian Zhao, Superior, CO (US); Joseph P. Lyssikatos, Superior, CO (US); Thomas D. Aicher, Superior, CO (US); Ellen R Laird, Longmont, CO (US); John Robinson, Commerce City, CO (US); Shelley Allen, Loveland, CO (US)

(73) Assignee: Array BioPharma Inc., Boulder, CO (US)

(*) Notice: Subject to any disclaimer, the term of this patent is extended or adjusted under 35 U.S.C. 154(b) by 0 days.

(21) Appl. No.: 13/538,698

(22) Filed: Jun. 29, 2012

(65) Prior Publication Data

US 2012/0270803 A1 Oct. 25, 2012

Related U.S. Application Data

(60) Continuation of application No. 13/093,729, filed on Apr. 25, 2011, now Pat. No. 8,236,825, which is a division of application No. 12/043,456, filed on Mar. 6, 2008, now Pat. No. 7,956,073, which is a division of application No. 11/252,232, filed on Oct. 17, 2005, now Pat. No. 7,449,486.

(60) Provisional application No. 60/620,048, filed on Oct. 19, 2004.

(51) Int. Cl.

| | |
|---|---|
| ***A61K 31/433*** | (2006.01) |
| ***A61K 31/4439*** | (2006.01) |
| ***C07D 417/12*** | (2006.01) |
| ***C07D 285/12*** | (2006.01) |

(52) U.S. Cl.
USPC ......... 514/363; 514/342; 548/136; 546/268.7

(58) Field of Classification Search
USPC ................. 548/136; 514/363, 342; 546/268.7
See application file for complete search history.

(56) References Cited

U.S. PATENT DOCUMENTS

| | | | |
|---|---|---|---|
| 2,702,803 | A | 2/1955 | Ainsworthh |
| 4,782,072 | A | 11/1988 | Stillings |
| 4,927,822 | A | 5/1990 | Brown et al. |
| 5,668,159 | A | 9/1997 | Jin et al. |
| 5,958,957 | A | 9/1999 | Andersen et al. |
| 5,972,937 | A | 10/1999 | Gaster et al. |
| 5,972,978 | A | 10/1999 | Andersen et al. |
| 6,159,938 | A | 12/2000 | Gyorkos et al. |
| 6,235,762 | B1 | 5/2001 | Takasugi et al. |
| 7,115,642 | B2 | 10/2006 | Singh et al. |
| 7,220,745 | B2 | 5/2007 | Singh et al. |
| 7,326,790 | B2 | 2/2008 | Singh et al. |
| 7,425,636 | B2 | 9/2008 | Murakata et al. |
| 7,795,282 | B2 | 9/2010 | Hans et al. |
| 7,956,073 | B2 | 6/2011 | Hans et al. |
| 8,236,825 | B2 | 8/2012 | Hans et al. |
| 8,268,871 | B2 | 9/2012 | Hans et al. |
| 8,324,257 | B2 | 12/2012 | Ahrendt et al. |
| 2002/0002193 | A1 | 1/2002 | Yu et al. |
| 2003/0229054 | A1 | 12/2003 | Belliotti et al. |
| 2004/0142985 | A1 | 7/2004 | Singh et al. |
| 2004/0167188 | A1 | 8/2004 | Xin et al. |
| 2004/0248950 | A1 | 12/2004 | Ishizuka et al. |
| 2004/0254227 | A1 | 12/2004 | Singh et al. |
| 2004/0266840 | A1 | 12/2004 | Singh et al. |
| 2005/0004186 | A1 | 1/2005 | Barrett et al. |
| 2005/0009877 | A1 | 1/2005 | Lu |
| 2005/0070538 | A1 | 3/2005 | Cheng et al. |
| 2005/0075375 | A1 | 4/2005 | Vourloumis et al. |
| 2005/0119484 | A1 | 6/2005 | Breslin et al. |
| 2007/0112044 | A1 | 5/2007 | Murakata et al. |
| 2007/0155804 | A1 | 7/2007 | Murakata et al. |
| 2007/0276017 | A1 | 11/2007 | Murakata et al. |
| 2008/0153887 | A1 | 6/2008 | Cox et al. |
| 2013/0109656 | A1 | 5/2013 | Hans et al. |

FOREIGN PATENT DOCUMENTS

| | | |
|---|---|---|
| EP | 0531906 | 3/1993 |
| EP | 1004241 | 5/2000 |
| EP | 1671957 | 6/2006 |
| JP | 2005232016 | 9/2005 |
| WO | WO 93/22311 | 11/1993 |
| WO | WO 98/38177 | 9/1998 |
| WO | WO 01/56994 | 8/2001 |
| WO | WO 03/051854 | 6/2003 |
| WO | WO 03/079973 | 10/2003 |
| WO | WO 2004/092147 | 10/2004 |
| WO | WO 2004/111023 | 12/2004 |
| WO | WO 2004/111024 | 12/2004 |
| WO | WO 2005/035512 | 4/2005 |
| WO | WO 2005/092304 | 10/2005 |
| WO | WO 2006/031348 | 3/2006 |
| WO | WO 2008/042928 | 4/2008 |

OTHER PUBLICATIONS

Clinical Trial record 1 for Multiple Myeloma (Feb. 14, 2013).*
Clinical Trial record 2 for Multiple Myeloma (Feb. 14, 2013).*
Clinical Trial record 3 for Multiple Myeloma (Feb. 14, 2013).*
Allen, Shelley, et al., "The Discovery and Optimization of Kinesin Spindle Protein (KSP) Inhibitors: Path to ARRY-520", 2012 Cambridge Healthtech Institute Conference. http://www.arraybiopharma.com/_documents/Publication/PubAttachment526.pdf.
Askari et al., "Thiadiazoles and Thiadizolines, Part 1, Reaction of Thiourea and Ethylenethiourea with Chlorodiazabutadienes: A New Route to 4-amidino-1,3,4-thiadiazolines"; Database CAPLUS on STN, Chem. Abstr., Accession No. 1981:174996, *Journal of the Chemical Society, Perkin Transactions 1: Organic and Bio-Organic Chemistry*, vol. 2, 360-365 abstract (1981).

(Continued)

*Primary Examiner* — Jason M Nolan
(74) *Attorney, Agent, or Firm* — Viksnins, Harris & Padys PLLP; Corey M. Williams

(57) ABSTRACT

This invention relates to inhibitors of mitotic kinesins, particularly KSP, and methods for producing these inhibitors. The invention also provides pharmaceutical compositions comprising the inhibitors of the invention and methods of utilizing the inhibitors and pharmaceutical compositions in the treatment and prevention of various disorders.

104 Claims, No Drawings

(56) References Cited

OTHER PUBLICATIONS

Bryn et al., "Chapter 11: Hydrates and Solvates" *Solid-State Chemistry of Drugs*, Second Edition, 233-247 (1999).

Carter, Bing Z., et al., "Inhibition of KSP by ARRY-520 Induces Cell Cycle Block and Cell Death via the Mitochondrial Pathway in AML Cells." 2007 American Center of Hematology. http://www.arraybiopharma.com/_documents/Publication/PubAttachment277.pdf.

Carter, Bing Z., et al., "Inhibition of KSP by ARRY-520 induces cell cycle block and cell death via the mitochondrial pathway in AML cells", *Leukemia*. 23(10) , 1755-62 (2009).

Chari, A., et al., "A Phase 1 Study of ARRY-520 with Bortezomib in Relapsed or Refractory Multiple Myeloma", 2013 International Myeloma Workshop, P-141. http://www.arraybiopharma.com/_documents/Publication/PubAttachment563.pdf.

Estrov, Z., et al., "A Phase 1 Dose-Escalation Study of the Novel KSP Inhibitor ARRY-520 in Advanced Leukemias", 2009 American Society of Clinical Oncology Annual Meeting. http://www.arraybiopharma.com/_documents/Publication/PubAttachment347.pdf.

Garcia-Manero, Guillermo, et al., "A Phase 1 Dose-Escalation Study of the Novel KSP Inhibitor ARRY-520 in Advanced Leukemias", 2009 51st American Society of Hematology Annual Meeting and Exposition. http://www.arraybiopharma.com/_documents/Publication/PubAttachment368.pdf.

Golub et al., "Molecular Classification of Cancer: Class Discovery and Class Prediction by Gene Expression Monitoring", *Science*, vol. 286, 537-537 (1999).

Goncalves, P., et al., "A Phase 1 Safety and Pharmacokinetic Study of ARRY-520 in Solid Tumors", 2010 American Society of Clinical Oncology Annual Meeting. http://www.arraybiopharma.com/_documents/Publication/PubAttachment387.pdf.

Humphries, Michael J., et al., "Human Tumor Explants are Better Predictors of Clinical Trial Outcome than Solid Tumor Cell Line Xenografts for the KSP Inhibitor ARRY-520", 2012 American Association of Cancer Research Annual Meeting. http://www.arraybiopharma.com/_documents/Publication/PubAttachment508.pdf.

Kim, Ki H., et al., "KSP inhibitor ARRY-520 as a substitute for Paclitaxel in Type I ovarian cancer cells", J. of Translational Medicine. vol. 7, 9 pages, Article 63 (2009).

Koch, Kevin, "ARRY-520: Novel KSP Inhibitor 2009", 2009 American Association of Cancer Research 100th Annual Meeting. http://www.arraybiopharma.com/_documents/Publication/PubAttachment575.pdf.

Lala et al., "Role of Nitric Oxide in Tumor Progression: Lessons from Experimental Tumors" *Cancer and Metastasis Reviews*, 17(1), 91-106 (1998).

Lemieux, Christine, et al., "ARRY-520, a Novel, Hightly Selective KSP Inhibitor with Potent Anti-Proliferative Activity", 2007 American Association of Cancer Research 98th Annual Meeting. http://www.arraybiopharma.com/_documents/Publication/PubAttachment223.pdf.

Lonial, S., et al., "The Novel KSP Inhibitor ARRY-520 Demonstrates Single-Agent Activity in Refractory Myeloma: Results From a Phase 2 Trial in Patients with Relapsed/Refractory Multiple Myeloma", 2011 American Society of Hematology Annual Meeting. http://www.arraybiopharma.com/_documents/Publication/PubAttachment563.pdf.

Moss, S.F. et al., "Thiadiazoles and Thiadiazolines Part 3. Synthesis of Triazol-3-yl-Δ-1,3,4-thiadiazolines and a New Synthesis of Unsymmetrical 2, 5-Di-substituted 1,3,4-Thiadiazoles", *Journal of the Chemical Society, Perkin Transactions, I*, 1987-1991 (1982).

Moss, S.F. et al., "Thiadiazoles and Thiadiazolines. Part 4. Acetylation, Hydrolysis, and Cyclocondensations of Δ2-1,3,4-Thiadiazolines-α-carboxamidines", *J. Chemical Society, Perkin Transactions I*, 1993-1998, (1982).

Shah, J.J., et al., "A Phase 1/2 Trial of the KSP Inhibitor ARRY-520 in Relapsed/Refractory Multiple Myeloma", 2010 American Society of Hematology Meeting, Publication No. 1959. http://www.arraybiopharma.com/_documents/Publication/PubAttachment428.pdf.

Shah, J., et al., "Phase 1 Trial of ARRY-520 in Relapsed/Refractory Multiple Myeloma", 2010 American Society of Clinical Oncology Annual Meeting. http://www.arraybiopharma.com/_documents/Publication/PubAttachment386.pdf.

Shah, J.J., et al., "ARRY-520 Shows Durable Responses in Patients with Relapsed/Refractory Multiple Myeloma in a Phase 1 Dose-Escalation Study", 2011 American Society of Hematology Annual Meeting. http://www.arraybiopharma.com/_documents/Publication/PubAttachment493.pdf.

Shah, Jatin J., et al., "Phase 1 Study of ARRY-520 and Carfilzomib in Patients With Relapsed/Refractory Multiple Myeloma (RRMM)", 2013 European Hematology Association Meeting. http://www.arraybiopharma.com/_documents/Publication/PubAttachment574.pdf.

Shah, J.J., et al., "Phase 1 Study of the Novel Kinesin Spindle Protein Inhibitor ARRY-520 + Carfilzomib in Patients with Relapsed and/or Refractory Multiple Myeloma", 2012 American Society of Hematology Meeting. http://www.arraybiopharma.com/_documents/Publication/PubAttachment555.pdf.

Shah, J.J., et al., "The Novel KSP Inhibitor ARRY-520 Is Active Both with and without Low-Dose Dexamethasone in Patients with Multiple Myeloma Refractory to Bortezomib and Lenalidomide: Results From a Phase 2 Study", 2012 American Society of Hematology Meeting. http://www.arraybiopharma.com/_documents/Publication/PubAttachment556.pdf.

Office Actionand translation thereof from Russian Application No. 2007144612/04(048882), 11 pages, received Feb. 11, 2010.

Szczepankiewicz et al., "New Antimitotic Agents with Activity in Multi-Drug Resistant Cell Lines and in Vivo Efficacy in Murine Tumor Models", *Journal of Medicinal Chemistry*, 44(25), 4416-4430 (2001).

Tunquist, Brian J., et al., "Degradation of the anti-apoptotic protein Mcl-1 correlates with mitotic cell death in response to the novel KSP inhibitor ARRY-520", 2009 American Association of Cancer Research 100th Annual Meeting. http://www.arraybiopharma.com/_documents/Publication/PubAttachment338.pdf.

Tunquist, Brian J., et al., "Mcl-1 Stability Determines Mitotic Cell Fate of Human Multiple Myeloma Tumor Cells Treated with the Kinesin Spindle Protein Inhibitor ARRY-520", *Mol. Cancer Ther*. 9(7) , 2046-56 (2010).

Tunquist, Brian, et al., "Alpha 1-Acis Glycoprotein (AAG) is a Potential Marker for Clinical Activity of ARRY-520 in Relapsed and Refractory Multiple Myeloma (MM)", 2013 European Hematology Association Meeting P786. http://www.arraybiopharma.com/_documents/Publication/PubAttachment575.pdf.

Tunquist, Brian, et al., "Identification of Alpha 1-Acid Glycoprotein (AAG) as a Potential Patient Selection Biomarker for Improved Clinical Activity of the Novel KSP Inhibitor ARRY-520 in Relapsed and Refractory Multiple Myeloma (MM)", 2012 American Society of Hematology Meeting. http://www.arraybiopharma.com/_documents/Publication/PubAttachment552.pdf.

Woessner, Rich, et al., "ARRY-520, a KSP Inhibitor, with Potent In Vitro and In Vivo Efficacy and Pharmacodynamic Activity in Models of Multiple Myeloma", 2008 European Organisation for Research and Treatment of Cancer Conference. http://www.arraybiopharma.com/_documents/Publication/PubAttachment314.pdf.

Woessner, Richard, et al., "Combination of the KSP Inhibitor ARRY-520 with Bortezomib or Revlimid Causes Sustained Tumor Regressions and Significantly Increased Time to Regrowth in Models of Multiple Myeloma", 2009 51st American Society of Hematology Annual Meeting and Exposition. http://www.arraybiopharma.com/_documents/Publication/PubAttachment366.pdf.

Woessner, Rich, et al., "In vivo and Pharmacodynamic Profiling of the KSP Inhibitor ARRY-520 Supports Potent Activity in Hematological Cancers and Drug Resistant Tumors", 2009 American Association of Cancer Research 100th Annual Meeting. \http://www.arraybiopharma.com/_documents/Publication/PubAttachment336.pdf.

(56) References Cited

OTHER PUBLICATIONS

Woessner, Richard, et al., "Combination of the KSP Inhibitor ARRY-520 with Bortezomib Causes Sustained Tumor Regressions and Significantly Increased Time to Regrowth in Bortezomib Sensitive and Resistant Models of Multiple Myeloma", 2011 American Association of Cancer Research 102nd Annual Meeting. http://www.arraybiopharma.com/_documents/Publication/PubAttachment457.pdf.

Woessner, Rich, et al., "ARRY-520, a KSP Inhibitor with Efficacy and Pharmacodynamic Activity in Animal Models of Solid Tumors", 2007 American Association of Cancer Research 98th Annual Meeting, #1433. http://www.arraybiopharma.com/_documents/Publication/PubAttachment222.pdf.

Office Action related to corresponding Chinese Patent Application No. 2005800436528.9 Jul. 6, 2009.

International Search Report related to corresponding PCT Application No. PCT/US2005/37305 Jul. 14, 2006.

European Search report related to corresponding EP Application No. 05819172.7 Sep. 18, 2009.

International Search Report related to corresponding PCT Application No. PCT/US2007/080246 Sep. 4, 2008.

Office Action corresponding to related Japanese Application No. 2007-537010. Aug. 10, 2011.

Office Action corresponding to related Philippine Application No. 12007500720. Sep. 16, 2011.

Examination Report corresponding to related Taiwanese Application No. 094136480. Jul. 29, 2011.

* cited by examiner

MITOTIC KINESIN INHIBITORS AND METHODS OF USE THEREOF

RELATED APPLICATION

This application is a Continuation application under 37 C.F.R. 1.53(b) of U.S. Ser. No. 13/093,729, filed Apr. 25, 2011, now U.S. Pat. No. 8,236,825, which is a Divisional application under 37 C.F.R. 1.53(b) of U.S. Ser. No. 12/043,456, filed Mar. 6, 2008, now U.S. Pat. No. 7,956,073, which is a Divisional application under 37 C.F.R. 1.53(b) of U.S. Ser. No. 11/252,232, filed Oct. 17, 2005, now U.S. Pat. No. 7,449,486, and claims priority of U.S. Provisional Patent Application No. 60/620,048 filed Oct. 19, 2004, which applications are incorporated by reference herein in their entirety.

BACKGROUND OF THE INVENTION

1. Field of the Invention

This invention relates to novel inhibitors of mitotic kinesins, in particular the mitotic kinesin KSP, pharmaceutical compositions containing the inhibitors, and methods for preparing these inhibitors. The compounds of this invention are useful for the treatment of diseases that can be treated by inhibiting mitosis, including cellular proliferative diseases, for example cancer, hyperplasias, restenosis, cardiac hypertrophy, immune disorders, fungal infections, and inflammation.

2. Description of the State of the Art

Among the therapeutic agents used to treat cancer are the taxanes and vinca alkaloids, which act on microtubules. Microtubules are the primary structural elements of the mitotic spindle, which is responsible for distribution of replicate copies of the genome to each of the two daughter cells that result from cell division. It is presumed that disruption of mitotic spindle by these drugs results in inhibition of cancer cell division and induction of cancer cell death. However, microtubules form other types of cellular structures, including tracks for intracellular transport in nerve processes. Because drugs such as taxanes and vinca alkaloids do not specifically target mitotic spindles, they have side effects that limit their usefulness.

Improvements in the specificity of agents used to treat cancer is of considerable interest, in part because of the improved therapeutic benefits which would be realized if the side effects associated with administration of these agents could be reduced. Traditionally, dramatic improvements in the treatment of cancer have been associated with identification of therapeutic agents acting through novel mechanisms. Examples include not only the taxanes, but also the camptothecin class of topoisomerase I inhibitors. From both of these perspectives, mitotic kinesins are attractive targets for new anti-cancer agents.

Mitotic kinesins are enzymes essential for assembly and function of the mitotic spindle, but are not generally part of other microtubule structures such as nerve processes. Mitotic kinesins play essential roles during all phases of mitosis. These enzymes are "molecular motors" that transform energy released by hydrolysis of ATP into mechanical force, which drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest and cell death.

Among the identified mitotic kinesins is kinesin spindle protein (KSP). KSP belongs to an evolutionarily conserved kinesin subfamily of plus end-directed microtubule motors that assemble into bipolar homotetramers consisting of antiparallel homodimers. During mitosis, KSP associates with microtubules of the mitotic spindle. Microinjection of antibodies directed against KSP into human cells prevents spindle pole separation during prometaphase, giving rise to monopolar spindles and causing mitotic arrest and induction of programmed cell death. KSP and related kinesins in other non-human organisms bundle antiparallel microtubules and slide them relative to one another, thus forcing the spindle poles apart. KSP may also mediate in anaphse B spindle elongation and focusing of microtubules at the spindle pole.

Human KSP (also termed HsEg5) has been described (Blangy, et al., *Cell,* 83:1159-69 (1995); Whitehead, et al., *Arthritis Rheum.,* 39:1635-42 (1996); Galtio, et al., *J. Cell Biol.,* 135:339-414 (1996); Blangy, et al., *J. Bio. Chem.,* 272:19418-24 (1997); Blangy, et al., *Cell Motil Cytoskeleton,* 40:174-82 (1998); Whitehead and Rattner, *J. Cell Sci.,* 111:2551-61 (1998); Kaiser, et al., *JBC,* 274:18925-31 (1999); GenBank accession numbers: X85137, NM004523 and U37426), and a fragment of the KP gene (TRIP5) has been described (Lee, et al., *Mol. Endocrinol.,* 9:243-54 (1995); GenBank accession number L40372). Xenopus KSP homologs (Eg5), as well as Drosophilia K-LP61 F/KRP 130 have been reported. Small molecule inhibitors of KSP have recently been described: Mayer, et al., *Science,* 286:971-4 (1999); Maliga, et al., *Chemistry and Biology,* 9:989-96 (2002) Sakowicz, et al., *Cancer Research* 64:3276-80 (2004); Yan, et al., *J. Mol. Biol.* 335:547-554 (2004); Coleman, et al., *Expert Opin. Ther. Patents* 14(12):1659-67 (2004); Cox, et al., *Bioorg. Med. Chem. Lett.* 15:2041-5 (2005); Gartner, et al., *ChemBioChem* 6:1173-7 (2005); Bergnes, et al., *Current Topics in Medicinal Chemistry* 5:127-45 (2005); and in PCT Publication Nos. WO 00/130,768, WO 01/30768, WO 01/98278, WO 03/050,064, WO 03/050,122, WO 03/049,527, WO 03/049,679, WO 03/049,678, WO 03/051854, WO 03/39460 WO 03/079,973, WO 03/088,903, WO 03/094,839, WO 03/097,053, WO 03/099,211, WO 03/099,286, WO 03/103,575, WO 03/105,855, WO 03/106,426, WO 04/032,840, WO 04/034,879, WO 04/037,171, WO 04/039,774, WO 04/055,008, WO 04/058,148, WO 04/058,700, WO 04/064,741, WO 04/092147, WO 04/111023, WO 04/111024, WO 05/035512, WO 05/017190, WO 05/018547, and WO 05/019206.

Mitotic kinesins are attractive targets for the discovery and development of novel mitotic chemotherapeutics. Accordingly, it is an object of the present invention to provide compounds, methods and compositions useful in the inhibition of the mitotic kinesin KSP.

SUMMARY OF THE INVENTION

This invention provides compounds that are useful in treating diseases that can be treated by inhibiting mitosis. In particular, one aspect of this invention provides compounds and pharmaceutical compositions thereof that inhibit mitotic kinesins, and in particular the mitotic kinesin KSP. Such compounds have utility as therapeutic agents for diseases that can be treated by the inhibition of the assembly and/or function of microtubule structures, including the mitotic spindle. In general, the invention relates to compounds of the general Formula I:

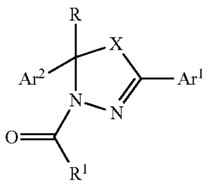

and metabolites, solvates, resolved enantiomers, diastereomers, racemic mixtures and pharmaceutically acceptable salts and prodrugs thereof, wherein:

X is O, S, S(O) or S(O)$_2$;

R is Z—NR$^2$R$^3$, Z—OH, or Z—OP(=O)(OR$^a$)(OR$^a$);

R$^1$ is alkyl, alkenyl, alkynyl, aryl, heteroaryl, saturated or partially unsaturated cycloalkyl, saturated or partially unsaturated heterocycloalkyl, —OR$^3$, —NR$^4$OR$^5$, CR$^b$(=NOR$^c$), C(=O)R$^a$, or —NR$^4$R$^5$, wherein said alkyl, alkenyl, alkynyl, aryl, heteroaryl, cycloalkyl, and heterocycloalkyl are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C=O)OR$^d$, —NR$^b$SO$_2$R$^d$, —SO$_2$NR$^a$R$^b$, —C(=O)R$^a$, —C(=O)OR$^a$, —OC(=O)R$^a$, —OCH$_2$C(=O)OR$^a$, —NR$^b$C(=O)OR$^d$, —NR$^b$C(=O)R$^a$, —C(=O)NR$^a$R$^b$, —NR$^a$R$^b$, —NR$^c$C(=O)NR$^a$R$^b$, —NR$^c$C(NCN)NR$^a$R$^b$, —OR$^a$, —OP(=O)(OR$^a$)$_2$, alkyl, alkenyl, alkynyl, cycloalkyl, aryl, heteroaryl, arylalkyl, heteroarylalkyl, heterocyclyl and heterocyclylalkyl;

Ar$^1$ and Ar$^2$ are independently aryl, heteroaryl, saturated or partially unsaturated cycloalkyl, or saturated or partially unsaturated heterocycloalkyl, wherein said aryl, heteroaryl, cycloalkyl, and heterocycloalkyl are optionally substituted with one or more groups independently selected from F, Cl, Br, I, cyano, nitro, alkyl, alkenyl, alkynyl, saturated or partially unsaturated cycloalkyl, saturated or partially unsaturated heterocycloalkyl, trifluoromethyl, difluoromethyl, fluoromethyl, fluoromethoxy, difluoromethoxy, trifluoromethoxy, OR$^a$, —O(C=O)OR$^d$, —OP(=O)(OR$^a$)(OR$^a$), NR$^a$R$^b$, —NR$^b$SO$_2$R$^d$, —SO$_2$NR$^a$R$^b$, SR$^6$, SOR$^6$, SO$_2$R$^6$, —C(=O)R$^a$, —C(=O)OR$^a$, —OC(=O)R$^a$, —OCH$_2$C(=O)OR$^a$, —NR$^b$C(=O)OR$^d$, —NR$^b$C(=O)R$^a$, —C(=O)NR$^a$R$^b$ and —NR$^c$C(=O)NR$^a$R$^b$;

R$^2$ is hydrogen, —C(=O)R$^4$, —SO$_2$R$^6$, —C(=O)NR$^4$R$^5$, —SO$_2$NR$^4$R$^5$, —C(=O)OR$^6$, alkyl, alkenyl, alkynyl, aryl, heteroaryl, saturated or partially unsaturated heterocycloalkyl, saturated or partially unsaturated cycloalkyl, a natural or unnatural amino acid, or a polypeptide of two or more amino acids independently selected from natural and unnatural amino acids, wherein said alkyl, alkenyl, alkynyl, aryl, heteroaryl, heterocycloalkyl, and cycloalkyl are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C=O)OR$^d$, —NR$^b$SO$_2$R$^d$, —SO$_2$NR$^a$R$^b$, —C(=O)R$^a$, —C(=O)OR$^a$, —OC(=O)R$^a$, —NR$^b$C(=O)OR$^d$, —NR$^b$C(=O)R$^a$, —C(=O)NR$^a$R$^b$, —NR$^a$R$^b$, —NR$^c$C(=O)NR$^a$R$^b$, —OR$^a$, alkyl, alkenyl, alkynyl, cycloalkyl, cycloalkenyl, cycloalkynyl, aryl, heteroaryl, arylalkyl, heteroarylalkyl, heterocycloalkyl and heterocyclylalkyl;

R$^3$ is hydrogen, —C(=O)R$^4$, —C(=O)NR$^4$R$^5$, alkyl, alkenyl, alkynyl, aryl, heteroaryl, saturated or partially unsaturated heterocycloalkyl, or saturated or partially unsaturated cycloalkyl, wherein said alkyl, alkenyl, alkynyl, aryl, heteroaryl, heterocycloalkyl and cycloalkyl are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C=O)OR$^d$, —OP(=O)(OR$^a$)$_2$, —NR$^b$SO$_2$R$^d$, —SO$_2$NR$^a$R$^b$, —C(=O)R$^a$, —C(=O)OR$^a$,—OC(=O)R$^a$, —NR$^b$C(=O)OR$^d$, —NR$^b$C(=O)R$^a$, —C(=O)NR$^a$R$^b$, —NR$^a$R$^b$, —NR$^c$C(=O)NR$^a$R$^b$, —OR$^a$, alkyl, alkenyl, alkynyl, cycloalkyl, cycloalkenyl, cycloalkynyl, aryl, heteroaryl, arylalkyl, heteroarylalkyl, heterocycloalkyl and heterocyclylalkyl, or R$^2$ and R$^3$ together with the nitrogen atom to which they are attached form a saturated or partially unsaturated heterocyclic ring which may include 1 to 3 additional heteroatoms, in addition to the nitrogen atom to which said R$^2$ and R$^3$ are attached, selected from N, O and S, wherein said heterocyclic ring is optionally substituted with one or more groups independently selected from oxo, halogen, cyano, nitro, trifluoromethyl, difluoromethyl, fluoromethyl, fluoromethoxy, difluoromethoxy, trifluoromethoxy, azido, —O(C=O)OR$^d$, —NR$^b$SO$_2$R$^d$, —SO$_2$NR$^a$R$^b$, —C(=O)R$^a$, —C(=O)OR$^a$, —OC(=O)R$^a$, —NR$^b$C(=O)OR$^d$, —NR$^b$C(=O)R$^a$, —C(=O)NR$^a$R$^b$, —NR$^a$R$^b$, —NR$^c$C(=O)NR$^a$R$^b$, —NR$^c$C(NCN)NR$^a$R$^b$, —OR$^a$, alkyl, alkenyl, alkynyl, cycloalkyl, aryl, heteroaryl, arylalkyl, heteroarylalkyl, heterocycloalkyl and heterocyclylalkyl;

R$^4$ and R$^5$ are independently H, OR$^a$, trifluoromethyl, difluoromethyl, fluoromethyl, alkyl, alkenyl, alkynyl, saturated or partially unsaturated cycloalkyl, saturated or partially unsaturated heterocycloalkyl, aryl or heteroaryl, wherein said alkyl, alkenyl, alkynyl, cycloalkyl, heterocycloalkyl, aryl and heteroaryl are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C=O)OR$^d$, —NR$^b$SO$_2$R$^d$, —SO$_2$NR$^a$R$^b$, —C(=O)R$^a$, —C(=O)OR$^a$, —OC(=O)R$^a$, —NR$^b$C(=O)OR$^d$, —NR$^b$C(=O)R$^a$, —C(=O)NR$^a$R$^b$, —NR$^a$R$^b$, —NR$^c$C(=O)NR$^a$R$^b$, —NR$^c$C(NCN)NR$^a$R$^b$, —OR$^a$, alkyl, alkenyl, alkynyl, cycloalkyl, aryl, heteroaryl, arylalkyl, heteroarylalkyl, heterocycloalkyl and heterocyclylalkyl, or R$^4$ and R$^5$ together with the atoms to which they are attached form a saturated or partially unsaturated heterocyclic ring which may include 1 to 3 additional heteroatoms, in addition to the heteroatoms to which said R$^4$ and R$^5$ are attached, selected from N, O and S, wherein said heterocyclic ring is optionally substituted with one or more groups independently selected from oxo, halogen, cyano, nitro, trifluoromethyl, difluoromethyl, fluoromethyl, fluoromethoxy, difluoromethoxy, trifluoromethoxy, azido, —O(C=O)OR$^d$, —NR$^b$SO$_2$R$^d$, —SO$_2$NR$^a$R$^b$, —C(=O)R$^a$, —C(=O)OR$^a$, —OC(=O)R$^a$, —NR$^b$C(=O)OR$^d$, —NR$^b$C(=O)R$^a$, —C(=O)NR$^a$R$^b$, —NR$^a$R$^b$, —NR$^c$C(=O)NR$^a$R$^b$, —NR$^c$C(NCN)NR$^a$R$^b$, —OR$^a$, alkyl, alkenyl, alkynyl, cycloalkyl, aryl, heteroaryl, arylalkyl, heteroarylalkyl, heterocycloalkyl and heterocyclylalkyl;

R$^6$ is alkyl, alkenyl, alkynyl, heteroalkyl, heteroalkenyl, heteroalkynyl, saturated or partially unsaturated cycloalkyl, saturated or partially unsaturated heterocycloalkyl, aryl or heteroaryl, wherein said alkyl, alkenyl, alkynyl, heteroalkyl, heteroalkenyl, heteroalkynyl, cycloalkyl, heterocycloalkyl, aryl and heteroaryl are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C═O)OR$^d$, —NR$^b$SO$_2$R$^d$, —SO$_2$NR$^a$R$^b$, —C(═O)R$^a$, —C(═O)OR$^a$, —OC(═O)R$^a$, —NR$^b$C(═O)OR$^d$, —NR$^b$C(═O)R$^a$, —C(═O)NR$^a$R$^b$, —NR$^a$R$^b$, —NR$^c$C(═O)NR$^a$R$^b$, —NR$^c$C(NCN)NR$^a$R$^b$, —OR$^a$, alkyl, alkenyl, alkynyl, cycloalkyl, aryl, heteroaryl, arylalkyl, heteroarylalkyl, heterocycloalkyl and heterocyclylalkyl;

R$^a$ is hydrogen, trifluoromethyl, alkyl, alkenyl, alkynyl, saturated or partially unsaturated cycloalkyl, cycloalkylalkyl, aryl, arylalkyl, heteroaryl, heteroarylalkyl, saturated or partially unsaturated heterocycloalkyl or heterocyclylalkyl, wherein said alkyl, alkenyl, alkynyl, cycloalkyl, cycloalkylalkyl, aryl, arylalkyl, heteroaryl, heteroarylalkyl, heterocycloalkyl and heterocyclylalkyl are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C═O)OR$^h$, —NR$^f$SO$_2$R$^h$, —SO$_2$NR$^e$R$^f$, —C(═O)R$^e$, —C(═O)OR$^e$, —OC(═O)R$^e$, —NR$^f$C(═O)OR$^h$, —NR$^f$C(═O)R$^e$, —C(═O)NR$^e$R$^f$, —NR$^e$R$^f$, —NR$^g$C(═O)NR$^e$R$^f$, —NR$^c$C(NCN)NR$^e$R$^f$, —OR$^e$, alkyl, alkenyl, alkynyl, saturated or partially unsaturated cycloalkyl, aryl, heteroaryl, arylalkyl, heteroarylalkyl, saturated or partially unsaturated heterocycloalkyl and heterocyclylalkyl;

R$^b$, R$^c$, R$^f$ and R$^g$ are independently are hydrogen or alkyl, or R$^a$ and R$^b$ together with the atom to which they are attached form a 4 to 10 membered saturated or partially unsaturated heterocyclic ring which may include 1 to 3 additional heteroatoms, in addition to the nitrogen atom to which said R$^a$ and R$^h$ are attached, selected from N, O and S;

R$^d$ and R$^h$ are independently trifluoromethyl, alkyl, saturated or partially unsaturated cycloalkyl, aryl, arylalkyl, heteroaryl, heteroarylalkyl, saturated or partially unsaturated heterocycloalkyl or heterocyclylalkyl;

R$^e$ is hydrogen, trifluoromethyl, alkyl, alkenyl, alkynyl, saturated or partially unsaturated cycloalkyl, cycloalkylalkyl, aryl, arylalkyl, heteroaryl, heteroarylalkyl, saturated or partially unsaturated heterocycloalkyl or heterocyclylalkyl; and Z is alkylene having from 1 to 6 carbons, or alkenylene or alkynylene each having from 2 to 6 carbons, wherein said alkylene, alkenylene and alkynylene are optionally substituted with one or more groups independently selected from oxo, halogen, cyano, nitro, trifluoromethyl, difluoromethyl, fluoromethyl, fluoromethoxy, difluoromethoxy, trifluoromethoxy, azido, —O(C═O)OR$^d$, —NR$^b$SO$_2$R$^d$, —SO$_2$NR$^a$R$^b$, —C(═O)R$^a$, —C(═O)OR$^a$, —OC(═O)R$^a$, —NR$^b$C(═O)OR$^d$, —NR$^b$C(═O)R$^a$, —C(═O)NR$^a$R$^b$, —NR$^a$R$^b$, —NR$^c$C(═O)NR$^a$R$^b$, —NR$^c$C(NCN)NR$^a$R$^b$, —OR$^a$, alkyl, alkenyl, $C_2$-$C_{10}$ alkynyl, cycloalkyl, aryl, heteroaryl, arylalkyl, heteroarylalkyl, heterocycloalkyl and heterocyclylalkyl.

Another aspect of this invention relates to kinesin inhibitors of the general Formula II:

II

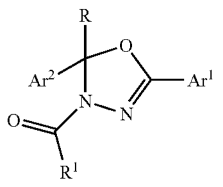

and metabolites, solvates, resolved enantiomers, diastereomers, racemic mixtures and pharmaceutically acceptable salts and prodrugs thereof, wherein R, R$^1$, Ar$^1$ and Ar$^2$ are as defined above.

Yet another aspect of this invention provides a compound of Formula III

III

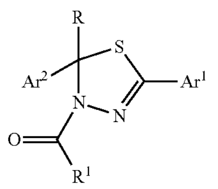

and metabolites, solvates, resolved enantiomers, diastereomers, racemic mixtures and pharmaceutically acceptable salts thereof, wherein R, R$^1$, Ar$^1$ and Ar$^2$ are as defined above.

Another aspect of this invention provides a compound of Formula IV

IV

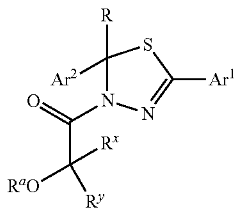

and metabolites, solvates, resolved enantiomers, diastereomers, racemic mixtures and pharmaceutically acceptable salts and prodrugs thereof, wherein R, R$^a$, Ar$^1$ and Ar$^2$ are as defined above, and R$^x$ and R$^y$ are independently H, alkyl, saturated or partially unsaturated cycloalkyl or aryl, wherein said alkyl, cycloalkyl and aryl are optionally substituted with one or more groups independently selected from oxo (with the proviso that it is not substituted on said aryl), halogen, cyano, nitro, trifluoromethyl, difluoromethyl, fluoromethyl, fluoromethoxy, difluoromethoxy, trifluoromethoxy, azido, —O(C═O)OR$^d$, —NR$^b$SO$_2$R$^d$, —SO$_2$NR$^a$R$^b$, —C(═O)R$^a$, —C(═O)OR$^a$, —OC(═O)R$^a$, —OCH$_2$C(═O)OR$^a$, —NR$^b$C(═O)OR$^d$, —NR$^b$C(═O)R$^a$, —C(═O)NR$^a$R$^b$, —NR$^a$R$^b$, —NR$^c$C(═O)NR$^a$R$^b$, —NR$^c$C(NCN)NR$^a$R$^b$, —OR$^a$, alkyl, alkenyl, alkynyl, cycloalkyl, aryl, heteroaryl, arylalkyl, heteroarylalkyl, heterocyclyl and heterocyclylalkyl, or R$^x$ and R$^y$ together with the atom to which they are attached form a saturated or partially unsaturated carbocyclic ring or heterocyclic ring having one or more heteroatoms independently selected from N, O and S, wherein said carbocyclic and heterocyclic rings are optionally substituted with one or more groups independently selected from oxo, halogen, cyano, nitro, trifluoromethyl, difluoromethyl, fluoromethyl, fluoromethoxy, difluoromethoxy, trifluoromethoxy, azido, —O(C═O)OR$^d$, —NR$^b$SO$_2$R$^d$, —SO$_2$NR$^a$R$^b$, —C(═O)R$^a$, —C(═O)OR$^a$, —OC(═O)R$^a$, —NR$^b$C(═O)OR$^d$, —NR$^b$C(═O)R$^a$, —C(═O)NR$^a$R$^b$, —NR$^a$R$^b$, —NR$^c$C(═O)NR$^a$R$^b$, —NR$^c$C(NCN)NR$^a$R$^b$, —OR$^a$, alkyl, alkenyl, alkynyl, cycloalkyl, aryl, heteroaryl, arylalkyl, heteroarylalkyl, heterocycloalkyl and heterocyclylalkyl;

wherein R$^a$, R$^b$, R$^c$ and R$^d$ are as defined above, or R$^a$ and R$^x$ together with the atoms to which they are attached form a saturated or partially unsaturated heterocyclic ring which may include 1 to 3 additional heteroatoms, in addition to the oxygen atom to which said R$^a$ is attached, selected from N, O and S, wherein said heterocyclic ring is optionally substituted with one or more groups independently selected from oxo, halogen, cyano, nitro, trifluoromethyl, difluoromethyl, fluoromethyl, fluoromethoxy, difluoromethoxy, trifluoromethoxy, azido, —O(C═O)OR$^h$, —NR$^f$SO$_2$R$^h$, —SO$_2$NR$^e$R$^f$, —C(═O)R$^e$, —C(═O)OR$^e$, —OC(═O)R$^e$, —NR$^f$C(═O)OR$^h$, —NR$^f$C(═O)R$^e$, —C(═O)NR$^e$R$^f$, —NR$^e$R$^f$, —NR$^g$C(═O)NR$^e$R$^f$, —NR$^c$C(NCN)NR$^e$R$^f$, —OR$^e$, alkyl, alkenyl, alkynyl, cycloalkyl, aryl, heteroaryl, arylalkyl, heteroarylalkyl, heterocycloalkyl and heterocyclylalkyl, wherein R$^e$, R$^f$, R$^g$ and R$^h$ are as defined above.

Methods of making compounds of Formulas I-IV are also described.

In a further aspect the present invention provides compounds that modulate mitotic spindle formation comprising compounds of Formulas I-IV, and metabolites, solvates, resolved enantiomers, diastereomers, racemic mixtures and pharmaceutically acceptable salts and in vivo cleavable prodrugs thereof.

In a further aspect the present invention provides a method of treating diseases that can be treated by blocking or inhibiting mitosis in a human or animal, which comprises administering to a warm-blooded animal an effective amount of a compound of Formula I-IV, or a metabolite, solvate, resolved enantiomer, diastereomer, racemic mixture or pharmaceutically acceptable salt or prodrug thereof, or a pharmaceutical composition comprising said compound. Examples of diseases that can be treated by administration of compounds of this invention include, but are not limited to, abnormal or unwanted cell growth conditions, such as, but not limited to, cellular proliferative diseases, for example, cancer, hyperplasias, restenosis, cardiac hypertrophy, immune disorders, infectious disease, fungal or other eukaryote infections, inflammatory diseases, arthritis, graft rejection, inflammatory bowel disease, proliferation induced after medical procedures, including, but not limited to, surgery, angioplasty, and the like.

In a further aspect the present invention provides a method of inhibiting abnormal or unwanted cell growth, comprises administering to said abnormal or unwanted cells an effective amount of a compound of Formula I-IV, or a metabolite, solvate, resolved enantiomer, diastereomer, racemic mixture or pharmaceutically acceptable salt or prodrug thereof.

In a further aspect the present invention provides a method of providing a mitotic kinesin inhibitory effect comprising administering to a warm-blooded animal an effective amount of a compound of Formula I-IV, or a metabolite, solvate, resolved enantiomer, diastereomer, racemic mixture or pharmaceutically acceptable salt or prodrug thereof.

The invention also relates to pharmaceutical compositions comprising a compound of Formula I-IV or a metabolite, solvate, resolved enantiomer, diastereomer, racemic mixture or pharmaceutically acceptable salt or prodrug thereof.

The inventive compounds may be used advantageously in combination with other known therapeutic agents. Accordingly, this invention also relates to pharmaceutical compositions comprising a therapeutically effective amount of a compound of Formula I-IV or a metabolite, solvate, resolved enantiomer, diastereomer, racemic mixture or pharmaceutically acceptable salt or prodrug thereof, in combination with a second therapeutic agent.

In a further aspect the present invention provides a method of using a compounds of this invention as a medicament to treat a disease or condition in a mammal that can be treated by blocking or inhibiting mitosis. For example, in certain aspects this invention provides a method for treatment of a hyperproliferative disorder in a mammal comprising administrating to said mammal one or more compounds of Formula I-IV, or a metabolite, solvate, resolved enantiomer, diastereomer, racemic mixture or pharmaceutically acceptable salt or prodrug thereof, in an amount effective to treat said disease or disorder. In other aspects, this invention provides a method of treating a fungal or other eukaryote infection in a mammal, comprising administrating to said mammal one or more compounds of Formula I-IV, or a metabolite, solvate, resolved enantiomer, diastereomer, racemic mixture or pharmaceutically acceptable salt or prodrug thereof, in an amount effective to treat said infection.

An additional aspect of the invention is the use of a compound of Formulas I-IV in the preparation of a medicament for the treatment or prevention of a disease or condition in a mammal that can be treated by blocking or inhibiting mitosis.

This invention further provides kits comprising one or more compounds of Formula I-IV. The kit may further comprise a second compound or formulation comprising a second pharmaceutical agent for treating a disease that can be treated by inhibiting mitosis. In certain embodiments, the second agent is a compound having, for example, anti-hyperproliferative or antifungal activity.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF THE INVENTION

The inventive compounds are useful for inhibiting mitotic kinesins and microtubule-mediated events such as mitotic spindle production. Such compounds have utility as therapeutic agents for diseases that can be treated by the inhibition of mitosis. In general, one aspect of the invention relates to compounds of the general Formula I:

I

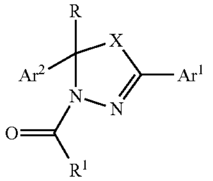

and metabolites, solvates, resolved enantiomers, diastereomers, racemic mixtures and pharmaceutically acceptable salts and prodrugs thereof, wherein:

X is O, S, S(O) or $S(O)_2$;

R is Z—$NR^2R^3$, Z—OH, or Z—OP(═O)($OR^a$)($OR^a$);

$R^1$ is alkyl, alkenyl, alkynyl, aryl, heteroaryl, saturated or partially unsaturated cycloalkyl, saturated or partially unsaturated heterocycloalkyl, —$OR^3$, —$NR^4OR^5$, $CR^b$(═$NOR^c$), C(═O)$R^a$, or —$NR^4R^5$, wherein said alkyl, alkenyl, alkynyl, aryl, heteroaryl, cycloalkyl, and heterocycloalkyl are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C═O)$OR^d$, —$NR^bSO_2R^d$, —$SO_2NR^aR^b$, —C(═O)$R^a$, —C(═O)$OR^a$, —OC(═O)$R^a$, —$OCH_2C$(═O)$OR^a$, —$NR^b$C(═O)$OR^d$, —$NR^b$C(═O)$R^a$, —C(═O)$NR^aR^b$, —$NR^aR^b$, —$NR^c$C(═O)$NR^aR^b$, —$NR^c$C(NCN)$NR^aR^b$, —$OR^a$, —OP(═O)$(OR^a)_2$, alkyl, alkenyl, alkynyl, cycloalkyl, aryl, heteroaryl, arylalkyl, heteroarylalkyl, heterocyclyl and heterocyclylalkyl;

$Ar^1$ and $Ar^2$ are independently aryl, heteroaryl, saturated or partially unsaturated cycloalkyl, or saturated or partially unsaturated heterocycloalkyl, wherein said aryl, heteroaryl, cycloalkyl, and heterocycloalkyl are optionally substituted with one or more groups independently selected from F, Cl, Br, I, cyano, nitro, alkyl, alkenyl, alkynyl, saturated or partially unsaturated cycloalkyl, saturated or partially unsaturated heterocycloalkyl, trifluoromethyl, difluoromethyl, fluoromethyl, fluoromethoxy, difluoromethoxy, trifluoromethoxy, $OR^a$, —O(C═O)$OR^d$, —OP(═O)($OR^a$)($OR^a$), $NR^aR^b$, —$NR^bSO_2R^d$, —$SO_2NR^aR^b$, $SR^6$, $SOR^6$, $SO_2R^6$, —C(═O)$R^a$, —C(═O)$OR^a$, —OC(═O)$R^a$, —$OCH_2C$(═O)$OR^a$, —$NR^b$C(═O)$OR^d$, —$NR^b$C(═O)$R^a$, —C(═O)$NR^aR^b$ and —$NR^c$C(═O)$NR^aR^b$;

$R^2$ is hydrogen, —C(═O)$R^4$, —$SO_2R^6$, —C(═O)$NR^4R^5$, —$SO_2NR^4R^5$, —C(═O)$OR^6$, alkyl, alkenyl, alkynyl, aryl, heteroaryl, saturated or partially unsaturated heterocycloalkyl, saturated or partially unsaturated cycloalkyl, a natural or unnatural amino acid, or a polypeptide of two or more amino acids independently selected from natural and unnatural amino acids, wherein said alkyl, alkenyl, alkynyl, aryl, heteroaryl, heterocycloalkyl, and cycloalkyl are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C═O)$OR^d$, —$NR^bSO_2R^d$, —$SO_2NR^aR^b$, —C(═O)$R^a$, —C(═O)$OR^a$, —OC(═O)$R^a$, —$NR^b$C(═O)$OR^d$, —$NR^b$C(═O)$R^a$, —C(═O)$NR^aR^b$, —$NR^aR^b$, —$NR^c$C(═O)$NR^aR^b$, —$OR^a$, alkyl, alkenyl, alkynyl, cycloalkyl, cycloalkenyl, cycloalkynyl, aryl, heteroaryl, arylalkyl, heteroarylalkyl, heterocycloalkyl and heterocyclylalkyl;

$R^3$ is hydrogen, —C(═O)$R^4$, —C(═O)$NR^4R^5$, alkyl, alkenyl, alkynyl, aryl, heteroaryl, saturated or partially unsaturated heterocycloalkyl, or saturated or partially unsaturated cycloalkyl, wherein said alkyl, alkenyl, alkynyl, aryl, heteroaryl, heterocycloalkyl, cycloalkyl, are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C═O)$OR^d$, —OP(═O)$(OR^a)_2$, —$NR^bSO_2R^d$, —$SO_2NR^aR^b$, —C(═O)$R^a$, —C(═O)$OR^a$, —OC(═O)$R^a$, —$NR^b$C(═O)$OR^d$, —$NR^b$C(═O)$R^a$, —C(═O)$NR^aR^b$, —$NR^aR^b$, —$NR^c$C(═O)$NR^aR^b$, —$OR^a$, alkyl, alkenyl, alkynyl, cycloalkyl, cycloalkenyl, cycloalkynyl, aryl, heteroaryl, arylalkyl, heteroarylalkyl, heterocycloalkyl and heterocyclylalkyl, or $R^2$ and $R^3$ together with the nitrogen atom to which they are attached form a saturated or partially unsaturated heterocyclic ring which may include 1 to 3 additional heteroatoms, in addition to the nitrogen atom to which said $R^2$ and $R^3$ are attached, selected from N, O and S, wherein said heterocyclic ring is optionally substituted with one or more groups independently selected from oxo, halogen, cyano, nitro, trifluoromethyl, difluoromethyl, fluoromethyl, fluoromethoxy, difluoromethoxy, trifluoromethoxy, azido, —O(C═O)$OR^d$, —$NR^bSO_2R^d$, —$SO_2NR^aR^b$, —C(═O)$R^a$, —C(═O)$OR^a$, —OC(═O)$R^a$, —$NR^b$C(═O)$OR^d$, —$NR^b$C(═O)$R^a$, —C(═O)$NR^aR^b$, —$NR^aR^b$, —$NR^c$C(═O)$NR^aR^b$, —$NR^c$C(NCN)$NR^aR^b$, —$OR^a$, alkyl, alkenyl, alkynyl, cycloalkyl, aryl, heteroaryl, arylalkyl, heteroarylalkyl, heterocycloalkyl and heterocyclylalkyl;

$R^4$ and $R^5$ are independently H, $OR^a$, trifluoromethyl, difluoromethyl, fluoromethyl, alkyl, alkenyl, alkynyl, saturated or partially unsaturated cycloalkyl, saturated or partially unsaturated heterocycloalkyl, aryl or heteroaryl, wherein said alkyl, alkenyl, alkynyl, cycloalkyl, heterocycloalkyl, aryl and heteroaryl are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C═O)$OR^d$, —$NR^bSO_2R^d$, —$SO_2NR^aR^b$, —C(═O)$R^a$, —C(═O)$OR^a$, —OC(═O)$R^a$, —$NR^b$C(═O)$OR^d$, —$NR^b$C(═O)$R^a$, —C(═O)$NR^aR^b$, —$NR^aR^b$, —$NR^c$C(═O)$NR^aR^b$, —$NR^c$C(NCN)$NR^aR^b$, —$OR^a$, alkyl, alkenyl, alkynyl, cycloalkyl, aryl, heteroaryl, arylalkyl, heteroarylalkyl, heterocycloalkyl and heterocyclylalkyl, or $R^4$ and $R^5$ together with the atoms to which they are attached form a saturated or partially unsaturated heterocyclic ring which may include 1 to 3 additional heteroatoms, in addition to the heteroatoms to which said $R^4$ and $R^5$ are attached, selected from N, O and S, wherein said heterocyclic ring is optionally substituted with one or more groups independently selected from oxo, halogen, cyano, nitro, trifluoromethyl, difluoromethyl, fluoromethyl, fluoromethoxy, difluoromethoxy, trifluoromethoxy, azido, —O(C═O)$OR^d$, —$NR^bSO_2R^d$, —$SO_2NR^aR^b$, —C(═O)$R^a$, —C(═O)$OR^a$, —OC(═O)$R^a$, —$NR^b$C(═O)$OR^d$, —$NR^b$C(═O)$R^a$, —C(═O)$NR^aR^b$, —$NR^aR^b$, —$NR^c$C(═O)$NR^aR^b$, —$NR^c$C(NCN)$NR^aR^b$, —$OR^a$, alkyl, alkenyl, alkynyl, cycloalkyl, aryl, heteroaryl, arylalkyl, heteroarylalkyl, heterocycloalkyl and heterocyclylalkyl;

$R^6$ is alkyl, alkenyl, alkynyl, heteroalkyl, heteroalkenyl, heteroalkynyl, saturated or partially unsaturated cycloalkyl, saturated or partially unsaturated heterocycloalkyl, aryl or heteroaryl, wherein said alkyl, alkenyl, alkynyl, heteroalkyl, heteroalkenyl, heteroalkynyl, cycloalkyl, heterocycloalkyl, aryl and heteroaryl are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C═O)OR$^d$, —NR$^b$SO$_2$R$^d$, —SO$_2$NR$^a$R$^b$, —C(═O)R$^a$, —C(═O)OR$^a$, —OC(═O)R$^a$, —NR$^b$C(═O)OR$^d$, —NR$^b$C(═O)R$^a$, —C(═O)NR$^a$R$^b$, —NR$^a$R$^b$, —NR$^c$C(═O)NR$^a$R$^b$, —NR$^c$C(NCN)NR$^a$R$^b$, —OR$^a$, alkyl, alkenyl, alkynyl, cycloalkyl, aryl, heteroaryl, arylalkyl, heteroarylalkyl, heterocycloalkyl and heterocyclylalkyl;

R$^a$ is hydrogen, trifluoromethyl, alkyl, alkenyl, alkynyl, saturated or partially unsaturated cycloalkyl, cycloalkylalkyl, aryl, arylalkyl, heteroaryl, heteroarylalkyl, saturated or partially unsaturated heterocycloalkyl or heterocyclylalkyl, wherein said alkyl, alkenyl, alkynyl, cycloalkyl, cycloalkylalkyl, aryl, arylalkyl, heteroaryl, heteroarylalkyl, heterocycloalkyl and heterocyclylalkyl are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C═O)OR$^h$, —NR$^f$SO$_2$R$^h$, —SO$_2$NR$^e$R$^f$, —C(═O)R$^e$, —C(═O)OR$^e$, —OC(═O)R$^e$, —NR$^f$C(═O)OR$^h$, —NR$^f$C(═O)R$^e$, —C(═O)NR$^e$R$^f$, —NR$^e$R$^f$, —NR$^g$C(═O)NR$^e$R$^f$, —NR$^c$C(NCN)NR$^e$R$^f$, —OR$^e$, alkyl, alkenyl, alkynyl, cycloalkyl, aryl, heteroaryl, arylalkyl, heteroarylalkyl, heterocycloalkyl and heterocyclylalkyl;

R$^b$, R$^c$, R$^f$ and R$^g$ are independently are hydrogen or alkyl, or R$^a$ and R$^b$ together with the atom to which they are attached form a 4 to 10 membered saturated or partially unsaturated heterocyclic ring which may include 1 to 3 additional heteroatoms, in addition to the nitrogen atom to which said R$^a$ and R$^b$ are attached, selected from N, O and S;

R$^d$ and R$^h$ are independently trifluoromethyl, alkyl, saturated or partially unsaturated cycloalkyl, aryl, arylalkyl, heteroaryl, heteroarylalkyl, saturated or partially unsaturated heterocycloalkyl or heterocyclylalkyl;

R$^e$ is hydrogen, trifluoromethyl, alkyl, alkenyl, alkynyl, saturated or partially unsaturated cycloalkyl, cycloalkylalkyl, aryl, arylalkyl, heteroaryl, heteroarylalkyl, saturated or partially unsaturated heterocycloalkyl or heterocyclylalkyl; and Z is alkylene having from 1 to 6 carbons, or alkenylene or alkynylene each having from 2 to 6 carbons, wherein said alkylene, alkenylene and alkynylene are optionally substituted with one or more groups independently selected from oxo, halogen, cyano, nitro, trifluoromethyl, difluoromethyl, fluoromethyl, fluoromethoxy, difluoromethoxy, trifluoromethoxy, azido, —O(C═O)OR$^d$, —NR$^b$SO$_2$R$^d$, —SO$_2$NR$^a$R$^b$, —C(═O)R$^a$, —C(═O)OR$^a$, —OC(═O)R$^a$, —NR$^b$C(═O)OR$^d$, —NR$^b$C(═O)R$^a$, —C(═O)NR$^a$R$^b$, —NR$^a$R$^b$, —NR$^c$C(═O)NR$^a$R$^b$, —NR$^c$C(NCN)NR$^a$R$^b$, —OR$^a$, alkyl, alkenyl, alkynyl, cycloalkyl, aryl, heteroaryl, arylalkyl, heteroarylalkyl, heterocycloalkyl and heterocyclylalkyl.

In certain embodiments of a compound of Formula I, Ar$^1$ is a substituted or unsubstituted phenyl, thienyl, imidazolyl, pyridyl or pyrazolyl. In particular embodiments, Ar$^1$ is optionally substituted with one or more groups independently selected from F, Cl, Br, I, OR$^a$, NR$^a$R$^b$, NO$_2$, CN, C(═O)OR$^a$, alkyl, and CF$_3$.

In certain embodiments of a compound of Formula I, Ar$^2$ is a substituted or unsubstituted phenyl, thienyl, imidazolyl, pyridyl or pyrazolyl. In particular embodiments, said Ar$^2$ is optionally substituted with one or more groups independently selected from F, Cl, Br, I, OR$^a$, NR$^a$R$^b$, NO$_2$, CN, C(═O)OH, alkyl, and CF$_3$.

In certain embodiments of a compound of Formula I, R is Z—NR$^2$R$^3$ or Z—OH. In certain embodiments, R$^2$ and R$^3$ are independently selected from H, alkyl, saturated or unsaturated cycloalkyl, SO$_2$Me, C(═O)alkyl, an amino acid, and a dipeptide, wherein said alkyl and cycloalkyl portions are optionally substituted. In certain embodiments of a compound of Formula I, Z is substituted or unsubstituted alkylene. In certain embodiments, Z is substituted or unsubstituted propylene.

In certain embodiments, R$^1$ is alkyl, cycloalkyl, heterocycloalkyl, O-alkyl, OR$^a$, aryl, heteroaryl, CR$^b$(═NOR$^c$), or C(═O)R$^a$, wherein said alkyl, cycloalkyl, heterocycloalkyl, aryl and heteroaryl are optionally substituted with one or more groups independently selected from OR$^a$, NR$^a$R$^b$, halogen, cycloalkyl, alkyl, aryl and CF$_3$. In certain embodiments, R$^a$ is alkyl, cycloalkyl, aryl, heteroaryl or CF$_3$, wherein said alkyl, cycloalkyl, aryl, and heteroaryl are optionally substituted with one or more groups selected from OR$^e$, C(═O)R$^e$, alkyl, or aryl.

In certain embodiments, R$^1$ is NR$^4$R$^5$. In certain embodiments, R$^4$ and R$^5$ are independently selected from H, alkyl, saturated or partially unsaturated cycloalkyl, and heteroaryl.

Another aspect of this invention relates to compounds of the general Formula II:

II

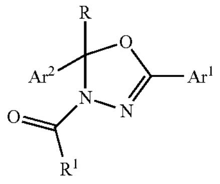

and metabolites, solvates, resolved enantiomers, diastereomers, racemic mixtures and pharmaceutically acceptable salts thereof, wherein R, R$^1$, Ar$^1$ and Ar$^2$ are as defined above.

In certain embodiments of a compound of Formula II, Ar$^1$ is a substituted or unsubstituted phenyl, thienyl, imidazolyl, pyridyl or pyrazolyl. In certain embodiments, Ar$^1$ is optionally substituted with one or more groups independently selected from F, Cl, Br, I, OR$^a$, NR$^a$R$^b$, NO$_2$, CN, C(═O)OH, alkyl and CF$_3$.

In certain embodiments of a compound of Formula II, Ar$^2$ is a substituted or unsubstituted phenyl, thienyl, imidazolyl, pyridyl or pyrazolyl. In certain embodiments, said Ar$^2$ is optionally substituted with one or more groups independently selected from F, Cl, Br, I, OR$^a$, NR$^a$R$^b$, NO$_2$, CN, C(═O)OH, alkyl, and CF$_3$.

In certain embodiments of a compound of Formula II, R is Z—NR$^2$R$^3$ or Z—OH. In certain embodiments, R$^2$ and R$^3$ are independently selected from H, alkyl, saturated or unsaturated cycloalkyl, SO$_2$Me, C(═O)alkyl, an amino acid, and a dipeptide, wherein said alkyl and cycloalkyl portions are optionally substituted. In certain embodiments of a compound of Formula II, Z is substituted or unsubstituted alkylene. In certain embodiments, Z is substituted or unsubstituted propylene.

In certain embodiments, R$^1$ is alkyl, cycloalkyl, heterocycloalkyl, O-alkyl, OR$^a$, aryl, heteroaryl, CR$^b$(═NOR$^c$), or C(═O)R$^a$, wherein said alkyl, cycloalkyl, heterocycloalkyl, aryl and heteroaryl are optionally substituted with one or more groups independently selected from OR$^a$, NR$^a$R$^b$, halogen, cycloalkyl, alkyl, aryl and $CF_3$. In certain embodiments, $R^a$ is alkyl, cycloalkyl, aryl, heteroaryl or $CF_3$, wherein said alkyl, cycloalkyl, aryl, and heteroaryl are optionally substituted with one or more groups selected from $OR^e$, $C(=O)R^e$, alkyl, or aryl.

In certain embodiments, $R^1$ is $NR^4R^5$. In certain embodiments, $R^4$ and $R^5$ are independently selected from H, alkyl, saturated or partially unsaturated cycloalkyl, and heteroaryl.

Yet another aspect of this invention provides a compound of Formula III

III

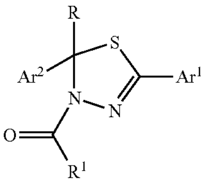

and metabolites, solvates, resolved enantiomers, diastereomers, racemic mixtures and pharmaceutically acceptable salts thereof, wherein R, $R^1$, $Ar^1$ and $Ar^2$ are as defined above.

In certain embodiments of a compound of Formula III, $Ar^1$ is a substituted or unsubstituted phenyl, thienyl, imidazolyl, pyridyl or pyrazolyl. In particular embodiments, $Ar^1$ is optionally substituted with one or more groups independently selected from F, Cl, Br, I, $OR^a$, $NR^aR^b$, $NO_2$, CN, $C(=O)OR^a$, alkyl, and $CF_3$.

In certain embodiments of a compound of Formula III, $Ar^2$ is a substituted or unsubstituted phenyl, thienyl, imidazolyl, pyridyl or pyrazolyl. In particular embodiments, said $Ar^2$ is optionally substituted with one or more groups independently selected from F, Cl, Br, I, $OR^a$, $NR^aR^b$, $NO_2$, CN, $C(=O)OH$, alkyl, and $CF_3$.

In certain embodiments of a compound of Formula III, R is $Z—NR^2R^3$ or Z—OH. In certain embodiments, $R^2$ and $R^3$ are independently selected from H, alkyl, saturated or unsaturated cycloalkyl, $SO_2Me$, $C(=O)$alkyl, an amino acid, and a dipeptide, wherein said alkyl and cycloalkyl portions are optionally substituted. In certain embodiments of a compound of Formula III, Z is substituted or unsubstituted alkylene. In certain embodiments, Z is substituted or unsubstituted propylene.

In certain embodiments, $R^1$ is alkyl, cycloalkyl, heterocycloalkyl, O-alkyl, $OR^a$, aryl, heteroaryl, $CR^b(=NOR^c)$, or $C(=O)R^a$, wherein said alkyl, cycloalkyl, heterocycloalkyl, aryl and heteroaryl are optionally substituted with one or more groups independently selected from $OR^a$, $NR^aR^b$, halogen, cycloalkyl, alkyl, aryl and $CF_3$. In certain embodiments, $R^a$ is alkyl, cycloalkyl, aryl, heteroaryl or $CF_3$, wherein said alkyl, cycloalkyl, aryl, and heteroaryl are optionally substituted with one or more groups selected from $OR^e$, $C(=O)R^e$, alkyl, or aryl.

In certain embodiments, $R^1$ is $NR^4R^5$. In certain embodiments, $R^4$ and $R^5$ are independently selected from H, alkyl, saturated or partially unsaturated cycloalkyl, and heteroaryl.

Another aspect of this invention provides a compound of Formula IV

IV

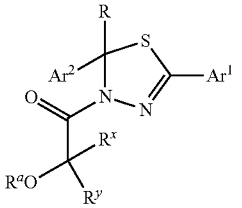

and metabolites, solvates, resolved enantiomers, diastereomers, racemic mixtures and pharmaceutically acceptable salts thereof, wherein R, $Ar^1$ and $Ar^2$ are as defined above, and $R^x$ and $R^y$ are independently H, alkyl, saturated or partially unsaturated cycloalkyl or aryl, wherein said alkyl, cycloalkyl and aryl are optionally substituted with one or more groups independently selected from oxo (with the proviso that it is not substituted on said aryl), halogen, cyano, nitro, trifluoromethyl, difluoromethyl, fluoromethyl, fluoromethoxy, difluoromethoxy, trifluoromethoxy, azido, $—O(C=O)OR^d$, $—NR^bSO_2R^d$, $—SO_2NR^aR^b$, $—C(=O)R^a$, $—C(=O)OR^a$, $—OC(=O)R^a$, $—OCH_2C(=O)OR^a$, $—NR^bC(=O)OR^d$, $—NR^bC(=O)R^a$, $—C(=O)NR^aR^b$, $—NR^aR^b$, $—NR^cC(=O)NR^aR^b$, $—NR^cC(NCN)NR^aR^b$, $—OR^a$, alkyl, alkenyl, alkynyl, cycloalkyl, aryl, heteroaryl, arylalkyl, heteroarylalkyl, heterocyclyl and heterocyclylalkyl, or $R^x$ and $R^y$ together with the atom to which they are attached form a saturated or partially unsaturated carbocyclic ring or heterocyclic ring having one or more heteroatoms independently selected from N, O and S, wherein said carbocyclic and heterocyclic rings are optionally substituted with one or more groups independently selected from oxo, halogen, cyano, nitro, trifluoromethyl, difluoromethyl, fluoromethyl, fluoromethoxy, difluoromethoxy, trifluoromethoxy, azido, $—O(C=O)OR^d$, $—NR^bSO_2R^d$, $—SO_2NR^aR^b$, $—C(=O)R^a$, $—C(=O)OR^a$, $—OC(=O)R^a$, $—NR^bC(=O)OR^d$, $—NR^bC(=O)R^a$, $—C(=O)NR^aR^b$, $—NR^aR^b$, $—NR^cC(=O)NR^aR^b$, $—NR^cC(NCN)NR^aR^b$, $—OR^a$, alkyl, alkenyl, alkynyl, cycloalkyl, aryl, heteroaryl, arylalkyl, heteroarylalkyl, heterocycloalkyl and heterocyclylalkyl;

and $R^a$, $R^b$, $R^c$ and $R^d$ are as defined above, or $R^a$ and $R^x$ together with the atoms to which they are attached form a saturated or partially unsaturated heterocyclic ring which may include 1 to 3 additional heteroatoms, in addition to the oxygen atom to which said $R^a$ is attached, selected from N, O and S, wherein said heterocyclic ring is optionally substituted with one or more groups independently selected from oxo, halogen, cyano, nitro, trifluoromethyl, difluoromethyl, fluoromethyl, fluoromethoxy, difluoromethoxy, trifluoromethoxy, azido, $—O(C=O)OR^h$, $—NR^fSO_2R^h$, $—SO_2NR^eR^f$, $—C(=O)R^e$, $—C(=O)OR^e$, $—OC(=O)R^e$, $—NR^fC(=O)OR^h$, $—NR^fC(=O)R^e$, $—C(=O)NR^eR^f$, $—NR^eR^f$, $—NR^gC(=O)NR^eR^f$, $—NR^cC(NCN)NR^eR^f$, $—OR^e$, alkyl, alkenyl, alkynyl, cycloalkyl, aryl, heteroaryl, arylalkyl, heteroarylalkyl, heterocycloalkyl and heterocyclylalkyl, wherein $R^e$, $R^f$, $R^g$ and $R^h$ are as defined above.

In certain embodiments of a compound of Formula IV, at least one of $R^x$ and $R^y$ is not H. In certain embodiments, $R^a$ is H or alkyl. In particular embodiments, $R^x$ and $R^a$ are alkyl.

In certain embodiments of a compound of Formula IV, $Ar^1$ is a substituted or unsubstituted phenyl, thienyl, imidazolyl, pyridyl or pyrazolyl. In particular embodiments, $Ar^1$ is optionally substituted with one or more groups independently selected from F, Cl, Br, I, $OR^a$, $NR^aR^b$, $NO_2$, CN, C(═O)$OR^a$, alkyl, and $CF_3$.

In certain embodiments of a compound of Formula IV, $Ar^2$ is a substituted or unsubstituted phenyl, thienyl, imidazolyl, pyridyl or pyrazolyl. In particular embodiments, said $Ar^2$ is optionally substituted with one or more groups independently selected from F, Cl, Br, I, $OR^a$, $NR^aR^b$, $NO_2$, CN, C(═O)OH, alkyl, and $CF_3$.

In certain embodiments of a compound of Formula IV, R is Z—$NR^2R^3$ or Z—OH. In certain embodiments, $R^2$ and $R^3$ are independently selected from H, alkyl, saturated or unsaturated cycloalkyl, $SO_2Me$, C(═O)alkyl, an amino acid, and a dipeptide, wherein said alkyl and cycloalkyl portions are optionally substituted. In certain embodiments of a compound of Formula IV, Z is substituted or unsubstituted alkylene. In certain embodiments, Z is substituted or unsubstituted propylene.

The term "alkyl" as used herein refers to a saturated linear or branched-chain monovalent hydrocarbon radical having one to ten carbon atoms, wherein the alkyl radical may be optionally substituted independently with one or more substituents described herein. Examples of alkyl radicals include $C_1$-$C_{12}$ hydrocarbon moieties such as: methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl, and 1-octyl.

The term "alkylene" as used herein refers to a linear or branched saturated divalent hydrocarbon radical of one to twelve carbon atoms, e.g., methylene (—$CH_2$—), 1,2-ethylene (—$CH_2CH_2$—), 1,3-propylene (—$CH_2CH_2CH_2$—), 1,4-butyl (—$CH_2CH_2CH_2CH_2$—), and the like, optionally substituted independently with one or more substituents described herein.

The term "alkenyl" refers to a linear or branched-chain monovalent hydrocarbon radical having two to 10 carbon atoms and at least one double bond, and include, but is not limited to, ethenyl, propenyl, 1-but-3-enyl, 1-pent-3-enyl, 1-hex-5-enyl and the like, wherein the alkenyl radical may be optionally substituted independently with one or more substituents described herein, and includes radicals having "cis" and "trans" orientations, or alternatively, "E" and "Z" orientations. The term "alkenyl" includes allyl.

The term "allyl" refers to a radical having the formula RC═CHCHR, wherein R is alkyl, alkenyl, alkynyl, cycloalkyl, heterocycloalkyl, aryl, or heteroaryl, wherein the allyl may be optionally substituted independently with one or more substituents described herein.

The term "alkenylene" refers to a linear or branched divalent hydrocarbon radical of two to twelve carbons containing at least one double bond, wherein the alkenylene radical may be optionally substituted independently with one or more substituents described herein. Examples include, but are not limited to, ethenylene (—CH═CH—), propenylene (—CH═$CHCH_2$—), and the like.

The term "alkynyl" refers to a linear or branched monovalent hydrocarbon radical of two to twelve carbon atoms containing at least one triple bond. Examples include, but are not limited to, ethynyl, propynyl, butynyl, pentyn-2-yl and the like, wherein the alkynyl radical may be optionally substituted independently with one or more substituents described herein.

The term "alkynylene" refers to a linear or branched divalent hydrocarbon radical of two to twelve carbons containing at least one triple bond, wherein the alkynylene radical may be optionally substituted independently with one or more substituents described herein. Alkynylene radicals include, but are not limited to: acetylene (—C≡C—), propargyl (—$CH_2$C≡C—), and 4-pentynyl (—$CH_2CH_2CH_2$C≡C—).

The terms "cycloalkyl," "carbocycle," and "carbocyclyl" are used interchangeably herein and refer to saturated or partially unsaturated (i.e., having one or more double and/or triple bonds within the carbocycle) cyclic hydrocarbon radical having from three to twelve carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl fused to a saturated or partially unsaturated cycloalkyl or heterocycloalkyl ring or an aryl or heteroaryl ring. Examples of cycloalkyl groups include, but are not limited to, cyclopropyl, cyclobutyl, cyclopentyl, cyclohexyl, cycloheptyl, and the like. Bicyclic carbocycles have 7 to 12 ring atoms, e.g. arranged as a bicyclo [4,5], [5,5], [5,6] or [6,6] system, or as bridged systems such as bicyclo[2.2.1]heptane, bicyclo[2.2.2]octane, and bicyclo[3.2.2]nonane. The cycloalkyl may be optionally substituted independently at one or more substitutable positions with one or more substituents described herein. Such cycloalkyl groups may be optionally substituted with, for example, one or more groups independently selected from $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl and di($C_1$-$C_6$)alkylamino($C_1$-$C_6$)alkyl.

The term "heteroalkyl" refers to a saturated linear or branched-chain monovalent hydrocarbon radical of one to twelve carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals.

The terms "heterocycloalkyl," "heterocycle" and "heterocyclyl" are used interchangeably herein and refer to a saturated or partially unsaturated (i.e., having one or more double and/or triple bonds within the carbocycle) carbocyclic radical of 3 to 8 ring atoms in which at least one ring atom is a heteroatom selected from nitrogen, oxygen and sulfur, the remaining ring atoms being C, where one or more ring atoms may be optionally substituted independently with one or more substituents described below. The radical may be a carbon radical or heteroatom radical. The term "heterocycle" includes heterocycloalkoxy. "Heterocycloalkyl" also includes radicals where heterocycle radicals are fused with a carbocyclic, heterocyclic, aromatic or heteroaromatic ring. Examples of heterocycloalkyl rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo [4.1.0]heptanyl, azabicyclo[2.2.2]hexanyl, 3H-indolyl quinolizinyl and N-pyridyl ureas. Spiro moieties are also included within the scope of this definition. The heterocycle may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl. The heterocycle groups herein are unsubstituted or substituted in one or more substitutable positions with various groups.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Further examples of carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

The term "aryl" refers to a monovalent aromatic carbocyclic radical having a single ring (e.g., phenyl), multiple rings (e.g., biphenyl), or multiple condensed rings in which at least one is aromatic, (e.g., 1,2,3,4-tetrahydronaphthyl, naphthyl, etc.), which is optionally substituted independently with one or more substituents described herein.

The term "heteroaryl" refers to a monovalent aromatic radical of 5-, 6-, or 7-membered rings and includes fused ring systems (at least one of which is aromatic) of 5-10 atoms containing one or more heteroatoms selected from nitrogen, oxygen, and sulfur. Examples of heteroaryl groups are pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups are optionally substituted independently with one or more substituents described herein.

The term "halogen" represents fluorine, bromine, chlorine, and iodine.

The term "arylalkyl" means an alkyl moiety (as defined above) substituted with one or more aryl moiety (also as defined above). Examples include, but are not limited to, aryl-$C_{1-3}$-alkyls such as benzyl, phenylethyl, and the like. The arylalkyl, may be optionally substituted independently with one or more substituents described herein.

The term "heteroarylalkyl" means an alkyl moiety (as defined above) substituted with a heteroaryl moiety (also as defined above). Examples include, but are not limited to, 5- or 6-membered heteroaryl-$C_{1-3}$-alkyls such as oxazolylmethyl, pyridylethyl and the like. The heteroarylalkyl may be optionally substituted independently with one or more substituents described herein.

The term "heterocyclylalkyl" means an alkyl moiety (as defined above) substituted with a heterocyclyl moiety (also defined above). Examples include, but are not limited to, 5- or 6-membered heterocyclyl-$C_{1-3}$-alkyls such as tetrahydropyranylmethyl. The heterocyclylalkyl may be optionally substituted independently with one or more substituents described herein.

The term "cycloalkylalkyl" means an alkyl moiety (as defined above) substituted with a cycloalkyl moiety (also defined above). Examples include 5- or 6-membered cycloalkyl-$C_{1-3}$-alkyls such as cyclopropylmethyl. The cycloalkylalkyl may be optionally substituted independently with one or more substituents described herein.

The term "amino acid" includes residues of natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr and Val) in D or L form, as well as unnatural amino acids (such as, but not limited to, phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, cirtulline, homocysteine, homoserine, methyl-alanine, para-benzoylphenylalanine, phenylglycine, propargylglycine, sarcosine, methionine sulfone and tert-butylglycine). An amino acid can be linked to the remainder of a compound of Formula I-IV through the carboxy terminus, the amino terminus, or through any other convenient point of attachment, such as, for example, through the sulfur of cysteine. In a particular embodiment, the amino acid is linked to the remainder of a compound of Formula I-IV through the carboxy terminus.

In general, the various moieties or functional groups of the compounds of Formulas I-IV may be optionally and independently substituted by one or more substituents. Examples of substituents suitable for purposes of this invention include, but are not limited to, oxo, halogen, cyano, nitro, trifluoromethyl, fluoromethoxy, difluoromethoxy, trifluoromethoxy, azido, —NR"$SO_2$R', —$SO_2$NR'R", —C(=O)R', —C(=O)OR', —OC(=O)R', —NR"C(=O)OR', —NR"C(=O)R', —C(=O)NR'R", —NR'R", —NR'"C(=O)N'R", —OR', alkyl, alkenyl, alkynyl, heteroalkyl, cycloalkyl, heterocycloalkyl, aryl, heteroaryl, arylalkyl, heteroarylalkyl, and heterocyclylalkyl, where R', R" and R'" are independently H, alkyl, alkenyl, alkynyl, heteroalkyl, saturated or partially unsaturated cycloalkyl, saturated or partially unsaturated heterocycloalkyl, aryl, or heteroaryl.

It is to be understood that in instances where two or more radicals are used in succession to define a substituent attached to a structure, the first named radical is considered to be terminal and the last named radical is considered to be attached to the structure in question. Thus, for example, an arylalkyl radical is attached to the structure in question by the alkyl group.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers, diastereomers mixtures, racemic or otherwise, thereof. Accordingly, this invention also includes all such isomers, including diastereomeric mixtures, pure diastereomers and pure enantiomers of the compounds of Formulas I-IV.

The term "enantiomer" refers to two stereoisomers of a compound which are non-superimposable mirror images of one another. The term "diastereomer" refers to a pair of optical isomers which are not mirror images of one another. Diastereomers have different physical properties, e.g. melting points, boiling points, spectral properties, and reactivities.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

In addition to compounds of Formulas I-IV, the invention also includes solvates, pharmaceutically acceptable prodrugs, and pharmaceutically acceptable salts of such compounds. The phrase "pharmaceutically acceptable" indicates that the substance or composition must be compatible chemically and/or toxicologically, with the other ingredients comprising a formulation, and/or the mammal being treated therewith.

The term "solvate" refers to an aggregate of a molecule with one or more solvent molecules.

A "pharmaceutically acceptable prodrug" is a compound that may be converted under physiological conditions or by solvolysis to the specified compound or to a pharmaceutically acceptable salt of such compound. Prodrugs include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, cirtulline, homocysteine, homoserine, methyl-alanine, para-benzoylphenylalanine, phenylglycine, propargylglycine, sarcosine, methionine sulfone and tert-butylglycine. Particular examples of prodrugs of this invention include a compound of Formula I-IV covalently joined to a phosphate residue or a valine residue.

Additional types of prodrugs are also encompassed. For instance, free carboxyl groups can be derivatized as amides or alkyl esters. As another example, compounds of this invention comprising free hydroxy groups may be derivatized as prodrugs by converting the hydroxy group into groups such as, but not limited to, phosphate ester, hemisuccinate, dimethylaminoacetate, or phosphoryloxymethyloxycarbonyl groups, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including, but not limited to, ether, amine and carboxylic acid functionalities, or where the acyl group is an amino acid ester as described above, are also encompassed. Prodrugs of this type are described in *J. Med. Chem.,* 1996, 39, 10. More specific examples include replacement of the hydrogen atom of the alcohol group with a group such as $(C_1-C_6)$alkanoyloxymethyl, 1-($(C_1-C_6)$alkanoyloxy)ethyl, 1-methyl-1-($(C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —P(O)(O$(C_1-C_6)$alkyl$)_2$ or glycosyl (the radical resulting from the removal of a hydroxyl group of the hemiacetal form of a carbohydrate).

Free amines of compounds of this invention can also be derivatized as amides, sulfonamides or phosphonamides. All of these prodrug moieties may incorporate groups including, but not limited to, ether, amine and carboxylic acid functionalities. For example, a prodrug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl-natural α-aminoacyl, —C(OH)C(O)OY wherein Y is H, $(C_1-C_6)$alkyl or benzyl, —C$(OY_0)Y_1$ wherein $Y_0$ is $(C_1-C_4)$ alkyl and $Y_1$ is $(C_1-C_6)$alkyl, carboxy $(C_1-C_6)$alkyl, amino$(C_1-C_4)$alkyl or mono-N- or di-N,N—$(C_1-C_6)$alkylamino alkyl, —C$(Y_2)Y_3$ wherein $Y_2$ is H or methyl and $Y_3$ is mono-N- or di-N,N—$(C_1-C_6)$alkylamino, morpholino, piperidin-1-yl or pyrrolidin-1-yl.

For additional examples of prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 *"Design and Application of Prodrugs*," by H. Bundgaard p. 113-191 (1991); c) H. Bundgaard, *Advanced Drug Delivery Reviews,* 8:1-38 (1992); d) H. Bundgaard, et al., *Journal of Pharmaceutical Sciences,* 77:285 (1988); and e) N. Kakeya, et al., *Chem. Pharm. Bull.,* 32:692 (1984), each of which is specifically incorporated herein by reference. Prodrugs of a compound may be identified using routine techniques known in the art.

A "pharmaceutically acceptable salt," unless otherwise indicated, includes salts that retain the biological effectiveness of the free acids and bases of the specified compound and that are not biologically or otherwise undesirable. A compound of the invention may possess a sufficiently acidic, a sufficiently basic, or both functional groups, and accordingly react with any of a number of inorganic or organic bases or acids to form a pharmaceutically acceptable salt. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moiety, the compounds of the present invention may include mono, di or tri-salts in a single compound.

If the inventive compound is a base, the desired pharmaceutically acceptable salt may be prepared by any suitable method available in the art, for example, treatment of the free base with an acidic compound, for example an inorganic acid such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alpha hydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base. Examples of suitable inorganic salts include those formed with alkali and alkaline earth metals such as lithium, sodium, potassium, barium and calcium. Examples of suitable organic base salts include, for example, ammonium, dibenzylammonium, benzylammonium, 2-hydroxyethylammonium, bis(2-hydroxyethyl) ammonium, phenylethylbenzylamine, dibenzyl-ethylenediamine, and the like salts. Other salts of acidic moieties may include, for example, those salts formed with procaine, quinine and N-methylglucosamine, plus salts formed with basic amino acids such as glycine, ornithine, histidine, phenylglycine, lysine and arginine.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified is contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Also falling within the scope of this invention are metabolites of compounds of Formulas I-IV. A "metabolite" is a pharmacologically active product produced through metabolism in the body of a specified compound or salt thereof. Metabolites may result, for example, from the oxidation, reduction, hydrolysis, amidation, deamidation, esterification, deesterification, enzymatic cleavage, and the like, of the administered compound. Accordingly, the invention includes metabolites of compounds of Formulas I-IV, including compounds produced by a process comprising contacting a compound of this invention with a mammal for a period of time sufficient to yield a metabolic product thereof.

Metabolites typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. Metabolites, so long as they are not otherwise found in vivo, are useful in diagnostic assays for therapeutic dosing of the compounds of the invention.

The inventive compounds may be prepared using the reaction routes and synthesis schemes as described below, employing the techniques available in the art using starting materials that are readily available or can be synthesized using methods known in the art. Illustrations of the preparation of certain compounds of the present invention are shown in Schemes I-III below.

Scheme I

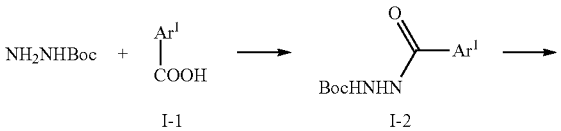

I-1

I-2

-continued

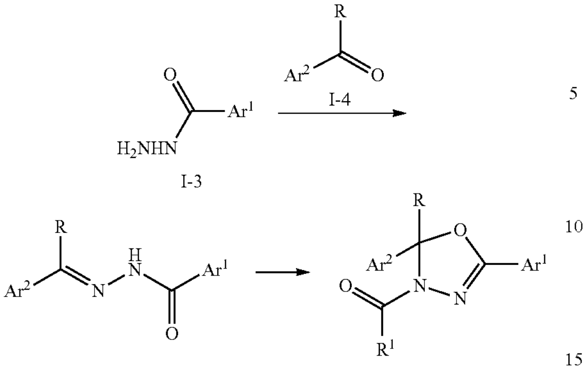

I-3 I-4 I-5 I-6

Scheme I illustrates a method of preparing compounds of Formula I-6. Acid I-1 can be coupled with tert-butyl carbazate using standard coupling procedures including, but not limited to, EDCI/HOBt, PyBOP, or DIC to produce intermediate I-2. Removal of the tert-butoxycarbonyl (Boc) group of I-2 can be achieved by treatment with a variety of acids including, but not limited to, TFA and HCl/dioxane to give acid hydrazide I-3. I-3 can then be condensed with ketone I-4 to provide intermediate I-5 utilizing a variety of acid catalysts. In one embodiment, compounds I-3 and I-4 are combined in ethanol with added acetic acid and heated at elevated temperature (95° C.) to provide compound I-5. Oxadiazolines I-6 can be prepared by combining I-5 with the appropriate anhydride or acid chloride or carboxylic acid in the presence of a standard coupling agent. For example, oxadiazoline I-6 can be prepared by treatment with excess anhydride at elevated temperatures in an appropriate organic solvent such as DCE. Alternatively, treatment of I-5 with acid chloride and an appropriate base, such as pyridine or $Et_3N$, in a variety of organic solvents such as DCM or DCE at room temperature affords oxadiazoline I-6. Alternatively, I-6 can be prepared through coupling with anhydrides, or through treatment of I-5 with the appropriate carboxylic acid and $Ac_2O$ in DCE at elevated temperature (80° C.). Oxadiazoline I-6 can be obtained by treatment of I-5 with a carboxylic acid and amide-coupling reagent, including but not limited to EDCI/HOBT or diethyl cyanophosphonate, and appropriate base, $Et_3N$ or DIEA, in a suitable organic solvent such as DCM, DCE, DMF, THF, or solvent mixture at room temperature or above. In certain embodiments, this coupling is accomplished with diethyl cyanophosphonate and TEA in DCE at elevated temperature (80° C.) to provide I-6.

Scheme II

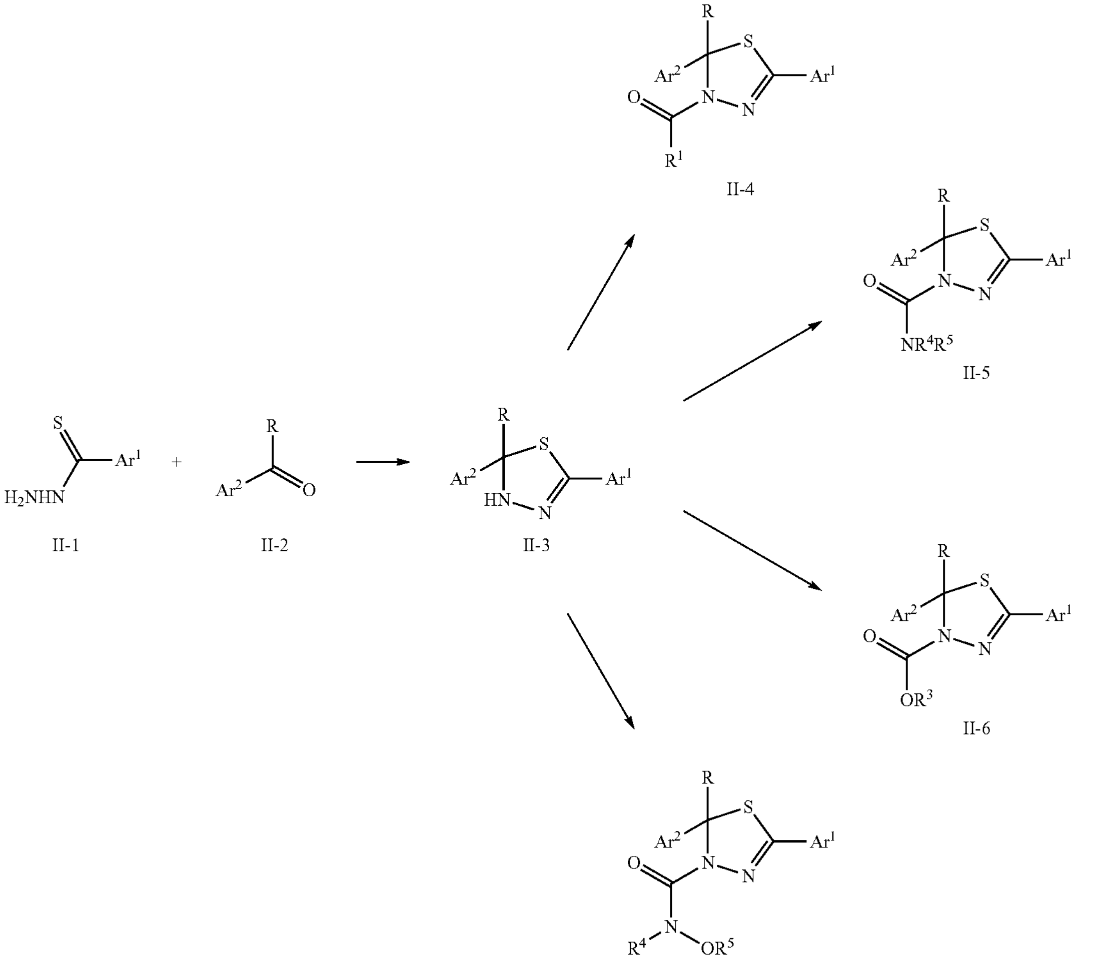

II-1 II-2 II-3 II-4 II-5 II-6 II-7

Scheme II illustrates a method of preparing thiodiazolines of Formulas II-3, II-4, II-5, II-6 and II-7. Thiohydrazide II-1 (Takasugi, J. J.; Buckwalter, B. L., EP Patent No. 1004241) can be condensed with ketone II-2 in an appropriate organic solvent such as ethanol to give thiodiazoline II-3. In certain embodiments, the condensation can be catalyzed by acetic acid. Thiodiazoline II-3 can be functionalized to produce II-4 by standard coupling procedures including, but not limited to, EDCI/HOBt, PyBOP, HATU, or DIC and the appropriate carboxylic acid. Alternatively, compound II-4 can be prepared by treatment of II-3 with the appropriate acid chloride and amine base in a suitable organic solvent such as THF. A compound of formula II-5 can be prepared by reacting compound II-3 with the appropriate carbamyl chloride in the presence of an amine base. Alternatively, a compound of formula II-5 can be prepared by treatment of a compound of formula II-3 with the appropriate isocyanate in an appropriate organic solvent such as THF. Another method for preparing compound II-5 comprises subjecting the appropriate amine to a carbonylating reagent such as, but not limited to, triphosgene, diphosgene, phosgene or carbonyldiimidazole, followed by treatment with II-3. In certain embodiments, the amine can be treated with triphosgene, $Et_3N$ and catalytic DMAP followed by II-3 to give II-5. Similarly, compounds of formula II-6 can be prepared by subjecting II-3 to a chloroformate in the presence of an amine base. Chloroformates can be prepared by subjecting alcohols to a carbonylating reagent, as described above. Alternatively, compounds of formulae II-5, II-6 and II-7 can be prepared by treating II-3 with carbonyldiimidazole followed by addition of MeI to generate the stable methylimidazolium iodide salt. Addition of an amine, alcohol, hydroxylamine or alkoxylamine in the presence of $Et_3N$ to the methylimidazolium iodide salt generates the analogs of formulae II-5, II-6, and II-7, respectively. Derivatives of formulae II-5, II-6 and II-7 can be prepared from an intermediate 4-nitrophenyl carboxylate. Thiadiazoline II-3 can be treated with 4-nitrophenylchloroformate in the presence of a suitable base such as DIEA or $Et_3N$ in a suitable organic solvent such as DCE or DCM at room temperature. Addition of amine, alcohol, hydroxylamine or alkoxylamine in the presence of a suitable base such as DIEA or $Et_3N$ to the 4-nitrophenyl carboxylate in a suitable organic solvent such as DCE or THF at elevated temperature affords the analogs of formulae II-5, II-6, and II-7, respectively.

In the above Schemes any of the substituents R, $R^1$, $Ar^1$, $Ar^2$, may contain functional groups that require protection in the reaction sequences described. The choice of protecting group and the deprotection conditions will depend on the functional group and is well known to those skilled in the art. Examples of use of protecting groups are described in Scheme III. These examples are representative only are not meant to limit the scope of this application in any way.

Scheme III

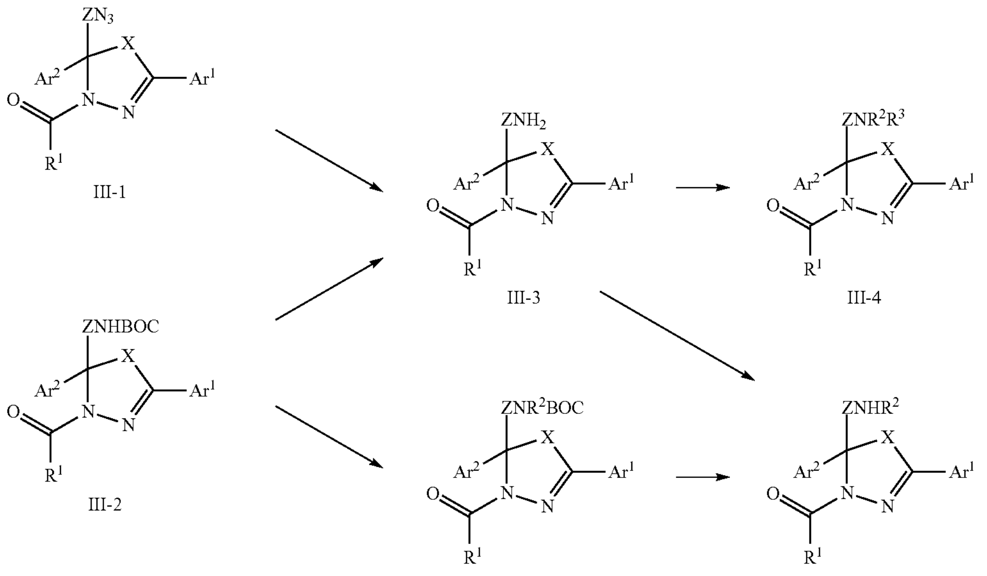

III-1 III-2 III-3 III-4 III-5 III-6

Scheme III shows a method of preparing compounds of Formulas III-4, III-5 and III-6. Compounds III-1 and III-2 can be prepared as described in Schemes I and II using the appropriate ketone containing an amino group either masked as an azide or protected as a t-butyl carbamate. Amine III-3 can be generated from azide III-1 by a variety of methods including, but not limited to, Staudinger reaction with $Ph_3P$/water and hydrogenation in the presence of Pd/C under 1 atm $H_2$. Amine III-3 can also be prepared from t-butyl carbamate III-2 by standard acidic deprotection conditions including but not limited to TFA in DCM, HCl in a suitable organic solvent such as dioxane or diethyl ether, and neat formic acid. Once unmasked amine III-3 can be further functionalized. Derivatives III-4, wherein $R^2$ and $R^3$ are independently selected from alkyl, alkenyl, alkynyl, cycloalkyl, cycloalkenyl and cycloalkynyl groups, can be made using standard reductive amination conditions. These conditions include but are not limited to treatment of amine III-3 with the appropriate aldehyde or ketone in the presence of dehydrating agents such as $MgSO_4$ followed by reduction with $NaBH_4$, $Na(OAc)_3BH$ or $NaCNBH_3$ in a suitable organic solvent such as DCM, DCE, acetonitrile or THF. Alternatively, amine III-3 can be treated with the appropriate aldehyde or ketone in the presence of acetic acid and reducing agent such as $Na(OAc)_3BH$ or $NaCNBH_3$ in suitable organic solvents such as DCM, DCE, acetonitrile or THF. In certain embodiments, III-3 and the appropriate aldehyde or ketone are combined in acetonitrile and stirred for 1 hour. Acetic acid and $Na(OAc)_3BH$ are then added and the reaction mixture is heated at an elevated temperature (45° C.) to afford III-4. Analogs III-4 where $R^2$ or $R^3$ is —C(═O)$R^6$, —$SO_2R^6$, —C(═O)$NR^4R^5$, —$SO_2NR^4R^5$, amino acid, or polypeptide can be prepared by standard methods known to those skilled in the art. These include but are not limited to treatment of amine III-3 with acid chloride, sulfamoyl chloride, sulfonyl chloride or isocyanate in the presence or absence of tertiary amine base, and treatment of III-3 with carboxylic acid, amino acid or polypeptide in the presence of standard coupling reagents including, but not limited to, EDCI/HOBt, PyBOP, HATU, or DIC. Derivatives of the formula III-5 may also be prepared by subjecting III-2 to a base such as NaH, KH, LiHMDS, NaHMDS, KHMDS or other suitable base and an appropriate alkylating agent which may include, but is not limited to, alkyl halides, (un)substituted benzyl halides, (un)substituted allyl halides, (un)substituted propargyl halides, sulfonate esters and sulfate esters in a suitable solvent such as DMF or THF to afford III-5. III-6 can be prepared from III-5 by standard acidic deprotection conditions including, but not limited to, TFA in DCM, HCl in a suitable organic solvent such as dioxane or diethyl ether, and neat formic acid. In certain embodiments, III-2 is treated with NaH in DMF followed by iodomethane to afford III-5 wherein $R^2$ is methyl. Removal of the BOC group is can be achieved, for example, with TFA in DCM to provide III-6. Alternatively, III-6 can be generated from III-3 by treatment with a suitable alkylating agent and a suitable base which may include, but is not limited to, a tertiary amine, $K_2CO_3$, $Na_2CO_3$, $Cs_2CO_3$, or CsOH in an appropriate solvent such as acetonitrile, DMF or THF to afford III-6.

In any of the synthetic methods for preparing compounds of Formula I-IV, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a reaction mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., *J. Chromatogr*., (1975), 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−)menthyl chloroformate in the presence of base, or Mosher ester, α-methoxy-α-(trifluoromethyl)phenyl acetate (Jacob III. *J. Org. Chem*., (1982) 47:4165), of the racemic mixture, and analyzing the $^1H$ NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, *J. of Chromatogr*., (1990) 513: 375-378). Enriched or purified enantiomers can be distinguished by methods used to distinguish other chiral molecules with asymmetric carbon atoms, such as optical rotation and circular dichroism.

The compounds of the invention find use in a variety of applications. According to certain embodiments, this invention provides methods of blocking or inhibiting mitosis by administering an effective amount of a compound of Formula I-IV. As will be appreciated by those skilled in the art, mitosis may be altered in a variety of ways; that is, one can affect mitosis either by increasing or decreasing the activity of a component in the mitotic pathway. Stated differently, mitosis may be affected (e.g., disrupted) by disturbing equilibrium, either by inhibiting or activating certain components using the compounds of the present invention, for example, by modulating spindle function or blocking mitotic kinesin. Similar approaches may be used to alter meiosis.

In certain embodiments, the compounds of the invention can be used to modulate mitotic spindle formation, thus causing prolonged cell cycle arrest in mitosis. By "modulate" herein is meant altering mitotic spindle formation, including increasing and decreasing spindle formation. By "mitotic spindle formation" herein is meant organization of microtubules into bipolar structures by mitotic kinesins. By "mitotic spindle dysfunction" herein is meant mitotic arrest and monopolar spindle formation.

In certain embodiments, the compounds of the invention can be used to bind to and/or modulate the activity of a mitotic kinesin. In an embodiment, the mitotic kinesin is a member of the bimC subfamily of mitotic kinesins as described in U.S. Pat. No. 6,284,480, which is incorporated herein by reference. In a further embodiment, the mitotic kinesin is human KSP, although the activity of mitotic kinesins from other organisms may also be modulated by the compounds of the present invention. In this context, modulate means either increasing or decreasing spindle pole separation, causing malformation, i.e., splaying, of mitotic spindle poles, or otherwise causing morphological perturbation of the mitotic spindle. Also included within the definition of KSP for these purposes are variants and/or fragments of KSP. In addition, other mitotic kinesins may be inhibited by the compounds of the present invention.

In certain embodiments, the compounds of the invention can be used to treat abnormal or unwanted cell growth conditions, such as, but not limited to, cellular proliferative diseases, for example, cancer, hyperplasias, restenosis, cardiac hypertrophy, immune disorders, infectious disease, fungal or other eukaryote infections, inflammatory diseases, arthritis, graft rejection, inflammatory bowel disease, proliferation induced after medical procedures, including, but not limited to, surgery, angioplasty, and the like, by administering a therapeutically effective amount of a compound of Formula I-IV, or a pharmaceutically acceptable salt, prodrug, metabolite or solvate thereof.

The terms "abnormal cell growth" and "hyperproliferative disorder" are used interchangeably in this application and, unless otherwise indicated, refer to cell growth that is independent of normal regulatory mechanisms (e.g., loss of contact inhibition). Examples of abnormal cell growth conditions include, but are not limited to, cancer, autoimmune disease, arthritis, graft rejection, inflammatory bowel disease, or proliferation induced after a medical procedure.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

It is appreciated that in some cases the cells may not be in a hyper- or hypoproliferation state (abnormal state) but still require treatment. For example, during wound healing, the cells may be proliferating "normally", but proliferation enhancement may be desired. Similarly, as discussed above, in the agriculture arena, cells may be in a "normal" state, but proliferation modulation may be desired to enhance a crop by directly enhancing growth of a crop, or by inhibiting the growth of a plant or organism which adversely affects the crop. Thus, in certain embodiments, the invention herein includes application to cells or individuals that are afflicted or may eventually become afflicted with any one of these disorders or states.

The invention also provides a pharmaceutical composition for the treatment of a hyperproliferative disorder in a mammal which comprises a therapeutically effective amount of a compound of the present invention, or a pharmaceutically acceptable salt, prodrug, metabolite or solvate thereof, and a pharmaceutically acceptable carrier. In certain embodiments, the invention provides a pharmaceutical composition for the treatment of solid tumors such as skin, breast, brain, cervical carcinomas, testicular carcinomas, etc. More particularly, cancers that may be treated by the compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. The term "cancerous cell" as provided herein, includes a cell afflicted by any one of the above identified conditions.

The invention also relates to a method of treating a hyperproliferative disorder in a mammal that comprises administering to said mammal a therapeutically effective amount of a compound of the present invention, or a pharmaceutically acceptable salt, prodrug, metabolite or solvate thereof. In certain embodiments, said method relates to the treatment of cancers, including the above identified conditions.

The invention also relates to a composition for the treatment of a hyperproliferative disorder in a mammal, comprising a therapeutically effective amount of a compound of the present invention, or a pharmaceutically acceptable salt, prodrug, metabolite or solvate thereof, in combination with an anti-tumor agent selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, anti-androgens, targeted antibodies, HMG-CoA reductase inhibitors, and prenyl-protein transferase inhibitors.

The invention also relates to a method for the treatment of a hyperproliferative disorder in a mammal that comprises administering to said mammal a therapeutically effective amount of a compound of the present invention, or a pharmaceutically acceptable salt, prodrug, metabolite or solvate thereof, in combination with an anti-tumor agent selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, anti-androgens, targeted antibodies, HMG-CoA reductase inhibitors, and prenyl-protein transferase inhibitors.

This invention also relates to a pharmaceutical composition for inhibiting abnormal cell growth in a mammal which comprises an amount of a compound of the present invention, or a pharmaceutically acceptable salt, solvate, metabolite or prodrug thereof, in combination with an amount of a chemotherapeutic, wherein the amounts of the compound, salt, solvate, or prodrug, and of the chemotherapeutic are together effective in inhibiting abnormal cell growth. Many chemotherapeutics are known in the art. In certain embodiments, the chemotherapeutic is selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, anti-androgens, targeted antibodies, HMG-CoA reductase inhibitors, and/or prenyl-protein transferase inhibitors.

This invention further relates to a method for inhibiting abnormal cell growth in a mammal or treating a hyperproliferative disorder which method comprises administering to the mammal an amount of a compound of the present invention, or a pharmaceutically acceptable salt, metabolite solvate or prodrug thereof, in combination with radiation therapy, wherein the amounts of the compound, salt, solvate, or prodrug, in combination with the radiation therapy is effective in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

It is believed that the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation, which comprises administering to the mammal an amount of a compound of the present invention or a pharmaceutically acceptable salt, solvate, metabolite or prodrug thereof, which amount is effective in sensitizing abnormal cells to radiation treatment. The amount of the compound, salt, solvate, metabolite or prodrug to be used in this method can be determined according to means for ascertaining effective amounts of such compounds as described herein or by methods know to those skilled in the art.

The invention also provides pharmaceutical compositions and methods of use thereof for inhibiting abnormal cell growth in a mammal, comprising administering to a mammal in need thereof an amount of a compound of the present invention, or a pharmaceutically acceptable salt, solvate, metabolite, or prodrug thereof, and an amount of one or more substances selected from anti-angiogenesis agents, signal transduction inhibitors, and antiproliferative agents, in amounts effective to inhibit abnormal cell growth.

For example, anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound or pharmaceutical compositions of the present invention. Examples of useful COX-II inhibitors include CELEBREX™ (alecoxib) BEXTRA® (valdecoxib), Arcoxia™ (etoricoxib), Prexige® (lumiracoxib) and Vioxx® (rofecoxib). Examples of MMP-2 and MMP-9 inhibitors are those that have little or no activity inhibiting MMP-1, and include those that selectively inhibit MMP-2 and/or MMP-9 relative to the other matrix-metalloproteinases (i.e., MMP-1, MMP-3, MMP-4, MMP-5, MMP-6, MMP-7, MMP-8, MMP-10, MMP-11, MMP-12, and MMP-13).

The invention also relates to a composition for the treatment of unwanted cell growth, for example a fungal infection, in a mammal, comprising a therapeutically effective amount of a compound of the present invention, or a pharmaceutically acceptable salt, prodrug, metabolite or solvate thereof. In certain embodiments the compositions of the present invention modulate the activity of the fungal members of the bimC kinesin subgroup, as is described in U.S. Pat. No. 6,284,480.

The invention also relates to a method of treating unwanted cell growth, for example a fungal infection, in a mammal, comprising administering a therapeutically effective amount of a compound of the present invention, or a pharmaceutically acceptable salt, prodrug, metabolite or solvate thereof.

The compounds of this invention may be used alone in combination with other drugs and therapies used in the treatment of disease states which would benefit from the inhibition of KSP kinesin. For example, a compound of this invention may be applied in combination with one or more other antitumor substances, including, but not limited to, mitotic inhibitors such as vinblastine; alkylating agents such as cisplatin, carboplatin and cyclophosphamide; anti-metabolites such as 5-fluorouracil, cytosine arabinside and hydroxyurea; one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; antisense RNA and DNA oligonucleotides such as G3139, ODN698, and GEM231; growth factor inhibitors; MEK inhibitors, signal transduction inhibitors, such as agents that can inhibit EGFR (epidermal growth factor receptor) responses, such as EGRF antibodies, EGF anitbodies and molecules that are EGFR inhibitors such as the compounds ZD-1839 (AstraZeneca) and BIBX-1382 (Boehringer Ingelheim); VEGF inhibitors such as SU-6668 (Sugen, Inc., South San Francisco, Calif.) or the anti-VEGF monoclonal antibody Avestin (Genentech, Inc., South San Francisco, Calif.); cell cycle inhibitors; intercalating antibiotics such as adriamycin and bleomycin; enzymes, for example, interferon; retinoid receptor modulators such as bexarotene, ILX23-7553, and N-4-carboxyphenyl retinamide; proteasome inhibitors such as lactacystin and bortezomib; topoisomerase inhibitors such as topotecan, rebutecan and teniposide; anti-hormone such as anti-estrogens such as Nolvadex™ (tamoxifen); anti-androgens such as Casodex™ (4'-cyano-3-(4-fluorophenylsulphonyl)-2-hydroxy-2-methyl-3'-(trifluoromethyl)propionanilide); monoclonal antibody targeted therapeutic agents which have cytotoxic agents or radioisotopes attached to a cancer cell specific or target cell specific monoclonal antibody; inhibitors of HMG-CoA reductase (3-hydroxy-3-methylglutrayl-CoA reductase) such as simvastatin (ZOCOR®) and atorvastatin (LIPITOR®); prenyl-protein transferase inhibitors; inhibitors of protein kinases that transduce cell cycle checkpoint signals (e.g. ART, ARM, the Chk1 and Chk2 kinases, cdk and cdc kinase) such as 7-hydroxystaurosporin, flavopiridol and CYC202 (Cyclacel); and inhibitors of kinases involved in mitotic progression where such kinases include, but are not limited to, Polo-like kinases and aurora kinase. Such conjoint treatment may be achieved by way of simultaneous, sequential or separate dosing of the individual components of treatment.

The compounds of the present invention may also be used in combination with other known inhibitors of mitotic kinesins. Examples of inhibitors of mitotic kinesins, and in particular the human mitotic kinesin KSP, include inhibitors described in PCT Publications WO 01/30768, WO 01/98278, WO 03/050,064, WO 03/050,122, WO 03/049,527, WO 03/049,679, WO 03/049,678, WO 03/051854, WO 03/39460 WO 03/079,973, WO 03/088,903, WO 03/094,839, WO 03/097,053, WO 03/099,211, WO 03/099,286, WO 03/103,575, WO 03/105,855, WO 03/106,426, WO 04/032,840, WO 04/034,879, WO 04/037,171, WO 04/039,774, WO 04/055,008, WO 04/058,148, WO 04/058,700, WO 04/064,741, WO 04/092147, WO 04/111023, WO 04/111024, WO 05/035512, WO 05/017190, WO 05/018547, and WO 05/019206, which are specifically incorporated herein by reference. Examples of such inhibitors include (2S)-4-(2,5-difluorophenyl)-N-[(3S,4S)-3-fluoro-1-methylpiperidin-4-yl]-2-(hydroxymethyl)-N-methyl-2phenyl-2,5-dihydro-1H-pyrrole-1-carboxamide; (2S)-4-(2,5-difluorophenyl)-N-[(3S,4R)-3-fluoro-1-methylpiperidin-4-yl]-2-(hydroxymethyl)-N-methyl-2-phenyl-2,5-dihydro-1H-pyrrole-1-carboxamide; (2S)-4-(2,5-difluorophenyl)-N-[(3R,4S)-3-fluoro-1-methylpiperidin-4-yl]-2-(hydroxymethyl)-N-methyl-2-phenyl-2,5-dihydro-1H-pyrrole-1-carboxamide, (2S)-4-(2,5-difluorophenyl)-N-[(2R,4R)-2-(fluoromethyl)-1-methylpiperidin-4-yl]-2-(hydroxymethyl)-N-methyl-2-phenyl-2,5-dihydro-1H-pyrrole-1-carboxamide, and (2S)-4-(2,5-Difluorophenyl)-N-[(3R,4S)-3-fluoro-1-methylpiperidin-4-yl]-N-methyl-2-phenyl-2,5-dihydro-1H-pyrrole-1-carboxamide.

The compounds of the present invention may also be used in the treatment of cancer in combination with compounds that are not anti-tumor compounds. For example, a compound of this invention may be applied in combination with one or more substances, including, but not limited to, PPAR-γ and PPAR-δ agonists such as troglitazone, gene therapy agents, and inhibitors of inherent multidrug resistance (e.g. p-glycoprotein inhibitors).

A compound of the present invention may also be employed in conjunction with anti-emetic agents to treat nausea or emesis, by way of simultaneous, sequential or separate dosing of the individual components of treatment.

A compound of the present invention may also be administered in combination with an agent useful in the treatment of anemia, such as epoetin alfa, by way of simultaneous, sequential or separate dosing of the individual components of treatment.

A compound of the present invention may also be administered in combination with an agent useful in the treatment of neutropenia, by way of simultaneous, sequential or separate dosing of the individual components of treatment. Such a neutropenia treatment agent is, for example, a hematopoietic growth factor that regulates the production and function of neutrophils such as a human granulocyte colony stimulating factor, (G-CSF). An example of a G-CSF is filgrastim.

A compound of the present invention may also be administered in combination with an immunologic-enhancing drug, such as levamisole, isoprinosine and Zadaxin®, by way of simultaneous, sequential or separate dosing of the individual components of treatment.

Further provided is a compound of Formula I-IV for use as a medicament in the treatment of the diseases or conditions described above in a warm-blooded animal, such as a mammal, for example, a human, suffering from such disease or condition. Also provided is the use of a compound of Formula I-IV in the preparation of a medicament for the treatment of the diseases and conditions described above in a warm-blooded animal, such as a mammal, for example a human, suffering from such disorder.

The term "treating," as used herein, unless otherwise indicated, means reversing, alleviating, inhibiting the progress of, or preventing the disorder or condition to which such term applies, or one or more symptoms of such disorder or condition. The term "treatment," as used herein, unless otherwise indicated, refers to the act of treating as "treating" is defined immediately above. "Treating" is intended to mean at least the mitigation of a disease condition in a mammal, such as a human, and includes, but is not limited to, modulating and/or inhibiting the disease condition, and/or alleviating the disease condition.

In treating a subject, it will be understood that the specific dosage level and frequency of dosage for any particular subject may be varied and will depend upon a variety of factors including the activity of the specific compound of Formula I-IV, the species, age, body weight, general health, sex and diet of the subject, the mode and time of administration, rate of excretion, drug combination, and severity of the particular condition, but can nevertheless be routinely determined by one skilled in the art.

The compounds of the invention may be administered by any route appropriate to the condition to be treated. Suitable routes include parenteral administration (including subcutaneous, intramuscular, intravenous, intraarterial, intradermal, intrathecal and epidural), transdermal, rectal, nasal, topical (including buccal and sublingual), e.g., by bolus injection or continuous infusion. Other suitable rounds include vaginal, intraperitoneal, intrapulmonary, oral, and intranasal administration. Alternatively, the compounds of the invention may be administered topically (e.g., to the skin) for the treatment of a topical condition such as a fungal skin infection. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

In order to use a compound of Formula I-IV or a pharmaceutically acceptable salt, solvate, metabolite or prodrug thereof for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of the Formula I-IV, or a pharmaceutically acceptable salt, solvate, metabolite or prodrug thereof, in association with a pharmaceutically acceptable diluent or carrier.

To prepare the pharmaceutical compositions according to this invention, a therapeutically or prophylactically effective amount of a compound of Formula I-IV or pharmaceutically acceptable salt, solvate, metabolite or prodrug thereof (alone or together with an additional therapeutic agent as disclosed herein) is intimately admixed, for example, with a pharmaceutically acceptable carrier according to conventional pharmaceutical compounding techniques to produce a dose. A carrier may take a wide variety of forms depending on the form of preparation desired for administration, e.g., oral or parenteral. Examples of suitable carriers include any and all solvents, dispersion media, adjuvants, coatings, antibacterial and antifungal agents, isotonic and absorption delaying agents, sweeteners, stabilizers (to promote long term storage), emulsifiers, binding agents, thickening agents, salts, preservatives, solvents, dispersion media, coatings, antibacterial and antifungal agents, isotonic and absorption delaying agents, flavoring agents, and miscellaneous materials such as buffers and absorbents that may be needed in order to prepare a particular therapeutic composition. The use of such media and agents with pharmaceutically active substances is well known in the art. Except insofar as any conventional media or agent is incompatible with a compound of Formula I-IV, its use in the therapeutic compositions and preparations is contemplated. Supplementary active ingredients can also be incorporated into the compositions and preparations as described herein.

The pharmaceutical compositions may be in the form of a sterile injectable aqueous or oily suspension, which may be formulated according to known procedures using one or more of the appropriate dispersing or wetting agents and suspending agents, which have been mentioned above. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the DeltecCADD-PLUS™ model 5400 intravenous pump.

The compositions of the invention may also be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain, for example, one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

Suppository formulations may be prepared by mixing the active ingredient with a suitable non-irritating excipient that is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 μm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

Compositions for transdermal administration may be in the form of those transdermal skin patches that are well known to those of ordinary skill in the art.

For further information on formulations, see Chapter 25.2 in Volume 5 of Comprehensive Medicinal Chemistry (Corwin Hansch; Chairman of Editorial Board), Pergamon Press 1990, which is specifically incorporated herein by reference.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The amount of a compound of this invention that is combined with one or more excipients to produce a single dosage form will necessarily vary depending upon the subject treated, the severity of the disorder or condition, the rate of administration, the disposition of the compound and the discretion of the prescribing physician. In certain embodiments, a suitable amount of a compound of Formula I-IV is administered to a mammal undergoing treatment for cancer. Administration in certain embodiments occurs in an amount between about 0.001 mg/kg of body weight to about 60 mg/kg of body weight per day. In another embodiment, administration occurs in an amount between 0.5 mg/kg of body weight to about 40 mg/kg of body weight per day. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

The size of the dose for therapeutic or prophylactic purposes of a compound of Formula I-IV will naturally vary according to the nature and severity of the conditions, the age and sex of the animal or patient and the route of administration, according to well known principles of medicine.

In another embodiment of the invention, an article of manufacture, or "kit", containing materials useful for the treatment of the disorders described above is provided. In certain embodiments, the kit comprises a container comprising a compound of Formula I-IV. In certain embodiments, the invention provides a kit for treating a hyperproliferative disorder. In another embodiment, the invention provides a kit for treating or preventing a fungal or other eukaryote infection. The kit may further comprise a label or package insert on or associated with the container. In certain embodiments, the label or package inserts indicates that the composition comprising a compound of Formula I-IV can be used, for example, to treat a hyperproliferative disorder or to treat a fungal or other eukaryote infection. The label or package insert may also indicate that the composition can be used to treat other disorders.

In certain embodiments, the kit further comprises a container. Suitable containers include, for example, bottles, vials, syringes, blister pack, etc. The container may be formed from a variety of materials such as glass or plastic. The container holds a compound of Formula I-IV or a pharmaceutical formulation thereof in an amount effective for treating the condition, and may have a sterile access port (for example, the container may be an intravenous solution bag or a vial having a stopper pierceable by a hypodermic injection needle).

Alternatively, or additionally, the kit may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I-IV and, if present, the second pharmaceutical formulation. For example, if the kit comprises a first composition comprising a compound of Formula I-IV and a second pharmaceutical formulation, the kit may further comprise directions for the simultaneous, sequential or separate administration of the first and second pharmaceutical compositions to a patient in need thereof.

According to certain embodiments, the kit may comprise (a) a first container with a compound of Formula I-IV contained therein; and optionally (b) a second container with a second pharmaceutical formulation contained therein, wherein the second pharmaceutical formulation comprises a second compound having, for example, anti-hyperproliferative or antifungal activity. Alternatively, or additionally, the kit may further comprise a third container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a pharmaceutical formulation of a compound of Formula I-IV and a second formulation comprising a second therapeutic agent, the kit may comprise a container for containing the separate formulations, such as a divided bottle or a divided foil packet; however, the separate compositions may also be contained within a single, undivided container. Typically, the kit comprises directions for the administration of the separate components. The kit form is particularly advantageous when the separate components are administered in different dosage forms (e.g., oral and parenteral), are administered at different dosage intervals, or when titration of the individual components of the combination is desired by the prescribing physician.

In another embodiment, the kits are suitable for the delivery of solid oral forms of a compound of Formula I-IV, such as tablets or capsules. Such a kit includes, for example, a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

Although the compounds of Formula I-IV are primarily of value as therapeutic agents for use in warm-blooded animals (including man), they are also useful whenever it is required to inhibit the effects of KSP kinesin. Thus, they are also useful as pharmacological standards in the development of new biological tests and in the search for new pharmacological agents.

Representative compounds of the present invention, which are encompassed by the present invention include, but are not limited to the compounds of the examples and their pharmaceutically acceptable salts, solvates, metabolites or prodrugs thereof. The examples presented below are intended to illustrate particular embodiments of the invention, and are not intended to limit the scope of the specification or the claims in any way.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other KSP inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), N,N-dimethylformamide (DMF), dichloromethane (DCM), toluene, dioxane and 1,2-dichloroethane (DCE) were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters).

$^1$H-NMR spectra were recorded on a Varian instrument operating at 400 MHz. $^1$H-NMR spectra were obtained as $CDCl_3$, $d_6$-DMSO, $CD_3OD$ or $CDCl_3$:$CD_3OD$ solutions (reported in ppm), using trimethylsilane as the reference standard (0.00 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

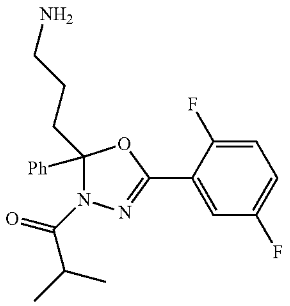 [SMILES: CC(C)C(=O)N1N=C(c2cc(F)ccc2F)OC1(CCCN)c1ccccc1]

Synthesis of 1-[2-(3-aminopropyl)-5-(2,5-difluorophenyl)-2-phenyl-[1,3,4]oxadiazol-3-yl]-2-methyl-propan-1-one Step A: Preparation of (4-oxo-4-phenylbutyl)-carbamic Acid Tert-butyl Ester To a solution of 2-oxo-pyrrolidine-1-carboxylic acid tert-butyl ester (7.03 g, 38 mmol) in THF (130 mL) was added phenylmagnesium bromide (1.0 M solution, 50 mL) at −78° C. After stirring for 2 hour at −78° C., HCl (2 M, 35 mL) was added to quench the reaction, which was then warmed to room temperature and the aqueous layer was extracted with EtOAc (2×100 mL). The combined organics were washed with brine (50 mL) and dried over $Na_2SO_4$, filtered and concentrated under reduced pressure to afford 9.56 g (96% yield) of the desired product.

Step B: Preparation of 2,5-difluorobenzoic Acid Hydrazide

To a solution of 2,5-difluorobenzoic acid (3.5 g, 22 mmol) in THF/DMF (20 mL/20 mL) was added EDCI (4.7 g, 24 mmol), DMAP (50 mg) and $NH_2NHBoc$ (3.07 g, 23.2 mmol). After stirring for 16 hours, the reaction was quenched with water (30 mL) and diluted with EtOAc (30 mL). The organic layer was then washed with HCl (0.5 M, 20 mL), saturated $NaHCO_3$ (20 mL), and brine (20 mL). The organic layer was then dried over $Na_2SO_4$, filtered and concentrated under reduced pressure to afford the crude Boc-protected product, which was then dissolved in DCM (60 mL) at 0° C. TFA (50 mL) was added to the above DCM solution. After stirring for 2 hours, the reaction mixture was concentrated and the residue was dissolved in DCM (60 mL). The solution was washed with saturated $NaHCO_3$ (40 mL) and dried over $Na_2SO_4$, filtered and concentrated under reduced pressure to afford the desired crude product.

Step C: Preparation of {4-[(2,5-difluorobenzoyl)-hydrazono]-4-phenylbutyl}-carbamic Acid Tert-butyl Ester To a solution of (4-oxo-4-phenylbutyl)-carbamic acid tert-butyl ester (3.2 g, 12.2 mmol) and 2,5-difluorobenzoic acid hydrazide (2.1 g, 12 mmol) in EtOH (40 mL) was added HOAc (0.5 mL). The reaction was then heated to reflux and stirred for 3 days. The reaction mixture was then cooled to room temperature and concentrated to give desired product (5.1 g).

Step D: Preparation of {3-[5-(2,5-difluorophenyl)-3-isobutyryl-2-phenyl-2,3-dihydro-[1,3,4]oxadiazol-2-yl]-propyl}-carbamic Acid Tert-butyl Ester To a solution of {4-[(2,5-difluorobenzoyl)-hydrazono]-4-phenylbutyl}-carbamic acid tert-butyl ester (420 mg, 1.01 mmol) in DCE (2 mL) was added isobutyric anhydride (2 mL). The reaction mixture was then sealed and heat to 110° C. and stirred for 5 hours. The reaction was then cooled and concentrated. The residue was purified by flash column chromatography (12:1 Hexanes/EtOAc) to provide the product (200 mg, 41%).

Step E: Preparation of 1-(2-(3-aminopropyl)-5-(2,5-difluorophenyl)-2-phenyl-1,3,4-oxadiazol-3(2H)-yl)-2-methylpropan-1-one To a solution of {3-[5-(2,5-difluorophenyl)-3-isobutyryl-2-phenyl-2,3-dihydro-[1,3,4]oxadiazol-2-yl]-propyl}-carbamic acid tert-butyl ester (60 mg, 0.123 mmol) in DCM (2 mL) at 0° C. was added TFA (1 mL). After stirring for 10 minutes, the reaction was concentrated and the residue was purified by preparative thin layer chromatography (10:1:0.2 EtOAc/MeOH/30% $NH_4OH$) to provide the desired product (25 mg, 53%). MS ESI (+) m/z 388 (M+1) detected; $^1H$ NMR (400 MHz, $CDCl_3$) δ 7.59 (m, 2H), 7.50 (m, 1H), 7.39 (m, 3H), 7.18 (m, 2H), 3.17 (m, 1H, J=7 Hz), 3.02 (m, 1H), 2.8 (br, 2H), 2.56 (m, 1H), 1.8 (br, 2H), 1.6 (m, 2H), 1.2 (d, 3H, J=7 Hz), 1.13 (d, 3H, J=7 Hz).

The following compounds were synthesized in a similar manner using the appropriate hydrazide and anhydride.

Example 2

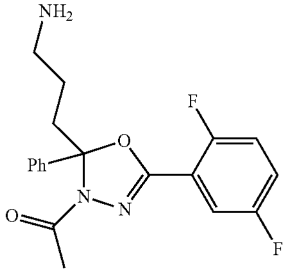 [SMILES: CC(=O)N1N=C(c2cc(F)ccc2F)OC1(CCCN)c1ccccc1]

1-[2-(3-Aminopropyl)-5-(2,5-difluorophenyl)-2-phenyl-[1,3,4]oxadiazol-3-yl]-ethanone MS ESI (+) m/z 360 (M+1) detected; $^1$H NMR (400 MHz, $CDCl_3$) δ 7.58 (m, 2H), 7.50 (m, 1H), 7.37 (m, 3H), 7.18 (m, 2H), 3.05 (m, 1H), 2.9 (m, 2H), 2.56 (m, 1H), 2.28 (s, 3H), 1.7 (m, 2H).

Example 3

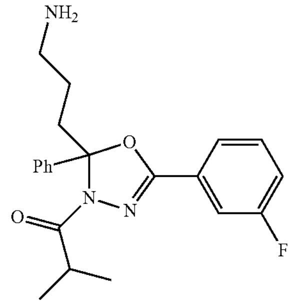 [SMILES: CC(C)C(=O)N1N=C(c2cccc(F)c2)OC1(CCCN)c1ccccc1]

1-[2-(3-Aminopropyl)-5-(3-fluorophenyl)-2-phenyl-[1,3,4]oxadiazol-3-yl]-2-methylpropan-1-one MS ESI (+) m/z 370 (M+1) detected; $^1$H NMR (400 MHz, $CDCl_3$) δ 7.67 (d, 1H, J=8 Hz), 7.56 (m, 1H), 7.52 (m, 2H), 7.42 (m, 1H), 7.35 (m, 3H), 7.2 (m, 1H), 3.35 (m, 1H, J=7 Hz), 3.05 (m, 1H), 2.85 (t, 2H, J=7 Hz), 2.52 (m, 1H), 1.62 (m, 2H), 1.17 (d, 3H, J=7 Hz), 1.11 (d, 3H, J=7 Hz).

Example 4

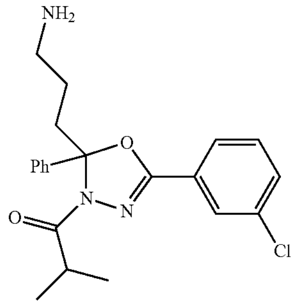 [SMILES: CC(C)C(=O)N1N=C(c2cccc(Cl)c2)OC1(CCCN)c1ccccc1]

1-[2-(3-Aminopropyl)-5-(3-chlorophenyl)-2-phenyl-[1,3,4]oxadiazol-3-yl]-2-methylpropan-1-one MS ESI (+) m/z 386 (M+1) detected; $^1$H NMR (400 MHz, $CDCl_3$) δ 7.86 (s, 1H), 7.77 (d, 1H, J=8 Hz), 7.54 (m, 2H), 7.46 (d, 1H, J=8 Hz), 7.4-7.34 (m, 4H), 3.37 (m, 1H, J=7 Hz), 3.05 (m, 1H), 2.81 (br, 2H), 2.52 (m, 1H), 2.39 (br, 3H), 1.61 (m, 2H), 1.19 (d, 3H, J=7 Hz), 1.13 (d, 3H, J=7 Hz).

Example 5

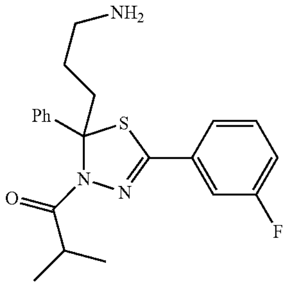 [SMILES: CC(C)C(=O)N1N=C(c2cccc(F)c2)SC1(CCCN)c1ccccc1]

Synthesis of 1-[2-(3-aminopropyl)-5-(3-fluorophenyl)-2-phenyl-[1,3,4]thiadiazol-3-yl]-2-methylpropan-1-one Step A: Preparation of {3-[5-(3-fluorophenyl)-2-phenyl-2,3-dihydro-[1,3,4]thiadiazol-2-yl]-propyl}-carbamic Acid Tert-butyl Ester To a solution of (4-oxo-4-phenylbutyl)-carbamic acid tert-butyl ester (2.2 g, 8.5 mmol) in ethanol/DCM (30 mL/10 mL) was added 3-fluorothiobenzoic acid hydrazide (Takasugi, J. J.; Buckwalter, B. L. European patent EP 1004241, 2004) (1.2 g, 7.1 mmol) at room temperature. After stirring for 3 days, the reaction mixture was concentrated and purified by flash column chromatography (20:1 Hexanes/EtOAc) to provide the product (2.65 g, 90%).

Step B: Preparation of {3-[5-(3-fluorophenyl)-3-isobutyryl-2-phenyl-2,3-dihydro-[1,3,4]thiadiazol-2-yl]-propyl}-carbamic Acid Tert-butyl Ester To a solution of {3-[5-(3-fluorophenyl)-2-phenyl-2,3-dihydro-[1,3,4]thiadiazol-2-yl]-propyl}-carbamic acid tert-butyl ester (400 mg, 0.96 mmol) in DCM (4 mL) was added triethylamine (130 mg, 1.3 mmol), followed by isobutyryl chloride (130 mg, 1.3 mmol). After stirring for 1 hour, the reaction was quenched by the addition of methanol (0.1 mL). The reaction mixture was concentrated and purified by flash column chromatography (15:1 Hexanes/EtOAc) to provide the product (350 mg, 75%).

Step C: Preparation of 1-[2-(3-aminopropyl)-5-(3-fluorophenyl)-2-phenyl-[1,3,4]thiadiazol-3-yl]-2-methylpropan-1-one HCl (1 mL, 4 M in dioxane) was added to {3-[5-(3-fluorophenyl)-3-isobutyryl-2-phenyl-2,3-dihydro-[1,3,4]thiadiazol-2-yl]-propyl}-carbamic acid tert-butyl ester (100 mg, 0.21 mmol) at 0° C. After stirring for 0.5 hours, the reaction was concentrated to give the desired product as the dihydrochloride salt. MS ESI (+) m/z 386 (M+1) detected; $^1$H NMR (400 MHz, $CDCl_3$) δ 8.51 (s, 2H), 7.55 (m, 2H), 7.4-7.2 (m, 6H), 7.15 (m, 1H), 3.43 (m, 2H), 3.06 (m, 2H), 2.4 (m, 1H), 2.1 (m, 1H), 1.8 (br, 1H), 1.2 (d, 3H, J=7 Hz), 1.1 (d, 3H, J=7 Hz).

Example 6

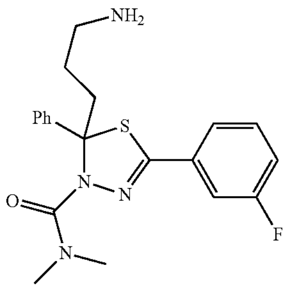 [SMILES: CN(C)C(=O)N1N=C(c2cccc(F)c2)SC1(CCCN)c1ccccc1]

2-(3-Aminopropyl)-5-(3-fluorophenyl)-2-phenyl-[1,3,4]thiadiazole-3-carboxylic Acid Dimethylamide This compound was synthesized in a manner similar to that described in Example 5, substituting dimethylcarbamyl chloride for isobutyryl chloride. MS ESI (+) m/z 387 (M+1) detected; $^1H$ NMR (di-TFA salt, 400 MHz, $CDCl_3$) δ 7.7 (s, 3H), 7.5-7.2 (m, 8H), 7.15 (m, 1H), 6.75 (br, 3H), 3.2-2.9 (m, 3H), 3.02 (s, 6H), 2.38 (m, 1H), 2.1 (m, 1H), 1.8 (m, 1H).

Example 7

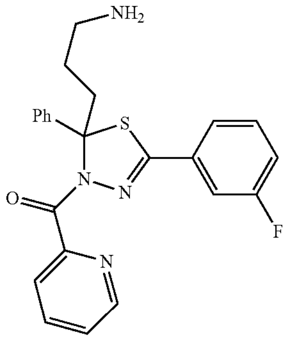 [SMILES: NCCCC1(c2ccccc2)SC(c2cccc(F)c2)=NN1C(=O)c1ccccn1]

Synthesis of [2-(3-aminopropyl)-5-(3-fluorophenyl)-2-phenyl-[1,3,4]thiadiazol-3-yl]-pyridin-2-yl-methanone To a solution of {3-[5-(3-fluorophenyl)-2-phenyl-2,3-dihydro-[1,3,4]thiadiazol-2-yl]-propyl}-carbamic acid tert-butyl ester (300 mg, 0.72 mmol) in DMF/THF (2 mL/2 mL) at room temperature were added picolinic acid (100 mg, 0.9 mmol), EDCI (170 mg, 0.87 mmol), HOBT monohydrate (130 mg, 0.87 mmol), triethylamine (88 mg, 0.87 mmol) and DMAP (2 mg). After stirring for 1 hour, EtOAc (20 mL) and saturated $NaHCO_3$ (10 mL) were added to the reaction solution. The phases were separated and the aqueous layer was extracted with EtOAc (2×10 mL). The combined organics were dried over $Na_2SO_4$, filtered and concentrated under reduced pressure. The residue was purified by flash column chromatography (8:1 hexanes/EtOAc) to provide the Boc-protected product (130 mg, 35%). 51 mg of the product was cooled to 0° C., to which HCl (1 mL, 4 M in dioxane) was added. After stirring for 0.5 hours, the reaction was concentrated to give the desired product as the trihydrochloride salt. MS ESI (+) m/z 421 (M+1) detected; $^1H$ NMR (400 MHz, $CDCl_3$) δ 9.05 (s, 1H), 8.6-8.2 (m, 5H), 7.85 (s, 1H), 7.7 (m, 2H), 7.4-7.2 (m, 9H), 7.1 (m, 1H), 3.7 (m, 1H), 3.2 (m, 1H), 3.06 (m, 1H), 2.5 (m, 1H), 2.1 (m, 2H).

Example 8

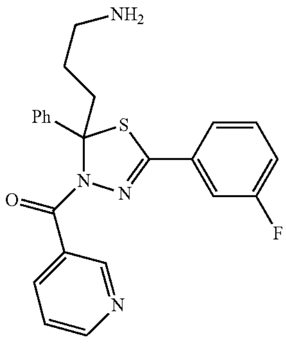 [SMILES: NCCCC1(c2ccccc2)SC(c2cccc(F)c2)=NN1C(=O)c1cccnc1]

[2-(3-Aminopropyl)-5-(3-fluorophenyl)-2-phenyl-[1,3,4]thiadiazol-3-yl]-pyridin-3-yl-methanone The trihydrochloride salt of this compound was synthesized in a manner similar to that described in Example 7. MS ESI (+) m/z 421 (M+1) detected; $^1H$ NMR (400 MHz, $CDCl_3$) δ 9.6 (s, 1H), 8.81 (s, 2H), 8.43 (s, 3H), 7.81 (br, 1H), 7.6 (m, 2H), 7.4-7.3 (m, 5H), 7.2 (m, 1H), 7.15 (m, 1H), 3.58 (m, 1H), 3.2 (m, 1H), 3.0 (m, 1H), 2.4 (m, 1H), 2.15 (m, 2H).

Example 9

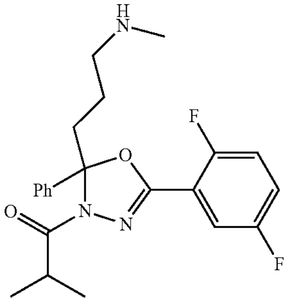 [SMILES: CNCCCC1(c2ccccc2)OC(c2cc(F)ccc2F)=NN1C(=O)C(C)C]

Synthesis of 1-[5-(2,5-difluorophenyl)-2-(3-methylaminopropyl)-2-phenyl-[1,3,4]oxadiazol-3-yl]-2-methylpropan-1-one To a solution of {3-[5-(2,5-difluorophenyl)-3-isobutyryl-2-phenyl-2,3-dihydro-[1,3,4]oxadiazol-2-yl]-propyl}-methylcarbamic acid tert-butyl ester (13 mg, 0.027 mmol) in DMF (0.5 mL) was added to NaH (14 mg, 0.58 mmol, 60% dispersion in mineral oil) that was previously washed with hexanes. After stirring at room temperature for 30 minutes, methyl iodide (23 mg, 0.16 mmol) was added. The reaction mixture was stirred at room temperature for 30 minutes and then diluted with saturated $NaHCO_3$ (20 mL). The mixture was extracted with ethyl acetate (2×30 mL). The combined organics were washed with brine (20 mL), dried over $Na_2SO_4$, filtered and concentrated under reduced pressure. The residue was purified by flash column chromatography (8% to 20% ethyl acetate in hexanes) to provide the Boc-protected product (6.6 mg, 48%). To this product in dichloromethane (1 mL) at 0° C. was added TFA (6 μL). After 30 minutes, more TFA (100 μL) was added and the mixture was stirred for 1 hour. The reaction mixture was concentrated under a stream of $N_2$, diluted with dichloromethane (20 mL) and washed with 10% $Na_2CO_3$ (20 mL). The mixture was extracted with dichloromethane (2×30 mL). The combined organics were dried over $Na_2SO_4$, filtered and concentrated under reduced pressure. The residue was purified by flash column chromatography (6:2:92 MeOH/triethylamine/ethyl acetate) to provide the final product (3.8 mg, 72%) as a yellow film. MS ESI (+) m/z 402 (M+1) detected; $^1H$ NMR (400 MHz, $CDCl_3$) δ 7.57 (m, 2H), 7.50 (m, 1H), 7.36 (m, 3H), 7.16 (m, 2H), 3.37 (m, 1H), 3.03 (m, 1H), 2.68 (m, 2H), 2.54 (m, 1H), 2.42 (s, 3H), 1.66 (m, 2H), 1.20 (d, 3H, J=6 Hz), 1.14 (d, 3H, J=7 Hz).

Example 10

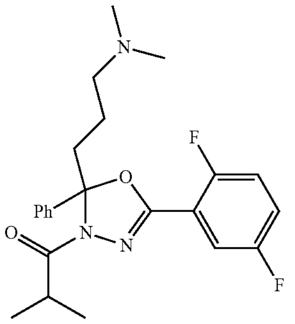 [SMILES: CC(C)C(=O)N1N=C(c2cc(F)ccc2F)OC1(CCCN(C)C)c1ccccc1]

Synthesis of 1-[5-(2,5-difluorophenyl)-2-(3-dimethylaminopropyl)-2-phenyl-[1,3,4]oxadiazol-3-yl]-2-methylpropan-1-one To a solution of 1-[2-(3-aminopropyl)-5-(2,5-difluorophenyl)-2-phenyl-[1,3,4]oxadiazol-3-yl]-2-methylpropan-1-one (9 mg, 0.023 mmol) in MeOH (0.5 mL) was added paraforamidehyde (11 mg, 0.35 mmol). The reaction mixture was heated to 70° C. and stirred for 2 hours. After cooling to room temperature, a solution of sodium cyanoborohydride (0.070 mL, 0.070 mmol, 1M in THF) was added. The mixture stirred for 20 minutes and then was diluted with half saturated NaCl (50 mL) and extracted with ethyl acetate (3×25 mL). The combined organics were washed with saturated NaCl, dried over $Na_2SO_4$, filtered and concentrated under reduced pressure. The residue was purified by flash column chromatography (2:40:60 triethylamine/ethyl acetate/hexanes) to provide the product (5.1 mg, 53%). MS ESI (+) m/z 416 (M+1) detected; $^1H$ NMR (400 MHz, $CDCl_3$) δ 7.57 (m, 2H), 7.50 (m, 1H), 7.36 (m, 3H), 7.16 (m, 2H), 3.37 (m, 1H) 3.01 (m, 1H), 2.51 (m, 1H), 2.34 (m, 2H), 2.20 (s, 6H), 1.66 (m, 2H), 1.20 (d, 3H, J=6 Hz), 1.14 (d, 3H, J=7 Hz).

Example 11

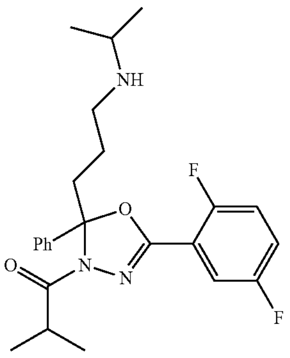 [SMILES: CC(C)NCCCC1(c2ccccc2)OC(c2cc(F)ccc2F)=NN1C(=O)C(C)C]

Synthesis of 1-[5-(2,5-difluorophenyl)-2-(3-isopropylaminopropyl)-2-phenyl-[1,3,4]oxadiazol-3-yl]-2-methylpropan-1-one To a solution of 1-[2-(3-aminopropyl)-5-(2,5-difluorophenyl)-2-phenyl-[1,3,4]oxadiazol-3-yl]-2-methylpropan-1-one (12 mg, 0.031 mmol) in acetonitrile (0.5 mL) was added acetone (60 μL, 0.082 mmol) and sodium triacetoxyborohydride (10 mg, 0.045 mmol). After stirring at room temperature for 45 minutes, more sodium triacetoxyborohydride (10 mg, 0.045 mmol) was added. The mixture stirred at room temperature for 5 hours. The reaction mixture was diluted with 10% $Na_2CO_3$ (30 mL) and extracted with ethyl acetate (3×30 mL). The combined organics were washed with brine (45 mL), dried over $Na_2SO_4$, filtered and concentrated under reduced pressure. The residue was purified by flash column chromatography (40% to 100% ethyl acetate in hexanes with 2% triethylamine) to provide the final product (3.3 mg, 25%). MS ESI (+) m/z 430 (M+1) detected; $^1H$ NMR (400 MHz, $CDCl_3$) δ 7.56 (m, 2H), 7.50 (m, 1H), 7.36 (m, 3H), 7.15 (m, 2H), 3.36 (m, 1H), 3.01 (m, 1H), 2.78 (m, 1H), 2.67 (m, 2H), 2.53 (m, 1H), 1.66 (m, 2H), 1.20 (d, 3H, J=7 Hz), 1.14 (d, 3H, J=6 Hz), 1.04 (d, 6H, J=6 Hz).

Example 12

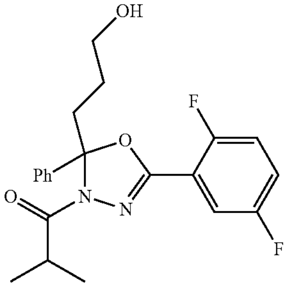 [SMILES: CC(C)C(=O)N1N=C(c2cc(F)ccc2F)OC1(CCCO)c1ccccc1]

Synthesis of 1-[5-(2,5-difluorophenyl)-2-(3-hydroxypropyl)-2-phenyl-[1,3,4]oxadiazol-3-yl]-2-methylpropan-1-one Step A: Preparation of 4-hydroxy-1-phenylbutan-1-one To a solution of dihydrofuran-2-one (5.71 g, 66 mmol) in diethyl ether (70 mL) at −78° C. was slowly added phenyl lithium (24 mL, 40 mmol, 1.67 M solution in cyclohexane/diethyl ether). After stirring at −78° C. for 2 hours, the reaction mixture was quenched by the addition of 10% $NH_4Cl$ (35 mL). The mixture was warmed to room temperature and the layers separated. The aqueous layer was extracted with diethyl ether (2×40 mL). The combined organics were washed with water (2×40 mL), dried over $Na_2SO_4$, filtered and concentrated under reduced pressure. The residue was purified by flash column chromatography (2:3 hexanes/ethyl acetate) to provide the product (6.4 g, 97%) as pale yellow oil.

Step B: Preparation of 4-(tert-butyldimethylsilanyloxy)-1-phenylbutan-1-one

To a solution of 4-hydroxy-1-phenyl-butan-1-one (3.29 g, 20 mmol) in DMF (20 mL) was added tert-butylchlorodimethyl-silane (4.5 g, 30 mmol) and imidazole (4.1 g, 60 mmol). After stirring at room temperature for 14 hours, the reaction mixture was diluted with diethyl ether (150 mL) and washed with 1M HCl (2×70 mL), water (2×70 mL) and brine (100 mL). The combined organics were dried over $Na_2SO_4$, filtered and concentrated under reduced pressure. The residue was purified by flash column chromatography (6% ethyl acetate in hexanes) to provide the product (5 g, 90%) as a colorless oil.

Step C: Preparation of 2,5-difluorobenzoic Acid [4-(tert-butyldimethylsilanyloxy)-1-phenylbutylidene]-hydrazide To a solution of 4-(tert-butyldimethylsilanyloxy)-1-phenylbutan-1-one (420 mg, 1.5 mmol) in EtOH (4 mL) was added 2,5-difluorobenzoic acid hydrazide (260 mg, 1.5 mmol) and acetic acid (0.07 mL, 1.2 mmol). After stirring the reaction mixture at 90° C. for 5 hours, more acetic acid (0.1 mL) was added. The mixture was stirred at 90° C. for 40 hours and then concentrated under reduced pressure. The mixture of starting material and product was carried forward without further purification.

Step D: Preparation of 1-[5-(2,5-difluorophenyl)-2-(3-hydroxypropyl)-2-phenyl-[1,3,4]oxadiazol-3-yl]-2-methylpropan-1-one To a solution of crude 2,5-difluorobenzoic acid [4-(tert-butyl-dimethylsilanyloxy)-1-phenylbutylidene]-hydrazide from the previous step (200 mg) in dichloroethane (1 mL) was added isobutyric anhydride (73 mg, 0.46 mmol). After heating at 110° C. for 8 hours, the mixture was concentrated under reduced pressure. The residue was chromatographed (7% ethyl acetate in hexanes) to provide the silane-protected product (44 mg). To a solution of this product (28 mg, 0.056 mmol) in acetonitrile (1 mL) was added 48% aq. HF (50 μL). After stirring at room temperature for 30 minutes, the mixture was diluted with saturated $NaHCO_3$ (30 mL) and extracted with ethyl acetate (3×20 mL). The combined organics were dried over $Na_2SO_4$, filtered and concentrated under reduced pressure. The residue was purified by flash column chromatography (30% ethyl acetate in hexanes) to provide the product (9 mg, 45%) as colorless film. MS ESI (+) m/z 389 (M+1) detected; $^1$H NMR (400 MHz, $CDCl_3$) δ 7.57 (m, 2H), 7.51 (m, 1H), 7.39 (m, 3H), 7.16 (m, 2H), 3.72 (m, 2H), 3.37 (m, 1H), 3.06 (m, 1H), 2.62 (m, 1H), 1.77 (m, 1H), 1.67 (m, 1H), 1.21 (d, 3H, J=7 Hz), 1.15 (d, 3H, J=7 Hz).

The following examples were prepared as previously described in Examples 5 or 6 using the appropriate thiohydrazide, ketone and acid chloride or carbamoyl chloride.

Example 13

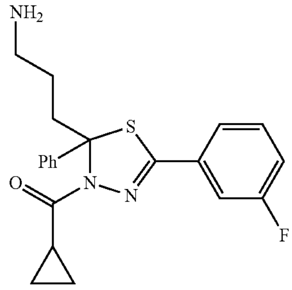 [SMILES: NCCCC1(c2ccccc2)SC(c2cccc(F)c2)=NN1C(=O)C1CC1]

[2-(3-Aminopropyl)-5-(3-fluorophenyl)-2-phenyl-[1,3,4]thiadiazol-3-yl]-cyclopropylmethanone MS APCI (+) m/z 384 (M+1) detected; $^1$H NMR (400 MHz, $CDCl_3$) δ 8.40 (br, 2H), 7.52 (m, 2H), 7.44 (m, 1H), 7.35 (m, 4H), 7.22 (m, 1H), 7.13 (m, 1H), 3.32 (m, 1H), 3.04 (m, 1H), 2.98 (m, 1H), 2.74 (m, 1H), 2.42 (m, 1H), 2.09 (m, 1H), 1.79 (m, 2H), 1.20 (m, 1H), 0.85 (m, 2H).

Example 14

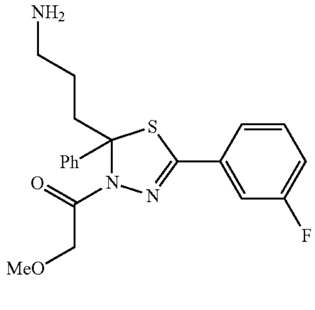 [SMILES: COCC(=O)N1N=C(c2cccc(F)c2)SC1(CCCN)c1ccccc1]

1-[2-(3-Aminopropyl)-5-(3-fluorophenyl)-2-phenyl-[1,3,4]thiadiazol-3-yl]-2-methoxyethanone MS APCI (+) m/z 387 (M+1) detected; $^1$H NMR (400 MHz, $CDCl_3$) δ 8.37 (br, 2H), 7.52 (m, 2H), 7.34 (m, 5H), 7.23 (m, 1H), 7.15 (m, 1H), 4.66 (d, 1H, J=16 Hz), 4.44 (d, 1H, J=16 Hz), 3.56 (m, 1H), 3.37 (s, 3H), 3.15 (m, 1H), 3.07 (m, 1H), 2.44 (m, 1H), 2.13 (m, 1H), 1.92 (m, 1H).

Example 15

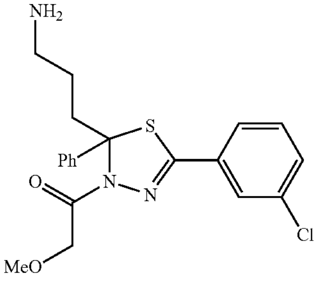 [SMILES: COCC(=O)N1N=C(c2cccc(Cl)c2)SC1(CCCN)c1ccccc1]

1-(2-(3-Aminopropyl)-5-(3-chlorophenyl)-2-phenyl-1,3,4-thiadiazol-3(2H)-yl)-2-methoxyethanone MS APCI (+) m/z 404, 406 (M+1, Cl pattern) detected; $^1$H NMR (400 MHz, $CDCl_3$) δ 8.38 (br, 2H), 7.65 (s, 1H), 7.52 (d, 2H, J=8 Hz), 7.47 (d, 1H, J=8 Hz), 7.41 (d, 1H, J=8 Hz), 7.32 (m, 3H), 7.24 (m, 1H), 4.67 (d, 1H, J=16 Hz), 7.45 (d, 1H, J=16 Hz), 3.57 (m, 1H), 3.37 (s, 3H), 3.16 (m, 1H), 3.07 (m, 1H), 2.44 (m, 1H), 2.13 (m, 1H), 1.93 (m, 1H).

Example 16

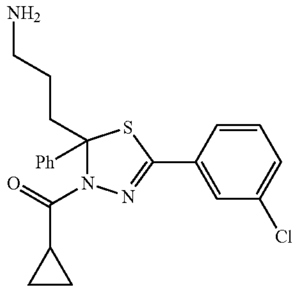 [SMILES: NCCCC1(c2ccccc2)SC(c2cccc(Cl)c2)=NN1C(=O)C1CC1]

(2-(3-Aminopropyl)-5-(3-chlorophenyl)-2-phenyl-1,3,4-thiadiazol-3(2H)-yl)(cyclopropyl)methanone MS APCI (+) m/z 400, 402 (M+1, Cl pattern) detected; $^1$H NMR (400 MHz, $CDCl_3$) δ 8.40 (br, 2H), 7.71 (s, 1H), 7.50 (m, 3H), 7.40 (d, 1H), 7.34 (m, 3H), 7.23 (m, 1H), 3.32 (m, 1H), 3.03 (m, 1H), 2.97 (m, 1H), 2.75 (m, 1H), 2.43 (m, 1H), 2.09 (m, 1H), 1.79 (m, 1H), 1.20 (m, 1H), 0.86 (m, 3H).

Example 17

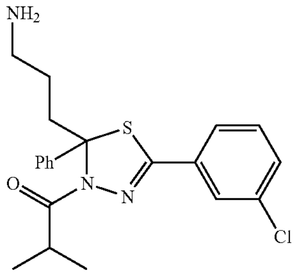 [SMILES: CC(C)C(=O)N1N=C(c2cccc(Cl)c2)SC1(CCCN)c1ccccc1]

1-(2-(3-Aminopropyl)-5-(3-chlorophenyl)-2-phenyl-1,3,4-thiadiazol-3(2H)-yl)-2-methylpropan-1-one MS APCI (+) m/z 402, 404 (M+1, Cl pattern) detected; $^1$H NMR (400 MHz, $CDCl_3$) δ 8.49 (br, 2H), 7.67 (s, 1H), 7.51 (m, 3H), 7.41 (d, 1H, J=8 Hz), 7.33 (m, 3H), 7.23 (m, 1H), 3.44 (m, 2H), 3.07 (m, 2H), 2.43 (m, 1H), 2.12 (m, 1H), 1.83 (m, 1H), 1.20 (d, 3H, J=6 Hz), 1.12 (d, 3H, J=7 Hz).

Example 18

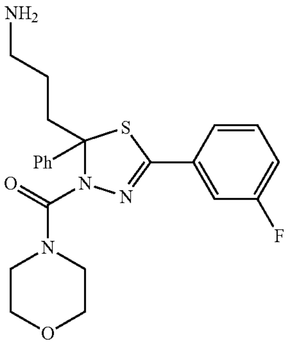 [SMILES: NCCCC1(c2ccccc2)SC(c2cccc(F)c2)=NN1C(=O)N1CCOCC1]

[2-(3-Aminopropyl)-5-(3-fluorophenyl)-2-phenyl-[1,3,4]thiadiazol-3-yl]-morpholin-4-yl-methanone MS APCI (+) m/z 429 (M+1) detected; $^1$H NMR (400 MHz, $CDCl_3$) δ 8.43 (br, 2H), 7.56 (d, 2H), 7.34 (m, 5H), 7.24

(m, 1H), 7.11 (m, 1H), 3.71 (m, 4H), 3.56 (m, 4H), 3.30 (m, 1H), 3.03 (m, 1H), 2.95 (m, 1H), 2.41 (m, 1H), 2.08 (m, 1H), 1.89 (m, 1H).

Example 19

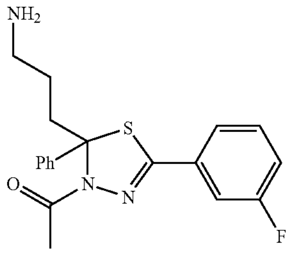 [SMILES: CC(=O)N1N=C(c2cccc(F)c2)SC1(CCCN)c1ccccc1]

Synthesis of 1-(2-(3-aminopropyl)-5-(3-fluorophenyl)-2-phenyl-1,3,4-thiadiazol-3(2H)-yl)ethanone MS ESI (+) m/z 358 (M+1) detected; $^{1}$H NMR (400 MHz, $CDCl_3$) δ 7.48 (s, 1H), 7.45 (s, 1H), 7.42 (d, 1H, J=9 Hz), 7.36 (m, 4H), 7.28 (d, 1H), 7.14 (m, 1H), 3.20 (m, 1H), 2.87 (m, 1H), 2.53 (m, 1H), 2.44 (s, 3H), 2.39 (m, 1H), 1.94 (m, 1H), 1.56 (m, 1H).

Example 20

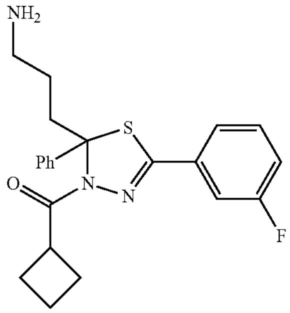 [SMILES: NCCCC1(c2ccccc2)SC(c2cccc(F)c2)=NN1C(=O)C1CCC1]

(2-(3-Aminopropyl)-5-(3-fluorophenyl)-2-phenyl-1,3,4-thiadiazol-3(2H)-yl)(cyclobutyl)methanone MS ESI (+) m/z 398 (M+1) detected; $^{1}$H NMR (400 MHz, $CDCl_3$) δ 7.46 (d, 2H, J=7 Hz), 7.41 (d, 1H, J=11 Hz), 7.35 (m, 4H), 7.27 (m, 1H), 7.13 (m, 1H), 3.87 (m, 1H), 3.22 (m, 1H), 2.95 (m, 1H), 2.88 (m, 1H), 2.39 (m, 1H), 2.26 (m, 4H), 2.02 (m, 1H), 1.92 (m, 1H), 1.82 (m, 1H), 1.56 (m, 1H).

Example 21

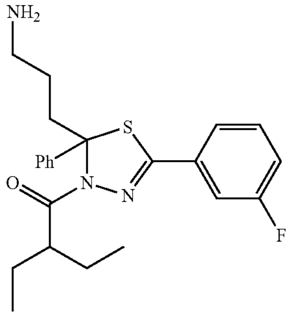 [SMILES: CCC(CC)C(=O)N1N=C(c2cccc(F)c2)SC1(CCCN)c1ccccc1]

1-(2-(3-Aminopropyl)-5-(3-fluorophenyl)-2-phenyl-1,3,4-thiadiazol-3(2H)-yl)-2-ethylbutan-1-one MS ESI (+) m/z 414 (M+1) detected; $^{1}$H NMR (400 MHz, $CDCl_3$) δ 7.50 (d, 2H, J=8 Hz), 7.40 (m, 3H), 7.33 (m, 2H), 7.25 (m, 1H), 7.14 (m, 1H), 3.26 (m, 2H), 2.98 (m, 2H), 2.58 (br, 2H), 2.42 (m, 1H), 1.96 (m, 1H), 1.71 (m, 1H), 1.63 (m, 1H), 1.51 (m, 3H), 0.95 (t, 3H, J=7 Hz), 0.83 (t, 3H, J=7 Hz).

Example 22

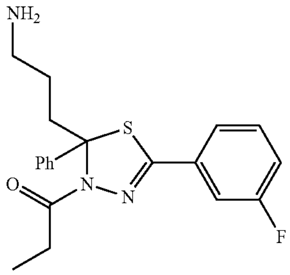 [SMILES: CCC(=O)N1N=C(c2cccc(F)c2)SC1(CCCN)c1ccccc1]

1-(2-(3-Aminopropyl)-5-(3-fluorophenyl)-2-phenyl-1,3,4-thiadiazol-3(2H)-yl)propan-1-one MS ESI (+) m/z 372 (M+1) detected; $^{1}$H NMR (400 MHz, $CDCl_3$) δ 7.44 (m, 2H), 7.37 (m, 5H), 7.27 (m, 1H), 7.14 (m, 1H), 3.21 (m, 1H), 2.84 (m, 4H), 2.58 (br, 2H), 2.39 (m, 1H), 1.92 (m, 1H), 1.55 (m, 1H), 1.15 (t, 3H, J=7 Hz).

Example 23

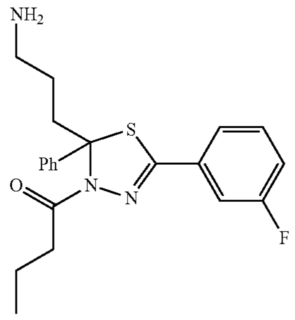 [SMILES: CCCC(=O)N1N=C(c2cccc(F)c2)SC1(CCCN)c1ccccc1]

1-(2-(3-Aminopropyl)-5-(3-fluorophenyl)-2-phenyl-1,3,4-thiadiazol-3(2H)-yl)butan-1-one MS ESI (+) m/z 386 (M+1) detected; $^1$H NMR (400 MHz, $CDCl_3$) δ 7.45 (m, 3H), 7.38 (m, 2H), 7.33 (d, 2H), 7.27 (m, 1H), 7.13 (m, 1H), 3.21 (m, 1H), 2.86 (br, 2H), 2.77 (m, 4H), 2.39 (m, 1H), 1.94 (m, 1H), 1.68 (m, 1H), 1.55 (m, 2H), 0.97 (t, 3H, J=7 Hz).

Example 24

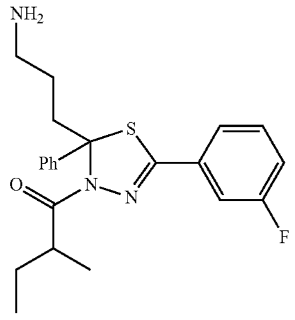 [SMILES: CCC(C)C(=O)N1N=C(c2cccc(F)c2)SC1(CCCN)c1ccccc1]

1-(2-(3-Aminopropyl)-5-(3-fluorophenyl)-2-phenyl-1,3,4-thiadiazol-3(2H)-yl)-2-methylbutan-1-one MS ESI (+) m/z 400 (M+1) detected; $^1$H NMR (400 MHz, $CDCl_3$) δ 7.44 (m, 3H), 7.34 (m, 4H), 7.26 (m, 1H), 7.14 (m, 1H), 3.36 (m, 1H), 3.23 (m, 1H), 2.86 (br, 2H), 2.39 (m, 3H), 1.93 (m, 1H), 1.75 (m, 1H), 1.54 (m, 1H), 1.43 (m, 1H), 1.17 (dd, 3H, J=6.9 Hz, 12.3 Hz), 0.90 (dt, 3H, J=7.4 Hz, 37.6 Hz).

Example 25

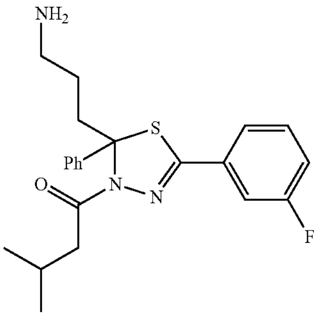 [SMILES: CC(C)CC(=O)N1N=C(c2cccc(F)c2)SC1(CCCN)c1ccccc1]

1-(2-(3-Aminopropyl)-5-(3-fluorophenyl)-2-phenyl-1,3,4-thiadiazol-3(2H)-yl)-3-methylbutan-1-one MS ESI (+) m/z 400 (M+1) detected; $^1$H NMR (400 MHz, $CDCl_3$) δ 7.45 (m, 2H), 7.38 (m, 3H), 7.32 (m, 2H), 7.26 (m, 1H), 7.14 (m, 1H), 3.45 (br, 2H), 3.23 (m, 1H), 2.87 (m, 2H), 2.74 (dd, 1H, J=7 Hz, 15 Hz), 2.63 (dd, 1H, J=7 Hz, 15 Hz), 2.39 (m, 1H), 2.17 (m, 1H), 1.95 (m, 1H), 1.56 (m, 1H), 0.95 (m, 6H).

Example 26

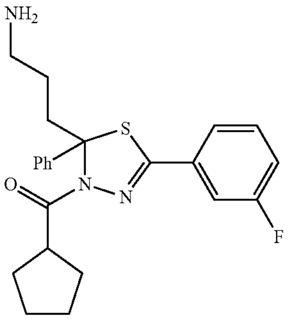 [SMILES: NCCCC1(c2ccccc2)SC(c2cccc(F)c2)=NN1C(=O)C1CCCC1]

(2-(3-Aminopropyl)-5-(3-fluorophenyl)-2-phenyl-1,3,4-thiadiazol-3(2H)-yl)(cyclopentyl)methanone MS ESI (+) m/z 412 (M+1) detected; $^1$H NMR (400 MHz, $CDCl_3$) δ 7.45 (m, 2H), 7.38 (m, 3H), 7.32 (m, 2H), 7.26 (m, 1H), 7.13 (m, 1H), 3.61 (m, 1H), 3.22 (m, 1H), 2.85 (m, 2H), 2.40 (m, 3H), 1.95 (m, 3H), 1.82 (m, 1H), 1.63 (m, 6H).

Example 27

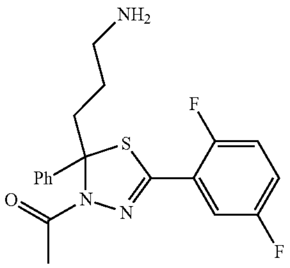 [SMILES: CC(=O)N1N=C(c2cc(F)ccc2F)SC1(CCCN)c1ccccc1]

1-(2-(3-Aminopropyl)-5-(2,5-difluorophenyl)-2-phenyl-1,3,4-thiadiazol-3(2H)-yl)ethanone MS ESI (+) m/z 376 (M+1) detected; $^1$H NMR (400 MHz, $CDCl_3$) δ 7.59 (m, 1H), 7.40 (m, 4H), 7.30 (m, 1H), 7.13 (m, 2H), 3.20 (m, 1H), 2.89 (m, 2H), 2.46 (s, 3H), 2.38 (m, 1H), 1.99 (m, 1H), 1.57 (m, 1H).

Example 28

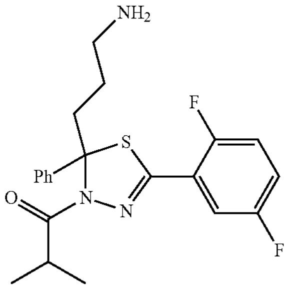 [SMILES: CC(C)C(=O)N1N=C(c2cc(F)ccc2F)SC1(CCCN)c1ccccc1]

1-(2-(3-Aminopropyl)-5-(2,5-difluorophenyl)-2-phenyl-1,3,4-thiadiazol-3(2H)-yl)-2-methylpropan-1-one MS ESI (+) m/z 404 (M+1) detected; $^1$H NMR (400 MHz, $CDCl_3$) δ 7.55 (m, 1H), 7.42 (m, 2H), 7.34 (m, 2H), 7.26 (m, 1H), 7.10 (m, 2H), 3.48 (m, 1H), 3.20 (m, 2H), 2.88 (m, 1H), 2.34 (m, 1H), 1.97 (m, 1H), 1.55 (m, 1H), 1.18 (d, 3H, J=8 Hz), 1.16 (d, 3H, J=8 Hz).

Example 29

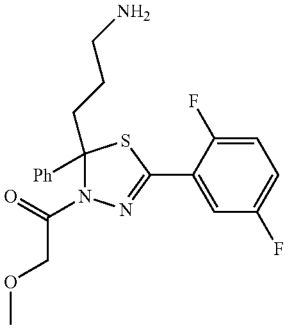 [SMILES: COCC(=O)N1N=C(c2cc(F)ccc2F)SC1(CCCN)c1ccccc1]

1-(2-(3-Aminopropyl)-5-(2,5-difluorophenyl)-2-phenyl-1,3,4-thiadiazol-3(2H)-yl)-2-methoxyethanone MS ESI (+) m/z 406 (M+1) detected; $^1$H NMR (400 MHz, $CDCl_3$) δ 7.53 (m, 1H), 7.45 (m, 2H), 7.35 (m, 2H), 7.28 (m, 1H), 7.12 (m, 2H), 4.55 (d, 1H, J=16 Hz), 4.48 (d, 1H, J=16 Hz), 3.46 (s, 3H), 3.28 (m, 1H), 2.89 (m, 2H), 2.40 (m, 1H), 1.96 (m, 1H), 1.58 (m, 1H).

Example 30

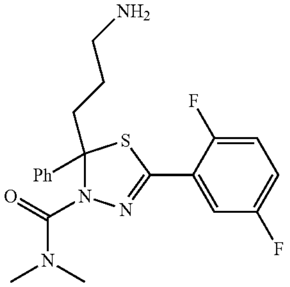 [SMILES: CN(C)C(=O)N1N=C(c2cc(F)ccc2F)SC1(CCCN)c1ccccc1]

2-(3-Aminopropyl)-5-(2,5-difluorophenyl)-N,N-dimethyl-2-phenyl-1,3,4-thiadiazole-3(2H)-carboxamide MS ESI (+) m/z 405 (M+1) detected; $^1$H NMR (400 MHz, $CDCl_3$) δ 7.51 (m, 2H), 7.45 (m, 1H), 7.34 (m, 2H), 7.26 (m, 1H), 7.07 (m, 2H), 3.12 (m, 1H), 3.01 (s, 6H), 2.85 (m, 1H), 2.36 (m, 1H), 1.95 (m, 1H), 1.65 (m, 1H), 1.26 (m, 1H).

Example 31

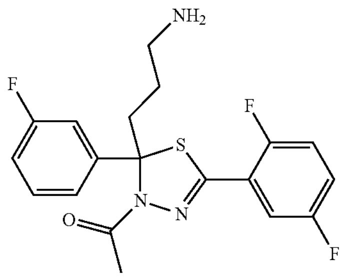 [SMILES: CC(=O)N1N=C(c2cc(F)ccc2F)SC1(CCCN)c1cccc(F)c1]

1-(2-(3-aminopropyl)-5-(2,5-difluorophenyl)-2-(3-fluorophenyl)-1,3,4-thiadiazol-3(2H)-yl)ethanone MS ESI (+) m/z 394 (M+1) detected; $^1$H NMR (400 MHz, $CDCl_3$) δ 7.57 (m, 1H), 7.32 (m, 1H), 7.23 (d, 1H, J=8 Hz), 7.11 (m, 3H), 6.97 (m, 1H), 3.31 (m, 2H) 3.19 (m, 1H), 2.89 (m, 2H), 2.43 (s, 3H), 2.31 (m, 1H), 1.95 (m, 1H), 1.58 (m, 1H).

Example 32

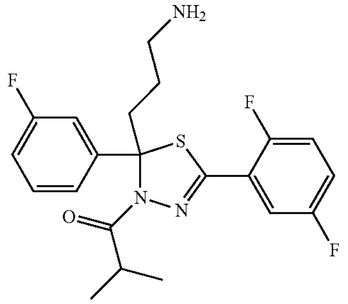 [SMILES: CC(C)C(=O)N1N=C(c2cc(F)ccc2F)SC1(CCCN)c1cccc(F)c1]

1-(2-(3-aminopropyl)-5-(2,5-difluorophenyl)-2-(3-fluorophenyl)-1,3,4-thiadiazol-3(2H)-yl)-2-methylpropan-1-one MS ESI (+) m/z 422 (M+1) detected; $^1$H NMR (400 MHz, $CDCl_3$) δ 7.55 (m, 1H), 7.32 (m, 1H), 7.23 (d, 1H, J=8 Hz), 7.11 (m, 3H), 6.96 (m, 1H), 3.48 (m, 1H), 3.18 (m, 1H), 2.92 (m, 1H), 2.88 (m, 1H), 2.45 (br, 2H), 2.31 (m, 1H), 1.93 (m, 1H), 1.52 (m, 1H), 1.20 (d, 3H, J=7 Hz), 1.18 (d, 3H, J=7 Hz).

Example 33

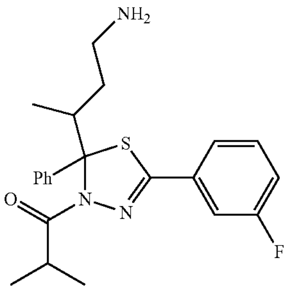 [SMILES: CC(C)C(=O)N1N=C(c2cccc(F)c2)SC1(c1ccccc1)C(C)CCN]

1-(2-(4-aminobutan-2-yl)-5-(3-fluorophenyl)-2-phenyl-1,3,4-thiadiazol-3(2H)-yl)-2-methylpropan-1-one (Diastereomer Pair A)

Step A: Preparation of tert-butyl 3-methyl-4-oxo-4-phenylbutylcarbamate

To a solution of 3-methyl-2-pyrrolidinone (5.0 g, 50.4 mmol) in anhydrous THF (100 mL) at −78° C. was added n-butyllithium (2.1 M solution, 25.2 mL, 53 mmol). The mixture was stirred for 30 min then treated with a solution of Boc-anhydride (11.01 g, 50.4 mmol) in anhydrous THF (50 mL). After 3 hours at −78° C., phenyl magnesium bromide (1.0 M solution, 65.6 mL, 65.6 mmol) was added via cannula. After a further 3 hours at −78° C. the mixture was treated with 2 N HCl (100 mL), warmed to room temperature and extracted with ethyl acetate (3×100 mL). The combined organic phases were washed with brine (100 mL), dried over $Na_2SO_4$ and concentrated under reduced pressure. The residue was chromatographed (9:1 to 4:1 hexanes/ethyl acetate) to provide the product (2.6 g, 18%) as a yellow oil.

Step B: Preparation of tert-butyl 3-(5-(3-fluorophenyl)-2-phenyl-2,3-dihydro-1,3,4-thiadiazol-2-yl)butylcarbamate To a solution of 3-fluorobenzothiohydrazide (300 mg, 1.76 mmol) in ethanol/DCM (6 mL/2 mL) was added tert-butyl 3-methyl-4-oxo-4-phenylbutylcarbamate (538 mg, 1.94 mmol). After stirring at room temperature for 16 hours, acetic acid (3 drops) was added and the mixture stirred for another 48 hours. The reaction mixture was then concentrated under reduced pressure and chromatographed (9:1 hexanes/ethyl acetate) to provide the product (366 mg, 48%) as a mixture of diastereomers as a yellow foam.

Step C: Preparation of tert-butyl 3-(5-(3-fluorophenyl)-3-isobutyryl-2-phenyl-2,3-dihydro-1,3,4-thiadiazol-2-yl)butylcarbamate To a solution of tert-butyl 3-(5-(3-fluorophenyl)-2-phenyl-2,3-dihydro-1,3,4-thiadiazol-2-yl)butylcarbamate (50 mg, 116 mmol) in anhydrous DCM (5 mL) was added isobutyryl chloride (16 μL, 151 mmol) followed by triethylamine (21 μL, 151 mmol). After stirring at room temperature for 16 hours the mixture was partitioned between sat. $NaHCO_3$ (20 mL) and DCM (20 mL). The aqueous layer was extracted with DCM (10 mL) and the combined organic phases were washed with brine (20 mL), dried over $Na_2SO_4$ and concentrated under reduced pressure. The residue was chromatographed (19:1, hexanes/ethyl acetate) to afford two diastereomeric pairs, diastereomer pair A (more polar, 13.1 mg) and diastereomer pair B (less polar, 11 mg).

Step D: Preparation of 1-(2-(4-aminobutan-2-yl)-5-(3-fluorophenyl)-2-phenyl-1,3,4-thiadiazol-3(2H)-yl)-2-methylpropan-1-one (Diastereomer Pair A)

To a solution of diastereomer pair A from the previous step (13.1 mg, 0.026 mmol) in DCM (2 mL) was added TFA (0.5 mL). After stirring at room temperature for 2 hours the mixture was concentrated under reduced pressure and partitioned between saturated $NaHCO_3$ (20 mL) and ethyl acetate (20 mL). The aqueous layer was extracted with ethyl acetate (10 mL) and the combined organic phases were washed with brine (10 mL), dried over $Na_2SO_4$ and concentrated under reduced pressure to provide the product as a diastereomer pair (10 mg, 96%) as a pale yellow oil.

MS ESI (+) m/z 400 (M+1) detected; $^1$H NMR (400 MHz, $CDCl_3$) δ 7.72 (m, 2H), 7.48 (m, 2H), 7.41 (m, 1H), 7.34 (m, 2H), 7.25 (m, 1H), 7.16 (m, 1H), 3.76 (m, 1H), 3.34 (m, 1H), 2.91 (br, 1H), 2.30 (br, 1H), 1.68 (m, 1H), 1.37 (m, 1H), 1.13 (m, 6H), 0.98 (m, 3H), 0.88 (m, 1H).

Example 34

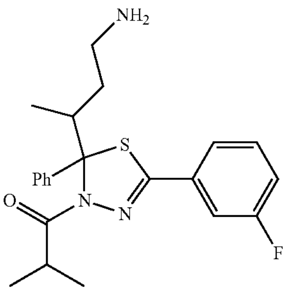 [SMILES: CC(C)C(=O)N1N=C(c2cccc(F)c2)SC1(c1ccccc1)C(C)CCN]

1-(2-(-4-aminobutan-2-yl)-5-(3-fluorophenyl)-2-phenyl-1,3,4-thiadiazol-3(2H)-yl)-2-methylpropan-1-one (Diastereomer Pair B)

Prepared as described in Example 33 using the less polar diastereomer pair B. MS ESI (+) m/z 400 (M+1) detected; $^1$H NMR (400 MHz, $CDCl_3$) δ 7.71 (m, 2H), 7.48 (m, 2H), 7.41 (m, 1H), 7.34 (m, 2H), 7.26 (m, 1H), 7.16 (m, 1H), 3.85 (m, 1H), 3.34 (m, 1H, J=6 Hz), 2.93 (br, 1H), 2.85 (br, 1H), 2.52 (br, 1H), 1.66 (m, 1H), 1.26 (m, 1H), 1.12 (dd, 6H, J=6.8 Hz, 14 Hz), 0.96 (d, 3H, J=7 Hz), 0.84 (m, 1H).

The following examples were prepared as previously described in Example 7 using the appropriate thiohydrazide, ketone and carboxylic acid.

Example 35

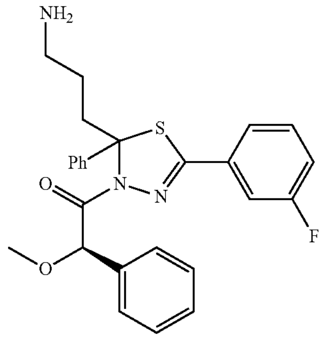 [SMILES: CO[C@@H](C(=O)N1N=C(c2cccc(F)c2)SC1(CCCN)c1ccccc1)c1ccccc1]

(2R)-1-(2-(3-aminopropyl)-5-(3-fluorophenyl)-2-phenyl-1,3,4-thiadiazol-3(2H)-yl)-2-methoxy-2-phenylethanone (Diastereomer A)

Coupling with (R)-2-methoxy-2-phenylacetic acid provided diastereomeric products that were isolated using silica gel chromatography (4:1 hexanes/ethyl acetate). The more polar diastereomer (Boc-protected diastereomer A) was subjected to t-butoxycarbonyl group removal as in Example 7 to afford the product as the di-HCl salt. MS ESI (+) m/z 464 (M+1) detected; $^1$H NMR (400 MHz, $CDCl_3$) δ 8.51 (br s, 3H), 7.4-7.0 (m, 14H), 5.60 (s, 1H), 3.8-3.1 (m, 6H), 2.6-1.9 (m, 3H).

Example 36

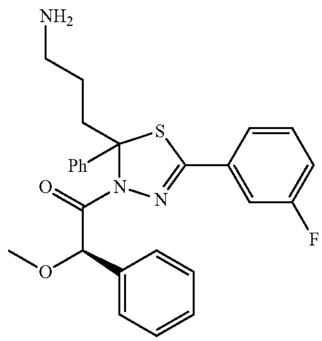 [SMILES: CO[C@@H](C(=O)N1N=C(c2cccc(F)c2)SC1(CCCN)c1ccccc1)c1ccccc1]

(2R)-1-(2-(3-aminopropyl)-5-(3-fluorophenyl)-2-phenyl-1,3,4-thiadiazol-3(2H)-yl)-2-methoxy-2-phenylethanone (Diastereomer B)

Prepared as described in Example 35 using the less polar diastereomer (Boc-protected diastereomer B). MS ESI (+)

m/z 464 (M+1) detected; $^1$H NMR (400 MHz, $CDCl_3$) δ 8.30 (br s, 3H), 7.6-7.1 (m, 14H), 5.54 (s, 1H), 3.4-2.3 (m, 8H), 1.7 (m, 1H).

Example 37

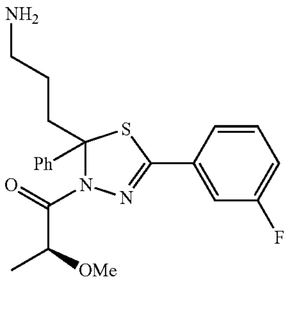 [SMILES: CO[C@@H](C)C(=O)N1N=C(c2cccc(F)c2)SC1(CCCN)c1ccccc1]

1-[2-(3-Aminopropyl)-5-(3-fluorophenyl)-2-phenyl-[1,3,4]thiadiazol-3-yl]-2-(S)-methoxypropan-1-one Obtained as a mixture of diastereomers. MS ESI (+) m/z 402 (M+1) detected; $^1$H NMR (400 MHz, $CDCl_3$) δ 8.47 (br, 4H), 7.50 (m, 4H), 7.35 (m, 10H), 7.22 (m, 2H), 7.15 (m, 2H), 4.66 (m, 2H), 3.54 (m, 2H), 3.38 (s, 3H), 3.22 (s, 3H), 3.12 (m, 4H), 2.50 (m, 2H), 2.15 (m, 2H), 1.88 (m, 1H), 1.78 (m, 1H), 1.54 (d, 3H, J=6 Hz), 1.37 (d, 3H, J=7 Hz).

Example 38

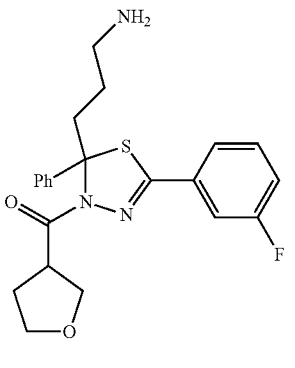 [SMILES: NCCCC1(c2ccccc2)SC(c2cccc(F)c2)=NN1C(=O)C1CCOC1]

[2-(3-Aminopropyl)-5-(3-fluorophenyl)-2-phenyl-[1,3,4]thiadiazol-3-yl]-(tetrahydrofuran-3-yl)-methanone Obtained as a mixture of diastereomers: MS ESI (+) m/z 414 (M+1) detected; $^1$H NMR (400 MHz, $CDCl_3$) δ 8.19 (br, 3H), 7.52 (m, 2H), 7.35 (m, 5H), 7.24 (m, 1H), 7.14 (m, 1H), 4.06-3.73 (m, 5H), 3.5-3.3 (m, 2H), 3.2-2.9 (m, 2H), 2.45-2.05 (m, 4H).

Example 39

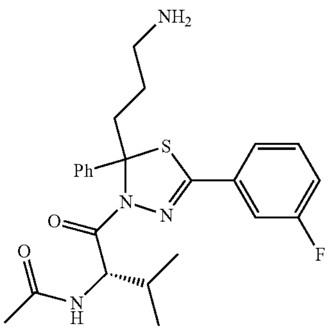 [SMILES: CC(=O)N[C@H](C(=O)N1N=C(c2cccc(F)c2)SC1(CCCN)c1ccccc1)C(C)C]

N—((S)-1-(2-(3-aminopropyl)-5-(3-fluorophenyl)-2-phenyl-1,3,4-thiadiazol-3(2H)-yl)-3-methyl-1-oxobutan-2-yl)acetamide (Diastereomer A)

Coupling with N-acetyl L-valine provided diastereomeric products that were isolated using silica gel chromatography (1:1 hexanes:ethyl acetate). The more polar diastereomer (Boc-protected diastereomer A) was subjected to t-butoxycarbonyl group removal as in Example 7 to afford the product as the di-HCl salt. MS ESI (+) m/z 457 (M+1) detected; $^1$H NMR (400 MHz, 10:1 $CDCl_3$:$CD_3OD$) δ 7.52-7.16 (m, 8H), 7.20 (m, 1H), 5.13 (d, 1H, J=4 Hz), 3.31-2.92 (m, 2H), 2.98 (m, 1H), 2.40 (m, 1H), 2.07 (s, 3H), 1.84 (m, 1H), 1.69 (m, 1H), 1.41 (m, 1H), 1.08 (d, 3H, J=6.3 Hz), 0.87 (d, 3H, J=7.0 Hz).

Example 40

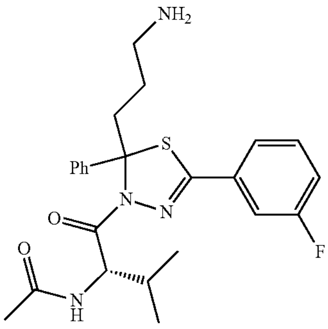 [SMILES: CC(=O)N[C@H](C(=O)N1N=C(c2cccc(F)c2)SC1(CCCN)c1ccccc1)C(C)C]

N—((S)-1-(2-(3-aminopropyl)-5-(3-fluorophenyl)-2-phenyl-1,3,4-thiadiazol-3(2H)-yl)-3-methyl-1-oxobutan-2-yl)acetamide (Diastereomer B)

Prepared as described in Example 39 using the less polar diastereomer (Boc-protected diastereomer B). MS ESI (+) m/z 457 (M+1) detected; $^1$H NMR (400 MHz, $CDCl_3$) δ 8.33 (br s, 3H), 7.50-7.13 (m, 8H), 6.76 (m, 1H), 5.43 (m, 1H), 3.31

(m, 1H), 3.19-2.81 (m, 2H), 2.57 (m, 1H), 2.36 (1H), 2.16 (m, 1H), 1.81 (m, 4H), 1.04 (m, 3H), 0.93 (d, 3H, J=7.8 Hz).

Example 41

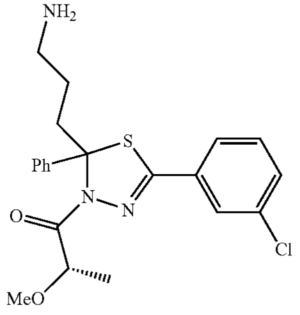 [SMILES: CO[C@@H](C)C(=O)N1N=C(c2cccc(Cl)c2)SC1(CCCN)c1ccccc1]

(2S)-1-(2-(3-Aminopropyl)-5-(3-chlorophenyl)-2-phenyl-1,3,4-thiadiazol-3(2H)-yl)-2-methoxypropan-1-one Obtained as a mixture of diastereomers. MS APCI (+) m/z 418, 420 (M+1, Cl pattern) detected; $^1$H NMR (400 MHz, $CDCl_3$) δ 8.46 (br, 4H), 7.65 (s, 2H), 7.50 (m, 6H), 7.42 (d, 2H, J=8 Hz), 7.32 (m, 6H), 7.22 (m, 2H), 4.66 (m, 2H), 3.52 (m, 2H), 3.38 (s, 3H), 3.22 (s, 3H), 3.12 (m, 4H), 2.50 (m, 2H), 2.15 (m, 2H), 1.74 (m, 2H), 1.54 (d, 3H, J=7 Hz), 1.37 (d, 3H, J=6 Hz).

Example 42

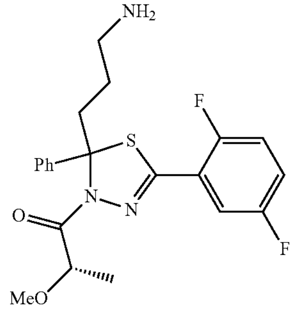 [SMILES: CO[C@@H](C)C(=O)N1N=C(c2cc(F)ccc2F)SC1(CCCN)c1ccccc1]

Synthesis of (2S)-1-(2-(3-aminopropyl)-5-(2,5-difluorophenyl)-2-phenyl-1,3,4-thiadiazol-3(2H)-yl)-2-methoxypropan-1-one To a solution of tert-butyl 3-(5-(2,5-difluorophenyl)-2-phenyl-2,3-dihydro-1,3,4-thiadiazol-2-yl)propylcarbamate (50 mg, 0.11 mmol) and (S)-2-methoxypropanoic acid (22 μL, 0.23 mmol) in DMF (1 mL) was added HOBt (44 mg, 0.29 mmol) followed by EDCI (55 mg, 0.29 mmol) and triethylamine (48 μL, 0.35 mmol). After stirring for 64 hours, the reaction mixture was partitioned between ethyl acetate (20 mL) and saturated $NaHCO_3$ (20 mL). The aqueous layer was extracted with ethyl acetate (20 mL) and the combined organics were washed with water (5×10 mL) and brine (10 mL). The solution was dried over $Na_2SO_4$ and concentrated under reduced pressure. The residue was chromatographed (9:1 to 4:1 hexanes/ethyl acetate) to provide the Boc-protected product (33 mg, 55%) as a pale yellow gum. To a solution of this product (33 mg, 0.06 mmol) in dichloromethane (4 mL) at 0° C. was added TFA (1 mL). After stirring for 20 minutes, the mixture was concentrated under reduced pressure and partitioned between ethyl acetate (20 mL) and saturated $NaHCO_3$ (20 mL). The aqueous layer was extracted with ethyl acetate (20 mL). The combined organics were washed with brine (10 mL), dried over $Na_2SO_4$, filtered and concentrated under reduced pressure to provide the product as a mixture of diastereomers as a colorless gum (26 mg, 97%). MS ESI (+) m/z 420 (M+1) detected; $^1$H NMR (400 MHz, $CDCl_3$) δ 7.52 (m, 1H), 7.45 (m, 2H), 7.37 (m, 2H), 7.27 (m, 1H), 7.14 (m, 2H), 4.71 (m, 1H), 3.35 (d, 3H, J=34 Hz), 3.28 (m, 1H), 2.91 (br, 2H), 2.72 (br, 2H), 2.43 (m, 1H), 1.98 (m, 1H), 1.56 (m, 1H), 1.47 (dd, 3H, J=6.6 Hz, 24.3 Hz).

The following examples were prepared as previously described in Example 42 using the appropriate thiohydrazide, ketone and acid.

Example 43

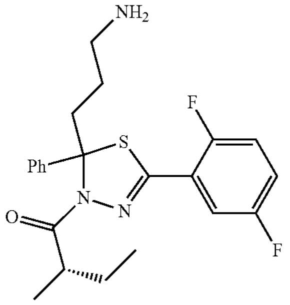 [SMILES: CC[C@H](C)C(=O)N1N=C(c2cc(F)ccc2F)SC1(CCCN)c1ccccc1]

(2S)-1-(2-(3-Aminopropyl)-5-(2,5-difluorophenyl)-2-phenyl-1,3,4-thiadiazol-3(2H)-yl)-2-methylbutan-1-one Obtained as a mixture of diastereomers. MS ESI (+) m/z 418 (M+1) detected; $^1$H NMR (400 MHz, $CDCl_3$) δ 7.55 (m, 1H), 7.45 (m, 2H), 7.34 (m, 2H), 7.26 (m, 1H), 7.11 (m, 2H), 3.34 (m, 1H), 3.22 (m, 1H), 2.87 (br, 2H), 2.73 (br, 2H), 2.38 (m, 1H), 1.96 (m, 1H), 1.74 (m, 1H), 1.54 (m, 1H), 1.43 (m, 1H), 1.16 (m, 3H), 0.91 (dt, 3H, J=7.4 Hz, 35.2 Hz).

Example 44

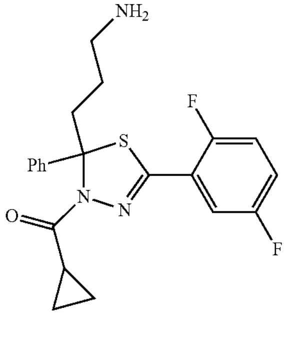 [SMILES: NCCCC1(c2ccccc2)SC(c2cc(F)ccc2F)=NN1C(=O)C1CC1]

(2-(3-Aminopropyl)-5-(2,5-difluorophenyl)-2-phenyl-1,3,4-thiadiazol-3(2H)-yl)(cyclopropyl)methanone MS ESI (+) m/z 402 (M+1) detected; $^1$H NMR (400 MHz, $CDCl_3$) δ 7.60 (m, 1H), 7.43 (m, 2H), 7.35 (m, 2H), 7.26 (m, 1H), 7.10 (m, 2H), 3.30 (br, 1H), 3.16 (m, 1H), 2.87 (br, 1H), 2.75 (m, 1H), 2.35 (m, 1H), 1.97 (m, 1H), 1.60 (m, 1H), 1.03 (m, 1H), 0.90 (m, 3H).

Example 45

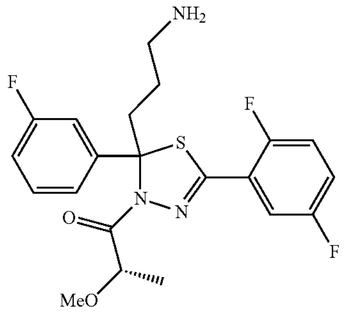 [SMILES: CO[C@@H](C)C(=O)N1N=C(c2cc(F)ccc2F)SC1(CCCN)c1cccc(F)c1]

(2S)-1-(2-(3-aminopropyl)-5-(2,5-difluorophenyl)-2-(3-fluorophenyl)-1,3,4-thiadiazol-3(2H)-yl)-2-methoxypropan-1-one Obtained as a mixture of diastereomers. MS ESI (+) m/z 438 (M+1) detected; $^1$H NMR (400 MHz, $CDCl_3$) δ 7.51 (m, 1H), 7.32 (m, 1H), 7.23 (d, 1H, J=8 Hz), 7.14 (m, 3H), 6.98 (m, 1H), 4.68 (m, 1H), 3.37 (m, 1H), 3.35 (d, 3H, J=34 Hz), 2.93 (m, 2H), 2.40 (m, 1H), 1.99 (m, 1H), 1.62 (m, 1H), 1.48 (dd, 3H, J=6.6 Hz, 26 Hz), 1.36 (m, 1H), 1.25 (m, 1H).

Example 46

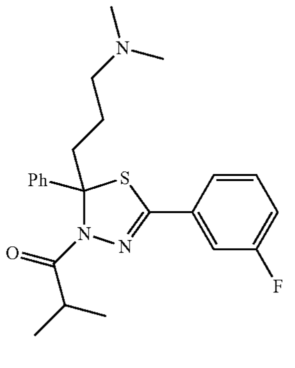 [SMILES: CC(C)C(=O)N1N=C(c2cccc(F)c2)SC1(CCCN(C)C)c1ccccc1]

Synthesis of 1-[2-(3-dimethylaminopropyl)-5-(3-fluorophenyl)-2-phenyl-[1,3,4]thiadiazol-3-yl]-2-methylpropan-1-one To a solution of 1-(2-(3-aminopropyl)-5-(3-fluorophenyl)-2-phenyl-1,3,4-thiadiazol-3(2H)-yl)-2-methylpropan-1-one (9.0 mg, 0.02 mmol) in MeOH (1 mL) was added paraformaldehyde (10 mg, 0.40 mmol). The mixture was heated to 70° C. for 2 hours. The mixture was allowed to cool to room temperature and sodium cyanoborohydride (0.07 mL, 0.07 mmol, 1M solution in THF) was added. After stirring for 40 minutes, the mixture was diluted with half saturated NaCl (50 mL) and extracted with ethyl acetate (3×25 mL). The combined organics were washed with saturated NaCl, dried over $Na_2SO_4$, filtered and concentrated under reduced pressure. The residue was purified by flash column chromatography (2% triethylamine, 40% ethyl acetate in hexanes) to provide the final product (3.0 mg, 30%) as pale yellow film. MS ESI (+) m/z 414 (M+1) detected; $^1$H NMR (400 MHz, $CDCl_3$) δ 7.44 (m, 3H), 7.36 (m, 5H), 7.14 (m, 1H), 3.51 (m, 1H), 3.17 (m, 1H), 2.40 (m, 3H), 2.23 (s, 6H), 1.92 (m, 1H), 1.53 (m, 1H), 1.20 (d, 3H, J=7 Hz), 1.18 (d, 3H, J=7 Hz).

Example 47

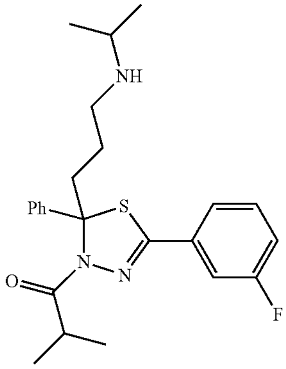 [SMILES: CC(C)NCCCC1(c2ccccc2)SC(c2cccc(F)c2)=NN1C(=O)C(C)C]

Synthesis of 1-[5-(3-fluorophenyl)-2-(3-isopropylaminopropyl)-2-phenyl-[1,3,4]thiadiazol-3-yl]-2-methylpropan-1-one A mixture of 1-(2-(3-aminopropyl)-5-(3-fluorophenyl)-2-phenyl-1,3,4-thiadiazol-3(2H)-yl)-2-methylpropan-1-one (9.0 mg, 0.02 mmol) and acetone (20 mg, 0.40 mmol) in acetonitrile (0.5 mL) was stirred at room temperature for 1 hour. To the mixture was added sodium triacetoxyborohydride (33 mg, 0.20 mmol). After stirring at room temperature for 16 hours, more acetone (50 μL) and sodium triacetoxyborohydride (14 mg) was added. The reaction mixture was heated to 45° C. for 40 hours and then diluted with 10% $Na_2CO_3$ (30 mL). The mixture was extracted with ethyl acetate (3×30 mL). The combined organics were dried over $Na_2SO_4$, filtered and concentrated under reduced pressure. The residue was purified by flash column chromatography (2% triethylamine, 40% ethyl acetate in hexanes) to provide the product (5.4 mg, 50%) as pale yellow film. MS ESI (+) m/z 428 (M+1) detected; $^1$H NMR (400 MHz, $CDCl_3$) δ 7.45 (d, 2H, J=8 Hz), 7.42 (d, 1H, J=7 Hz), 7.37 (m, 4H), 7.27 (m, 1H), 7.14 (m, 1H), 3.50 (m, 1H), 3.21 (m, 1H), 2.80 (m, 1H), 2.73 (m, 2H), 2.39 (m, 1H), 1.95 (m, 1H), 1.56 (m, 1H), 1.19 (d, 3H, J=6 Hz), 1.17 (d, 3H, J=6 Hz), 1.05 (d, 6H, J=6 Hz).

Example 48

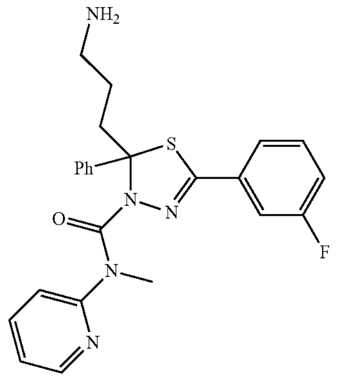 [SMILES: CN(C(=O)N1N=C(c2cccc(F)c2)SC1(CCCN)c1ccccc1)c1ccccn1]

Synthesis of 2-(3-aminopropyl)-5-(3-fluorophenyl)-2-phenyl-[1,3,4]thiadiazole-3-carboxylic Acid methyl-pyridin-2-yl-amide To a solution of methyl-pyridin-2-yl-amine (77 mg, 0.71 mmol) and triethylamine (150 mg, 0.15 mmol) in dichloroethane (3 mL) was added triphosgene (110 mg, 0.37 mmol). After stirring at room temperature for 1 hour, the reaction mixture was concentrated under reduced pressure and diluted with dichloroethane (3 mL). To the solution was added {3-[5-(3-fluorophenyl)-2-phenyl-2,3-dihydro-[1,3,4]thiadiazol-2-yl]-propyl}-carbamic acid tert-butyl ester (250 mg, 0.60 mmol) and DMAP (20 mg). After stirring at room temperature for 3 hours, the reaction mixture was concentrated under reduced pressure and purified by flash column chromatography (1:8 ethyl acetate/hexanes) to provide the Boc-protected product (210 mg, 54%). To this product (65 mg, 0.12 mmol) was added HCl (3 mL, 4M in dioxane) at 0° C. After warming to room temperature and stirring for 3 minutes, the mixture was concentrated to provide the final product as the trihydrochloride salt (64 mg, 97%). MS APCI (+) m/z 450 (M+1) detected; $^1$H NMR (400 MHz, $CDCl_3$) δ 8.62 (m, 3H), 7.60 (d, 2H, J=6 Hz), 7.35 (m, 5H), 7.19 (d, 1H, J=7 Hz), 7.13 (m, 1H), 7.06 (d, 1H, J=8 Hz), 3.67 (s, 3H), 3.50 (m, 1H), 3.25 (m, 1H), 3.13 (m, 1H), 2.50 (m, 1H), 2.23 (m, 2H).

Example 49

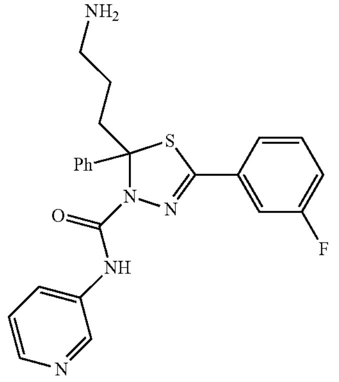 [SMILES: NCCCC1(c2ccccc2)SC(c2cccc(F)c2)=NN1C(=O)Nc1cccnc1]

2-(3-Aminopropyl)-5-(3-fluorophenyl)-2-phenyl-[1,3,4]thiadiazole-3-carboxylic Acid pyridin-3-ylamide Prepared as previously described in Example 48 using pyridin-3-amine in place of methylpyridin-2-yl-amine. MS APCI (+) m/z 436 (M+1) detected; $^1$H NMR (400 MHz, $CDCl_3$) δ 9.31 (s, 1H), 8.75 (d, 1H), 8.29 (m, 1H), 7.78 (m, 1H), 7.73 (m, 1H), 7.52 (m, 3H), 7.40 (m, 3H), 7.35 (m, 2H), 7.18 (m, 1H), 3.39 (m, 2H), 3.23 (m, 1H), 3.13 (m, 1H), 3.06 (m, 1H), 2.58 (m, 1H), 2.25 (br, 1H), 2.00 (br, 1H).

Example 50

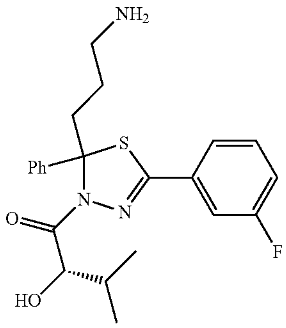 [SMILES: CC(C)[C@H](O)C(=O)N1N=C(c2cccc(F)c2)SC1(CCCN)c1ccccc1]

Synthesis of (2S)-1-(2-(3-aminopropyl)-5-(3-fluorophenyl)-2-phenyl-1,3,4-thiadiazol-3(2H)-yl)-2-hydroxy-3-methylbutan-1-one (Diastereomer A)

(S)-2-hydroxy-3-methylbutyric acid (13.5 mg, 0.11 mmol) and PyBOP (60 mg, 0.12 mmol) were combined in THF (0.4 mL) and stirred for 10 minutes. To this mixture was added {3-[5-(3-fluorophenyl)-2-phenyl-2,3-dihydro-[1,3,4]thiadiazol-2-yl]-propyl}-carbamic acid tert-butyl ester (20 mg, 0.05 mmol) and DIEA (31 mg, 0.24 mmol). After stirring at room temperature for 24 hours, the reaction mixture was diluted with 10% $Na_2CO_3$ (20 mL) and extracted with ethyl acetate (3×20 mL). The combined organics were dried over $Na_2SO_4$, filtered and concentrated under reduced pressure.

The residue was chromatographed (1:4 ethyl acetate/hexanes) to provide Boc-protected diastereomer A (less polar, 2.0 mg) and Boc-protected diastereomer B (more polar, 4.2 mg). To the Boc-protected diastereomer A was added HCl (1 mL, 4M in dioxane) at 0° C. After warming to room temperature and stirring for 1 hour, the mixture was concentrated under a stream of $N_2$. The residue was dissolved in an ether/dioxane mixture and precipitated with hexanes. The solid was filtered and washed with hexanes to provide the final product as yellow solid. MS ESI (+) m/z 416 (M+1) detected; $^1$H NMR (400 MHz, $CDCl_3$) δ 8.4 (br s, 3H), 7.5 (m, 2H), 7.43-7.28 (m, 4H), 7.24-7.11 (m, 3H), 4.66 (br s, 1H), 3.30 (br s, 1H), 3.15-2.92 (m, 2H), 2.73 (m, 1H), 2.30 (m, 1H), 2.18 (m, 1H), 1.81-1.49 (m, 2H), 1.10 (br m, 3H), 0.9 (br m, 3H).

Example 51

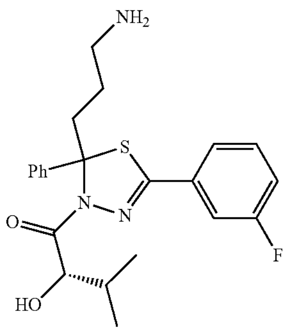 [SMILES: CC(C)[C@H](O)C(=O)N1N=C(c2cccc(F)c2)SC1(CCCN)c1ccccc1]

(2S)-1-(2-(3-aminopropyl)-5-(3-fluorophenyl)-2-phenyl-1,3,4-thiadiazol-3(2H)-yl)-2-hydroxy-3-methylbutan-1-one (Diastereomer B)

Prepared as previously described in Example 50 using the more polar Boc-protected diastereomer B. MS ESI (+) m/z 416 (M+1) detected; $^1$H NMR (400 MHz, $CDCl_3$) δ 8.3 (br s, 3H), 7.65 (m, 2H), 7.45-7.30 (m, 5H), 7.28-7.12 (m, 2H), 4.89 (br s, 1H), 3.86 (br m, 1H), 3.13 (br m, 1H) 3.05-2.82 (m, 2H), 2.27-2.14 (m, 2H), 2.05 (br m, 1H), 1.91 (br m, 1H), 1.02 (d, 3H, J=7.0 Hz), 0.60 (d, 3H, J=6.3 Hz).

Example 52

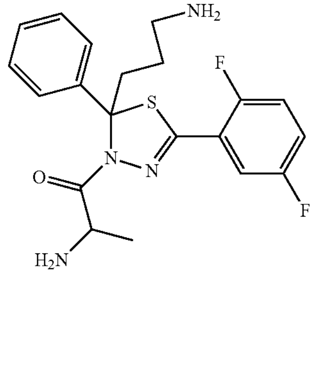 [SMILES: CC(N)C(=O)N1N=C(c2cc(F)ccc2F)SC1(CCCN)c1ccccc1]

2-amino-1-(2-(3-aminopropyl)-5-(2,5-difluorophenyl)-2-phenyl-1,3,4-thiadiazol-3(2H)-yl)propan-1-one Step A: Preparation of tert-butyl 1-(2-(3-azidopropyl)-5-(2,5-difluorophenyl)-2-phenyl-1,3,4-thiadiazol-3(2H)-yl)-1-oxopropan-2-ylcarbamate 2-(3-Azidopropyl)-5-(2,5-difluorophenyl)-2-phenyl-2,3-dihydro-1,3,4-thiadiazole (50 mg, 0.139 mmol; as prepared in example 70) was dissolved in 2.0 mL of DMF. 2-(tert-Butoxycarbonyl)propanoic acid (39 mg, 0.208 mmol), EDCI (40 mg, 0.208 mmol), HOBt (28 mg, 0.208 mmol) and TEA (0.058 mL, 0.417 mmol) were then added and the reaction allowed to stir at 23° C. Following 12 hours, the reaction was quenched by addition of saturated $NaHCO_3$ solution, extracted (3×15 mL ethyl acetate), combined organics washed with water (1×50 mL) then dried over $Na_2SO_4$, and concentrated in vacuo. The crude reaction was purified by chromatography (20% ethyl acetate/Hex) affording the product as a white foam (70 mg, 94%). MS APCI (−) m/z 529 (M−1) detected; $^1$H NMR (400 MHz, $CDCl_3$) δ 7.59 (m, 1H), 7.43 (m, 2H), 7.37 (t, 2H, J=8 Hz), 7.30 (m, 1H), 7.12 (m, 2H), 5.23 (brs, 0.5H), 5.12 (brs, 0.5H), 3.44 (m, 2H), 3.19 (m, 1H), 2.47 (m, 1H), 1.57 (d, 2H, J=9 Hz), 1.43 (m, 12H), 0.89 (m, 1H).

Step B: Preparation of 2-amino-1-(2-(3-azidopropyl)-5-(2,5-difluorophenyl)-2-phenyl-1,3,4-thiadiazol-3(2H)-yl)propan-1-one tert-Butyl 1-(2-(3-azidopropyl)-5-(2,5-difluorophenyl)-2-phenyl-1,3,4-thiadiazol-3(2H)-yl)-1-oxopropan-2-ylcarbamate (70 mg, 0.131 mmol) was dissolved in 7.0 mL of EtOH. HCl (0.65 mL, 0.659 mmol) was then added and the reaction stirred at 23° C. for 4 hours. The reaction was then concentrated and purified by chromatography (2-10% MeOH/DCM), yielding the product (54 mg, 95%) as a yellow oil. MS ESI (+) m/z 431 (M+1) detected; $^1$H NMR (400 MHz, $CD_3OD$) δ7.69 (m, 1H), 7.53 (d, 2H, J=8 Hz), 7.42 (t, 2H, J=7 Hz), 7.34 (m, 3H), 4.91 (m, 3H), 3.21 (m, 1H), 3.17 (m, 2H), 2.68 (m, 1H), 2.19 (m, 1H), 1.99 (m, 1H), 1.73 (d, 1.5H, J=8 Hz), 1.64 (d, 1.5H, J=8 Hz).

Step C: Preparation of 2-amino-1-(2-(3-aminopropyl)-5-(2,5 difluorophenyl)-2-phenyl-1,3,4-thiadiazol-3(2H)-yl)propan-1-one 2-Amino-1-(2-(3-azidopropyl)-5-(2,5-difluorophenyl)-2-phenyl-1,3,4-thiadiazol-3(2H)-yl)propan-1-one (50 mg, 0.116 mmol) was dissolved in 5.0 mL of MeOH. HCl (0.46 ml, 0.464 mmol) was added followed by evacuation/re-vacuation with $N_2$. Pd/C (12 mg, 0.011 mmol) was then added followed by $H_2$ balloon. Following 40 hours at 23° C., the reaction was concentrated in vacuo, affording the product (41 mg, 87%) as a cream/yellow colored foam. MS ESI (+) m/z 405 (M+1) detected; $^1$H NMR (400 MHz, $CD_3OD$) δ7.68 (m, 1H), 7.53 (m, 2H), 7.42 (t, 2H, J=9 Hz), 7.34 (m, 3H), 4.92 (m, 1H), 3.22 (m, 2H), 3.17 (m, 4H), 2.65 (m, 2H), 2.20 (m, 1H), 1.99 (m, 1H), 1.72 (d, 1.5H, J=8 Hz), 1.66 d, 1.5H, J=8 Hz).

Example 53

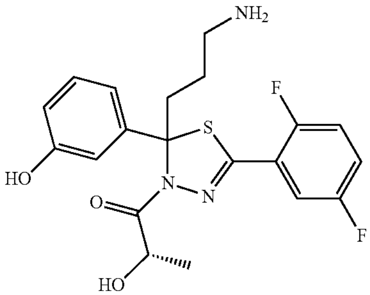 [SMILES: C[C@H](O)C(=O)N1N=C(c2cc(F)ccc2F)SC1(CCCN)c1cccc(O)c1]

(2S)-1-(2-(3-aminopropyl)-5-(2,5-difluorophenyl)-2-(3-hydroxyphenyl)-1,3,4-thiadiazol-3(2H)-yl)-2-hydroxypropan-1-one Prepared as previously described in Example 52 using the appropriate thiohydrazide, ketone and carboxylic acid to provide the Boc-protected product. To this product (0.087 g, 0.167 mmol) dissolved in ether (5 mL) was added HCl (0.654 mL, 1.67 mmol, solution in ether). After stirring at room temperature for 1 hour, the mixture was concentrated under reduced pressure to provide the final product as a mixture of diastereomers. MS ESI (+) m/z 422 (M+1) detected; $^{1}$H NMR (400 MHz, $CDCl_3$) δ 7.43 (m, 2H), 7.36 (m, 3H), 7.33 (m, 1H), 7.15 (m, 2H), 5.03 (s, 1H), 4.83 (m, 1H), 3.19 (m, 1H), 2.93 (m, 2H), 2.42 (m, 1H), 1.57 (m, 4H), 1.49 (d, 3H).

Example 54

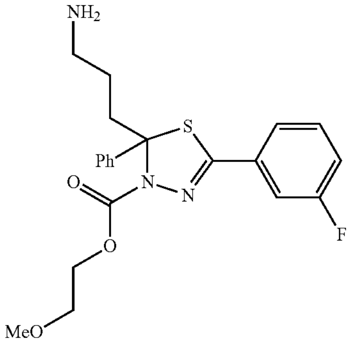 [SMILES: COCCOC(=O)N1N=C(c2cccc(F)c2)SC1(CCCN)c1ccccc1]

Synthesis of 2-(3-aminopropyl)-5-(3-fluorophenyl)-2-phenyl-[1,3,4]thiadiazole-3-carboxylic Acid 2-methoxyethyl Ester To a solution of 2-methoxyethanol (30 mg, 0.4 mmol) in acetonitrile (3 mL) at 0° C. was added phosgene (54 mg, 0.54 mmol, 20% wt in toluene). After warming to room temperature and stirring for 6 hours, the mixture was concentrated under reduced pressure. To the residue was added dichloromethane (4 mL), {3-[5-(3-fluorophenyl)-2-phenyl-2,3-dihydro-[1,3,4]thiadiazol-2-yl]-propyl}-carbamic acid tert-butyl ester (90 mg, 0.22 mmol), triethylamine (33 mg, 0.32 mmol) and DMAP (10 mg). After stirring for 1 hour, MeOH (0.5 mL) was added to quench the reaction. The mixture was concentrated under reduced pressure and purified by flash column chromatography (8:1 hexanes/ethyl acetate) to provide the Boc-protected product (90 mg, 80%). To 41 mg of this product was added HCl (3 mL, 4M in dioxane) at 0° C. After warming to room temperature and stirring for 1 hour, the mixture was concentrated to provide the final product as the dihydrochloride salt (39 mg, 100%). MS APCI (+) m/z 418 (M+1) detected; $^{1}$H NMR (400 MHz, $CDCl_3$) δ 8.45 (br, 2H), 7.55 (m, 2H), 7.36 (m, 5H), 7.25 (m, 1H), 7.10 (m, 1H), 4.25 (m, 1H), 3.58 (m, 1H), 3.33 (s, 3H), 3.22 (m, 1H), 3.10 (m, 2H), 2.53 (m, 1H), 2.18 (m, 1H), 1.91 (m, 1H), 1.77 (s, 2H).

Example 55

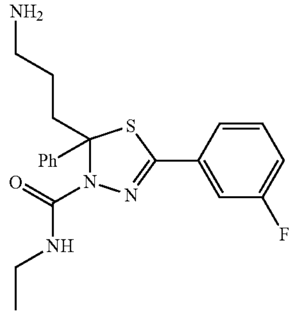 [SMILES: CCNC(=O)N1N=C(c2cccc(F)c2)SC1(CCCN)c1ccccc1]

Synthesis of 2-(3-aminopropyl)-5-(3-fluorophenyl)-2-phenyl-[1,3,4]thiadiazole-3-carboxylic Acid Ethylamide To a solution of {3-[5-(3-fluorophenyl)-2-phenyl-2,3-dihydro-[1,3,4]thiadiazol-2-yl]-propyl}-carbamic acid tert-butyl ester (40 mg, 0.096 mmol) in dichloroethane (3 mL) was added ethyl isocyanate (140 mg, 1.9 mmol). After stirring at 60° C. for 1 hour, the reaction mixture was cooled to room temperature and concentrated under reduced pressure. The residue was purified by flash column chromatography (8:1 hexanes/ethyl acetate) to provide the Boc-protected product (40 mg, 85%). To this product was added HCl (3 mL, 4M in dioxane) at 0° C. After warming to room temperature and stirring for 1 hour, the mixture was concentrated to provide the final product as the dihydrochloride salt (37 mg, 98%). MS APCI (+) m/z 387 (M+1) detected; $^{1}$H NMR (400 MHz, $CDCl_3$) δ 8.44 (br, 2H), 7.49 (m, 2H), 7.34 (m, 5H), 7.24 (m, 1H), 7.10 (m, 1H), 6.19 (m, 1H), 3.26 (m, 3H), 3.04 (m, 1H), 2.99 (m, 1H), 2.44 (m, 1H), 2.11 (m, 1H), 1.92 (m, 1H), 1.15 (t, 3H).

Example 56

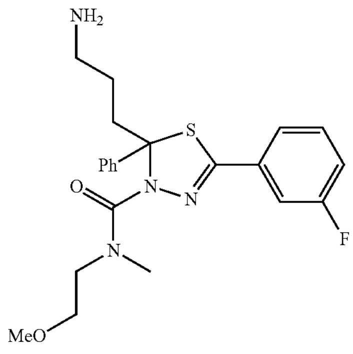 [SMILES: COCCN(C)C(=O)N1N=C(c2cccc(F)c2)SC1(CCCN)c1ccccc1]

Synthesis of 2-(3-aminopropyl)-5-(3-fluorophenyl)-N-(2-methoxyethyl)-N-methyl-2-phenyl-1,3,4-thiadiazole-3(2H)-carboxamide

Step A: Preparation of 4-nitrophenyl 2-(3-(tert-butoxycarbonyl)propyl)-5-(3-fluorophenyl)-2-phenyl-1,3,4-thiadiazole-3(2H)-carboxylate To a solution of tert-butyl 3-(5-(3-fluorophenyl)-2-phenyl-2,3-dihydro-1,3,4-thiadiazol-2-yl)propylcarbamate (350 mg, 0.84 mmol) in dichloromethane (3 mL) was added triethylamine (110 mg, 1.10 mmol) and 4-nitrophenylchloroformate (220 mg, 1.00 mmol). After stirring for 1 hour, the reaction mixture was diluted with 1M HCl (5 mL) and dichloromethane (10 mL). The organic layer was dried over $Na_2SO_4$, filtered, and concentrated under reduced pressure to provide the product.

Step B: Preparation of 2-(3-aminopropyl)-5-(3-fluorophenyl)-N-(2-methoxyethyl)-N-methyl-2-phenyl-1,3,4-thiadiazole-3(2H)-carboxamide To a solution of 4-nitrophenyl 2-(3-(tert-butoxycarbonyl)propyl)-5-(3-fluorophenyl)-2-phenyl-1,3,4-thiadiazole-3(2H)-carboxylate (90 mg, 0.20 mmol) in dichloroethane (3 mL) was added 2-methoxy-N-methylethanamine (70 mg, 0.80 mmol) and DIEA (100 mg, 0.80 mmol). After stirring at 50° C. for 6 hours, the mixture was cooled to room temperature and concentrated under reduced pressure. The residue was purified by flash column chromatography (1:10 ethyl acetate/hexanes) to provide the Boc-protected product (60 mg, 70%). To this product was added HCl (3 mL, 4M in dioxane) at 0° C. After warming to room temperature and stirring for 1 hour, the mixture was concentrated to provide the final product as the dihydrochloride salt (50 mg, 83%). MS APCI (+) m/z 431 (M+1) detected; $^1$H NMR (400 MHz, $CDCl_3$) δ 8.41 (br, 2H), 7.55 (m, 2H), 7.32 (m, 6H), 7.09 (m, 1H), 3.63 (m, 3H), 3.35 (s, 3H), 3.01 (s, 3H), 2.41 (m, 1H), 2.05 (m, 1H), 1.80 (m, 2H), 1.26 (m, 2H) 0.88 (m, 1H).

The following examples were prepared as previously described in Example 56 using the appropriate amine.

Example 57

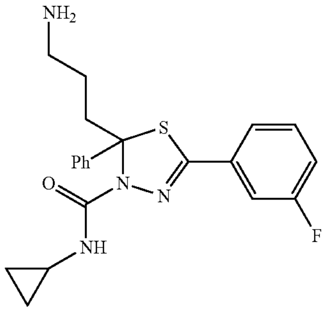 [SMILES: NCCCC1(c2ccccc2)SC(c2cccc(F)c2)=NN1C(=O)NC1CC1]

2-(3-Aminopropyl)-N-cyclopropyl-5-(3-fluorophenyl)-2-phenyl-1,3,4-thiadiazole-3(2H)-carboxamide MS APCI (+) m/z 399 (M+1) detected.

Example 58

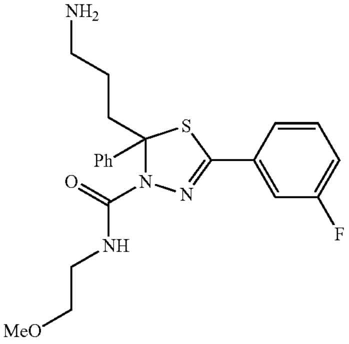 [SMILES: COCCNC(=O)N1N=C(c2cccc(F)c2)SC1(CCCN)c1ccccc1]

2-(3-Aminopropyl)-5-(3-fluorophenyl)-N-(2-methoxyethyl)-2-phenyl-1,3,4-thiadiazole-3(2H)-carboxamide MS APCI (+) m/z 417 (M+1) detected; $^1$H NMR (400 MHz, $CDCl_3$) δ 8.30 (br, 2H), 7.47 (m, 2H), 7.32 (m, 5H), 7.23 (m, 1H), 7.10 (m, 1H), 6.58 (m, 1H), 3.42 (m, 3H), 3.35 (s, 3H), 3.25 (m, 1H), 3.01 (m, 2H), 2.46 (m, 2H), 2.10 (m, 1H), 1.88 (m, 1H).

Example 59

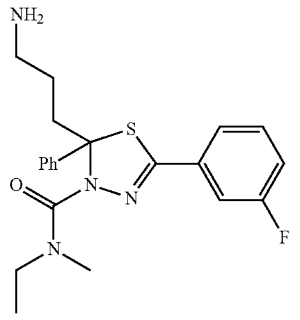 [SMILES: CCN(C)C(=O)N1N=C(c2cccc(F)c2)SC1(CCCN)c1ccccc1]

2-(3-Aminopropyl)-N-ethyl-5-(3-fluorophenyl)-N-methyl-2-phenyl-1,3,4-thiadiazole-3(2H)-carboxamide MS APCI (+) m/z 401 (M+1) detected; $^1$H NMR (400 MHz, $CDCl_3$) δ 8.36 (br, 2H), 7.52 (m, 2H), 7.32 (m, 5H), 7.21 (m, 1H), 7.09 (m, 1H), 3.39 (m, 2H), 3.25 (m, 1H), 2.97 (m, 1H), 2.92 (s, 3H), 2.39 (m, 1H), 2.16 (m, 1H), 2.06 (m, 1H), 1.84 (m, 1H), 1.22 (m, 3H).

Example 60

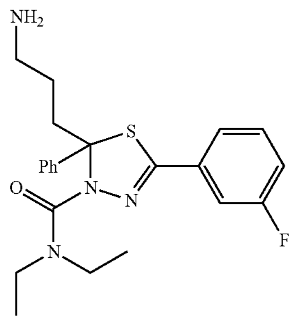 [SMILES: CCN(CC)C(=O)N1N=C(c2cccc(F)c2)SC1(CCCN)c1ccccc1]

2-(3-Aminopropyl)-N,N-diethyl-5-(3-fluorophenyl)-2-phenyl-1,3,4-thiadiazole-3(2H)-carboxamide MS APCI (+) m/z 415 (M+1) detected; $^1$H NMR (400 MHz, $CDCl_3$) δ 8.42 (br, 2H), 7.52 (m, 2H), 7.33 (m, 5H), 7.21 (m, 1H), 7.08 (m, 1H), 3.35 (m, 4H), 3.24 (m, 1H), 2.96 (m, 2H), 2.46 (m, 1H), 2.07 (m, 1H), 1.85 (m, 1H), 1.20 (m, 6H).

Example 61

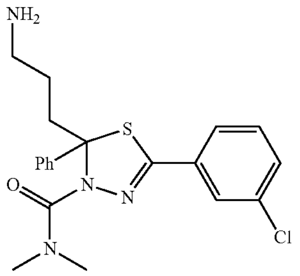 [SMILES: CN(C)C(=O)N1N=C(c2cccc(Cl)c2)SC1(CCCN)c1ccccc1]

2-(3-Aminopropyl)-5-(3-chlorophenyl)-N,N-dimethyl-2-phenyl-1,3,4-thiadiazole-3(2H)-carboxamide MS APCI (+) m/z 403, 405 (M+1, Cl pattern) detected; $^1$H NMR (400 MHz, $CDCl_3$) δ 8.44 (br, 2H), 7.62 (s, 1H), 7.54 (d, 2H), 7.45 (d, 1H), 7.36 (d, 1H), 7.32 (m, 3H), 7.23 (m, 1H), 3.29 (m, 1H), 3.00 (s, 6H), 2.91 (m, 1H), 2.38 (m, 1H), 2.07 (m, 1H), 1.87 (m, 1H), 1.72 (m, 1H).

Example 62

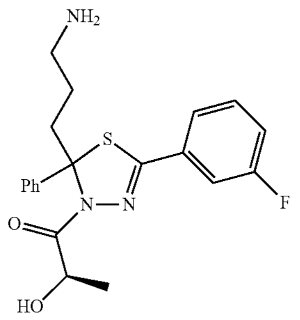 [SMILES: C[C@@H](O)C(=O)N1N=C(c2cccc(F)c2)SC1(CCCN)c1ccccc1]

Synthesis of (2R)-1-(2-(3-aminopropyl)-5-(3-fluorophenyl)-2-phenyl-1,3,4-thiadiazol-3(2H)-yl)-2-hydroxypropan-1-one (Diastereomer A)

Step A: Preparation of tert-butyl 3-(3-((R)-2-((2,2-dimethyl-1,1-diphenylpropyl)dimethylsilyloxy)propanoyl)-5-(3-fluorophenyl)-2-phenyl-2,3-dihydro-1,3,4-thiadiazol-2-yl)propylcarbamate To a solution of (R)-2-((2,2-dimethyl-1,1-diphenylpropyl)dimethylsilyloxy)propanoic acid (181 mg, 0.36 mmol) and DIEA (78 mg, 0.60 mmol) in acetonitrile (1 mL) was added HATU (137 mg, 0.36 mmol). After stirring at room temperature for 10 minutes, a solution of tert-butyl 3-(5-(3-fluorophenyl)-2-phenyl-2,3-dihydro-1,3,4-thiadiazol-2-yl)propylcarbamate (100 mg, 0.24 mmol) in acetonitrile (1 mL) was added. After stirring for 3 hours, PyBOP (150 mg), DIEA (100 μL), and more tert-butyl 3-(5-(3-fluorophenyl)-2-phenyl-2,3-dihydro-1,3,4-thiadiazol-2-yl)propylcarbamate (45 mg) was added. After stirring for 16 hours, the reaction mixture was diluted with 10% $Na_2CO_3$ (30 mL) and extracted with ethyl acetate (3×20 mL). The combined organics were washed with brine (40 mL), dried over $Na_2SO_4$, filtered, and concentrated under reduced pressure. The residue was chromatographed (1:9 ethyl acetate/hexanes) to provide the N-Boc-O-TBDPS-protected diastereomer A (more polar, 74 mg, 40%) and the N-Boc-O-TBDPS-protected diastereomer B (less polar, 35 mg, 19%)

Step B: Preparation of (2R)-1-(2-(3-aminopropyl)-5-(3-fluorophenyl)-2-phenyl-1,3,4-thiadiazol-3(2H)-yl)-2-hydroxypropan-1-one (Diastereomer A)

To a solution of the N-Boc-O-TBDPS-protected diastereomer A (36 mg, 0.047 mmol) in THF (0.5 mL) was added TBAF (94 μL of 1.0 M solution in THF). After stirring for 3 hours at room temperature, the mixture was diluted with half saturated $NaHCO_3$ (30 mL) and extracted with ethyl acetate (3×20 mL). The combined organics were washed with brine (30 mL), dried over $Na_2SO_4$, filtered, and concentrated under reduced pressure. The residue was chromatographed (30% ethyl acetate in hexanes) to provide the N-Boc-protected diastereomer A (18 mg, 80%). To a cooled (0° C.) solution of this product in dioxane (0.5 mL) was added HCl (0.5 mL of 4.0 M solution in dioxane). After warming to room temperature, the mixture was stirred for 4.5 hours. The reaction mixture was concentrated under reduced pressure and dissolved in minimal dioxane and then precipitated with ether to provide the final product (3.9 mg, 70%). MS ESI (+) m/z 388 (M+1) detected; $^1H$ NMR (400 MHz, 10:1 $CDCl_3$:$CD_3OD$) δ 7.40 (m, 8H), 7.19 (m, 1H), 4.98 (m, 1H), 3.32 (m, 1H), 3.05 (m, 2H), 2.56 (m, 1H), 2.18 (m, 1H), 1.70 (m, 1H), 1.57 (m, 3H).

Example 63

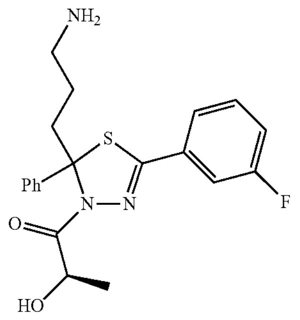 [SMILES: C[C@@H](O)C(=O)N1N=C(c2cccc(F)c2)SC1(CCCN)c1ccccc1]

(2R)-1-(2-(3-aminopropyl)-5-(3-fluorophenyl)-2-phenyl-1,3,4-thiadiazol-3(2H)-yl)-2-hydroxypropan-1-one (Diastereomer B)

Prepared as previously described in Example 62 using the N-Boc-O-TBDPS-protected diastereomer B from Step A of Example 62. MS ESI (+) m/z 388 (M+1) detected; $^1H$ NMR (400 MHz, 10:1 $CDCl_3$:$CD_3OD$) δ 7.53-7.30 (m, 8H), 7.19 (m, 1H), 5.10 (m, 1H), 3.53 (m, 1H), 3.24-2.95 (m, 2H), 2.55 (m, 1H), 2.19 (m, 1H), 1.87 (m, 1H), 1.49 (m, 3H).

Example 64

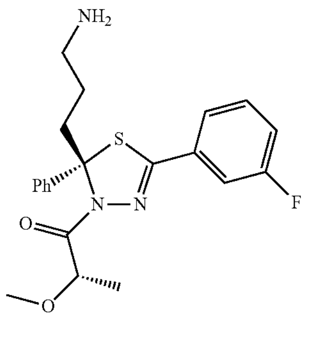 [SMILES: CO[C@@H](C)C(=O)N1N=C(c2cccc(F)c2)S[C@@]1(CCCN)c1ccccc1]

Synthesis of (S)-1-((S)-2-(3-aminopropyl)-5-(3-fluorophenyl)-2-phenyl-1,3,4-thiadiazol-3(2H)-yl)-2-methoxypropan-1-one Step A: Preparation of tert-butyl 3-((S)-3-((S)-2-(tert-butyldiphenylsilyloxy)propanoyl)-5-(3-fluorophenyl)-2-phenyl-2,3-dihydro-1,3,4-thiadiazol-2-yl)propylcarbamate To a solution of tert-butyl 3-(5-(3-fluorophenyl)-2-phenyl-2,3-dihydro-1,3,4-thiadiazol-2-yl)propylcarbamate (0.54 g, 1.30 mmol) and (S)-2-(tert-butyldiphenylsilyloxy)propanoic acid (0.64 g, 1.95 mmol) in DMF (10 mL) was added PyBOP (1.01 g, 1.95 mmol) followed by DIEA (0.34 g, 2.60 mmol). After stirring at room temperature for 14 hours, the reaction mixture was partitioned between 10% $Na_2CO_3$ (100 mL) and ethyl acetate (100 mL). The aqueous layer was extracted with ethyl acetate (40 mL). The combined organics were washed with brine (100 mL), dried over $Na_2SO_4$, filtered and concentrated under reduced pressure. The residue was chromatographed (1:9 to 1:4 ethyl acetate/hexanes) to provide the less polar diastereomer product (180 mg, 19%) as a yellow syrup.

Step B: Preparation of tert-butyl 3-((S)-5-(3-fluorophenyl)-3-((S)-2-hydroxypropanoyl)-2-phenyl-2,3-dihydro-1,3,4-thiadiazol-2-yl)propylcarbamate To a cooled (0° C.) solution of tert-butyl 3-(3-((S)-2-(tert-butyldiphenylsilyloxy)propanoyl)-5-(3-fluorophenyl)-2-phenyl-2,3-dihydro-1,3,4-thiadiazol-2-yl)propylcarbamate (180 mg, 0.25 mmol) in THF (2.5 mL) was added TBAF (0.40 mL of 1M solution in THF). After stirring at room temperature for 2 hours, the volume was reduced in vacuo and the mixture was diluted with half-saturated $NaHCO_3$ (30 mL). The mixture was extracted with ethyl acetate (3×20 mL) and the combined organics were washed with brine (30 mL), dried over $Na_2SO_4$, filtered and concentrated under reduced pressure. The residue was chromatographed (30% ethyl acetate in hexanes) to provide the product (95 mg, 79%) as a viscous, yellow syrup.

Step C: Preparation of (S)-1-((S)-2-(3-aminopropyl)-5-(3-fluorophenyl)-2-phenyl-1,3,4-thiadiazol-3(2H)-yl)-2-methoxypropan-1-one To a solution of tert-butyl 3-((S)-5-(3-fluorophenyl)-3-((S)-2-hydroxypropanoyl)-2-phenyl-2,3-dihydro-1,3,4-thiadiazol-2-yl)propylcarbamate (64 mg, 0.13 mmol) in acetonitrile (1.3 mL) was added $Ag_2O$ (150 mg, 0.66 mmol) followed by iodomethane (190 mg, 1.3 mmol). After stirring at room temperature for 9 hours, the mixture was filtered, concentrated under reduced pressure and chromatographed (20% ethyl acetate in hexanes) to provide the Boc-protected product (30 mg, 45%). To this product was added HCl (0.5 mL of 4 M solution in dioxane). After stirring at 0° C. for 10 minutes and then at room temperature for 90 minutes, the mixture was concentrated under reduced pressure to provide the product (26 mg, 95%) as the di-HCl salt. MS ESI (+) m/z 402 (M+1) detected; $^1$H NMR (400 MHz, 10:1 $CDCl_3$:$CD_3OD$) δ 7.38 (m, 6H), 7.30 (m, 2H), 7.19 (m, 1H), 4.86 (br q, 1H, J=6.3 Hz), 3.43 (s, 3H), 3.36 (m, 1H), 3.12 (m, 2H), 2.56 (m, 1H), 2.21 (m, 2H), 1.44 (m, 3H).

Absolute stereochemistry was assigned by examination of the protein:inhibitor co-crystal structure of Eg5 and (S)-1-(S)-2-(3-aminopropyl)-5-(3-fluorophenyl)-2-phenyl-1,3,4-thiadiazol-3(2H)-yl)-2-methoxypropan-1-one.

Example 65

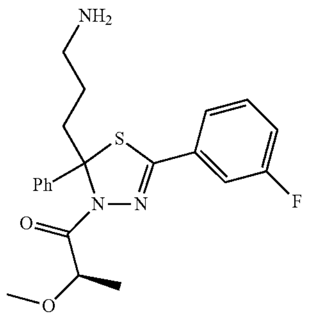 [SMILES: CO[C@H](C)C(=O)N1N=C(c2cccc(F)c2)SC1(CCCN)c1ccccc1]

(2R)-1-(2-(3-aminopropyl)-5-(3-fluorophenyl)-2-phenyl-1,3,4-thiadiazol-3(2H)-yl)-2-methoxypropan-1-one Prepared as in Example 42 using appropriately substituted reagents. MS (+) m/z 402 (M+1) detected; $^1$H NMR (400 MHz, 10:1 $CDCl_3$:$CD_3OD$) δ 7.49-7.29 (m, 8H), 7.20 (m, 1H), 4.77 (br 1, 1H, J=6.3 Hz), 3.35-3.26 (m, 4H), 3.10 (m, 2H), 2.61 (m, 1H), 2.22 (m, 1H), 1.68 (m, 1H), 1.52 (m, 3H).

Example 66

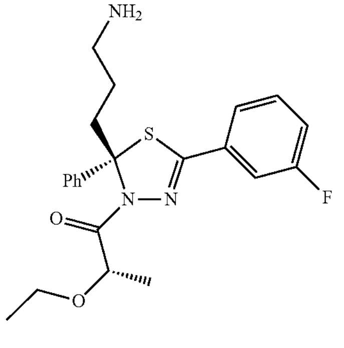 [SMILES: CCO[C@@H](C)C(=O)N1N=C(c2cccc(F)c2)S[C@@]1(CCCN)c1ccccc1]

(S)-1-((S)-2-(3-aminopropyl)-5-(3-fluorophenyl)-2-phenyl-1,3,4-thiadiazol-3(2H)-yl)-2-ethoxypropan-1-one Prepared as described in Example 64 using ethyl iodide in place of methyl iodide. MS (+) m/z 416 (M+1) detected; $^1$H NMR (400 MHz, 10:1 $CDCl_3$:$CD_3OD$) δ 7.39 (m, 7H), 7.30 (m 1H), 7.20 (m, 1H), 4.85 (br q, 1H, J=6.3 Hz), 3.68-3.53 (m, 2H), 3.27 (m, 1H), 3.11 (m, 2H), 2.58 (m, 1H), 2.21 (m, 1H), 1.72 (m, 1H), 1.47 (d, 3H, J=6.3 Hz), 1.24 (m, 3H). Stereochemistry was assigned by inference from (S)-1-((S)-2-(3-aminopropyl)-5-(3-fluorophenyl)-2-phenyl-1,3,4-thiadiazol-3(2H)-yl)-2-methoxypropan-1-one.

Example 67

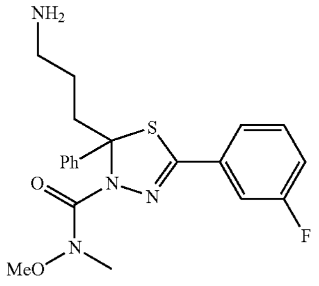 [SMILES: CON(C)C(=O)N1N=C(c2cccc(F)c2)SC1(CCCN)c1ccccc1]

Synthesis of 2-(3-aminopropyl)-5-(3-fluorophenyl)-N-methoxy-N-methyl-2-phenyl-1,3,4-thiadiazole-3(2H)-carboxamide Step A: Preparation of tert-butyl 3-(5-(3-fluorophenyl)-3-(1-carbonyl-3-methylimidazolium Iodide)-2-phenyl-2,3-dihydro-1,3,4-thiadiazol-2-yl)propylcarbamate To a solution of tert-butyl 3-(5-(3-fluorophenyl)-2-phenyl-2,3-dihydro-1,3,4-thiadiazol-2-yl)propylcarbamate (500 mg, 1.20 mmol) in THF (8 mL) was added 1,1'-carbonyl diimidazole (234 mg, 1.44 mmol). After heating to 70° C. in a sealed vessel for 2 hours, the mixture was cooled to room temperature and concentrated under reduced pressure. The residue was dissolved in dichloromethane (20 mL) and washed with 0.5 M HCl (2×10 mL). The organic layer was dried over $Na_2SO_4$, filtered, and concentrated under reduced pressure to provide the crude imidazole intermediate. To this product was added acetonitrile (3 mL) followed by methyl iodide (854 mg, 6.02 mmol). After stirring at room temperature for 24 hours, the mixture was concentrated under reduced pressure to provide the crude product (778 mg, 99%).

Step B: Preparation of 2-(3-aminopropyl)-5-(3-fluorophenyl)-N-methoxy-N-methyl-2-phenyl-1,3,4-thiadiazole-3(2H)-carboxamide To a solution of tert-butyl 3-(5-(3-fluorophenyl)-3-(1-carbonyl-3-methylimidazolium iodide)-2-phenyl-2,3-dihydro-1,3,4-thiadiazol-2-yl)propylcarbamate (157 mg, 0.241 mmol) and triethylamine (122 mg, 1.21 mmol) in THF (3 mL) was added N-methoxymethanamine hydrochloride (47 mg, 0.48 mmol). After stirring at room temperature for 2 hours, the mixture was concentrated under reduced pressure and chromatographed (10:1 hexanes/ethyl acetate) to provide the Boc-protected product (87 mg, 72%). To this product was added HCl (2 mL of 4M in dioxane). After stirring at room temperature for 30 minutes, the mixture was concentrated under reduced pressure to provide the final product as the dihydrochloride salt. MS APCI (+) m/z 403 (M+1) detected; $^1$H NMR (400 MHz, $CDCl_3$) δ 8.43 (br, 2H), 7.54 (br, 2H), 7.36 (m, 5H), 7.22 (m, 1H), 7.11 (m, 1H), 3.74 (s, 3H), 3.34 (br, 1H), 3.16 (s, 3H), 3.06 (br, 2H), 2.50 (br, 1H), 2.12 (br, 1H), 1.91 (br, 1H).

The following examples were prepared as previously described in Example 67 using the appropriate thiohydrazide, ketone, and alkoxyamine or alcohol.

Example 68

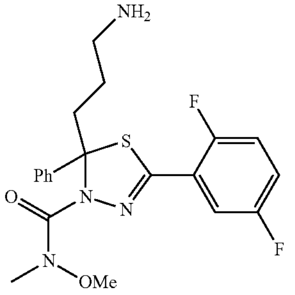 [SMILES: CON(C)C(=O)N1N=C(c2cc(F)ccc2F)SC1(CCCN)c1ccccc1]

2-(3-aminopropyl)-5-(2,5-difluorophenyl)-N-methoxy-N-methyl-2-phenyl-1,3,4-thiadiazole-3(2H)-carboxamide MS ESI (+) m/z 421 (M+1) detected; $^1$H NMR (400 MHz, $CDCl_3$) δ 7.79 (br, 3H), 7.47 (m, 1H), 7.40 (d, 2H), 7.34 (m, 2H), 7.28 (d, 1H), 7.11 (m, 2H), 3.68 (s, 3H), 3.17 (s, 3H), 3.13 (m, 1H), 3.06 (m, 1H), 2.97 (m, 1H), 2.31 (m, 1H), 2.11 (m, 1H), 1.74 (m, 1H).

Example 69

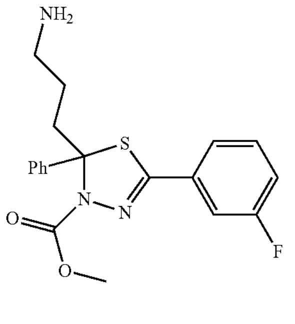 [SMILES: COC(=O)N1N=C(c2cccc(F)c2)SC1(CCCN)c1ccccc1]

Methyl 2-(3-aminopropyl)-5-(3-fluorophenyl)-2-phenyl-1,3,4-thiadiazole-3(2H)-carboxylate MS APCI (+) m/z 374 (M+1) detected.

Example 70

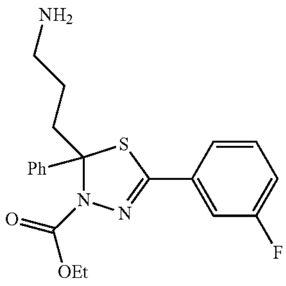 [SMILES: CCOC(=O)N1N=C(c2cccc(F)c2)SC1(CCCN)c1ccccc1]

Ethyl 2-(3-aminopropyl)-5-(3-fluorophenyl)-2-phenyl-1,3,4-thiadiazole-3(2H)-carboxylate MS APCI (+) m/z 388 (M+1) detected; $^1$H NMR (400 MHz, $CDCl_3$) δ 8.44 (br, 2H), 7.55 (br, 2H), 7.35 (m, 5H), 7.24 (m, 1H), 7.10 (m, 1H), 4.22 (br, 1H), 4.11 (br, 1H), 3.26 (br, 1H), 3.08 (br, 2H), 2.50 (br, 1H), 2.17 (br, 1H), 1.91 (br, 1H), 1.26 (br, 3H).

Example 71

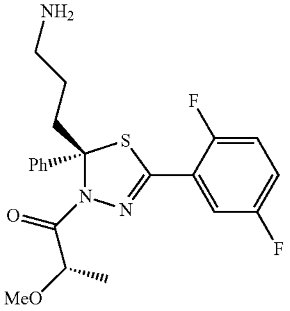 [SMILES: CO[C@@H](C)C(=O)N1N=C(c2cc(F)ccc2F)S[C@@]1(CCCN)c1ccccc1]

Synthesis of (S)-1-((S)-2-(3-aminopropyl)-5-(2,5-difluorophenyl)-2-phenyl-1,3,4-thiadiazol-3(2H)-yl)-2-methoxypropan-1-one Step A: Preparation of 4-azido-1-phenylbutan-1-one To a solution of 4-chloro-1-phenylbutan-1-one (26.4 mL, 164 mmol) in DMSO (200 mL) was added sodium azide (12.8 g, 197 mmol). The solution was warmed to 55° C. and stirred for 16 hours. The cooled mixture was then treated with water (600 mL) and extracted with ether (3×200 mL). The combined organics were washed with water (8×100 mL) and brine (100 mL) then dried over $MgSO_4$ and concentrated to provide the product as an orange oil (30.7 g, 99%).

Step B: Preparation of 2-(3-azidopropyl)-5-(2,5-difluorophenyl)-2-phenyl-2,3-dihydro-1,3,4-thiadiazole To a solution of 2,5-difluorobenzothiohydrazide (1.5 g, 7.97 mmol) in EtOH/dichloromethane (3:1, 16 mL) was added 4-azido-1-phenylbutan-1-one (1.36 g, 7.17 mmol). After stirring at room temperature for 16 hours, acetic acid (2 drops) was added and the mixture was stirred for another 16 hours. The reaction mixture was then concentrated under reduced pressure and chromatographed (9:1 hexanes/ethyl acetate) to provide the product (1.41 g, 41%) as a bright yellow syrup.

Step C: Preparation of (S)-1-((S)-2-(3-azidopropyl)-5-(2,5-difluorophenyl)-2-phenyl-1,3,4-thiadiazol-3(2H)-yl)-2-(t-butyldiphenylsilyloxy)propan-1-one and (S)-1-((R)-2-(3-azidopropyl)-5-(2,5-difluorophenyl)-2-phenyl-1,3,4-thiadiazol-3(2H)-yl)-2-(t-butyldiphenylsilyloxy)propan-1-one To a solution of (S)-2-(t-butyldiphenylsilyloxy)propanoic acid (339 mg, 1.09 mmol) in acetonitrile (6 mL) was added HATU (550 mg, 1.45 mmol) followed by DIEA (0.378 mL, 2.17 mmol). After stirring at room temperature for 15 minutes, a solution of 2-(3-azidopropyl)-5-(2,5-difluorophenyl)-2-phenyl-2,3-dihydro-1,3,4-thiadiazole (260 mg, 0.72 mmol) in acetonitrile (4 mL) was added. After stirring at room temperature for 16 hours, the mixture was concentrated under reduced pressure and partitioned between saturated $NaHCO_3$ (50 mL) and ethyl acetate (50 mL). The aqueous layer was extracted with ethyl acetate (2×30 mL) and the combined organic phases were washed with brine (20 mL), dried over $Na_2SO_4$, filtered, and concentrated under reduced pressure. The brown oil was chromatographed (9:1 hexanes/ethyl acetate) to provide the less polar diastereomer, (S)-1-((S)-2-(3-azidopropyl)-5-(2,5-difluorophenyl)-2-phenyl-1,3,4-thiadiazol-3(2H)-yl)-2-(t-butyldiphenylsilyloxy)propan-1-one (121 mg) and the more polar diastereomer, (S)-1-((R)-2-(3-azidopropyl)-5-(2,5-difluorophenyl)-2-phenyl-1,3,4-thiadiazol-3(2H)-yl)-2-(t-butyldiphenylsilyloxy)propan-1-one (175 mg) as pale yellow oils. Absolute stereochemistry was assigned by examination of a protein:inhibitor co-crystal structure of Eg5 and (S)-1-((S)-2-(3-aminopropyl)-5-(2,5-difluorophenyl)-2-phenyl-1,3,4-thiadiazol-3(2H)-yl)-2-methoxypropan-1-one.

Step D: Preparation of (S)-1-((S)-2-(3-azidopropyl)-5-(2,5-difluorophenyl)-2-phenyl-1,3,4-thiadiazol-3(2H)-yl)-2-hydroxypropan-1-one To a solution of (S)-1-((S)-2-(3-azidopropyl)-5-(2,5-difluorophenyl)-2-phenyl-1,3,4-thiadiazol-3(2H)-yl)-2-(t-butyldiphenylsilyloxy)propan-1-one (121 mg, 0.18 mmol) in THF (5 mL) at 0° C. was added TBAF (0.31 mL, 1M, 0.31 mmol). After stirring at 0° C. for 1 hour and at room temperature for 1 hour, the mixture was treated with saturated $NaHCO_3$ (20 mL) and extracted with ethyl acetate (3×20 mL). The combined organics were washed with brine (20 mL), dried over $Na_2SO_4$, filtered, and concentrated. The brown oil was chromatographed (4:1 hexanes/ethyl acetate) to provide the product (41 mg, 53%) as a pale yellow oil.

Step E: Preparation of (S)-1-((S)-2-(3-azidopropyl)-5-(2,5-difluorophenyl)-2-phenyl-1,3,4-thiadiazol-3(2H)-yl)-2-methoxypropan-1-one To a solution of (S)-1-((S)-2-(3-azidopropyl)-5-(2,5-difluorophenyl)-2-phenyl-1,3,4-thiadiazol-3(2H)-yl)-2-hydroxypropan-1-one (41 mg, 0.095 mmol) in DMF (2 mL) at 0° C. was added methyl iodide (50 µL, 0.48 mmol) followed by sodium hydride (10 mg, 60%). After stirring at 0° C. for 30 minutes and room temperature for 3 hours, the mixture was treated with saturated $NH_4Cl$ (20 mL) and extracted with ethyl acetate (3×20 mL). The combined organic phases were washed with water (6×10 mL) and brine (10 mL), dried over $Na_2SO_4$, filtered, and concentrated under reduced pressure to provide the product (40 mg, 94%) as a yellow oil.

Step F: Preparation of (S)-1-((S)-2-(3-aminopropyl)-5-(2,5-difluorophenyl)-2-phenyl-1,3,4-thiadiazol-3(2H)-yl)-2-methoxypropan-1-one To a suspension of (S)-1-((S)-2-(3-azidopropyl)-5-(2,5-difluorophenyl)-2-phenyl-1,3,4-thiadiazol-3(2H)-yl)-2-hydroxypropan-1-one (102 mg, 0.23 mmol) in MeOH (2.2 mL) was added conc. HCl (57 µL, 0.69 mmol) followed by 10% Pd/C (10 mg, wet, Degussa type). After stirring under a $H_2$ balloon for 1 hour, the mixture was filtered and concentrated under reduced pressure. The colorless glass was triturated with diethyl ether and filtered to provide the di-HCl salt product as a white solid (89 mg, 79%). MS ESI (+) m/z 420 (M+1) detected; $^1H$ NMR (400 MHz, $CDCl_3$) δ 7.52 (m, 1H), 7.45 (m, 2H), 7.35 (m, 2H), 7.28 (m, 1H), 7.13 (m, 2H), 4.70 (m, 1H), 3.40 (s, 3H), 3.27 (m, 1H), 2.88 (m, 2H), 2.43 (m, 1H), 1.96 (m, 1H), 1.57 (m, 1H), 1.45 (d, 3H, J=7 Hz). Absolute stereochemistry assigned by examination of a protein:inhibitor co-crystal structure of Eg5 and (S)-1-((S)-2-(3-aminopropyl)-5-(2,5-difluorophenyl)-2-phenyl-1,3,4-thiadiazol-3(2H)-yl)-2-methoxypropan-1-one.

Example 72

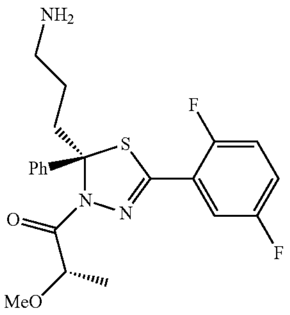 [SMILES: CO[C@@H](C)C(=O)N1N=C(c2cc(F)ccc2F)S[C@]1(CCCN)c1ccccc1]

(S)-1-((R)-2-(3-aminopropyl)-5-(2,5-difluorophenyl)-2-phenyl-1,3,4-thiadiazol-3(2H)-yl)-2-methoxypropan-1-one Prepared as previously described in Example 71 using (S)-1-((R)-2-(3-azidopropyl)-5-(2,5-difluorophenyl)-2-phenyl-1,3,4-thiadiazol-3(2H)-yl)-2-(tert-butyldiphenylsilyloxy)propan-1-one from Step C. MS ESI (+) m/z 420 (M+1) detected; $^1H$ NMR (400 MHz, $CDCl_3$) δ 7.51 (m, 1H), 7.44 (m, 2H), 7.36 (m, 2H), 7.29 (m, 1H), 7.12 (m, 2H), 4.71 (q, 1H, J=6 Hz), 3.32 (s, 3H), 3.23 (m, 1H), 2.84 (m, 2H), 2.43 (m, 1H), 1.93 (m, 1H), 1.50 (d, 3H, J=6 Hz), 1.44 (m, 2H), 1.34 (m, 1H). Stereochemistry was assigned by inference from (S)-1-((S)-2-(3-aminopropyl)-5-(2,5-difluorophenyl)-2-phenyl-1,3,4-thiadiazol-3(2H)-yl)-2-methoxypropan-1-one.

Example 73

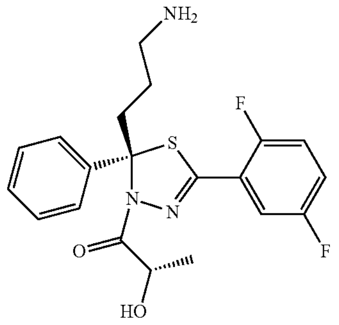 [SMILES: C[C@H](O)C(=O)N1N=C(c2cc(F)ccc2F)S[C@@]1(CCCN)c1ccccc1]

Synthesis of (S)-1-((S)-2-(3-aminopropyl)-5-(2,5-difluorophenyl)-2-phenyl-1,3,4-thiadiazol-3(2H)-yl)-2-hydroxypropan-1-one To a solution of (S)-1-((S)-2-(3-azidopropyl)-5-(2,5-difluorophenyl)-2-phenyl-1,3,4-thiadiazol-3(2H)-yl)-2-hydroxypropan-1-one prepared as described in Example 71 (74 mg, 0.172 mmol) in MeOH (5 mL) was added 1N HCl/MeOH (0.5 mL) followed by 10% Pd/C (10 mg, wet, Degussa type). After stirring under a $H_2$ balloon for 1 hour, the mixture was filtered and concentrated under reduced pressure. The colorless glass was triturated with diethyl ether and filtered to provide the di-HCl salt product as a white solid (54 mg, 66%). MS ESI (+) m/z 406 (M+1) detected; $^1$H NMR (400 MHz, $CDCl_3$) δ 7.51 (m, 1H), 7.47 (m, 2H), 7.39 (t, 2H, J=7 Hz), 7.32 (t, 1H, J=7 Hz), 7.15 (m, 2H), 4.89 (q, 1H, J=6 Hz), 3.18 (m, 1H), 2.84 (m, 2H), 2.42 (m, 1H), 1.92 (m, 1H), 1.58 (br, 2H), 1.52 (d, 2H, J=6.7 Hz), 1.48 (d, 3H, J=6.7 Hz). Stereochemistry was assigned by inference from (S)-1-((S)-2-(3-aminopropyl)-5-(2,5-difluorophenyl)-2-phenyl-1,3,4-thiadiazol-3(2H)-yl)-2-methoxypropan-1-one.

Example 74

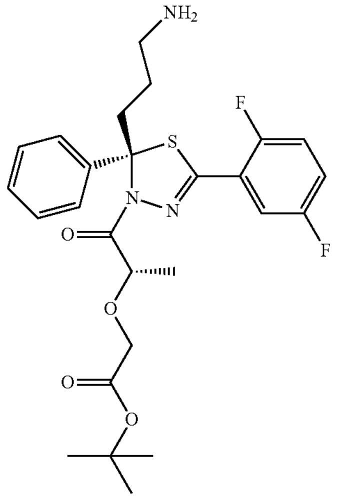 [SMILES: C[C@H](OCC(=O)OC(C)(C)C)C(=O)N1N=C(c2cc(F)ccc2F)S[C@@]1(CCCN)c1ccccc1]

Tert-Butyl 2-((S)-1-((S)-2-(3-aminopropyl)-5-(2,5-difluorophenyl)-2-phenyl-1,3,4-thiadiazol-3(2H)-yl)-1-oxopropan-2-yloxy)acetate Prepared as previously described in Example 71 using tert-butyl 2-bromoacetate in place of methyl iodide. MS ESI (+) m/z 520 (M+1) detected; $^1$H NMR (400 MHz, $CDCl_3$) δ 7.50 (m, 1H), 7.46 (d, 2H, J=8 Hz), 7.34 (m, 2H), 7.27 (m, 1H), 7.13 (m, 2H), 4.93 (q, 1H, J=6 Hz), 4.18 (d, 1H, J=16 Hz), 3.96 (d, 1H, J=16 Hz), 3.30 (m, 1H), 2.96 (m, 2H), 2.45 (m, 1H), 2.01 (m, 1H), 1.63 (m, 1H), 1.50 (d, 3H, J=6 Hz), 1.46 (s, 9H). Stereochemistry was assigned by inference from (S)-1-((S)-2-(3-aminopropyl)-5-(2,5-difluorophenyl)-2-phenyl-1,3,4-thiadiazol-3(2H)-yl)-2-methoxypropan-1-one.

Example 75

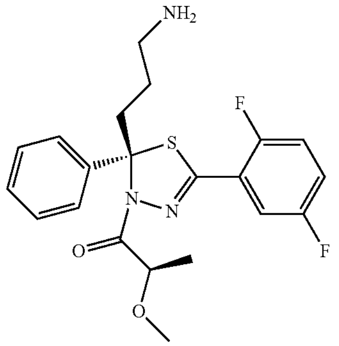 [SMILES: CO[C@H](C)C(=O)N1N=C(c2cc(F)ccc2F)S[C@@]1(CCCN)c1ccccc1]

(R)-1-((S)-2-(3-aminopropyl)-5-(2,5-difluorophenyl)-2-phenyl-1,3,4-thiadiazol-3(2H)-yl)-2-methoxypropan-1-one Prepared as previously described in Example 71 using (R)-2-(t-butyldiphenylsilyloxy)propanoic acid in place of (S)-2-(t-butyldiphenylsilyloxy)propanoic acid. MS ESI (+) m/z 420 (M+1) detected; $^1$H NMR (400 MHz, $CDCl_3$) δ 7.52 (m, 1H), 7.46 (d, 2H, J=7 Hz), 7.37 (t, 2H, J=8 Hz), 7.30 (t, 1H, J=7 Hz), 7.13 (m, 2H), 4.71 (q, 1H, J=6 Hz), 3.32 (s, 3H), 3.24 (m, 1H), 2.83 (m, 2H), 2.43 (m, 1H), 1.92 (m, 1H), 1.51 (d, 3H, J=6 Hz), 1.45 (m, 1H). Stereochemistry was assigned by comparison to (S)-1-((S)-2-(3-aminopropyl)-5-(2,5-difluorophenyl)-2-phenyl-1,3,4-thiadiazol-3(2H)-yl)-2-methoxypropan-1-one and (S)-1-((R)-2-(3-aminopropyl)-5-(2,5-difluorophenyl)-2-phenyl-1,3,4-thiadiazol-3(2H)-yl)-2-methoxypropan-1-one.

Example 76

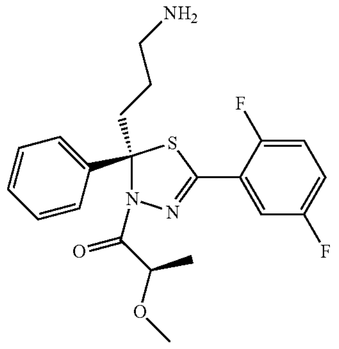 [SMILES: CO[C@H](C)C(=O)N1N=C(c2cc(F)ccc2F)S[C@]1(CCCN)c1ccccc1]

(R)-1-((R)-2-(3-aminopropyl)-5-(2,5-difluorophenyl)-2-phenyl-1,3,4-thiadiazol-3(2H)-yl)-2-methoxypropan-1-one Prepared as previously described in Example 75 using (R)-1-((R)-2-(3-azidopropyl)-5-(2,5-difluorophenyl)-2-phenyl-1,3,4-thiadiazol-3(2H)-yl)-2-methoxypropan-1-one. MS ESI (+) m/z 420 (M+1) detected; $^1$H NMR (400 MHz, $CDCl_3$) δ 7.52 (m, 1H), 7.44 (d, 2H, J=7 Hz), 7.35 (t, 2H, J=8 Hz), 7.29 (t, 1H, J=7 Hz), 7.13 (m, 2H), 4.68 (q, 1H, J=6 Hz), 3.41 (s, 3H), 3.24 (m, 1H), 2.85 (m, 2H), 2.43 (m, 1H), 1.95 (m, 1H), 1.54 (br, 3H), 1.46 (d, 3H, J=6 Hz). Stereochemistry was assigned by comparison to (S)-1-((S)-2-(3-aminopropyl)-5-(2,5-difluorophenyl)-2-phenyl-1,3,4-thiadiazol-3(2H)-yl)-2-methoxypropan-1-one and (S)-1-((R)-2-(3-aminopropyl)-5-(2,5-difluorophenyl)-2-phenyl-1,3,4-thiadiazol-3(2H)-yl)-2-methoxypropan-1-one.

Example 77

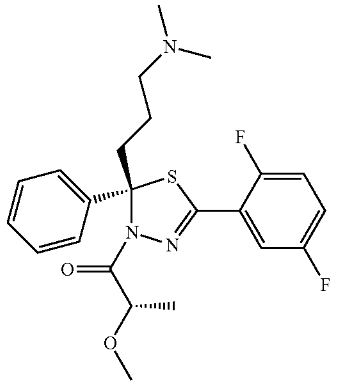 [SMILES: CO[C@@H](C)C(=O)N1N=C(c2cc(F)ccc2F)S[C@@]1(CCCN(C)C)c1ccccc1]

(S)-1-((S)-5-(2,5-difluorophenyl)-2-(3-(dimethylamino)propyl)-2-phenyl-1,3,4-thiadiazol-3(2H)-yl)-2-methoxypropan-1-one Prepared as previously described in Example 47 using (S)-1-((S)-2-(3-aminopropyl)-5-(2,5-difluorophenyl)-2-phenyl-1,3,4-thiadiazol-3(2H)-yl)-2-methoxypropan-1-one in place of 1-(2-(3-aminopropyl)-5-(3-fluorophenyl)-2-phenyl-1,3,4-thiadiazol-3(2H)-yl)-2-methylpropan-1-one. MS ESI (+) m/z 448 (M+1) detected; $^1$H NMR (400 MHz, $CDCl_3$) δ 7.56 (m, 1H), 7.49 (d, 2H, J=7 Hz), 7.39 (m, 2H), 7.32 (m, 1H), 7.17 (m, 2H), 4.73 (m, 1H), 3.44 (s, 3H), 3.26 (m, 1H), 2.56 (m, 1H), 2.49 (m, 2H), 2.34 (s, 6H), 2.05 (m, 1H), 1.63 (m, 1H), 1.50 (d, 3H, J=7 Hz).

Example 78

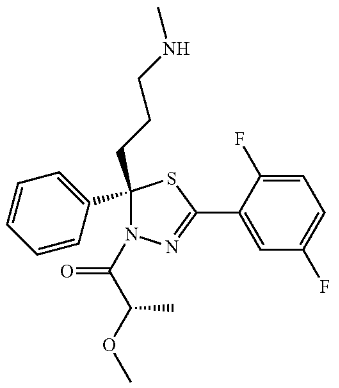 [SMILES: CNCCC[C@@]1(c2ccccc2)SC(c2cc(F)ccc2F)=NN1C(=O)[C@H](C)OC]

Synthesis of (S)-1-((S)-5-(2,5-difluorophenyl)-2-(3-(methylamino)propyl)-2-phenyl-1,3,4-thiadiazol-3(2H)-yl)-2-methoxypropan-1-one Step A: Preparation of tert-butyl 3-((S)-5-(2,5-difluorophenyl)-3-((S)-2-methoxypropanoyl)-2-phenyl-2,3-dihydro-1,3,4-thiadiazol-2-yl)propylcarbamate To a cooled (0° C.) solution of (S)-1-((S)-2-(3-aminopropyl)-5-(2,5-difluorophenyl)-2-phenyl-1,3,4-thiadiazol-3(2H)-yl)-2-methoxypropan-1-one (50 mg, 0.12 mmol) in THF (2 mL) was added Boc-anhydride (31 mg, 0.14 mmol). After warming slowly to room temperature and stirring for 64 hours, the reaction mixture was concentrated under reduced pressure and chromatographed (DCM to 2% MeOH in DCM) to provide the product as a colorless oil (62 mg, 100%).

Step B: Preparation of (S)-1-((S)-5-(2,5-difluorophenyl)-2-(3-(methylamino)propyl)-2-phenyl-1,3,4-thiadiazol-3(2H)-yl)-2-methoxypropan-1-one To a cooled (0° C.) solution of tert-butyl 3-((S)-5-(2,5-difluorophenyl)-3-((S)-2-methoxypropanoyl)-2-phenyl-2,3-dihydro-1,3,4-thiadiazol-2-yl)propylcarbamate (62 mg, 0.12 mmol) in DMF (2 mL) was added methyl iodide (37 μL, 0.6 mmol) followed by NaH (10 mg, 60%). After slowly warming to room temperature and stirring for 16 hours, the mixture was quenched with saturated $NH_4Cl$ (20 mL) and extracted with ethyl acetate (3×20 mL). The combined organics were washed with water (5×20 mL) and brine (20 mL), and then dried over $Na_2SO_4$. The mixture was concentrated under reduced pressure and chromatographed (9:1 to 4:1 hexanes/ethyl acetate) to provide the Boc-protected product (38 mg, 0.071 mmol). To this product was added DCM (2 mL) and TFA (0.5 mL). After stirring at room temperature for 1 hour, the mixture was concentrated under reduced pressure and partitioned between saturated $NaHCO_3$ (10 mL) and ethyl acetate (10 mL). The aqueous layer was extracted with ethyl acetate (2×10 mL). The combined organics were washed with $NaHCO_3$ (10 mL), brine (10 mL), dried over $Na_2SO_4$, and concentrated under reduced pressure to provide a yellow oil. The oil was dissolved in ether (2 mL) and treated with 2N HCl in ether (2 mL). The mixture was stirred for 30 minutes, concentrated and triturated with ether to provide the di-HCl product as a yellow solid (31 mg, 51%). MS ESI (+) m/z 434 (M+1) detected; $^1H$ NMR (400 MHz, $CDCl_3$) δ 7.51 (m, 1H), 7.44 (d, 2H), 7.35 (m, 2H), 7.27 (m, 1H), 7.12 (m, 2H), 4.68 (q, 1H, J=6 Hz), 3.40 (s, 3H), 3.25 (m, 1H), 2.76 (m, 2H), 2.46 (s, 3H), 2.45 (m, 1H), 2.00 (m, 2H), 1.61 (m, 1H), 1.45 (d, 3H, J=6 Hz).

Example 79

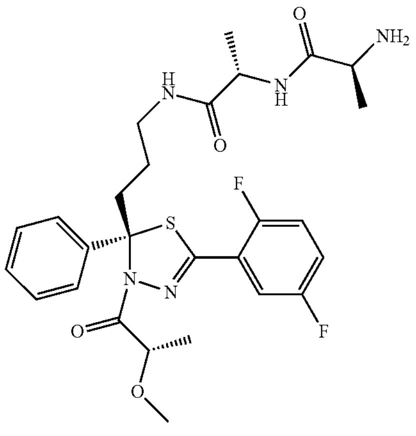 [SMILES: CO[C@@H](C)C(=O)N1N=C(c2cc(F)ccc2F)S[C@@]1(CCCNC(=O)[C@H](C)NC(=O)[C@H](C)N)c1ccccc1]

Synthesis of (S)-1-((S)-1-(3-((S)-5-(2,5-difluorophenyl)-3-((S)-2-methoxypropanoyl)-2-phenyl-2,3-dihydro-1,3,4-thiadiazol-2-yl)propylamino)-1-oxopropan-2-ylamino)-1-oxopropan-2-ylamine To a solution of (S)-1-((S)-2-(3-aminopropyl)-5-(2,5-difluorophenyl)-2-phenyl-1,3,4-thiadiazol-3(2H)-yl)-2-methoxypropan-1-one (25 mg, 0.051 mmol) and Boc-Ala-Ala-OH (19.8 mg, 0.0766 mmol) in DMF (1 mL) was added PyBOP (52.8 mg, 0.102 mmol) followed by DIEA (44 μL, 0.25 mmol). After stirring at room temperature for 64 hours, the mixture was partitioned between saturated $NaHCO_3$ (20 mL) and ethyl acetate. The aqueous layer was extracted with ethyl acetate (10 mL). The combined organics were washed with water (5×10 mL), brine (10 mL), dried over $Na_2SO_4$, and concentrated under reduced pressure. The orange residue was chromatographed (0-3% MeOH in DCM) to provide the Boc-protected product as a colorless glass (30 mg, 89%). To a cooled (0° C.) solution of this product in DCM (2 mL) was added TFA (0.5 mL). After stirring for 5 hours, the mixture was concentrated under reduced pressure and partitioned between saturated $NaHCO_3$ (10 mL) and ethyl acetate. The aqueous layer was extracted with ethyl acetate (10 mL) and the combined organics were washed with brine (10 mL), dried over $Na_2SO_4$, and concentrated under reduced pressure to provide the product as a colorless glass (25 mg, 98%). MS ESI (+) m/z 562 (M+1) detected; $^1H$ NMR (400 MHz, $CDCl_3$) δ 7.79 (br, 1H), 7.50 (m, 1H), 7.42 (d, 2H, J=8 Hz), 7.36 (t, 2H, J=7 Hz), 7.30 (t, 1H, J=7 Hz), 7.13 (m, 2H), 7.04 (t, 1H, J=5 Hz), 4.65 (q, 1H, J=6 Hz), 4.39 (m, 1H), 3.70 (m, 1H), 3.45 (m, 1H), 3.36 (s, 3H), 3.23 (m, 1H), 3.07 (m, 1H), 2.24 (m, 1H), 1.96 (m, 1H), 1.56 (m, 1H), 1.41 (d, 3H, J=7 Hz), 1.34 (d, 3H, J=7 Hz), 1.26 (m, 3H).

Example 80

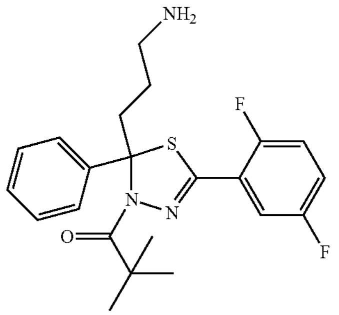 [SMILES: CC(C)(C)C(=O)N1N=C(c2cc(F)ccc2F)SC1(CCCN)c1ccccc1]

Synthesis of 1-(2-(3-aminopropyl)-5-(2,5-difluorophenyl)-2-phenyl-1,3,4-thiadiazol-3(2H)-yl)-2,2-dimethylpropan-1-one

Step A: Preparation of 1-(2-(3-azidopropyl)-5-(2,5-difluorophenyl)-2-phenyl-1,3,4-thiadiazol-3(2H)-yl)-2,2-dimethylpropan-1-one To a cooled (0° C.) solution of 2-(3-azidopropyl)-5-(2,5-difluorophenyl)-2-phenyl-2,3-dihydro-1,3,4-thiadiazole (100 mg, 0.278 mmol) in DCM (5 mL) was added triethylamine (50.4 μL, 0.362 mmol) followed by pivaloyl chloride (45 μL, 0.362 mmol). After warming slowly to room temperature and stirring for 16 hours, the mixture was partitioned between DCM (10 mL) and saturated $NaHCO_3$ (10 mL). The aqueous layer was extracted with DCM (10 mL) and the combined organics were washed with brine (10 mL), dried over $Na_2SO_4$, and concentrated under reduced pressure. The residue was chromatographed (19:1 hexanes/ethyl acetate) to provide the product as a pale yellow oil (114 mg, 92%).

Step B: Preparation of 1-(2-(3-aminopropyl)-5-(2,5-difluorophenyl)-2-phenyl-1,3,4-thiadiazol-3(2H)-yl)-2,2-dimethylpropan-1-one To a solution of 1-(2-(3-azidopropyl)-5-(2,5-difluorophenyl)-2-phenyl-1,3,4-thiadiazol-3(2H)-yl)-2,2-dimethylpropan-1-one (100 mg, 0.225 mmol) in MeOH (3 mL) was added 1N HCl/MeOH (1 mL) followed by 10% Pd/C (40 mg, wet, Degussa type). After stirring under a $H_2$ balloon for 3 hours, the mixture was filtered and concentrated under reduced pressure to provide the product as a white foam. MS ESI (+) m/z 418 (M+1) detected; $^1H$ NMR (400 MHz, $CDCl_3$) δ 7.47 (m, 1H), 7.43 (d, 2H, J=7 Hz), 7.35 (t, 2H, J=7 Hz), 7.25 (m, 1H), 7.11 (m, 2H), 3.47 (m, 1H), 3.22 (m, 1H), 2.85 (m, 2H), 2.33 (m, 1H), 1.92 (m, 1H), 1.48 (m, 2H), 1.39 (s, 9H).

Example 81

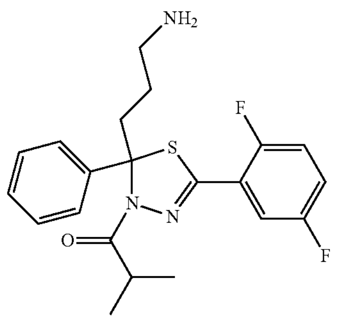 [SMILES: CC(C)C(=O)N1N=C(c2cc(F)ccc2F)SC1(CCCN)c1ccccc1]

1-(2-(3-aminopropyl)-5-(2,5-difluorophenyl)-2-phenyl-1,3,4-thiadiazol-3(2H)-yl)-2-methylpropan-1-one (Enantiomer A)

Prepared as previously described in Example 80 using isobutyryl chloride in place of pivaloyl chloride. The 1-(2-(3-azidopropyl)-5-(2,5-difluorophenyl)-2-phenyl-1,3,4-thiadiazol-3(2H)-yl)-2-methylpropan-1-one enantiomers were separated on a chiral column (Chiralcel OJ-H 250×10 mm) eluting with 1:1 EtOH/hexanes to provide the more polar enantiomer A and the less polar enantiomer B. Reduction of the azide group of enantiomer A provided the final product. MS ESI (+) m/z 404 (M+1) detected; $^1$H NMR (400 MHz, $CDCl_3$) δ 7.55 (m, 1H), 7.45 (d, 2H, J=8 Hz), 7.35 (t, 2H, J=7 Hz), 7.25 (m, 1H), 7.11 (m, 2H), 3.48 (m, 1H), 3.22 (m, 1H), 2.87 (m, 2H), 2.36 (m, 1H), 1.95 (m, 1H), 1.57 (m, 3H), 1.18 (dd, 6H, J=11 Hz, 6 Hz).

Example 82

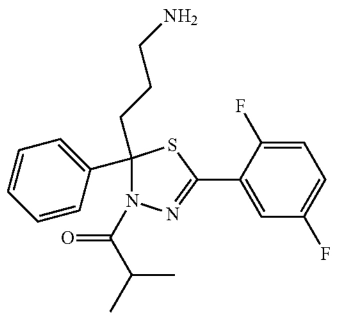 [SMILES: CC(C)C(=O)N1N=C(c2cc(F)ccc2F)SC1(CCCN)c1ccccc1]

1-(2-(3-aminopropyl)-5-(2,5-difluorophenyl)-2-phenyl-1,3,4-thiadiazol-3(2H)-yl)-2-methylpropan-1-one (Enantiomer B)

Prepared as in Example 81 using the less polar enantiomer B. MS ESI (+) m/z 404 (M+1) detected; $^1$H NMR (400 MHz, $CDCl_3$) δ 7.55 (m, 1H), 7.45 (d, 2H, J=8 Hz), 7.35 (t, 2H, J=8 Hz), 7.28 (m, 1H), 7.10 (m, 2H), 3.48 (m, 1H), 3.24 (m, 1H), 2.88 (m, 2H), 2.36 (m, 1H), 2.11 (br, 2H), 1.96 (m, 1H), 1.57 (m, 1H), 1.18 (dd, 6H, J=7 Hz, 13 Hz).

Example 83

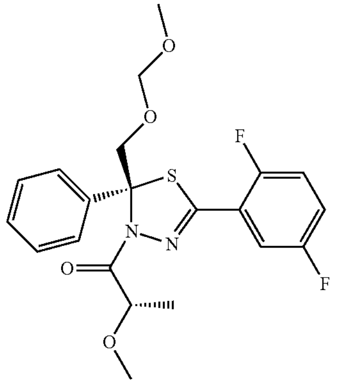 [SMILES: COCOC[C@@]1(c2ccccc2)SC(c2cc(F)ccc2F)=NN1C(=O)[C@H](C)OC]

Synthesis of (S)-1-((R)-5-(2,5-difluorophenyl)-2-((methoxymethoxy)methyl)-2-phenyl-1,3,4-thiadiazol-3(2H)-yl)-2-methoxypropan-1-one Step A: Preparation of 2-(methoxymethoxy)-1-phenylethanone To a cooled (0° C.) solution of 2-hydroxyacetophenone (1.0 g, 7.3 mmol) in DMF (50 mL) was added lithium hydride (74 mg, 95%, 8.8 mmol). After stirring for 30 minutes, MOM-Cl (0.73 mL, 9.5 mmol) was added slowly via syringe and the mixture was allowed to warm slowly to room temperature and was stirred for 16 hours. The reaction mixture was treated with saturated $NH_4Cl$ (100 mL) and extracted with ethyl acetate (3×50 mL). The combined organics were washed with water (6×50 mL) and brine (50 mL), dried over $Na_2SO_4$ and concentrated under reduced pressure. The brown residue was chromatographed (9:1 to 4:1 hexanes/ethyl acetate) to provide the product as a colorless oil (0.60 g, 45%).

Step B: Preparation of 5-(2,5-difluorophenyl)-2-((methoxymethoxy)methyl)-2-phenyl-2,3-dihydro-1,3,4-thiadiazole To a solution of 2-(methoxymethoxy)-1-phenylethanone (0.60 g, 3.33 mmol) in EtOH/DCM (3:1, 12 mL) was added 2,5-difluorobenzothiohydrazide (0.63 g, 3.33 mmol). After stirring at room temperature for 16 hours, the mixture was concentrated under reduced pressure. The brown residue was chromatographed (9:1 hexanes/ethyl acetate) to provide the product as a yellow oil (0.73 g, 63%).

Step C: Preparation of (S)-2-(t-butyldiphenylsilyloxy)-1-((R)-5-(2,5-difluorophenyl)-2-((methoxymethoxy)methyl)-2-phenyl-1,3,4-thiadiazol-3(2H)-yl)propan-1-one To a solution of (S)-2-(tert-butyldiphenylsilyloxy)propanoic acid (0.70 g, 2.14 mmol) in DMF (20 mL) was added 5-(2,5-difluorophenyl)-2-((methoxymethoxy)methyl)-2-phenyl-2,3-dihydro-1,3,4-thiadiazole (0.50 g, 1.43 mmol) followed by PyBOP (1.11 g, 2.14 mmol) and DIEA (497 μL, 2.85 mmol). After stirring at room temperature for 16 hours, the mixture was treated with saturated $NaHCO_3$ (50 mL) and extracted with ethyl acetate (3×30 mL). The combined organics were washed with water (6×30 mL) and brine (30 mL), dried over $Na_2SO_4$, and concentrated under reduced pressure. The yellow residue was chromatographed (19:1 to 9:1 hexanes/ethyl acetate) to afford the less polar diastereomer (S)-2-(tert-butyldiphenylsilyloxy)-1-((R)-5-(2,5-difluorophenyl)-2-((methoxymethoxy)methyl)-2-phenyl-1,3,4-thiadiazol-3(2H)-yl)propan-1-one (110 mg, 12%), and the more polar diastereomer (S)-2-(tert-butyldiphenylsilyloxy)-1-((S)-5-(2,5-difluorophenyl)-2-((methoxy-methoxy)methyl)-2-phenyl-1,3,4-thiadiazol-3(2H)-yl)propan-1-one (146 mg of a 1:1 mixture with starting material) as yellow oils. Absolute stereochemistry was assigned by inference from (S)-1-((R)-5-(2,5-difluorophenyl)-2-(hydroxymethyl)-2-phenyl-1,3,4-thiadiazol-3(2H)-yl)-2-methoxypropan-1-one.

Step D: Preparation of (S)-1-((R)-5-(2,5-difluorophenyl)-2-((methoxy-methoxy)methyl)-2-phenyl-1,3,4-thiadiazol-3(2H)-yl)-2-hydroxypropan-1-one To a cooled (0° C.) solution of (S)-2-(tert-butyldiphenylsilyloxy)-1-((R)-5-(2,5-difluorophenyl)-2-((methoxymethoxy)methyl)-2-phenyl-1,3,4-thiadiazol-3(2H)-yl) propan-1-one (110 mg, 0.17 mmol) in THF (10 mL) was added TBAF (0.28 mL, 1.0 M, 0.28 mmol). After slowly warming to room temperature and stirring for 16 hours, the mixture was treated with 0.5 N HCl (30 mL) and extracted with ethyl acetate (2×30 mL). The combined organics were washed with $NaHCO_3$ (30 mL) and brine (30 mL), dried over $Na_2SO_4$, and concentrated under reduced pressure. The pale yellow residue was chromatographed (9:1 to 4:1 hexanes/ethyl acetate) to provide the product as a white solid (0.045 g, 64%).

Step E: Preparation of (S)-1-((R)-5-(2,5-difluorophenyl)-2-((methoxymethoxy)methyl)-2-phenyl-1,3,4-thiadiazol-3(2H)-yl)-2-methoxypropan-1-one To a cooled (0° C.) solution of (S)-1-((R)-5-(2,5-difluorophenyl)-2-((methoxymethoxy)methyl)-2-phenyl-1,3,4-thiadiazol-3(2H)-yl)-2-hydroxypropan-1-one (45 mg, 0.11 mmol) in DMF was added methyl iodide (100 μL, 1.6 mmol) followed by sodium hydride (10 mg). After slowly warming to room temperature and stirring for 16 hours, the mixture was treated with saturated $NH_4Cl$ (10 mL) and extracted with ethyl acetate (2×10 mL). The combined organics were washed with water (6×10 mL) and brine (10 mL), dried over $Na_2SO_4$ and concentrated under reduced pressure. The pale yellow residue was chromatographed (4:1 to 2:1 hexanes/ethyl acetate) to provide the product as a pale yellow oil (0.040 g, 86%). MS ESI (+) m/z 437 (M+1) detected; $^1H$ NMR (400 MHz, $CDCl_3$) δ 7.54 (m, 1H), 7.42 (m, 2H), 7.35 (m, 2H), 7.29 (m, 1H), 7.12 (m, 2H), 4.80 (s, 2H), 4.78 (d, 1H, J=10 Hz), 4.71 (q, 1H, J=7 Hz), 4.59 (d, 1H, J=10 Hz), 3.43 (s, 3H), 3.39 (s, 3H), 1.48 (d, 3H, J=7 Hz). Stereochemistry was assigned by inference from (S)-1-((R)-5-(2,5-difluorophenyl)-2-(hydroxymethyl)-2-phenyl-1,3,4-thiadiazol-3(2H)-yl)-2-methoxypropan-1-one.

Example 84

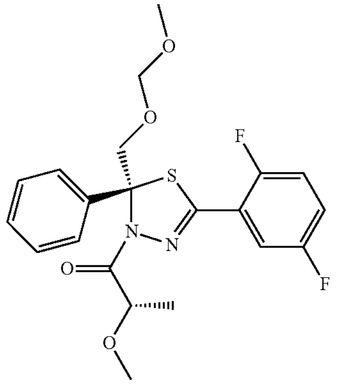 [SMILES: COCOC[C@]1(c2ccccc2)SC(c2cc(F)ccc2F)=NN1C(=O)[C@H](C)OC]

(S)-1-((S)-5-(2,5-difluorophenyl)-2-((methoxymethoxy)methyl)-2-phenyl-1,3,4-thiadiazol-3(2H)-yl)-2-methoxypropan-1-one Prepared as previously described in Example 83 using (S)-2-(tert-butyldiphenylsilyloxy)-1-((S)-5-(2,5-difluorophenyl)-2-((methoxymethoxy)methyl)-2-phenyl-1,3,4-thiadiazol-3(2H)-yl)propan-1-one from Step C. MS ESI (+) m/z 437 (M+1) detected; $^1H$ NMR (400 MHz, $CDCl_3$) δ 7.53 (m, 1H), 7.43 (m, 2H), 7.37 (m, 2H), 7.31 (m, 1H), 7.11 (m, 2H), 4.76 (m, 4H), 4.47 (d, 1H, J=10 Hz), 3.41 (s, 3H), 3.35 (s, 3H), 1.47 (d, 3H, J=7 Hz). Stereochemistry was assigned by inference from (S)-1-((R)-5-(2,5-difluorophenyl)-2-(hydroxymethyl)-2-phenyl-1,3,4-thiadiazol-3(2H)-yl)-2-methoxypropan-1-one.

Example 85

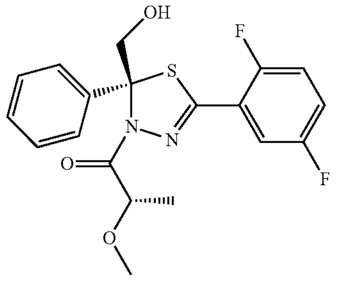 [SMILES: CO[C@@H](C)C(=O)N1N=C(c2cc(F)ccc2F)S[C@@]1(CO)c1ccccc1]

Synthesis of (S)-1-((R)-5-(2,5-difluorophenyl)-2-(hydroxymethyl)-2-phenyl-1,3,4-thiadiazol-3(2H)-yl)-2-methoxypropan-1-one To a solution of (S)-1-((R)-5-(2,5-difluorophenyl)-2-((methoxymethoxy)methyl)-2-phenyl-1,3,4-thiadiazol-3(2H)-yl)-2-methoxypropan-1-one (16 mg, 0.037 mmol) in MeOH (2 mL) was added HCl (300 μL of 6 M solution). After stirring at 50° C. for 5 hours, the mixture was cooled to room temperature and partitioned between saturated $NaHCO_3$ (20 mL) and ethyl acetate (10 mL). The aqueous phase was extracted with ethyl acetate (2×10 mL). The combined organics were washed with brine (10 mL), dried over $Na_2SO_4$, and concentrated under reduced pressure. The pale yellow residue was chromatographed (9:1 to 2:1 hexanes/ethyl acetate) to provide the product as a colorless gum (4.2 mg, 29%). MS ESI (+) m/z 393 (M+1) detected; $^1$H NMR (400 MHz, $CDCl_3$) δ 7.52 (m, 1H), 7.37 (m, 5H), 7.13 (m, 2H), 4.74 (m, 2H), 4.48 (d, 1H, J=11 Hz), 4.19 (d, 1H, J=10 Hz), 3.44 (s, 3H), 1.59 (m, 3H). Absolute stereochemistry was assigned by examination of a protein:inhibitor co-crystal structure of Eg5 and (S)-1-((R)-5-(2,5-difluorophenyl)-2-(hydroxymethyl)-2-phenyl-1,3,4-thiadiazol-3(2H)-yl)-2-methoxypropan-1-one.

Example 86

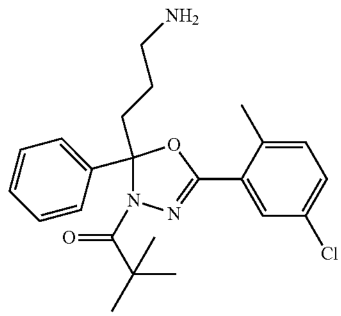 [SMILES: Cc1ccc(Cl)cc1C1=NN(C(=O)C(C)(C)C)C(CCCN)(c2ccccc2)O1]

Synthesis of 1-(2-(3-aminopropyl)-5-(5-chloro-2-methylphenyl)-2-phenyl-1,3,4-oxadiazol-3(2H)-yl)-2,2-dimethylpropan-1-one Step A: Preparation of N'-(4-azido-1-phenylbutylidene)-5-chloro-2-methyl benzohydrazide To a solution of 5-chloro-2-methylbenzohydrazide (2.70 g, 14.62 mmol) prepared as in Example 1, Step B, in toluene (100 mL) was added 4-azido-1-phenylbutan-1-one (3.04 g, 16.1 mmol) prepared as in Example 70, Step A, followed by p-toluenesulfonic acid monohydrate (0.28 g, 1.46 mmol). The reaction was heated to reflux and stirred under a Dean-Stark trap for 16 hours. The cooled mixture was diluted with EtOAc (300 mL) and washed with $NaHCO_3$ (100 mL). The aqueous layer was extracted with EtOAc (100 mL) and the combined organics were washed with brine (100 mL), dried over $Na_2SO_4$ and concentrated. The residue was triturated with ether and filtered to afford the product (3.09 g, 59%) as a tan solid.

Step B: Preparation of 1-(2-(3-azidopropyl)-5-(5-chloro-2-methylphenyl)-2-phenyl-1,3,4-oxadiazol-3(2H)-yl)-2,2-dimethylpropan-1-one To a solution of N'-(4-azido-1-phenylbutylidene)-5-chloro-2-methyl benzohydrazide (100 mg, 0.28 mmol) in pyridine (1 mL) was added pivaloyl chloride (70 μL, 0.56 mmol). After stirring at room temperature for 16 hours the heterogeneous mixture was treated with water (10 mL) and extracted with EtOAc (3×10 mL). The combined organic phases were washed successively with 10% $NaHSO_4$ (2×10 mL), $NaHCO_3$ (10 mL) and brine (10 mL) then dried over $Na_2SO_4$ and concentrated. The residue was purified by preparative TLC (9:1 hexanes/EtOAc) to afford the product (62 mg, 50%) as a colorless oil.

Step C: Preparation of 1-(2-(3-aminopropyl)-5-(5-chloro-2-methylphenyl)-2-phenyl-1,3,4-oxadiazol-3(2H)-yl)-2,2-dimethylpropan-1-one To a solution of 1-(2-(3-azidopropyl)-5-(5-chloro-2-methylphenyl)-2-phenyl-1,3,4-oxadiazol-3(2H)-yl)-2,2-dimethylpropan-1-one (62 mg, 0.141 mmol) in methanol (2 mL) was added $PtO_2$ (5 mg) followed by 1N HCl/MeOH (0.42 mL, 0.42 mmol). The mixture was hydrogenated under a balloon atmosphere for 4 hours then filtered through GF paper and the filtrate concentrated. The residue was purified by flash column chromatography ($CH_2Cl_2$ to 3% MeOH/$CH_2Cl_2$ to 10%) to afford the di-HCl product which was triturated with hexanes and filtered to afford a white solid (18 mg, 26%). MS ESI (+) m/z 414 (M+1) detected; $^1$H NMR (400 MHz, $CDCl_3$) δ 7.74 (s, 1H), 7.54 (d, 2H, J=7 Hz), 7.33 (m, 4H), 7.22 (d, 1H, J=9 Hz), 3.36 (m, 1H), 3.08 (m, 1H), 2.99 (m, 1H), 2.63 (s, 3H), 2.46 (m, 1H), 1.78 (m, 2H), 1.33 (s, 9H).

The following examples were prepared using the appropriately substituted benzohydrazides, ketones and acid chlorides:

Example 87

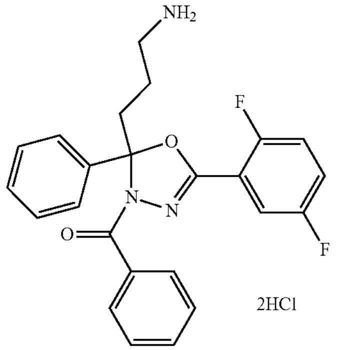 [SMILES: NCCCC1(c2ccccc2)OC(c2cc(F)ccc2F)=NN1C(=O)c1ccccc1]

(2-(3-aminopropyl)-5-(2,5-difluorophenyl)-2-phenyl-1,3,4-oxadiazol-3(2H)-yl)(phenyl)methanone Dihydrochloride MS ESI (+) m/z 421.9 (M+1) detected; $^1$H NMR (400 MHz, $CDCl_3$) δ 7.95 (d, 2H, J=8 Hz), 7.67 (d, 2H, J=8 Hz), 7.46 (m, 1H), 7.36 (m, 6H), 7.12 (m, 2H), 3.37 (m, 1H), 3.00 (brs, 2H), 2.63 (m, 1H), 1.86 (m, 2H).

Example 88

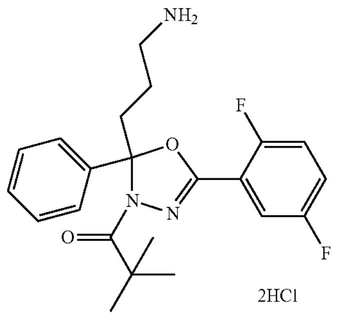 [SMILES: CC(C)(C)C(=O)N1N=C(c2cc(F)ccc2F)OC1(CCCN)c1ccccc1]

1-(2-(3-aminopropyl)-5-(2,5-difluorophenyl)-2-phenyl-1,3,4-oxadiazol-3(2H)-yl)-2,2-dimethylpropan-1-one Dihydrochloride MS ESI (+) m/z 402 (M+1) detected; $^1$H NMR (400 MHz, $CDCl_3$) δ 7.54 (m, 2H), 7.45 (m, 1H), 7.33 (m, 3H), 7.14 (m, 2H), 3.29 (m, 1H), 3.04 (m, 2H), 2.51 (m, 1H), 1.79 (m, 2H), 1.33 (s, 9H).

Example 89

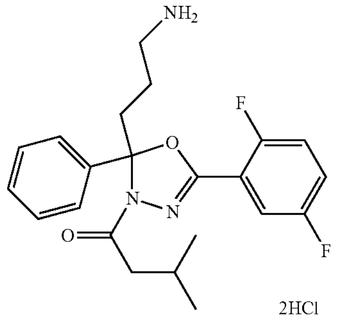 [SMILES: CC(C)CC(=O)N1N=C(c2cc(F)ccc2F)OC1(CCCN)c1ccccc1]

1-(2-(3-aminopropyl)-5-(2,5-difluorophenyl)-2-phenyl-1,3,4-oxadiazol-3(2H)-yl)-3-methylbutan-1-one Dihydrochloride MS ESI (+) m/z 402 (M+1) detected; $^1$H NMR (400 MHz, $CDCl_3$) δ 7.59 (d, 2H, J=8 Hz), 7.51 (m, 1H), 7.34 (m, 3H), 7.15 (t, 2H, J=8 Hz), 3.20 (m, 1H), 3.02 (m, 2H), 2.64 (m, 2H), 2.49 (m, 1H), 2.11 (m, 1H), 1.82 (m, 2H), 0.89 (t, 6H, J=7 Hz).

Example 90

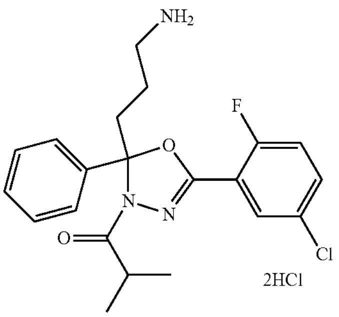 [SMILES: CC(C)C(=O)N1N=C(c2cc(Cl)ccc2F)OC1(CCCN)c1ccccc1]

1-(2-(3-aminopropyl)-5-(5-chloro-2-fluorophenyl)-2-phenyl-1,3,4-oxadiazol-3(2H)-yl)-2-methylpropan-1-one Dihydrochloride MS ESI (+) m/z 404.4 (M+1) detected; $^1$H NMR (400 MHz, $CDCl_3$) δ 7.77 (m, 1H), 7.57 (m, 2H), 7.41 (m, 1H), 7.35 (m, 3H), 7.13 (t, 1H, J=9), 3.31 (m, 1H), 3.21 (m, 1H), 3.04 (brs, 2H), 2.56 (m, 1H), 1.80 (m, 2H), 1.17 (d, 3H, J=7 Hz), 1.07 (d, 3H, J=7 Hz).

Example 91

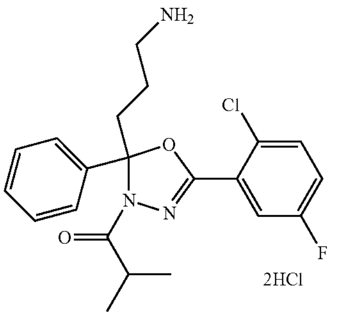 [SMILES: CC(C)C(=O)N1N=C(c2cc(F)ccc2Cl)OC1(CCCN)c1ccccc1]

1-(2-(3-aminopropyl)-5-(2-chloro-5-fluorophenyl)-2-phenyl-1,3,4-oxadiazol-3(2H)-yl)-2-methylpropan-1-one Dihydrochloride MS ESI (+) m/z 404 (M+1) detected; $^1$H NMR (400 MHz, $CDCl_3$) δ 7.56 (m, 3H), 7.45 (m, 1H), 7.33 (m, 3H), 7.11 (m, 1H), 3.30 (m, 1H), 3.21 (m, 1H), 3.06 (brs, 2H), 2.58 (m, 1H), 1.83 (m, 2H), 1.19 (d, 3H, J=7 Hz), 1.09 (d, 3H, J=7 Hz).

Example 92

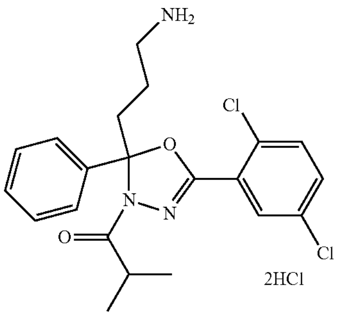 [SMILES: CC(C)C(=O)N1N=C(c2cc(Cl)ccc2Cl)OC1(CCCN)c1ccccc1]

1-(2-(3-aminopropyl)-5-(2,5-dichlorophenyl)-2-phenyl-1,3,4-oxadiazol-3(2H)-yl)-2-methylpropan-1-one Dihydrochloride MS ESI (+) m/z 420 (M+1) detected; $^1$H NMR (400 MHz, $CDCl_3$) δ 7.80 (d, 1H, J=2 Hz), 7.57 (d, 2H, J=8 Hz), 7.42 (d, 1H, J=8 Hz), 7.34 (m, 4H), 3.30 (m, 2H), 3.21 (m, 1H), 3.07 (brs, 1H), 2.57 (m, 1H), 1.82 (m, 2H), 1.19 (d, 3H, J=7 Hz), 1.09 (d, 3H, J=7 Hz).

Example 93

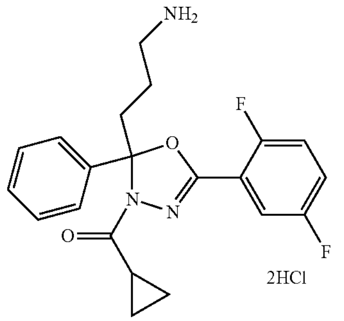 [SMILES: NCCCC1(c2ccccc2)OC(c2cc(F)ccc2F)=NN1C(=O)C1CC1]

(2-(3-aminopropyl)-5-(2,5-difluorophenyl)-2-phenyl-1,3,4-oxadiazol-3(2H)-yl)(cyclopropyl)methanone Dihydrochloride MS ESI (+) m/z 386 (M+1) detected; $^1$H NMR (400 MHz, $CDCl_3$) δ 7.58 (m, 2H), 7.52 (m, 1H), 7.36 (m, 3H), 7.16 (m, 2H), 3.02 (m, 1H), 2.84 (brs, 2H), 2.58 (m, 3H), 1.65 (m, 2H), 1.05 (m, 1H), 1.05 (m, 1H), 0.98 (m, 1H), 0.87 (m, 2H).

Example 94

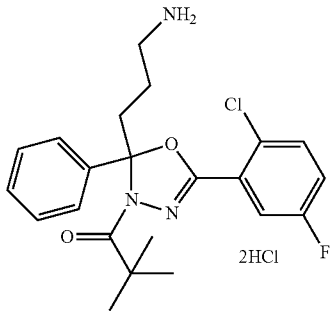 [SMILES: CC(C)(C)C(=O)N1N=C(c2cc(F)ccc2Cl)OC1(CCCN)c1ccccc1]

1-(2-(3-aminopropyl)-5-(2-chloro-5-fluorophenyl)-2-phenyl-1,3,4-oxadiazol-3(2H)-yl)-2,2-dimethylpropan-1-one Dihydro Chloride MS ESI (+) m/z 418 (M+1) detected; $^1$H NMR (400 MHz, $CDCl_3$) δ 7.54 (m, 3H), 7.47 (m, 1H), 7.33 (m, 3H), 7.10 (m, 1H), 3.28 (m, 1H), 3.02 (m, 2H), 2.52 (m, 1H), 1.79 (m, 2H), 1.35 (s, 9H).

Example 95

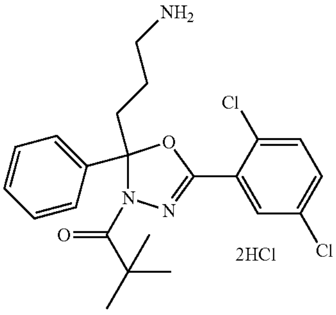 [SMILES: CC(C)(C)C(=O)N1N=C(c2cc(Cl)ccc2Cl)OC1(CCCN)c1ccccc1]

1-(2-(3-aminopropyl)-5-(2,5-dichlorophenyl)-2-phenyl-1,3,4-oxadiazol-3(2H)-yl)-2,2-dimethylpropan-1-one Dihydrochloride MS ESI (+) m/z 435 (M+1) detected; $^1$H NMR (400 MHz, $CDCl_3$) δ 7.77 (d, 1H, J=2 Hz), 7.55 (d, 2H, J=6), 7.40 (d, 1H, J=9 Hz), 7.34 (m, 4H), 3.32 (m, 1H), 3.08 (m, 1H), 3.00 (m, 1H), 2.50 (m, 1H), 1.79 (m, 2H), 1.35 (s, 9H).

Example 96

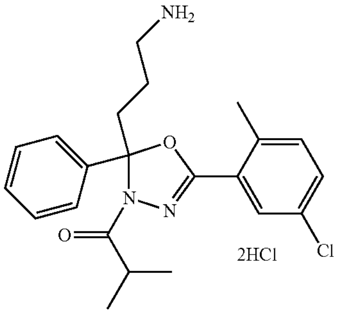 [SMILES: Cc1ccc(Cl)cc1C1=NN(C(=O)C(C)C)C(CCCN)(c2ccccc2)O1]

2HCl 1-(2-(3-aminopropyl)-5-(5-chloro-2-methylphenyl)-2-phenyl-1,3,4-oxadiazol-3(2H)-yl)-2-methylpropan-1-one Dihydrochloride MS ESI (+) m/z 400 (M+1) detected; $^{1}$H NMR (400 MHz, $CDCl_3$) δ 7.78 (s, 1H), 7.56 (d, 2H, J=8 Hz), 7.33 (m, 4H), 7.22 (d, 1H, J=9 Hz), 3.26 (m, 2H), 3.03 (m, 2H), 2.58 (s, 3H), 2.53 (m, 1H), 1.80 (m, 2H), 1.18 (d, 3H, J=7 Hz), 1.07 (d, 3H, J=7 Hz).

Example 97

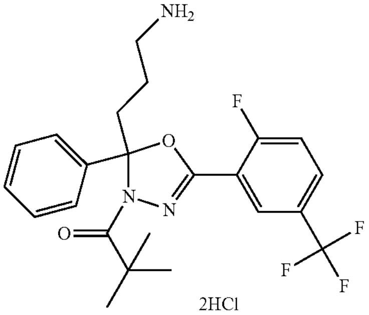 [SMILES: CC(C)(C)C(=O)N1N=C(c2cc(C(F)(F)F)ccc2F)OC1(CCCN)c1ccccc1]

2HCl 1-(2-(3-aminopropyl)-5-(2-fluoro-5-(trifluoromethyl)phenyl)-2-phenyl-1,3,4-oxadiazol-3(2H)-yl)-2,2-dimethylpropan-1-one Dihydrochloride MS ESI (+) m/z 452 (M+1) detected; $^{1}$H NMR (400 MHz, $CDCl_3$) δ 8.01 (d, 1H, J=6 Hz), 7.73 (m, 1H), 7.55 (d, 2H, J=6 Hz), 7.34 (m, 4H), 3.38 (m, 1H), 3.12 (m, 1H), 3.01 (m, 1H), 2.48 (m, 1H), 1.82 (m, 2H), 1.34 (s, 9H).

Example 98

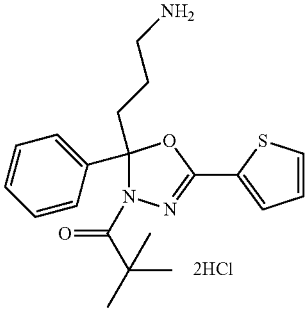 [SMILES: CC(C)(C)C(=O)N1N=C(c2cccs2)OC1(CCCN)c1ccccc1]

2HCl 1-(2-(3-aminopropyl)-2-phenyl-5-(thiophen-2-yl)-1,3,4-oxadiazol-3(2H)-yl)-2,2-dimethylpropan-1-one Dihydrochloride MS ESI (+) m/z 372 (M+1) detected; $^{1}$H NMR (400 MHz, $CDCl_3$) δ 7.53 (m, 3H), 7.46 (d, 1H, J=6 Hz), 7.32 (m, 3H), 7.07 (m, 1H), 3.20 (m, 1H), 2.95 (m, 2H), 2.50 (m, 1H), 1.72 (m, 2H), 1.33 (s, 9H).

Example 99

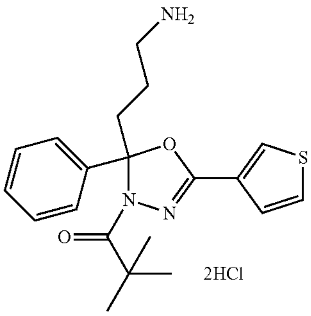 [SMILES: CC(C)(C)C(=O)N1N=C(c2ccsc2)OC1(CCCN)c1ccccc1]

2HCl 1-(2-(3-aminopropyl)-2-phenyl-5-(thiophen-3-yl)-1,3,4-oxadiazol-3(2H)-yl)-2,2-dimethylpropan-1-one Dihydrochloride MS ESI (+) m/z 372 (M+1) detected; $^{1}$H NMR (400 MHz, $CDCl_3$) δ 7.80 (d, 1H, J=3 Hz), 7.53 (d, 2H, J=6 Hz), 7.48 (d, 1H, J=5 Hz), 7.33 (m, 4H), 3.24 (m, 1H), 2.99 (brs, 2H), 2.48 (m, 1H), 1.73 (m, 2H), 1.33 (s, 9H).

Example 100

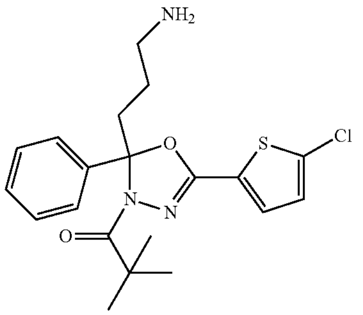 [SMILES: CC(C)(C)C(=O)N1N=C(c2ccc(Cl)s2)OC1(CCCN)c1ccccc1]

1-(2-(3-aminopropyl)-5-(5-chlorothiophen-2-yl)-2-phenyl-1,3,4-oxadiazol-3(2H)-yl)-2,2-dimethylpropan-1-one MS ESI (+) m/z 406 (M+1) detected; $^1$H NMR (400 MHz, $CDCl_3$) δ 7.52 (d, 2H, J=9 Hz), 7.33 (m, 3H), 7.30 (d, 1H, J=4 Hz), 6.89 (d, 1H, J=4 Hz), 3.23 (m, 1H), 2.95 (m, 2H), 2.47 (m, 1H), 1.72 (m, 2H), 1.31 (s, 9H).

Example 101

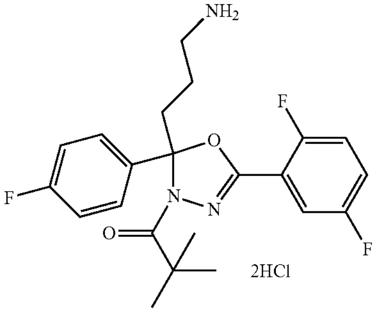 [SMILES: CC(C)(C)C(=O)N1N=C(c2cc(F)ccc2F)OC1(CCCN)c1ccc(F)cc1]

1-(2-(3-aminopropyl)-5-(2,5-difluorophenyl)-2-(4-fluorophenyl)-1,3,4-oxadiazol-3(2H)-yl)-2,2-dimethylpropan-1-one Dihydrochloride MS ESI (+) m/z 420 (M+1) detected; $^1$H NMR (400 MHz, $CDCl_3$) δ 7.54 (m, 2H), 7.45 (m, 1H), 7.15 (m, 2H), 7.02 (m, 2H), 3.19 (m, 1H), 2.97 (brs, 2H), 2.48 (m, 1H), 1.70 (m, 2H), 1.34 (s, 9H).

Example 102

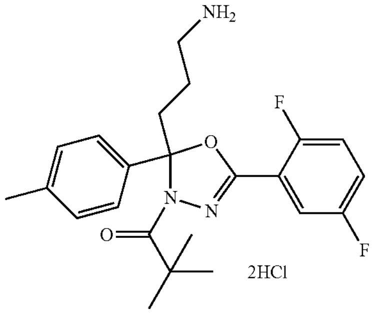 [SMILES: Cc1ccc(C2(CCCN)OC(c3cc(F)ccc3F)=NN2C(=O)C(C)(C)C)cc1]

1-(2-(3-aminopropyl)-5-(2,5-difluorophenyl)-2-p-tolyl-1,3,4-oxadiazol-3(2H)-yl)-2,2-dimethylpropan-1-one Dihydrochloride MS ESI (+) m/z 416 (M+1) detected; $^1$H NMR (400 MHz, $CDCl_3$) δ 7.42 (m, 3H), 7.13 (m, 4H), 3.26 (m, 1H), 3.04 (m, 2H), 2.51 (m, 1H), 2.29 (s, 3H), 1.78 (m, 2H), 1.33 (s, 9H).

Example 103

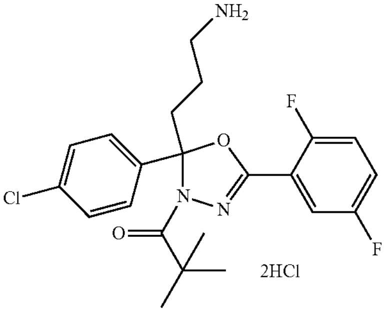 [SMILES: CC(C)(C)C(=O)N1N=C(c2cc(F)ccc2F)OC1(CCCN)c1ccc(Cl)cc1]

1-(2-(3-aminopropyl)-2-(4-chlorophenyl)-5-(2,5-difluorophenyl)-1,3,4-oxadiazol-3(2H)-yl)-2,2-dimethylpropan-1-one Dihydrochloride MS ESI (+) m/z 436 (M+1) detected; $^1$H NMR (400 MHz, $CDCl_3$) δ 7.51 (d, 2H, J=9 Hz), 7.44 (m, 1H), 7.30 (d, 2H, J=9 Hz), 7.15 (m, 2H), 3.25 (m, 1H), 3.01 (m, 2H), 2.48 (m, 1H), 1.74 (m, 2H), 1.33 (s, 9H).

Example 104

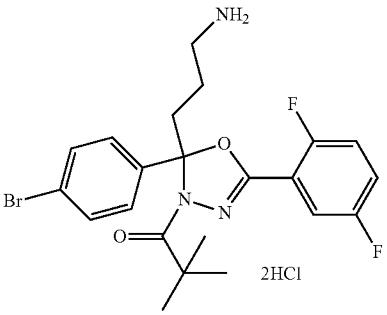 [SMILES: CC(C)(C)C(=O)N1N=C(c2cc(F)ccc2F)OC1(CCCN)c1ccc(Br)cc1]

1-(2-(3-aminopropyl)-2-(4-bromophenyl)-5-(2,5-difluorophenyl)-1,3,4-oxadiazol-3(2H)-yl)-2,2-dimethylpropan-1-one Dihydrochloride MS ESI (+) m/z 480 (M+1) detected; $^1$H NMR (400 MHz, $CDCl_3$) δ 7.45 (m, 5H), 7.15 (m, 2H), 3.28 (m, 1H), 3.05 (brs, 2H), 2.48 (m, 1H), 1.77 (m, 2H), 1.33 (s, 9H).

Example 105

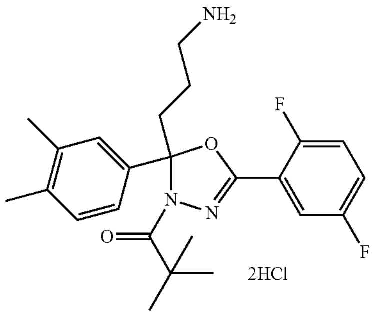 [SMILES: Cc1ccc(C2(CCCN)OC(c3cc(F)ccc3F)=NN2C(=O)C(C)(C)C)cc1C]

1-(2-(3-aminopropyl)-5-(2,5-difluorophenyl)-2-(3,4-dimethylphenyl)-1,3,4-oxadiazol-3(2H)-yl)-2,2-dimethylpropan-1-one Dihydrochloride MS ESI (+) m/z 429.9 (M+1) detected; $^1$H NMR (400 MHz, $CDCl_3$) δ 7.44 (m, 1H), 7.30 (s, 1H), 7.25 (m, 1H), 7.10

(m, 3H), 3.25 (m, 1H), 3.04 (m, 2H), 2.50 (m, 1H), 2.22 (s, 3H), 2.19 (s, 3H), 1.80 (m, 2H), 1.33 (s, 9H).

Example 106

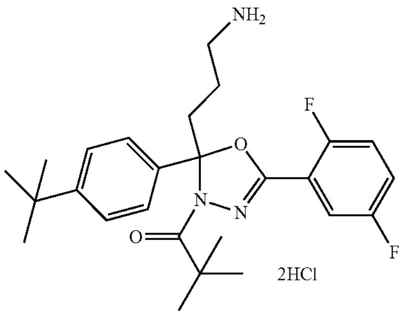 [SMILES: CC(C)(C)C(=O)N1N=C(c2cc(F)ccc2F)OC1(CCCN)c1ccc(C(C)(C)C)cc1]

1-(2-(3-aminopropyl)-2-(4-tert-butylphenyl)-5-(2,5-difluorophenyl)-1,3,4-oxadiazol-3(2H)-yl)-2,2-dimethylpropan-1-one Dihydrochloride MS ESI (+) m/z 458 (M+1) detected; $^1$H NMR (400 MHz, $CDCl_3$) δ 7.47 (d, 2H, J=9 Hz), 7.41 (m, 1H), 7.34 (d, 2H, J=9 Hz), 7.12 (m, 2H), 3.29 (m, 1H), 3.04 (brs, 2H), 2.52 (m, 1H), 1.78 (m, 2H), 1.35 (s, 9H), 1.24 (s, 9H).

Example 107

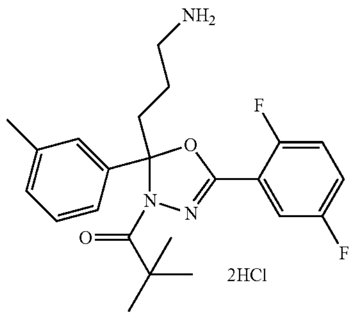 [SMILES: Cc1cccc(C2(CCCN)OC(c3cc(F)ccc3F)=NN2C(=O)C(C)(C)C)c1]

1-(2-(3-aminopropyl)-5-(2,5-difluorophenyl)-2-m-totyl-1,3,4-oxadiazol-3(2H)-yl)-2,2-dimethylpropan-1-one Dihydrochloride MS ESI (+) m/z 416 (M+1) detected; $^1$H NMR (400 MHz, $CDCl_3$) δ 7.44 (m, 1H), 7.32 (d, 2H, J=9 Hz), 7.22 (t, 1H, J=7

Hz), 7.13 (m, 3H), 3.25 (m, 1H), 3.04 (brs, 2H), 2.50 (m, 1H), 2.33 (s, 3H), 1.78 (m, 2H), 1.33 (s, 9H).

Example 108

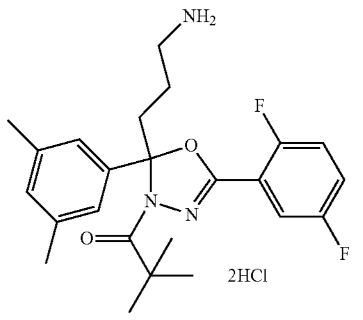 [SMILES: Cc1cc(C)cc(C2(CCCN)OC(c3cc(F)ccc3F)=NN2C(=O)C(C)(C)C)c1]

1-(2-(3-aminopropyl)-5-(2,5-difluorophenyl)-2-(3,5-dimethylphenyl)-1,3,4-oxadiazol-3(2H)-yl)-2,2-dimethylpropan-1-one Dihydrochloride MS ESI (+) m/z 429.9 (M+1) detected; $^1$H NMR (400 MHz, $CDCl_3$) δ 7.45 (m, 1H), 7.14 (m, 4H), 6.95 (s, 1H), 3.24 (m, 1H), 3.04 (m, 2H), 2.49 (m, 1H), 2.28 (s, 6H), 1.99 (m, 2H), 1.33 (s, 9H).

Example 109

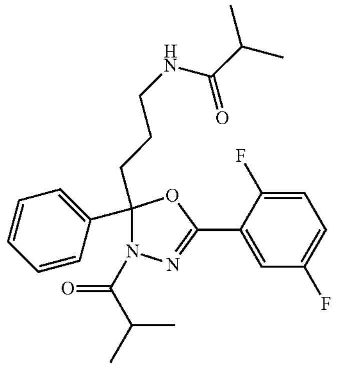 [SMILES: CC(C)C(=O)NCCCC1(c2ccccc2)OC(c2cc(F)ccc2F)=NN1C(=O)C(C)C]

Synthesis of N-(3-(5-(2,5-difluorophenyl)-3-isobutyryl-2-phenyl-2,3-dihydro-1,3,4-oxadiazol-2-yl)propyl)isobutyramide To a solution of 1-(2-(3-aminopropyl)-5-(2,5-difluorophenyl)-2-phenyl-1,3,4-oxadiazol-3(2H)-yl)-2-methylpropan-1-one dihydrochloride, prepared as in the above examples, (50 mg, 0.11 mmol) in anhydrous $CH_2Cl_2$ (1 mL) was added DIEA (95 μL, 0.54 mmol) followed by isobutyryl chloride (17 μL, 0.16 mmol). After stirring at room temperature for 16 hours the mixture was treated with 1N HCl (10 mL) and extracted with $CH_2Cl_2$ (2×10 mL). The combined organic phases were washed with brine (10 mL) then dried over $Na_2SO_4$ and concentrated. The residue was chromatographed (4:1 to 2:1 hexanes/EtOAc) to afford the product (31 mg, 62%) as a colorless gum. MS ESI (+) m/z 458.1 (M+1) detected; $^1$H NMR (400 MHz, $CDCl_3$) δ 7.55 (m, 3H), 7.36 (m, 3H), 7.17 (m, 2H), 3.33 (m, 3H), 3.04 (m, 1H), 2.53 (m, 1H), 2.35 (m, 1H), 1.77 (m, 1H), 1.56 (m, 1H), 1.16 (m, 12H).

Example 110

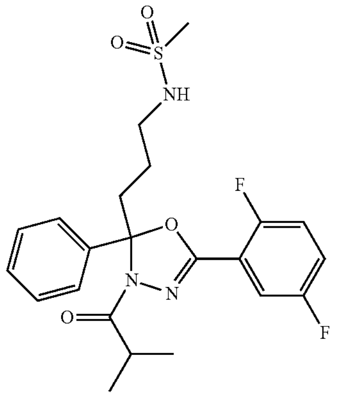 [SMILES: CC(C)C(=O)N1N=C(c2cc(F)ccc2F)OC1(CCCNS(C)(=O)=O)c1ccccc1]

N-(3-(5-(2,5-difluorophenyl)-3-isobutyryl-2-phenyl-2,3-dihydro-1,3,4-oxadiazol-2-yl)propyl)methanesulfonamide Prepared as in Example 109 using methanesulfonyl chloride in place of isobutyryl chloride. MS ESI (+) m/z 466.1 (M+1) detected; $^1$H NMR (400 MHz, $CDCl_3$) δ 7.51 (m, 3H), 7.38 (m, 3H), 7.17 (m, 2H), 3.41 (m, 1H), 3.21 (m, 2H), 3.04 (m, 1H), 2.95 (s, 3H), 2.59 (m, 1H), 1.74 (m, 2H), 1.21 (d, 3H, J=6.8 Hz), 1.15 (d, 3H, J=6.8 Hz).

Example 111

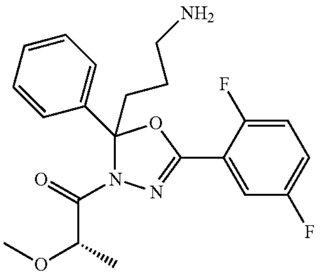 [SMILES: CO[C@@H](C)C(=O)N1N=C(c2cc(F)ccc2F)OC1(CCCN)c1ccccc1]

Synthesis of (2S)-1-(2-(3-aminopropyl)-5-(2,5-difluorophenyl)-2-phenyl-1,3,4-oxadiazol-3(2H)-yl)-2-methoxypropan-1-one Step A: Preparation of (S)-2-methoxypropanoic Anhydride To a solution of (S)-2-methoxy propanoic acid (0.25 g, 4.80 mmol) in $CH_2Cl_2$ (2 mL) was added EDCI (0.46 g, 2.38 mmol). After stirring at room temperature for 1 hour, hexanes were added and the mixture filtered to obtain the product (0.24 g, 53%).

Step B: Preparation of (2S)-1-(2-(3-azidopropyl)-5-(2,5-difluorophenyl)-2-phenyl-1,3,4-oxadiazol-3(2H)-yl)-2-methoxypropan-1-one To a solution of N'-(4-azido-1-phenylbutylidene)-2,5-difluorobenzohydrazide (100 mg, 0.29 mmol), prepared as in Example 85, Step A, in DCE (1 mL) was added (S)-2-methoxypropanoic anhydride from the previous step (277 mg, 1.46 mmol). After stirring at reflux for 48 hours the crude mixture was chromatographed ($CH_2Cl_2$ to 2.5% MeOH/$CH_2Cl_2$) to afford the product (81 mg, 65%) as a clear oil.

Step C: Preparation of (2S)-1-(2-(3-aminopropyl)-5-(2,5-difluorophenyl)-2-phenyl-1,3,4-oxadiazol-3(2H)-yl)-2-methoxypropan-1-one (2S)-1-(2-(3-azidopropyl)-5-(2,5-difluorophenyl)-2-phenyl-1,3,4-oxadiazol-3(2H)-yl)-2-methoxypropan-1-one (50 mg, 0.11 mmol) was reduced as in Example 86, Step C, to afford the product (32 mg, 68%) as a colorless oil. MS ESI (+) m/z 404 (M+1) detected; $^1$H NMR (400 MHz, $CDCl_3$) δ 7.62 (m, 1H), 7.56 (m, 1H), 7.52 (m, 1H), 7.34 (m, 3H), 7.17 m, 2H), 4.58 (q, 0.5H, J=7 Hz), 4.52 (q, 0.5H, J=7 Hz), 3.38 (s, 1.5H), 3.22 (s, 1.5H), 3.10 (m, 2H), 2.60 (m, 1H), 1.90 (m, 3H), 1.49 (d, 1.5H, J=7 Hz), 1.27 (d, 1.5H, J=7 Hz). 1:1 mixture of diastereomers.

Example 112

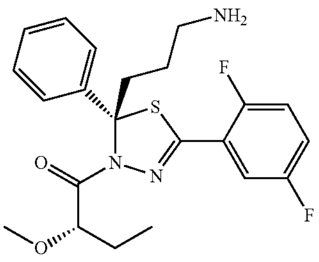 [SMILES: CC[C@H](OC)C(=O)N1N=C(c2cc(F)ccc2F)S[C@@]1(CCCN)c1ccccc1]

(S)-1-((S)-2-(3-aminopropyl)-5-(2,5-difluorophenyl)-2-phenyl-1,3,4-thiadiazol-3(2H)-yl)-2-methoxybutan-1-one Prepared as in Example 71 using (S)-2-(tert-butyldiphenylsilyloxy)butanoic acid in place of (S)-2-(tert-butyldiphenylsilyloxy)propanoic acid. MS APCI (+) m/z 434 (M+1) detected; $^1$H NMR (400 MHz, $CDCl_3$) δ 7.48 (m, 3H), 7.35 (app t, 2H, J=8 Hz), 7.28 (m, 1H), 7.13 (m, 2H), 4.53 (dd, 1H, J=7 Hz, 4 Hz), 3.40 (s, 3H), 3.26 (m, 1H), 2.86 (m, 2H), 2.42 (m, 1H), 1.94 (m, 2H), 1.74 (m, 2H), 0.96 (t, 3H, J=8 Hz). Stereochemistry was assigned by comparison to (S)-1-((S)-2-(3-aminopropyl)-5-(2,5-difluorophenyl)-2-phenyl-1,3,4-thiadiazol-3(2H)-yl)-2-methoxypropan-1-one.

Example 113

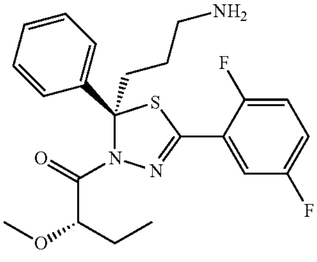 [SMILES: CC[C@H](OC)C(=O)N1N=C(c2cc(F)ccc2F)S[C@]1(CCCN)c1ccccc1]

(S)-1-((R)-2-(3-aminopropyl)-5-(2,5-difluorophenyl)-2-phenyl-1,3,4-thiadiazol-3(2H)-yl)-2-methoxybutan-1-one Prepared as in Example 71 using (S)-2-(tert-butyldiphenylsilyloxy)butanoic acid in place of (S)-2-(tert-butyldiphenylsilyloxy)propanoic acid. MS APCI (+) m/z 434 (M+1) detected; $^1$H NMR (400 MHz, $CDCl_3$) δ 7.46 (m, 3H), 7.36 (app t, 2H, J=8 Hz), 7.13 (m, 2H), 4.54 (dd, 1H, J=8 Hz, 4 Hz), 3.31 (s, 3H), 3.23 (m, 1H), 2.84 (m, 2H), 2.44 (m, 1H), 1.94 (m, 2H), 1.78 (m, 1H), 1.48 (m, 1H), 1.08 (t, 3H, J=7 Hz). Stereochemistry was assigned by comparison to (S)-1-((S)-2-(3-aminopropyl)-5-(2,5-di fluorophenyl)-2-phenyl-1,3,4-thiadiazol-3(2H)-yl)-2-methoxypropan-1-one.

Example 114

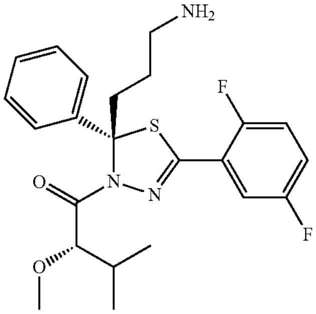 [SMILES: CO[C@H](C(=O)N1N=C(c2cc(F)ccc2F)S[C@@]1(CCCN)c1ccccc1)C(C)C]

(S)-1-((S)-2-(3-aminopropyl)-5-(2,5-difluorophenyl)-2-phenyl-1,3,4-thiadiazol-3(2H)-yl)-2-methoxy-3-methylbutan-1-one Prepared as in Example 71 using 2-(tert-butyldiphenylsilyloxy)-3-methylbutanoic acid in place of (S)-2-(tert-butyldiphenylsilyloxy)propanoic acid. Product obtained as a 2:1 mixture of diastereomers. MS APCI (+) m/z 448 (M+1) detected; $^1$H NMR (400 MHz, $CDCl_3$) δ 7.49 (m, 3H), 7.35 (m, 2H), 7.29 (m, 1H), 7.13 (m, 2H), 4.45 (d, 0.33H, J=5 Hz), 4.10 (d, 0.66H, J=5 Hz), 3.39 (s, 2H), 3.27 (m, 2H), 2.87 (m, 2H), 2.44 (m, 1H), 2.22 (m, 1H), 1.95 (m, 1H), 1.53 (m, 1H), 1.09 (d, 0.85H, J=7 Hz), 0.99 (m, 3H), 0.82 (d, 2.15H, J=7 Hz).

Example 115

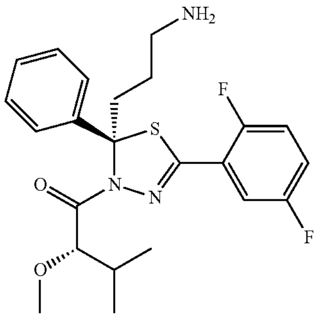 [SMILES: CO[C@H](C(=O)N1N=C(c2cc(F)ccc2F)S[C@]1(CCCN)c1ccccc1)C(C)C]

(S)-1-((R)-2-(3-aminopropyl)-5-(2,5-difluorophenyl)-2-phenyl-1,3,4-thiadiazol-3(2H)-yl)-2-methoxy-3-methylbutan-1-one Prepared as in Example 71 using 2-(tert-butyldiphenylsilyloxy)-3-methylbutanoic acid in place of (S)-2-(tert-butyldiphenylsilyloxy)propanoic acid. MS APCI (+) m/z 448 (M+1) detected; ¹H NMR (400 MHz, $CDCl_3$) δ 7.47 (m, 3H), 7.35 (m, 2H), 7.28 (m, 1H), 7.12 (m, 2H), 4.45 (d, 1H, J=4 Hz), 3.27 (s, 3H), 3.25 (m, 1H), 2.87 (m, 2H), 2.49 (m, 1H), 2.23 (m, 1H), 1.97 (m, 1H), 1.52 (m, 1H), 1.09 (d, 3H, J=7 Hz), 0.99 (d, 3H, J=7 Hz). Stereochemistry was assigned by comparison to (S)-1-((S)-2-(3-aminopropyl)-5-(2,5-difluorophenyl)-2-phenyl-1,3,4-thiadiazol-3(2H)-yl)-2-methoxypropan-1-one.

Example 116

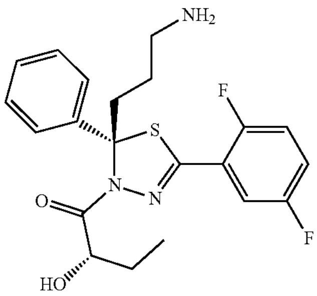 [SMILES: CC[C@H](O)C(=O)N1N=C(c2cc(F)ccc2F)S[C@@]1(CCCN)c1ccccc1]

(S)-1-((S)-2-(3-aminopropyl)-5-(2,5-difluorophenyl)-2-phenyl-1,3,4-thiadiazol-3(2H)-yl)-2-hydroxybutan-1-one Prepared as in Example 73. MS APCI (+) m/z 420 (M+1) detected; ¹H NMR (400 MHz, $CDCl_3$) δ 7.50 (m, 3H), 7.38 (m, 2H), 7.32 (m, 1H), 7.14 (m, 2H), 4.78 (dd, 1H, J=7 Hz, 4 Hz), 3.19 (m, 1H), 2.86 (m, 2H), 2.41 (m, 1H), 1.98 (m, 2H), 1.64 (m, 2H), 0.96 (t, 3H, J=7 Hz). Stereochemistry was assigned by comparison to (S)-1-((S)-2-(3-aminopropyl)-5-(2,5-difluorophenyl)-2-phenyl-1,3,4-thiadiazol-3(2H)-yl)-2-methoxypropan-1-one.

Example 117

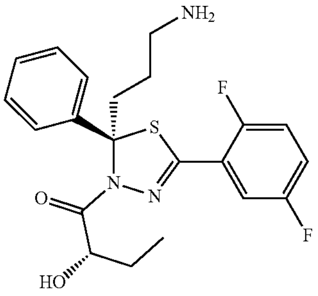 [SMILES: CC[C@H](O)C(=O)N1N=C(c2cc(F)ccc2F)S[C@]1(CCCN)c1ccccc1]

(S)-1-((R)-2-(3-aminopropyl)-5-(2,5-difluorophenyl)-2-phenyl-1,3,4-thiadiazol-3(2H)-yl)-2-hydroxybutan-1-one Prepared as in Example 73. MS APCI (+) m/z 420 (M+1) detected; ¹H NMR (400 MHz, $CDCl_3$) δ 7.45 (m, 3H), 7.38 (app t, 2H, J=8 Hz), 7.31 (m, 1H), 7.14 (m, 2H), 4.77 (dd, 1H, J=7 Hz, 3 Hz), 3.16 (m, 1H), 2.85 (m, 2H), 2.49 (m, 1H), 1.99 (m, 2H), 1.70 (m, 2H), 1.07 (t, 3H, J=7 Hz). Stereochemistry was assigned by comparison to (S)-1-((S)-2-(3-aminopropyl)-5-(2,5-difluorophenyl)-2-phenyl-1,3,4-thiadiazol-3(2H)-yl)-2-methoxypropan-1-one.

Example 118

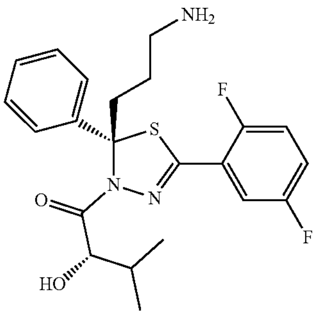 [SMILES: CC(C)[C@H](O)C(=O)N1N=C(c2cc(F)ccc2F)S[C@@]1(CCCN)c1ccccc1]

(S)-1-((S)-2-(3-aminopropyl)-5-(2,5-difluorophenyl)-2-phenyl-1,3,4-thiadiazol-3(2H)-yl)-2-hydroxy-3-methylbutan-1-one Prepared as in Example 73. Product obtained as a 2:1 mixture of diastereomers. MS APCI (+) m/z 434 (M+1) detected; ¹H NMR (400 MHz, $CDCl_3$) δ 7.49 (m, 3H), 7.38 (app t, 2H, J=8 Hz), 7.32 (m, 1H), 7.15 (m, 2H), 4.71 (m, 1H), 3.20 (m, 1H), 2.86 (m, 2H), 2.41 (m, 2H), 1.92 (m, 1H), 1.51

(m, 1H), 1.14 (d, 1H, J=7 Hz), 1.12 (m, 3H), 0.87 (d, 1.4H, J=7 Hz), 0.66 (d, 1.6H, J=6 Hz).

Example 119

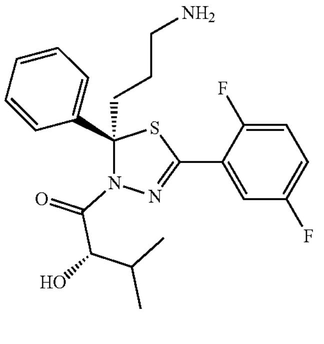 [SMILES: CC(C)[C@H](O)C(=O)N1N=C(c2cc(F)ccc2F)S[C@]1(CCCN)c1ccccc1]

(S)-1-((R)-2-(3-aminopropyl)-5-(2,5-difluorophenyl)-2-phenyl-1,3,4-thiadiazol-3(2H)-yl)-2-hydroxy-3-methylbutan-1-one Prepared as in Example 73. MS APCI (+) m/z 434 (M+1) detected; $^1$H NMR (400 MHz, $CDCl_3$) δ 7.46 (m, 3H), 7.34 (app t, 2H, J=8 Hz), 7.26 (m, 1H), 7.11 (m, 2H), 4.65 (d, 1H, J=3 Hz), 3.24 (m, 1H), 2.98 (t, 2H, J=6 Hz), 2.64 (m, 1H), 2.28 (m, 1H), 2.12 (m, 1H), 1.66 (m, 1H), 1.08 (d, 3H, J=7 Hz), 0.86 (d, 3H, J=7 Hz). Stereochemistry was assigned by comparison to (S)-1-(S)-2-(3-aminopropyl)-5-(2,5-difluorophenyl)-2-phenyl-1,3,4-thiadiazol-3(2H)-yl)-2-methoxypropan-1-one.

Example 120

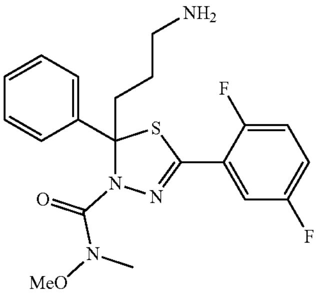 [SMILES: CON(C)C(=O)N1N=C(c2cc(F)ccc2F)SC1(CCCN)c1ccccc1]

2-(3-aminopropyl)-5-(2,5-difluorophenyl)-N-methoxy-N-methyl-2-phenyl-1,3,4-thiadiazole-3(2H)-carboxamide (Enantiomer A)

Prepared as previously described in Example 68. The tert-butyl 3-(5-(2,5-difluorophenyl)-3-(methoxy(methyl)carbamoyl)-2-phenyl-2,3-dihydro-1,3,4-thiadiazol-2-yl)propylcarbamate enantiomers were separated on a chiral column (Chiralcel ODH 250×20 mm) eluting with 2% EtOH/hexanes to provide the less polar enantiomer A and the more polar enantiomer B. Boc-deprotection of enantiomer A provided the final product. MS ESI (+) m/z 421 (M+1) detected; $^1$H NMR (400 MHz, $CDCl_3$) δ 8.44 (br, 3H), 7.52 (m, 3H), 7.34 (m, 2H), 7.24 (m, 1H), 7.08 (m, 2H), 3.35 (m, 1H), 3.16 (s, 3H), 3.06 (m, 2H), 2.42 (m, 1H), 2.13 (m, 1H), 1.88 (m, 1H), 1.61 (s, 3H).

Example 121

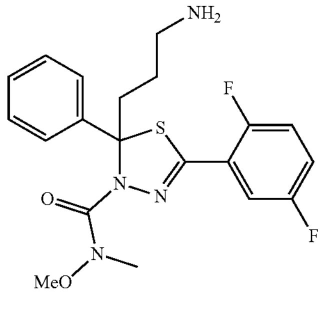 [SMILES: CON(C)C(=O)N1N=C(c2cc(F)ccc2F)SC1(CCCN)c1ccccc1]

2-(3-aminopropyl)-5-(2,5-difluorophenyl)-N-methoxy-N-methyl-2-phenyl-1,3,4-thiadiazole-3(2H)-carboxamide (Enantiomer B)

Prepared as in Example 120 using the more polar enantiomer, B. MS ESI (+) m/z 421 (M+1) detected; $^1$H NMR (400 MHz, $CDCl_3$) δ 8.44 (br, 3H), 7.52 (m, 3H), 7.34 (m, 2H), 7.24 (m, 1H), 7.08 (m, 2H), 3.35 (m, 1H), 3.16 (s, 3H), 3.06 (m, 2H), 2.42 (m, 1H), 2.13 (m, 1H), 1.88 (m, 1H), 1.61 (s, 3H).

Example 122

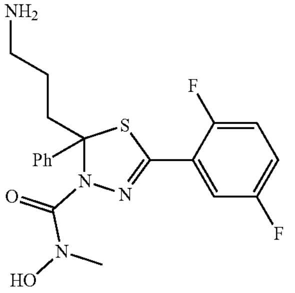 [SMILES: CN(O)C(=O)N1N=C(c2cc(F)ccc2F)SC1(CCCN)c1ccccc1]

Synthesis of 2-(3-aminopropyl)-5-(2,5-difluorophenyl)-N-hydroxy-N-methyl-2-phenyl-1,3,4-thiadiazole-3(2H)-carboxamide Step A: Preparation of (2-(3-azidopropyl)-5-(2,5-difluorophenyl)-2-phenyl-1,3,4-thiadiazol-3(2H)-yl)(1H-imidazol-1-yl)methanone To a solution of 2-(3-azidopropyl)-5-(2,5-difluorophenyl)-2-phenyl-2,3-dihydro-1,3,4-thiadiazole (0.492 g, 1.37 mmol) in THF (8 mL) was added 1,1'-carbonyl diimidazole (0.266 g, 1.64 mmol). After stirring at 75° C. for 2 hours, the reaction mixture was concentrated under reduced pressure and dissolved in dichloromethane (20 mL). The solution was washed with HCl (0.5 M), dried over $Na_2SO_4$ and concentrated to provide the crude product.

Step B: Preparation of (2-(3-azidopropyl)-5-(2,5-difluorophenyl)-2-phenyl-1,3,4-thiadiazol-3(2H)-yl)(3-methylimidazolium iodide-1-yl)methanone To a solution of (2-(3-azidopropyl)-5-(2,5-difluorophenyl)-2-phenyl-1,3,4-thiadiazol-3(2H)-yl)(1H-imidazol-1-yl)methanone (0.621 g, 1.37 mmol) in acetonitrile (5 mL) was added iodomethane (0.972 g, 6.85 mmol). After stirring in a sealed flask for 24 hours, the mixture was concentrated to provide the crude product.

Step C: Preparation of 2-(3-azidopropyl)-N-tert-butoxy-5-(2,5-difluorophenyl)-2-phenyl-1,3,4-thiadiazole-3(2H)-carboxamide To a solution of (2-(3-azidopropyl)-5-(2,5-difluorophenyl)-2-phenyl-1,3,4-thiadiazol-3(2H)-yl)(3-methylimidazolium iodide-1-yl)methanone (0.112 g, 0.188 mmol) and O-(tert-buty)hydroxylamine hydrochloride (0.047 g, 0.376 mmol) in dichloromethane (3 mL) was added triethylamine (0.095 g, 0.941 mmol). After stirring for 1 hour, the mixture was concentrated under reduced pressure and chromatographed (10:1 hexanes/ethyl acetate) to provide the product (0.078 g, 87%).

Step D: Preparation of 2-(3-azidopropyl)-N-tert-butoxy-5-(2,5-difluorophenyl)-N-methyl-2-phenyl-1,3,4-thiadiazole-3(2H)-carboxamide To a cooled (0° C.) solution of 2-(3-azidopropyl)-N-tert-butoxy-5-(2,5-difluorophenyl)-2-phenyl-1,3,4-thiadiazole-3(2H)-carboxamide (0.061 g, 0.13 mmol) and iodomethane (0.18 g, 1.3 mmol) in DMF (4 mL) was added sodium hydride (0.006 g, 0.26 mmol). After stirring at 0° C. for 30 minutes and then at room temperature for 1 hour, the mixture was partitioned between ethyl acetate (10 mL) and saturated $NH_4Cl$ (5 mL). The organic layer was washed with water (2×5 mL), dried and concentrated under reduced pressure to provide the crude product.

Step E: Preparation of 2-(3-aminopropyl)-N-tert-butoxy-5-(2,5-difluorophenyl)-N-methyl-2-phenyl-1,3,4-thiadiazole-3(2H)-carboxamide To a solution of 2-(3-azidopropyl)-N-tert-butoxy-5-(2,5-difluorophenyl)-N-methyl-2-phenyl-1,3,4-thiadiazole-3(2H)-carboxamide (0.032 g, 0.065 mmol) and platinum oxide (15 mg) in methanol (3 mL) was added HCl (5.3 M solution in dioxane, 0.05 mL). After stirring under a hydrogen balloon for 1 hour, the mixture was filtered and the filtrate was concentrated under reduced pressure to provide the product.

Step F: Preparation of 2-(3-aminopropyl)-5-(2,5-difluorophenyl)-N-hydroxy-N-methyl-2-phenyl-1,3,4-thiadiazole-3(2H)-carboxamide To 2-(3-aminopropyl)-N-tert-butoxy-5-(2,5-difluorophenyl)-N-methyl-2-phenyl-1,3,4-thiadiazole-3(2H)-carboxamide (0.023 g, 0.05 mmol) was added TFA (2 mL). After stirring for 18 hours, the mixture was concentrated and chromatographed (10:1:0.2 dichloromethane/methanol/30% $NH_4OH$) to provide the product (0.01 g, 49%). MS ESI (+) m/z 407 (M+1) detected; $^1H$ NMR (400 MHz, $CDCl_3$) δ 7.45 (d, 2H), 7.36 (m, 3H), 7.29 (m, 1H), 7.11 (m, 2H), 3.28 (s, 3H), 3.12 (m, 1H), 2.90 (m, 1H), 2.78 (m, 1H), 2.24 (m, 1H), 1.98 (m, 1H), 1.62 (m, 1H).

The following compounds are prepared by using the procedures described above, utilizing the appropriately substituted reagents.

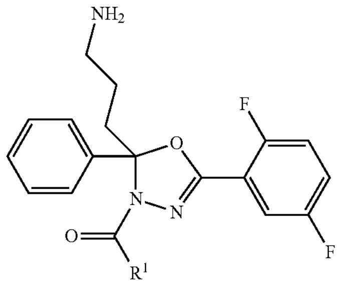

| $R^1$ | Name |
|---|---|
| 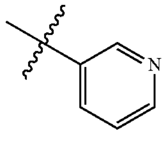 | (2-(3-aminopropyl)-5-(2,5-difluorophenyl)-2-phenyl-1,3,4-oxadiazol-3(2H)-yl)(pyridin-3-yl)methanone |
| 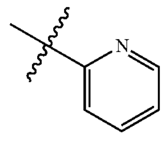 | (2-(3-aminopropyl)-5-(2,5-difluorophenyl)-2-phenyl-1,3,4-oxadiazol-3(2H)-yl)(pyridin-2-yl)methanone |

-continued

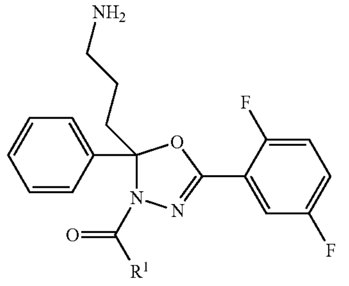

| R1 | Name |
| --- | --- |
| 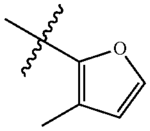 | (2-(3-aminopropyl)-5-(2,5-difluorophenyl)-2-phenyl-1,3,4-oxadiazol-3(2H)-yl)(3-methylfuran-2-yl)methanone |
| 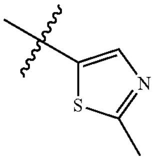 [SMILES: *c1cnc(C)s1] | (2-(3-aminopropyl)-5-(2,5-difluorophenyl)-2-phenyl-1,3,4-oxadiazol-3(2H)-yl)(2-methylthiazol-5-yl)methanone |
| 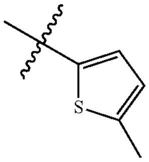 [SMILES: *c1ccc(C)s1] | (2-(3-aminopropyl)-5-(2,5-difluorophenyl)-2-phenyl-1,3,4-oxadiazol-3(2H)-yl)(5-methylthiophen-2-yl)methanone |
| 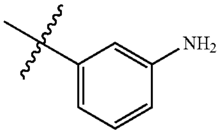 [SMILES: *c1cccc(N)c1] | (3-aminophenyl)(2-(3-aminopropyl)-5-(2,5-difluorophenyl)-2-phenyl-1,3,4-oxadiazol-3(2H)-yl)methanone |
| 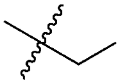 [SMILES: *CC] | 1-(2-(3-aminopropyl)-5-(2,5-difluorophenyl)-2-phenyl-1,3,4-oxadiazol-3(2H)-yl)propan-1-one |
| 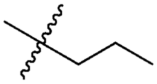 [SMILES: *CCC] | 1-(2(3-aminopropyl)-5-(2,5-difluorophenyl)-2-phenyl-1,3,4-oxadiazol-3(2H)-yl)butan-1-one |
| 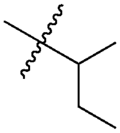 [SMILES: *C(C)CC] | 1-(2(3-aminopropyl)-5-(2,5-difluorophenyl)-2-phenyl-1,3,4-oxadiazol-3(2H)-yl)-2-methylbutan-1-one |
| 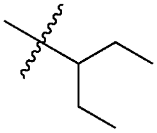 [SMILES: *C(CC)CC] | 1-(2-(3-aminopropyl)-5-(2,5-difluorophenyl)-2-phenyl-1,3,4-oxadiazol-3(2H)-yl)-2-ethylbutan-1-one |
| 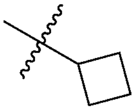 [SMILES: *C1CCC1] | (2-(3-aminopropyl)-5-(2,5-difluorophenyl)-2-phenyl-1,3,4-oxadiazol-3(2H)-yl)(cyclobutyl)methanone |

-continued

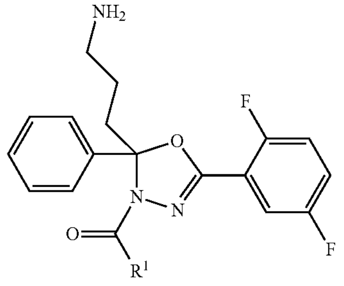

| $R^1$ | Name |
|---|---|
| 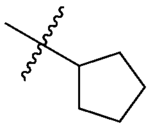 [SMILES: *C1CCCC1] | (2-(3-aminopropyl)-5-(2,5-difluorophenyl)-2-phenyl-1,3,4-oxadiazol-3(2H)-yl)(cyclopentyl)methanone |
| 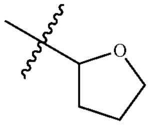 [SMILES: *C1CCCO1] | (2-(3-aminopropyl)-5-(2,5-difluorophenyl)-2-phenyl-1,3,4-oxadiazol-3(2H)-yl)(tetrahydrofuran-2-yl)methanone |
| 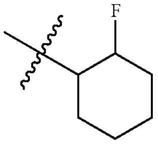 [SMILES: *C1CCCCC1F] | (2-(3-aminopropyl)-5-(2,5-difluorophenyl)-2-phenyl-1,3,4-oxadiazol-3(2H)-yl)(2-fluorocyclohexyl)methanone |
| 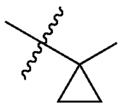 [SMILES: *C1(C)CC1] | (2-(3-aminopropyl)-5-(2,5-difluorophenyl)-2-phenyl-1,3,4-oxadiazol-3(2H)-yl)(1-methylcyclopropyl)methanone |
| 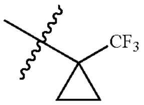 [SMILES: *C1(C(F)(F)F)CC1] | (2-(3-aminopropyl)-5-(2,5-difluorophenyl)-2-phenyl-1,3,4-oxadiazol-3(2H)-yl)(1-(trifluoromethyl)cyclopropyl)methanone |
| 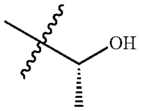 [SMILES: *[C@@H](C)O] | (2R)-1-(2-(3-aminopropyl)-5-(2,5-difluorophenyl)-2-phenyl-1,3,4-oxadiazol-3(2H)-yl)-2-hydroxypropan-1-one |
| 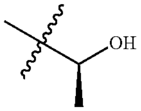 [SMILES: *[C@H](C)O] | (2S)-1-(2-(3-aminopropyl)-5-(2,5-difluorophenyl)-2-phenyl-1,3,4-oxadiazol-3(2H)-yl)-2-hydroxypropan-1-one |
| 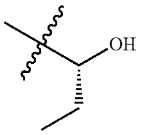 [SMILES: *[C@H](O)CC] | (2R)-1-(2-(3-aminopropyl)-5-(2,5-difluorophenyl)-2-phenyl-1,3,4-oxadiazol-3(2H)-yl)-2-hydroxybutan-1-one |
| 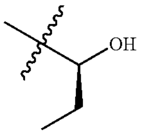 [SMILES: *[C@@H](O)CC] | (2S)-1-(2-(3-aminopropyl)-5-(2,5-difluorophenyl)-2-phenyl-1,3,4-oxadiazol-3(2H)-yl)-2-hydroxybutan-1-one |

-continued

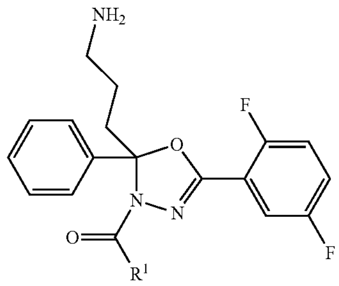

| $R^1$ | Name |
|---|---|
| 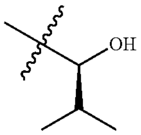 [SMILES: *[C@@H](O)C(C)C] | (2S)-1-(2-(3-aminopropyl)-5-(2,5-difluorophenyl)-2-phenyl-1,3,4-oxadiazol-3(2H)-yl)-2-hydroxy-3-methylbutan-1-one |
| 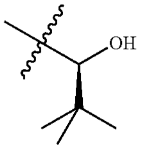 [SMILES: *[C@@H](O)C(C)(C)C] | (2S)-1-(2-(3-aminopropyl)-5-(2,5-difluorophenyl)-2-phenyl-1,3,4-oxadiazol-3(2H)-yl)-2-hydroxy-3,3-dimethylbutan-1-one |
| 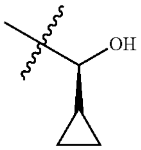 [SMILES: *[C@@H](O)C1CC1] | (2S)-1-(2-(3-aminopropyl)-5-(2,5-difluorophenyl)-2-phenyl-1,3,4-oxadiazol-3(2H)-yl)-2-cyclopropyl-2-hydroxyethanone |
| 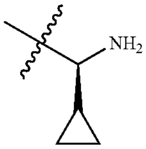 [SMILES: *[C@@H](N)C1CC1] | (2S)-2-amino-1-(2-(3-aminopropyl)-5-(2,5-difluorophenyl)-2-phenyl-1,3,4-oxadiazol-3(2H)-yl)-2-cyclopropylethanone |
| 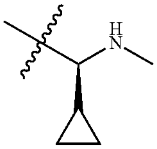 [SMILES: *[C@@H](NC)C1CC1] | (2S)-1-(2-(3-aminopropyl)-5-(2,5-difluorophenyl)-2-phenyl-1,3,4-oxadiazol-3(2H)-yl)-2-cyclopropyl-2-(methylamino)ethanone |
| 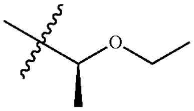 [SMILES: *[C@H](C)OCC] | (2S)-1-(2-(3-aminopropyl)-5-(2,5-difluorophenyl)-2-phenyl-1,3,4-oxadiazol-3(2H)-yl)-2-ethoxypropan-1-one |
| 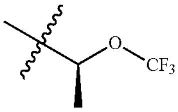 [SMILES: *[C@H](C)OC(F)(F)F] | (2S)-1-(2-(3-aminopropyl)-5-(2,5-difluorophenyl)-2-phenyl-1,3,4-oxadiazol-3(2H)-yl)-2-(trifluoromethoxy)propan-1-one |
| 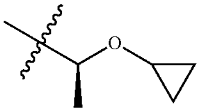 [SMILES: *[C@H](C)OC1CC1] | (2S)-1-(2-(3-aminopropyl)-5-(2,5-difluorophenyl)-2-phenyl-1,3,4-oxadiazol-3(2H)-yl)-2-cyclopropoxypropan-1-one |
| 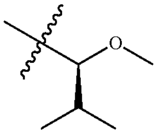 [SMILES: *[C@@H](OC)C(C)C] | (2S)-1-(2-(3-aminopropyl)-5-(2,5-difluorophenyl)-2-phenyl-1,3,4-oxadiazol-3(2H)-yl)-2-methoxy-3-methylbutan-1-one |

-continued

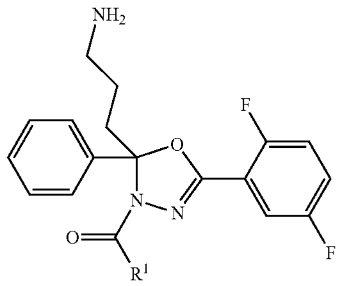

| $R^1$ | Name |
|---|---|
| 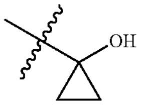 [SMILES: *C1(O)CC1] | (2-(3-aminopropyl)-5-(2,5-difluorophenyl)-2-phenyl-1,3,4-oxadiazol-3(2H)-yl)(1-hydroxycyclopropyl)methanone |
| 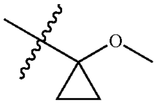 [SMILES: *C1(OC)CC1] | (2-(3-aminopropyl)-5-(2,5-difluorophenyl)-2-phenyl-1,3,4-oxadiazol-3(2H)-yl)(1-methoxycyclopropyl)methanone |
| 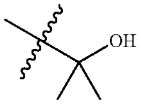 [SMILES: *C(C)(C)O] | 1-(2-(3-aminopropyl)-5-(2,5-difluorophenyl)-2-phenyl-1,3,4-oxadiazol-3(2H)-yl)-2-hydroxy-2-methylpropan-1-one |
| 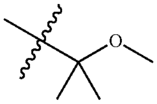 [SMILES: *C(C)(C)OC] | 1-(2-(3-aminopropyl)-5-(2,5-difluorophenyl)-2-phenyl-1,3,4-oxadiazol-3(2H)-yl)-2-methoxy-2-methylpropan-1-one |
| 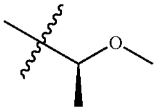 [SMILES: *[C@H](C)OC] | (2S)-1-(2-(3-aminopropyl)-5-(2,5-difluorophenyl)-2-phenyl-1,3,4-oxadiazol-3(2H)-yl)-2-methoxypropan-1-one |
| 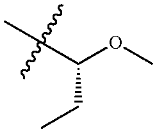 [SMILES: *[C@@H](CC)OC] | (2R)-1-(2-(3-aminopropyl)-5-(2,5-difluorophenyl)-2-phenyl-1,3,4-oxadiazol-3(2H)-yl)-2-methoxybutan-1-one |
| 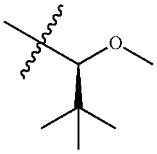 [SMILES: *[C@@H](OC)C(C)(C)C] | (2S)-1-(2-(3-aminopropyl)-5-(2,5-difluorophenyl)-2-phenyl-1,3,4-oxadiazol-3(2H)-yl)-2-methoxy-3,3-dimethylbutan-1-one |
| 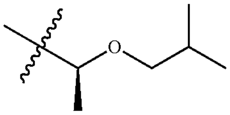 [SMILES: *[C@H](C)OCC(C)C] | (2S)-1-(2-(3-aminopropyl)-5-(2,5-difluorophenyl)-2-phenyl-1,3,4-oxadiazol-3(2H)-yl)-2-isobutoxypropan-1-one |
| 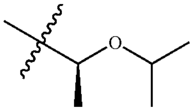 [SMILES: *[C@H](C)OC(C)C] | (2S)-1-(2-(3-aminopropyl)-5-(2,5-difluorophenyl)-2-phenyl-1,3,4-oxadiazol-3(2H)-yl)-2-isopropoxypropan-1-one |
| 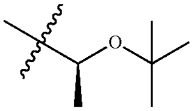 [SMILES: *[C@H](C)OC(C)(C)C] | (2S)-1-(2-(3-aminopropyl)-5-(2,5-difluorophenyl)-2-phenyl-1,3,4-oxadiazol-3(2H)-yl)-2-tert-butoxypropan-1-one |

-continued

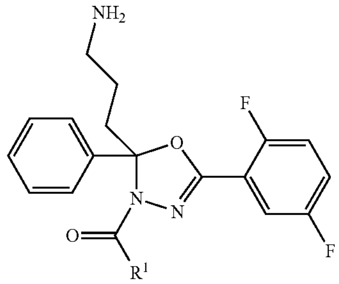

| R[1] | Name |
|---|---|
| 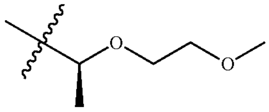 [SMILES: *[C@H](C)OCCOC] | (2S)-1-(2-(3-aminopropyl)-5-(2,5-difluorophenyl)-2-phenyl-1,3,4-oxadiazol-3(2H)-yl)-2-(2-methoxyethoxy)propan-1-one |
| 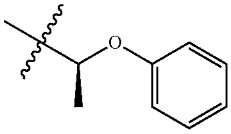 [SMILES: *[C@H](C)Oc1ccccc1] | (2S)-1-(2-(3-aminopropyl)-5-(2,5-difluorophenyl)-2-phenyl-1,3,4-oxadiazol-3(2H)-yl)-2-phenoxypropan-1-one |
| 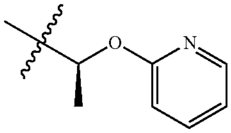 [SMILES: *[C@H](C)Oc1ccccn1] | (2S)-1-(2-(3-aminopropyl)-5-(2,5-difluorophenyl)-2-phenyl-1,3,4-oxadiazol-3(2H)-yl)-2-(pyridin-2-yloxy)propan-1-one |
| 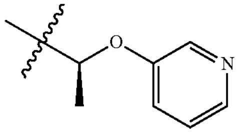 [SMILES: *[C@H](C)Oc1cccnc1] | (2S)-1-(2-(3-aminopropyl)-5-(2,5-difluorophenyl)-2-phenyl-1,3,4-oxadiazol-3(2H)-yl)-2-(pyridin-3-yloxy)propan-1-one |
| 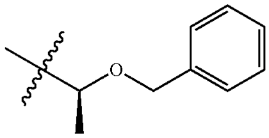 [SMILES: *[C@H](C)OCc1ccccc1] | (2S)-1-(2-(3-aminopropyl)-5-(2,5-difluorophenyl)-2-phenyl-1,3,4-oxadiazol-3(2H)-yl)-2-(benzyloxy)propan-1-one |
| 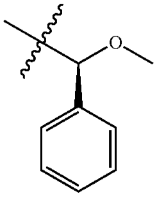 [SMILES: *[C@@H](OC)c1ccccc1] | (2S)-1-(2-(3-aminopropyl)-5-(2,5-difluorophenyl)-2-phenyl-1,3,4-oxadiazol-3(2H)-yl)-2-methoxy-2-phenylethanone |
| 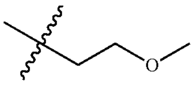 [SMILES: *CCOC] | 1-(2-(3-aminopropyl)-5-(2,5-difluorophenyl)-2-phenyl-1,3,4-oxadiazol-3(2H)-yl)-3-methoxypropan-1-one |
| 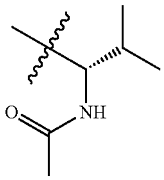 [SMILES: *[C@@H](NC(C)=O)C(C)C] | N-((S)-1-(2-(3-aminopropyl)-5-(2,5-difluorophenyl)-2-phenyl-1,3,4-oxadiazol-3(2H)-yl)-3-methyl-1-oxobutan-2-yl)acetamide |

-continued

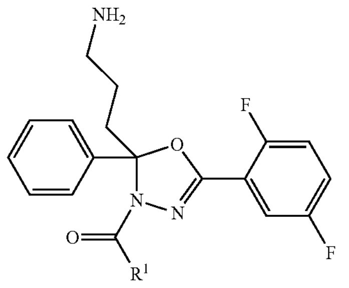

| $R^1$ | Name |
|---|---|
| 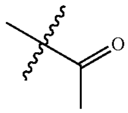 [SMILES: *C(C)=O] | 1-(2-(3-aminopropyl)-5-(2,5-difluorophenyl)-2-phenyl-1,3,4-oxadiazol-3(2H)-yl)propane-1,2-dione |
| 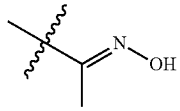 [SMILES: */C(C)=N/O] | (Z)-1-(2-(3-aminopropyl)-5-(2,5-difluorophenyl)-2-phenyl-1,3,4-oxadiazol-3(2H)-yl)-2-(hydroxyimino)propan-1-one |
| 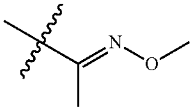 [SMILES: */C(C)=N/OC] | (Z)-1-(2-(3-aminopropyl)-5-(2,5-difluorophenyl)-2-phenyl-1,3,4-oxadiazol-3(2H)-yl)-2-(methoxyimino)propan-1-one |

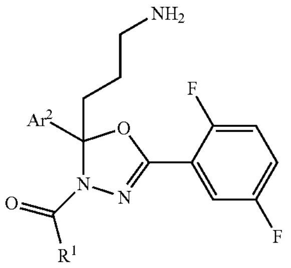

| $Ar^2$ | $R^1$ | Name |
|---|---|---|
| 4-methylphenyl | (S)-1-methoxyethyl | (2S)1-(2-(3-aminopropyl)-5-(2,5-difluorophenyl)-2-p-tolyl-1,3,4-oxadiazol-3(2H)-yl)-2-methoxypropan-1-one |
| 4-chlorophenyl | (S)-1-methoxyethyl | 1-(2-(3-aminopropyl)-2-(4-chlorophenyl)-5-(2,5-difluorophenyl)-1,3,4-oxadiazol-3(2H)-yl)-2,2-dimethylpropan-1-one |
| 4-bromophenyl | (S)-1-methoxyethyl | 1-(2-(3-aminopropyl)-2-(4-bromophenyl)-5-(2,5-difluorophenyl)-1,3,4-oxadiazol-3(2H)-yl)-2-methoxypropan-1-one |
| 4-t-butylphenyl | (S)-1-methoxyethyl | 1-(2-(3-aminopropyl)-2-(4-tert-butylphenyl)-5-(2,5-difluorophenyl)-1,3,4-oxadiazol-3(2H)-yl)-2-methoxypropan-1-one |
| 3,4-dimethylphenyl | (S)-1-methoxyethyl | 1-(2-(3-aminopropyl)-5-(2,5-difluorophenyl)-2-(3,4-dimethylphenyl)-1,3,4-oxadiazol-3(2H)-yl)-2,2-dimethylpropan-1-one |
| 3-methylphenyl | (S)-1-methoxyethyl | 1-(2-(3-aminopropyl)-5-(2,5-difluorophenyl)-2-m-tolyl-1,3,4-oxadiazol-3(2H)-yl)-2-methoxypropan-1-one |
| 3,5-dimethylphenyl | (S)-1-methoxyethyl | 1-(2-(3-aminopropyl)-5-(2,5-difluorophenyl)-2-(3,5-dimethylphenyl)-1,3,4-oxadiazol-3(2H)-yl)-2-methoxypropan-1-one |
| 2-chlorophenyl | t-butyl | 1-(2-(3-aminopropyl)-2-(2-chlorophenyl)-5-(2,5-difluorophenyl)-1,3,4-oxadiazol-3(2H)-yl)-2,2-dimethylpropan-1-one |

-continued

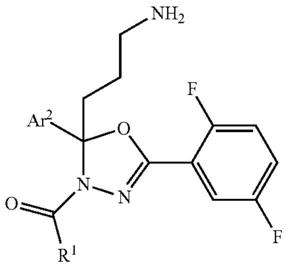

| Ar2 | R1 | Name |
|---|---|---|
| 2-ethylphenyl | t-butyl | 1-(2-(3-aminopropyl)-5-(2,5-difluorophenyl)-2-(2-ethylphenyl)-1,3,4-oxadiazol-3(2H)-yl)-2,2-dimethylpropan-1-one |
| 3-nitrophenyl | t-butyl | 1-(2-(3-aminopropyl)-5-(2,5-difluorophenyl)-2-(3-nitrophenyl)-1,3,4-oxadiazol-3(2H)-yl)-2,2-dimethylpropan-1-one |
| 3-hydroxyphenyl | t-butyl | 1-(2-(3-aminopropyl)-5-(2,5-difluorophenyl)-2-(3-hydroxyphenyl)-1,3,4-oxadiazol-3(2H)-yl)-2,2-dimethylpropan-1-one |
| 3-aminophenyl | t-butyl | 1-(2-(3-aminophenyl)-2-(3-aminopropyl)-5-(2,5-difluorophenyl)-1,3,4-oxadiazol-3(2H)-yl)-2,2-dimethylpropan-1-one |
| 3-carboxyphenyl | t-butyl | 3-(2-(3-aminopropyl)-5-(2,5-difluorophenyl)-3-pivaloyl-2,3-dihydro-1,3,4-oxadiazol-2-yl)benzoic acid |
| 3-cyanophenyl | t-butyl | 4-(2-(3-aminopropyl)-5-(2,5-difluorophenyl)-3-pivaloyl-2,3-dihydro-1,3,4-oxadiazol-2-yl)benzonitrile |
| 3,4-dichlorophenyl | t-butyl | 1-(2-(3-aminopropyl)-2-(3,4-dichlorophenyl)-5-(2,5-difluorophenyl)-1,3,4-oxadiazol-3(2H)-yl)-2,2-dimethylpropan-1-one |
| 3-fluorophenyl | t-butyl | 1-(2-(3-aminopropyl)-5-(2,5-difluorophenyl)-2-(3-fluorophenyl)-1,3,4-oxadiazol-3(2H)-yl)-2,2-dimethylpropan-1-one |
| 3-chlorophenyl | t-butyl | 1-(2-(3-aminopropyl)-2-(3-chlorophenyl)-5-(2,5-difluorophenyl)-1,3,4-oxadiazol-3(2H)-yl)-2,2-dimethylpropan-1-one |
| 4-fluorophenyl | (S)-2-methoxyethyl | (2S)-1-(2-(3-aminopropyl)-5-(2,5-difluorophenyl)-2-(4-fluorophenyl)-1,3,4-oxadiazol-3(2H)-yl)-2-methoxypropan-1-one |
| 3-fluorophenyl | (S)-2-methoxyethyl | (2S)-1-(2-(3-aminopropyl)-5-(2,5-difluorophenyl)-2-(3-fluorophenyl)-1,3,4-oxadiazol-3(2H)-yl)-2-methoxypropan-1-one |
| 2-chlorophenyl | (S)-2-methoxyethyl | (2S)-1-(2-(3-aminopropyl)-2-(2-chlorophenyl)-5-(2,5-difluorophenyl)-1,3,4-oxadiazol-3(2H)-yl)-2-methoxypropan-1-one |
| 3-methylphenyl | iso-Propyl | 1-(2-(3-aminopropyl)-5-(2,5-difluorophenyl)-2-m-tolyl-1,3,4-oxadiazol-3(2H)-yl)-2-methylpropan-1-one |
| 3-ethylphenyl | iso-Propyl | 1-(2-(3-aminopropyl)-5-(2,5-difluorophenyl)-2-(3-ethylphenyl)-1,3,4-oxadiazol-3(2H)-yl)-2-methylpropan-1-one |
| 3-pyridyl | iso-Propyl | 1-(2-(3-aminopropyl)-5-(2,5-difluorophenyl)-2-(pyridin-3-yl)-1,3,4-oxadiazol-3(2H)-yl)-2-methylpropan-1-one |
| 5-methylthiophen-2-yl | iso-Propyl | 1-(2-(3-aminopropyl)-5-(2,5-difluorophenyl)-2-(5-methylthiophen-2-yl)-1,3,4-oxadiazol-3(2H)-yl)-2-methylpropan-1-one |
| 1-methyl-1H-imidazol-2-yl) | iso-Propyl | 1-(2-(3-aminopropyl)-5-(2,5-difluorophenyl)-2-(1-methyl-1H-imidazol-2-yl)-1,3,4-oxadiazol-3(2H)-yl)-2-methylpropan-1-one |
| 2-methylthiazol-4-yl | iso-Propyl | 1-(2-(3-aminopropyl)-5-(2,5-difluorophenyl)-2-(2-methylthiazol-4-yl)-1,3,4-oxadiazol-3(2H)-yl)-2-methylpropan-1-one |
| 2-methylphenyl | iso-Propyl | 1-(2-(3-aminopropyl)-5-(2,5-difluorophenyl)-2-o-tolyl-1,3,4-oxadiazol-3(2H)-yl)-2-methylpropan-1-one |
| 2-pyridyl | iso-Propyl | 1-(2-(3-aminopropyl)-5-(2,5-difluorophenyl)-2-(pyridin-2-yl)-1,3,4-oxadiazol-3(2H)-yl)-2-methylpropan-1-one |
| 2-(1H-imidazol-4-yl)- | iso-Propyl | 1-(2-(3-aminopropyl)-5-(2,5-difluorophenyl)-2-(1H-imidazol-4-yl)-1,3,4-oxadiazol-3(2H)-yl)-2-methylpropan-1-one |
| 3-amino-1H-pyrazol-5-yl | iso-Propyl | 1-(2-(3-amino-1H-pyrazol-5-yl)-2-(3-aminopropyl)-5-(2,5-difluorophenyl)-1,3,4-oxadiazol-3(2H)-yl)-2-methylpropan-1-one |

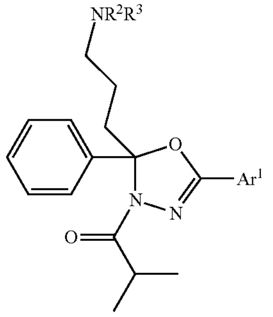

| $NR^2R^3$ | $Ar^1$ | Name |
|---|---|---|
| $NH_2$ | 2-fluorophenyl | 1-(2-(3-aminopropyl)-5-(2-fluorophenyl)-2-phenyl-1,3,4-oxadiazol-3(2H)-yl)-2-methylpropan-1-one |
| $NH_2$ | 2-chlorophenyl | 1-(2-(3-aminopropyl)-5-(2-chlorophenyl)-2-phenyl-1,3,4-oxadiazol-3(2H)-yl)-2-methylpropan-1-one |
| NH-Ala-Ala | 2,5-difluorophenyl | |
| $NHC(=O)(CH_2)_2NMe_2$ | 2,5-difluorophenyl | N-(3-(5-(2,5-difluorophenyl)-3-isobutyryl-2-phenyl-2,3-dihydro-1,3,4-oxadiazol-2-yl)propyl)-3-(dimethylamino)propanamide |
| 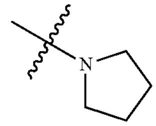 [SMILES: *N1CCCC1] | 2,5-difluorophenyl | 1-(5-(2,5-difluorophenyl)-2-phenyl-2-(3-(pyrrolidin-1-yl)propyl)-1,3,4-oxadiazol-3-(2H)-yl)-2-methylpropan-1-one |
| 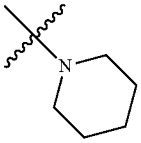 [SMILES: *N1CCCCC1] | 2,5-difluorophenyl | 1-(5-(2,5-difluorophenyl)-2-phenyl-2-(3-(piperidin-l-yl)propyl)-1,3,4-oxadiazol-3(2H)-yl)-2-methylpropan-1-one |
| 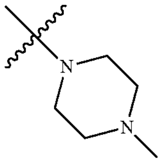 [SMILES: *N1CCN(C)CC1] | 2,5-difluorophenyl | 1-(5-(2,5-difluorophenyl)-2-(3-(4-methylpiperazin-1-yl)propyl)-2-phenyl-1,3,4-oxadiazol-3(2H)-yl)-2-methylpropan-1-one |

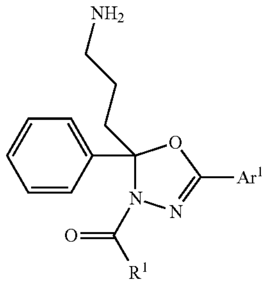

| $R^1$ | $Ar^1$ | Name |
|---|---|---|
| t-butyl | 2-fluorophenyl | 1-(2-(3-aminopropyl)-5-(2-fluorophenyl)-2-phenyl-1,3,4-oxadiazol-3(2H)-yl)-2,2-dimethylpropan-1-one |
| t-butyl | 2-chlorophenyl | 1-(2-(3-aminopropyl)-5-(2-chlorophenyl)-2-phenyl-1,3,4-oxadiazol-3(2H)-yl)-2,2-dimethylpropan-1-one |

-continued

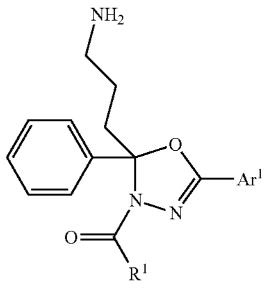

| $R^1$ | $Ar^1$ | Name |
|---|---|---|
| t-butyl | 3-fluorophenyl | 1-(2-(3-aminopropyl)-5-(3-fluorophenyl)-2-phenyl-1,3,4-oxadiazol-3(2H)-yl)-2,2-dimethylpropan-1-one |
| t-butyl | 3-chlorophenyl | 1-(2-(3-aminopropyl)-5-(3-chlorophenyl)-2-phenyl-1,3,4-oxadiazol-3(2H)-yl)-2,2-dimethylpropan-1-one |
| t-butyl | 2-fluoro-5-chlorophenyl | 1-(2-(3-aminopropyl)-5-(5-chloro-2-fluorophenyl)-2-phenyl-1,3,4-oxadiazol-3(2H)-yl)-2,2-dimethylpropan-1-one |
| t-butyl | 2-chloro-5-methylphenyl | 1-(2-(3-aminopropyl)-5-(2-chloro-5-methylphenyl)-2-phenyl-1,3,4-oxadiazol-3(2H)-yl)-2,2-dimethylpropan-1-one |
| t-butyl | 2-trifluoro methyl-5-fluorophenyl | 1-(2-(3-aminopropyl)-5-(5-fluoro-2-(trifluoromethyl)phenyl)-2-phenyl-1,3,4-oxadiazol-3(2H)-yl)-2,2-dimethylpropan-l-one |
| (S)-2-methoxyethyl | 2-chloro-5-fluorophenyl | (2S)-1-(2-(3-aminopropyl)-5-(2-chloro-5-fluorophenyl)-2-phenyl-1,3,4-oxadiazol-3(2H)-yl)-2-methoxypropan-1-one |
| (S)-2-methoxyethyl | 2,5-dichlorophenyl | (2S)-1-(2-(3-aminopropyl)-5-(2,5-dichlorophenyl)-2-phenyl-1,3,4-oxadiazol-3(2H)-yl)-2-methoxypropan-1-one |
| (S)-2-methoxyethyl | 2-chlorophenyl | (2S)-1-(2-(3-aminopropyl)-5-(2-chlorophenyl)-2-phenyl-1,3,4-oxadiazol-3(2H)-yl)-2-methoxypropan-1-one |
| (S)-2-methoxyethyl | 2-fluorophenyl | (2S)-1-(2-(3-aminopropyl)-5-(2-fluorophenyl)-2-phenyl-1,3,4-oxadiazol-3(2H)-yl)-2-methoxypropan-1-one |
| (S)-2-methoxyethyl | 3-chlorophenyl | (2S)-1-(2-(3-aminopropyl)-5-(3-chlorophenyl)-2-phenyl-1,3,4-oxadiazol-3(2H)-yl)-2-methoxypropan-1-one |
| (S)-2-methoxyethyl | 3-fluorophenyl | (2S)-1-(2-(3-aminopropyl)-5-(3-fluorophenyl)-2-phenyl-1,3,4-oxadiazol-3(2H)-yl)-2-methoxypropan-1-one |
| (S)-2-methoxyethyl | 2-fluoro-5-methoxyphenyl | (2S)-1-(2-(3-aminopropyl)-5-(2-fluoro-5-methoxyphenyl)-2-phenyl-1,3,4-oxadiazol-3(2H)-yl)-2-methoxypropan-1-one |
| (S)-2-methoxyethyl | 2,3-dichlorophenyl | (2S)-1-(2-(3-aminopropyl)-5-(2,3-dichlorophenyl)-2-phenyl-1,3,4-oxadiazol-3(2H)-yl)-2-methoxypropan-1-one |
| (S)-2-methoxyethyl | 3,4-dichlorophenyl | (2S)-1-(2-(3-aminopropyl)-5-(3,4-dichlorophenyl)-2-phenyl-1,3,4-oxadiazol-3(2H)-yl)-2-methoxypropan-1-one |
| (S)-2-methoxyethyl | 3,5-dichlorophenyl | (2S)-1-(2-(3-aminopropyl)-5-(3,5-dichlorophenyl)-2-phenyl-1,3,4-oxadiazol-3(2H)-yl)-2-methoxypropan-1-one |
| (S)-2-methoxyethyl | thiophen-2-yl | (2S)-1-(2-(3-aminopropyl)-2-phenyl-5-(thiophen-2-yl)-1,3,4-oxadiazol-3(2H)-yl)-2-methoxypropan-1-one |
| (S)-2-methoxyethyl | thiophen-3-yl | (2S)-1-(2-(3-aminopropyl)-2-phenyl-5-(thiophen-3-yl)-1,3,4-oxadiazol-3(2H)-yl)-2-methoxypropan-1-one |
| (S)-2-methoxyethyl | 5-chlorothiophen-2-yl | (2S)-1-(2-(3-aminopropyl)-5-(5-chlorothiophen-2-yl)-2-phenyl-1,3,4-oxadiazol-3(2H)-yl)-2-methoxypropan-1-one |
| (S)-2-methoxyethyl | 2-pyridyl | (2S)-1-(2-(3-aminopropyl)-2-phenyl-5-(pyridin-2-yl)-1,3,4-oxadiazol-3(2H)-yl)-2-methoxypropan-1-one |
| (S)-2-methoxyethyl | 3-pyridyl | (2S)-1-(2-(3-aminopropyl)-2-phenyl-5-(pyridin-3-yl)-1,3,4-oxadiazol-3(2H)-yl)-2-methoxypropan-1-one |
| (S)-2-methoxyethyl | 4-chloropyridin-3-yl | (2S)-1-(2-(3-aminopropyl)-5-(4-chloropyridin-3-yl)-2-phenyl-1,3,4-oxadiazol-3(2H)-yl)-2-methoxypropan-1-one |
| (S)-2-methoxyethyl | 3-chloropyridin-2-yl | (2S)-1-(2-(3-aminopropyl)-5-(3-chloropyridin-2-yl)-2-phenyl-1,3,4-oxadiazol-3(2H)-yl)-2-methoxypropan-1-one |

-continued

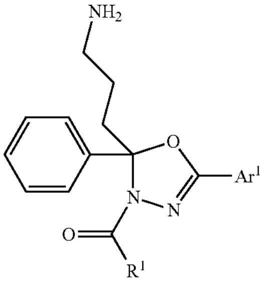

| $R^1$ | $Ar^1$ | Name |
|---|---|---|
| acetyl | 2,5-difluorophenyl | 1-(2-(3-aminopropyl)-5-(2,5-difluorophenyl)-2-phenyl-1,3,4-oxadiazol-3(2H)-yl)ethanone |
| t-butyl | 2-fluoro-5-methoxyphenyl | 1-(2-(3-aminopropyl)-5-(2-fluoro-5-methoxyphenyl)-2-phenyl-1,3,4-oxadiazol-3(2H)-yl)-2,2-dimethylpropan-1-one |
| t-butyl | 3,6-difluoropyridin-2-yl | 1-(2-(3-aminopropyl)-5-(3,6-difluoropyridin-2-yl)-2-phenyl-1,3,4-oxadiazol-3(2H)-yl)-2,2-dimethylpropan-l-one |
| t-butyl | 4-fluoropyridin-3-yl | 1-(2-(3-aminopropyl)-5-(4-fluoropyridin-3-yl)-2-phenyl-1,3,4-oxadiazol-3(2H)-yl)-2,2-dimethylpropan-1-one |

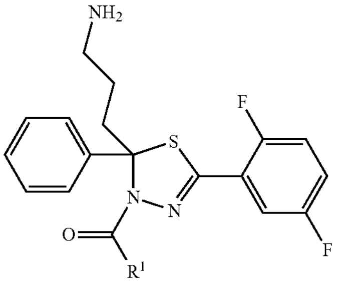

| $R^1$ | Name |
|---|---|
| 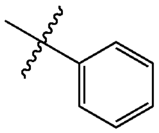 [SMILES: *c1ccccc1] | (2-(3-aminopropyl)-5-(2,5-difluorophenyl)-2-phenyl-1,3,4-thiadiazol-3(2H)-yl)(phenyl)methanone |
| 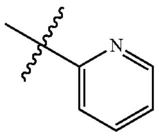 [SMILES: *c1ccccn1] | (2-(3-aminopropyl)-5-(2,5-difluorophenyl)-2-phenyl-1,3,4-thiadiazol-3(2H)-yl)(pyridin-2-yl)methanone |
| 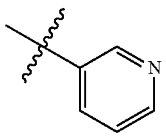 [SMILES: *c1cccnc1] | (2-(3-aminopropyl)-5-(2,5-difluorophenyl)-2-phenyl-1,3,4-thiadiazol-3(2H)-yl)(pyridin-3-yl)methanone |
| 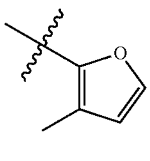 [SMILES: *c1occc1C] | (2-(3-aminopropyl)-5-(2,5-difluorophenyl)-2-phenyl-1,3,4-thiadiazol-3(2H)-yl)(3-methylfuran-2-yl)methanone |

-continued

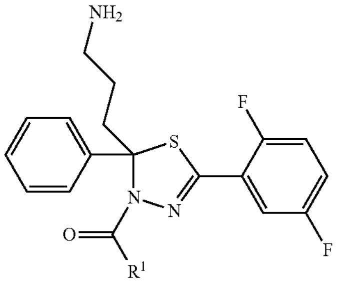

| $R^1$ | Name |
|---|---|
| 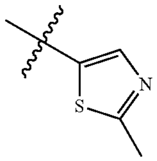 [SMILES: *c1cnc(C)s1] | (2-(3-aminopropyl)-5-(2,5-difluorophenyl)-2-phenyl-1,3,4-thiadiazol-3(2H)-yl)(2-methylthiazol-5-yl)methanone |
| 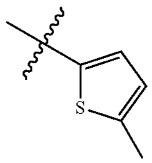 [SMILES: *c1ccc(C)s1] | (2-(3-aminopropyl)-5-(2,5-difluorophenyl)-2-phenyl-1,3,4-thiadiazol-3(2H)-yl)(5-methylthiophen-2-yl)methanone |
| 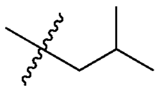 [SMILES: *CC(C)C] | 1-(2-(3-aminopropyl)-5-(2,5-difluorophenyl)-2-phenyl-1,3,4-thiadiazol-3(2H)-yl)-3-methylbutan-1-one |
| 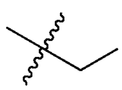 | 1-(2-(3-aminopropyl)-5-(2,5-difluorophenyl)-2-phenyl-1,3,4-thiadiazol-3(2H)-yl)propan-1-one |

-continued

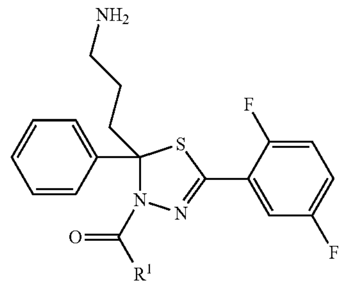

| R1 | Name |
|---|---|
| 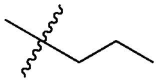 [SMILES: *CCC] | 1-(2-(3-aminopropyl)-5-(2,5-difluorophenyl)-2-phenyl-1,3,4-thiadiazol-3(2H)-yl)butan-1-one |
| 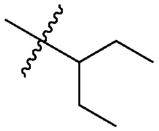 [SMILES: *C(CC)CC] | 1-(2-(3-aminopropyl)-5-(2,5-difluorophenyl)-2-phenyl-1,3,4-thiadiazol-3(2H)-yl)-2-ethylbutan-1-one |
| 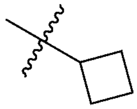 [SMILES: *C1CCC1] | (2-(3-aminopropyl)-5-(2,5-difluorophenyl)-2-phenyl-1,3,4-thiadiazol-3(2H)-yl)(cyclobutyl)methanone |
| 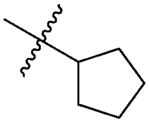 [SMILES: *C1CCCC1] | (2-(3-aminopropyl)-5-(2,5-difluorophenyl)-2-phenyl-1,3,4-thiadiazol-3(2H)-yl)(cyclopentyl)methanone |
| 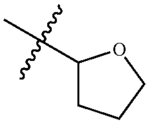 [SMILES: *C1CCCO1] | (2-(3-aminopropyl)-5-(2,5-difluorophenyl)-2-phenyl-1,3,4-thiadiazol-3(2H)-yl)(tetrahydrofuran-2-yl)methanone |
| 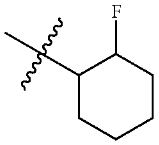 [SMILES: *C1CCCCC1F] | (2-(3-aminopropyl)-5-(2,5-difluorophenyl)-2-phenyl-1,3,4-thiadiazol-3(2H)-yl)(2-fluorocyclohexyl)methanone |
| 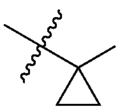 [SMILES: *C1(C)CC1] | (2-(3-aminopropyl)-5-(2,5-difluorophenyl)-2-phenyl-1,3,4-thiadiazol-3(2H)-yl)(1-methylcyclopropyl)methanone |
| 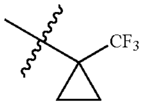 [SMILES: *C1(C(F)(F)F)CC1] | (2-(3-aminopropyl)-5-(2,5-difluorophenyl)-2-phenyl-1,3,4-thiadiazol-3(2H)-yl)(1-trifluoromethyl)cyclopropyl)methanone |
| 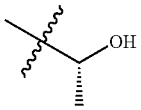 [SMILES: *[C@@H](C)O] | (2R)-1-(2-(3-aminopropyl)-5-(2,5-difluorophenyl)-2-phenyl-1,3,4-thiadiazol-3(2H)-yl)-2-hydroxypropan-1-one |

-continued

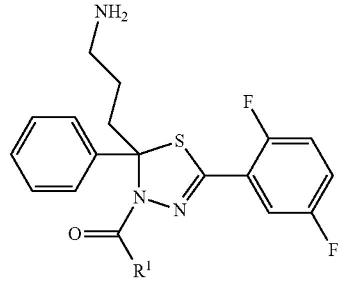

| R1 | Name |
|---|---|
| 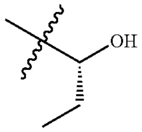 [SMILES: *[C@H](O)CC] | (2R)-1-(2-(3-aminopropyl)-5-(2,5-difluorophenyl)-2-phenyl-1,3,4-thiadiazol-3(2H)-yl)-2-hydroxybutan-1-one |
| 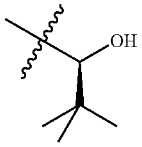 [SMILES: *[C@@H](O)C(C)(C)C] | (2S)-1-(2-(3-aminopropyl)-5-(2,5-difluorophenyl)-2-phenyl-1,3,4-thiadiazol-3(2H)-yl)-2-hydroxy-3,3-dimethylbutan-1-one |
| 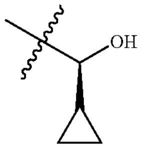 [SMILES: *[C@@H](O)C1CC1] | (2S)-1-(2-(3-aminopropyl)-5-(2,5-difluorophenyl)-2-phenyl-1,3,4-thiadiazol-3(2H)-yl)-2-cyclopropyl-2-hydroxyethanone |
| 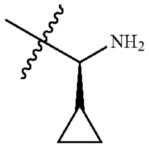 [SMILES: *[C@@H](N)C1CC1] | (2S)-2-amino-1-(2-(3-aminopropyl)-5-(2,5-difluorophenyl)-2-phenyl-1,3,4-thiadiazol-3(2H)-yl)-2-cyclopropylethanone |
| 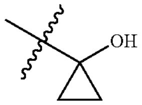 [SMILES: *C1(O)CC1] | (2-(3-aminopropyl)-5-(2,5-difluorophenyl)-2-phenyl-1,3,4-thiadiazol-3(2H)-yl)(1-hydroxycyclopropyl)methanone |
| 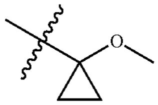 [SMILES: *C1(OC)CC1] | (2-(3-aminopropyl)-5-(2,5-difluorophenyl)-2-phenyl-1,3,4-thiadiazol-3(2H)-yl)(1-methoxycyclopropyl)methanone |
| 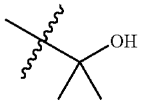 [SMILES: *C(C)(C)O] | 1-(2-(3-aminopropyl)-5-(2,5-difluorophenyl)-2-phenyl-1,3,4-thiadiazol-3(2H)-yl)-2-hydroxy-2-methylpropan-1-one |
| 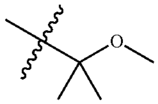 [SMILES: *C(C)(C)OC] | 1-(2-(3-aminopropyl)-5-(2,5-difluorophenyl)-2-phenyl-1,3,4-thiadiazol-3(2H)-yl)-2-methoxy-2-methylpropan-1-one |
| 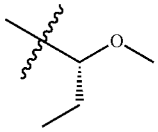 [SMILES: *[C@@H](CC)OC] | (2R)-1-(2-(3-aminopropyl)-5-(2,5-difluorophenyl)-2-phenyl-1,3,4-thiadiazol-3(2H)-yl)-2-methoxybutan-1-one |

-continued

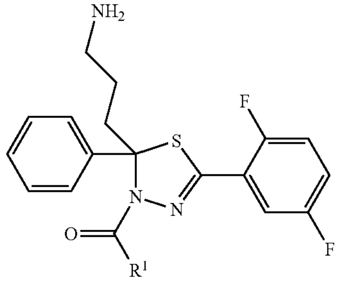

| R1 | Name |
|---|---|
| 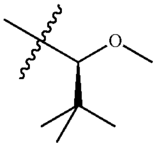 [SMILES: *[C@@H](OC)C(C)(C)C] | (2S)-1-(2-(3-aminopropyl)-5-(2,5-difluorophenyl)-2-phenyl-1,3,4-thiadiazo-3(2H)-yl)-2-methoxy-3,3-dimethylbutan-1-one |
| 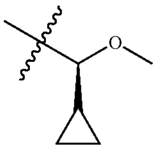 [SMILES: *[C@@H](OC)C1CC1] | (2S)-1-(2-(3-aminopropyl)-5-(2,5-difluorophenyl)-2-phenyl-1,3,4-thiadiazol-3(2H)-yl)-2-cyclopropyl-2-methoxyethanone |
| 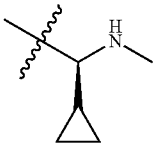 [SMILES: *[C@@H](NC)C1CC1] | (2S)-1-(2-(3-aminopropyl)-5-(2,5-difluorophenyl)-2-phenyl-1,3,4-thiadiazol-3(2H)-yl)-2-cyclopropyl-2-(methylamino)ethanone |
| 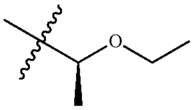 [SMILES: *[C@H](C)OCC] | (2S)-1-(2-(3-aminopropyl)-5-(2,5-difluorophenyl)-2-phenyl-1,3,4-thiadiazol-3(2H)-yl)-2-ethoxypropan-1-one |
| 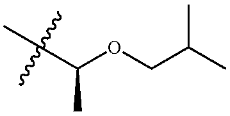 [SMILES: *[C@H](C)OCC(C)C] | (2S)-1-(2-(3-aminopropyl)-5-(2,5-difluorophenyl)-2-phenyl-1,3,4-thiadiazol-3(2H)-yl)-2-isobutoxypropan-1-one |
| 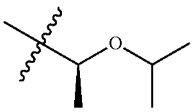 [SMILES: *[C@H](C)OC(C)C] | (2S)-1-(2-(3-aminopropyl)-5-(2,5-difluorophenyl)-2-phenyl-1,3,4-thiadiazol-3(2H)-yl)-2-isopropoxypropan-1-one |
| 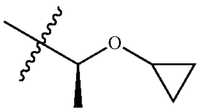 [SMILES: *[C@H](C)OC1CC1] | (2S)-1-(2-(3-aminopropyl)-5-(2,5-difluorophenyl)-2-phenyl-1,3,4-thiadiazol-3(2H)-yl)-2-cyclopropoxypropan-1-one |
| 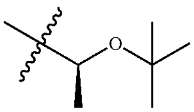 [SMILES: *[C@H](C)OC(C)(C)C] | (2S)-1-(2-(3-aminopropyl)-5-(2,5-difluorophenyl)-2-phenyl-1,3,4-thiadiazol-3(2H)-yl)-2-tert-butoxypropan-1-one |
| 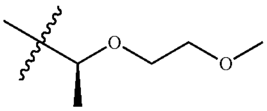 [SMILES: *[C@H](C)OCCOC] | (2S)-1-(2-(3-aminopropyl)-5-(2,5-difluorophenyl)-2-phenyl-1,3,4-thiadiazol-3(2H)-yl)-2-(2-methoxyethoxy)propan-1-one |

-continued

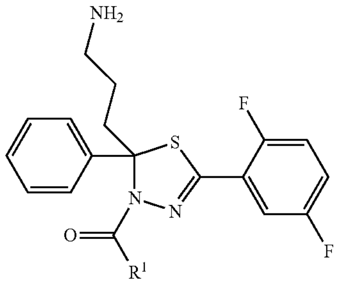

| R1 | Name |
|---|---|
| 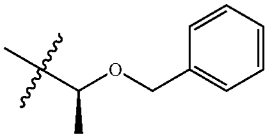 [SMILES: *[C@H](C)OCc1ccccc1] | (2S)-1-(2-(3-aminopropyl)-5-(2,5-difluorophenyl)-2-phenyl-1,3,4-thiadiazol-3(2H)-yl)-2-(benzyloxy)propan-1-one |
| 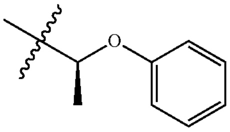 [SMILES: *[C@H](C)Oc1ccccc1] | (2S)-1-(2-(3-aminopropyl)-5-(2,5-difluorophenyl)-2-phenyl-1,3,4-thiadiazol-3(2H)-yl)-2-phenoxypropan-1-one |
| 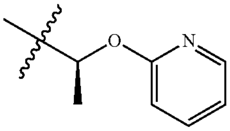 [SMILES: *[C@H](C)Oc1ccccn1] | (2S)-1-(2-(3-aminopropyl)-5-(2,5-difluorophenyl)-2-phenyl-1,3,4-thiadiazol-3(2H)-yl)-2-(pyridin-2-yloxy)propan-1-one |
| 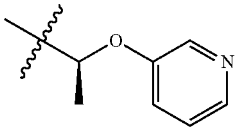 [SMILES: *[C@H](C)Oc1cccnc1] | (2S)-1-(2-(3-aminopropyl)-5-(2,5-difluorophenyl)-2-phenyl-1,3,4-thiadiazol-3(2H)-yl)-2-(pyridin-3-yloxy)propan-1-one |
| 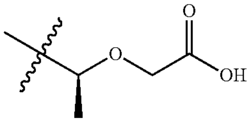 [SMILES: *[C@H](C)OCC(=O)O] | 2-((2S)-1-(2-(3-aminopropyl)-5-(2,5-difluorophenyl)-2-phenyl-1,3,4-thiadiazol-3(2H)-yl)-1-oxopropan-2-yloxy)acetic acid |
| 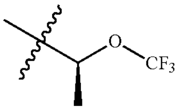 [SMILES: *[C@H](C)OC(F)(F)F] | (2S)-1-(2-(3-aminopropyl)-5-(2,5-difluorophenyl)-2-phenyl-1,3,4-thiadiazol-3(2H)-yl)-2-(trifluoromethoxy)propan-1-one |
| 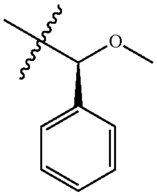 [SMILES: *[C@@H](OC)c1ccccc1] | (2S)-1-(2-(3-aminopropyl)-5-(2,5-difluorophenyl)-2-phenyl-1,3,4-thiadiazol-3(2H)-yl)-2-methoxy-2-phenylethanone |
| 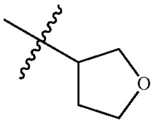 [SMILES: *C1CCOC1] | (2-(3-aminopropyl)-5-(2,5-difluorophenyl)-2-phenyl-1,3,4-thiadiazol-3(2H)-yl)(tetrahydrofuran-3-yl)methanone |
| 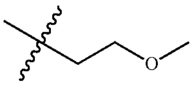 [SMILES: *CCOC] | 1-(2-(3-aminopropyl)-5-(2,5-difluorophenyl)-2-phenyl-1,3,4-thiadiazol-3(2H)-yl)-3-methoxypropan-1-one |

-continued

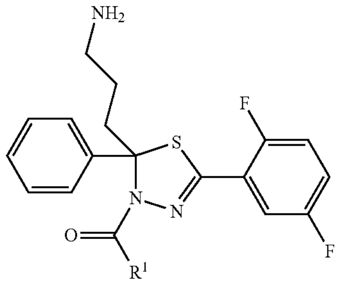

| $R^1$ | Name |
|---|---|
| 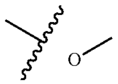 | methyl 2-(3-aminopropyl)-5-(2,5-difluorophenyl)-2-phenyl-1,3,4-thiadiazole-3(2H)-carboxylate |
| 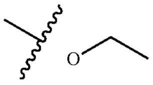 | ethyl 2-(3-aminopropyl)-5-(2,5-difluorophenyl)-2-phenyl-1,3,4-thiadiazole-3(2H)-carboxylate |
| 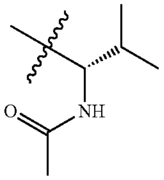 [SMILES: *[C@@H](NC(C)=O)C(C)C] | N-((2S)-1-(2-(3-aminopropyl)-5-(2,5-difluorophenyl)-2-phenyl-1,3,4-thiadiazol-3(2H)-yl)-3-methyl-1-oxobutan-2-yl)acetamide |

-continued

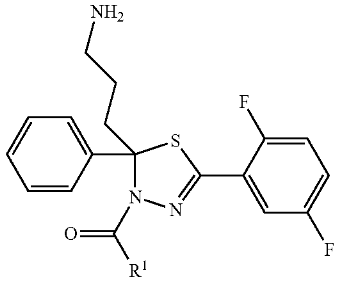

| $R^1$ | Name |
|---|---|
| 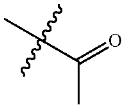 [SMILES: *C(C)=O] | 1-(2-(3-aminopropyl)-5-(2,5-difluorophenyl)-2-phenyl-1,3,4-thiadiazol-3(2H)-yl) propane-1,2-dione |
| 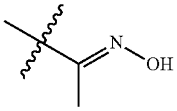 [SMILES: */C(C)=N/O] | (Z)-1-(2-(3-aminopropyl)-5-(2,5-difluorophenyl)-2-phenyl-1,3,4-thiadiazol-3(2H)-yl)-2-(hydroxyimino)propan-1-one |
| 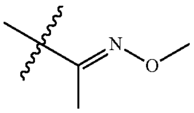 [SMILES: */C(C)=N/OC] | (Z)-1-(2-(3-aminopropyl)-5-(2,5-difluorophenyl)-2-phenyl-1,3,4-thiadiazol-3(2H)-yl)-2-(methoxyimino)propan-1-one |

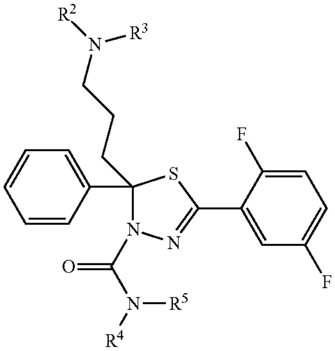

| $R^4$ | $R^5$ | $NR^2R^3$ | Name |
|---|---|---|---|
| H | H | $NH_2$ | 2-(3-aminopropyl)-5-(2,5-difluorophenyl)-2-phenyl-1,3,4-thiadiazole-3(2H)-carboxamide |
| H | Me | $NH_2$ | 2-(3-aminopropyl)-5-(2,5-difluorophenyl)-N-methyl-2-phenyl-1,3,4-thiadiazole-3(2H)-carboxamide |
| Me | Et | $NH_2$ | 2-(3-aminopropyl)-5-(2,5-difluorophenyl)-N-ethyl-N-methyl-2-phenyl-1,3,4-thiadiazole-3(2H)-carboxamide |
| Et | Et | $NH_2$ | 2-(3-aminopropyl)-5-(2,5-difluorophenyl)-N,N-diethyl-2-phenyl-1,3,4-thiadiazole-3(2H)-carboxamide |
| H | Et | $NH_2$ | 2-(3-aminopropyl)-5-(2,5-difluorophenyl)-N-ethyl-2-phenyl-1,3,4-thiadiazole-3(2H)-carboxamide |

-continued

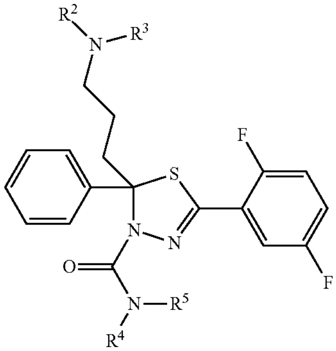

| $R^4$ | $R^5$ | $NR^2R^3$ | Name |
| --- | --- | --- | --- |
| H | 3-pyridyl | $NH_2$ | 2-(3-aminopropyl)-5-(2,5-difluorophenyl)-2-phenyl-N-(pyridin-3-yl)-1,3,4-thiadiazole-3(2H)-carboxamide |
| H | cyclopropyl | $NH_2$ | 2-(3-aminopropyl)-N-cyclopropyl-5-(2,5-difluorophenyl)-2-phenyl-1,3,4-thiadiazole-3(2H)-carboxamide |
| Me | 2-pyridyl | $NH_2$ | 2-(3-aminopropyl)-5-(2,5-difluorophenyl)-N-methyl-2-phenyl-N-(pyridin-2-yl)-1,3,4-thiadiazole-3(2H)-carboxamide |
| H | 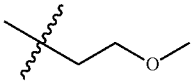 [SMILES: *CCOC] | $NH_2$ | 2-(3-aminopropyl)-5-(2,5-difluorophenyl)-N-(2-methoxyethyl)-2-phenyl-1,3,4-thiadiazole-3(2H)-carboxamide |
| Me | 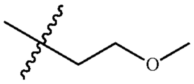 [SMILES: *CCOC] | $NH_2$ | 2-(3-aminopropyl)-5-(2,5-difluorophenyl)-N-(2-methoxyethyl)-N-methyl-2-phenyl-1,3,4-thiadiazole-3(2H)-carboxamide |
| Me | 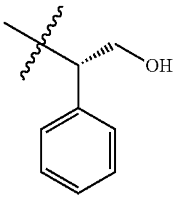 [SMILES: *[C@H](CO)c1ccccc1] | $NH_2$ | 2-(3-aminopropyl)-5-(2,5-difluorophenyl)-N-((S)-2-hydroxy-1-phenylethyl)-N-methyl-2-phenyl-1,3,4-thiadiazole-3(2H)-carboxamide |
| 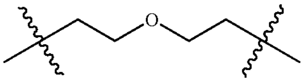 [SMILES: *CCOCC*] | | $NH_2$ | (2-(3-aminopropyl)-5-(2,5-difluorophenyl)-2-phenyl-1,3,4-thiadiazol-3(2H)-yl)(morpholino)methanone |
| H | OH | $NH_2$ | 2-(3-aminopropyl)-5-(2,5-difluorophenyl)-N-hydroxy-2-phenyl-1,3,4-thiadiazole-3(2H)-carboxamide |
| H | OMe | $NH_2$ | 2-(3-aminopropyl)-5-(2,5-difluorophenyl)-N-methoxy-2-phenyl-1,3,4-thiadiazole-3(2H)-carboxamide |
| H | OEt | $NH_2$ | 2-(3-aminopropyl)-5-(2,5-difluorophenyl)-N-ethoxy-2-phenyl-1,3,4-thiadiazole-3(2H)-carboxamide |
| H | 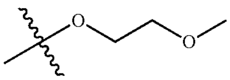 [SMILES: *OCCOC] | $NH_2$ | 2-(3-aminopropyl)-5-(2,5-difluorophenyl)-N-(2-methoxyethoxy)-2-phenyl-1,3,4-thiadiazole-3(2H)-carboxamide |

-continued

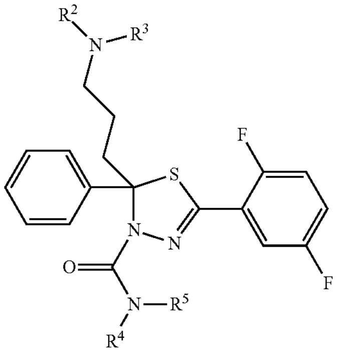

| $R^4$ | $R^5$ | $NR^2R^3$ | Name |
|---|---|---|---|
| H | 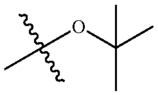 [SMILES: *OC(C)(C)C] | $NH_2$ | 2-(3-aminopropyl)-N-tert-butoxy-5-(2,5-difluorophenyl)-2-phenyl-1,3,4-thiadiazole-3(2H)-carboxamide |
| H | 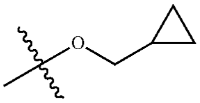 [SMILES: *OCC1CC1] | $NH_2$ | 2-(3-aminopropyl)-N-(cyclopropylmethoxy)-5-(2,5-difluorophenyl)-2-phenyl-1,3,4-thiadiazole-3(2H)-carboxamide |
| Me | OH | $NH_2$ | 2-(3-aminopropyl)-5-(2,5-difluorophenyl)-N-hydroxy-N-methyl-2-phenyl-1,3,4-thiadiazole-3(2H)-carboxamide |
| Me | OEt | $NH_2$ | 2-(3-aminopropyl)-5-(2,5-difluorophenyl)-N-ethoxy-N-methyl-2-phenyl-1,3,4-thiadiazole-3(2H)-carboxamide |
| Me | 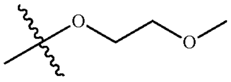 [SMILES: *OCCOC] | $NH_2$ | 2-(3-aminopropyl)-5-(2,5-difluorophenyl)-N-(2-methoxyethoxy)-N-methyl-2-phenyl-1,3,4-thiadiazole-3(2H)-carboxamide |
| Me | 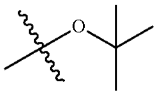 [SMILES: *OC(C)(C)C] | $NH_2$ | 2-(3-aminopropyl)-N-tert-butoxy-5-(2,5-difluorophenyl)-N-methyl-2-phenyl-1,3,4-thiadiazole-3(2H)-carboxamide |
| Me | 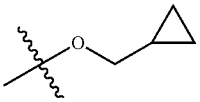 [SMILES: *OCC1CC1] | $NH_2$ | 2-(3-aminopropyl)-N-(cyclopropylmethoxy)-5-(2,5-difluorophenyl)-N-methyl-2-phenyl-1,3,4-thiadiazole-3(2H)-carboxamide |
| iPropyl | OH | $NH_2$ | 2-(3-aminopropyl)-5-(2,5-difluorophenyl)-N-hydroxy-N-isopropyl-2-phenyl-1,3,4-thiadiazole-3(2H)-carboxamide |
| | 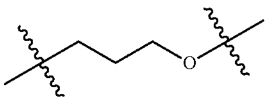 [SMILES: *CCCO*] | $NH_2$ | (2-(3-aminopropyl)-5-(2,5-difluorophenyl)-2-phenyl-1,3,4-thiadiazol-3(2H)-yl)(isoxazolidin-2-yl)methanone |
| Phenyl | 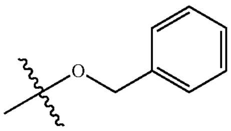 [SMILES: *OCc1ccccc1] | $NH_2$ | 2-(3-aminopropyl)-N-(benzyloxy)-5-(2,5-difluorophenyl)-N,2-diphenyl-1,3,4-thiadiazole-3(2H)-carboxamide |
| H | 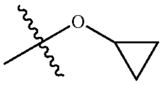 [SMILES: *OC1CC1] | $NH_2$ | 2-(3-aminopropyl)-N-cyclopropoxy-5-(2,5-difluorophenyl)-2-phenyl-1,3,4-thiadiazole-3(2H)-carboxamide |

-continued

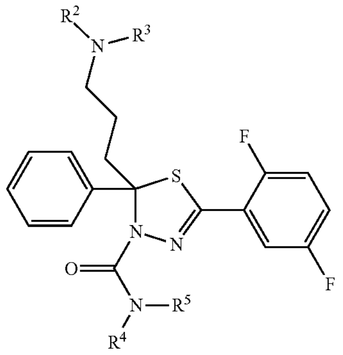

| $R^4$ | $R^5$ | $NR^2R^3$ | Name |
|---|---|---|---|
| H | 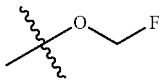 [SMILES: *OCF] | $NH_2$ | 2-(3-aminopropyl)-5-(2,5-difluorophenyl)-N-(fluoromethoxy)-2-phenyl-1,3,4-thiadiazole-3(2H)-carboxamide |
| Me | 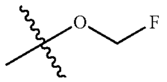 | $NH_2$ | 2-(3-aminopropyl)-5-(2,5-difluorophenyl)-N-(fluoromethoxy)-N-methyl-2-phenyl-1,3,4-thiadiazole-3(2H)-carboxamide |
| H | 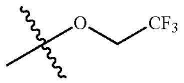 [SMILES: *OCC(F)(F)F] | $NH_2$ | 2-(3-aminopropyl)-5-(2,5-difluorophenyl)-2-phenyl-N-(2,2,2-trifluoroethoxy)-1,3,4-thiadiazole-3(2H)-carboxamide |
| Me | 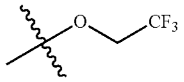 [SMILES: *OCC(F)(F)F] | $NH_2$ | 2-(3-aminopropyl)-5-(2,5-difluorophenyl)-N-methyl-2-phenyl-N-(2,2,2-trifluoroethoxy)-1,3,4-thiadiazole-3(2H)-carboxamide |
| Me | OMe | NHMe | 5-(2,5-difluorophenyl)-N-methoxy-N-methyl-2-(3-(methylamino)propyl)-2-phenyl-1,3,4-thiadiazole-3(2H)-carboxamide |
| Me | OMe | NHMe | 5-(2,5-difluorophenyl)-2-(3-(dimethylamino)propyl)-N-methoxy-N-methyl-2-phenyl-1,3,4-thiadiazole-3(2H)-carboxamide |
| Me | OMe | 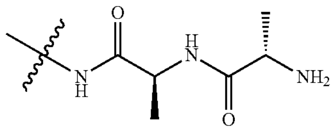 [SMILES: *NC(=O)[C@H](C)NC(=O)[C@H](C)N] | 2-(3-((S)-2-((S)-2-amonopropanamido)propanamido)propyl)-5-(2,5-difluorophenyl)-N-methoxy-N-methyl-2-phenyl-1,3,4-thiadiazole-3(2H)-carboxamide |
| Me | OEt | NHMe | 5-(2,5-difluorophenyl)-N-ethoxy-N-methyl-2-(3-(methylamino)propyl)-2-phenyl-1,3,4-thiadiazole-3(2H)-carboxamide |
| Me | OEt | $NMe_2$ | 5-(2,5-difluorophenyl)-2-(3-(dimethylamino)propyl)-N-ethoxy-N-methyl-2-phenyl-1,3,4-thiadiazole-3(2H)-carboxamide |
| Me | OEt | 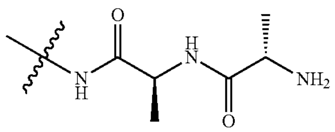 [SMILES: *NC(=O)[C@H](C)NC(=O)[C@H](C)N] | 2-(3-((S)-2-((S)-2-aminopropanamido)propanamido)propyl)-5-(2,5-difluorophenyl)-N-ethoxy-N-methyl-2-phenyl-1,3,4-thiadiazole-3(2H)-carboxamide |

-continued

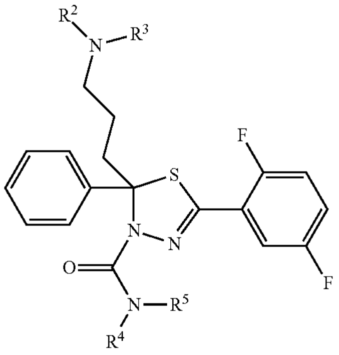

| R⁴ | R⁵ | NR²R³ | Name |
|---|---|---|---|
| Me | OEt | 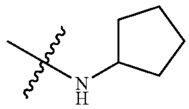 [SMILES: *NC1CCCC1] | 2-(3-((S)-2-((S)-2-aminopropanamido)propanamido)propyl)-5-(2,5-difluorophenyl)-N-ethoxy-N-methyl-2-phenyl-1,3,4-thiadiazole-3(2H)-carboxamide |

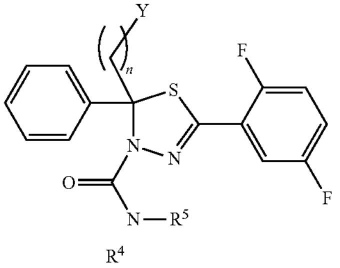

| $R^4$ | $R^5$ | n | Y | Name |
|---|---|---|---|---|
| H | OH | 2 | OH | 5-(2,5-difluorophenyl)-N-hydroxy-2-(2-hydroxethyl)-2-phenyl-1,3,4-thiadiazole-3(2H)-carboxamide |
| H | OH | 3 | OH | 5-(2,5-difluorophenyl)-N-hydroxy-2-(3-hydroxypropyl)-2-phenyl-1,3,4-thiadiazole-3(2H)-carboxamide |
| H | OH | 2 | $OP(O)(OH)_2$ | 2-(5-(2,5-difluorophenyl)-3-(hydroxycarbamoyl)-2-phenyl-2,3-dihydro-1,3,4-thiadiazol-2-yl)ethyl dihydrogen phosphate |
| H | OH | 3 | $OP(O)(OH)_2$ | 3-(5-(2,5-difluorophenyl)-3-(hydroxycarbamoyl)-2-phenyl-2,3-dihydro-1,3,4-thiadiazol-2-yl)propyl dihydrogen phosphate |
| Me | OH | 1 | OH | 5-(2,5-difluorophenyl)-N-hydroxy-2-(hydroxymethyl)-N-methyl-2-phenyl-1,3,4-thiadiazole-3(2H)-carboxamide |
| Me | OH | 2 | OH | 5-(2,5-difluorophenyl)-N-hydroxy-2-(2-hydroxyethyl)-N-methyl-2-phenyl-1,3,4-thiadiazole-3(2H)-carboxamide |
| Me | OH | 3 | OH | 5-(2,5-difluorophenyl)-N-hydroxy-2-(3-hydroxypropyl)-N-methyl-2-phenyl-1,3,4-thiadiazole-3(2H)-carboxamide |
| Me | OH | 1 | $OP(O)(OH)_2$ | (5-(2,5-difluorophenyl)-3-(hydroxy(methyl)carbamoyl)-2-phenyl-2,3-dihydro-1,3,4-thiadiazol-2-yl)methyl dihydrogen phosphate |
| Me | OH | 2 | $OP(O)(OH)_2$ | 2-(5-(2,5-difluorophenyl)-3-(hydroxy(methyl)carbamoyl)-2-phenyl-2,3-dihydro-1,3,4-thiadiazol-2-yl)ethyl dihydrogen phosphate |

-continued

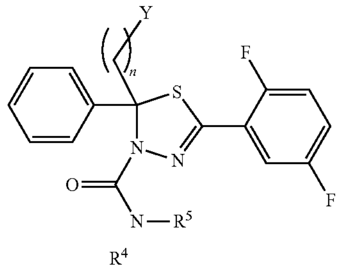

| $R^4$ | $R^5$ | n | Y | Name |
|---|---|---|---|---|
| Me | OH | 3 | $OP(O)(OH)_2$ | 3-(5-(2,5-difluorophenyl)-3-(hydroxy(methyl)carbamoyl)-2-phenyl-2,3-dihydro-1,3,4-thiadiazol-2-yl)propyl dihydrogen phosphate |
| H | OMe | 1 | OH | 5-(2,5-difluorophenyl)-2-(hydroxymethyl)-N-methoxy-2-phenyl-1,3,4-thiadiazole-3(2H)-carboxamide |
| H | OMe | 2 | OH | 5-(2,5-difluorophenyl)-2-(2-hydroxyethyl)-N-methoxy-2-phenyl-1,3,4-thiadiazole-3(2H)-carboxamide |
| H | OMe | 3 | OH | 5-(2,5-difluorophenyl)-2-(3-hydroxypropyl)-N-methoxy-2-phenyl-1,3,4-thiadiazole-3(2H)-carboxamide |
| H | OMe | 1 | $OP(O)(OH)_2$ | (5-(2,5-difluorophenyl)-3-(methoxycarbamoyl)-2-phenyl-2,3-dihydro-1,3,4-thiadiazol-2-yl)methyl dihydrogen phosphate |
| H | OMe | 2 | $OP(O)(OH)_2$ | 2-(5-(2,5-difluorophenyl)-3-(methoxycarbamoyl)-2-phenyl-2,3-dihydro-1,3,4-thiadiazol-2-yl)ethyl dihydrogen phosphate |
| H | OMe | 3 | $OP(O)(OH)_2$ | 3-(5-(2,5-difluorophenyl)-3-(methoxycarbamoyl)-2-phenyl-2,3-dihydro-1,3,4-thiadiazol-2-yl)propyl dihydrogen phosphate |
| Me | OMe | 1 | OH | 5-(2,5-difluorophenyl)-2-(hydroxymethyl)-N-methoxy-N-methyl-2-phenyl-1,3,4-thiadiazole-3(2H)-carboxamide |
| Me | OMe | 2 | OH | 5-(2,5-difluorophenyl)-2-(2-hydroxyethyl)-N-methoxy-N-methyl-2-phenyl-1,3,4-thiadiazole-3(2H)-carboxamide |
| Me | OMe | 3 | OH | 5-(2,5-difluorophenyl)-2-(3-hydroxypropyl)-N-methoxy-N-methyl-2-phenyl-1,3,4-thiadiazole-3(2H)-carboxamide |
| Me | OMe | 4 | OH | 5-(2,5-difluorophenyl)-2-(4-hydroxybutyl)-N-methoxy-N-methyl-2-phenyl-1,3,4-thiadiazole-3(2H)-carboxamide |
| Me | OMe | 1 | $OP(O)(OH)_2$ | (5-(2,5-difluorophenyl)-3-(methoxy(methyl)carbamoyl)-2-phenyl-2,3-dihydro-1,3,4-thiadiazol-2-yl)methyl dihydrogen phosphate |
| Me | OMe | 2 | $OP(O)(OH)_2$ | 2-(5-(2,5-difluorophenyl)-3-(methoxy(methyl)carbamoyl)-2-phenyl-2,3-dihydro-1,3,4-thiadiazol-2-yl)ethyl dihydrogen phosphate |
| Me | OMe | 3 | $OP(O)(OH)_2$ | 3-(5-(2,5-difluorophenyl)-3-(methoxy(methyl)carbamoyl)-2-phenyl-2,3-dihydro-1,3,4-thiadiazol-2-yl)propyl dihydrogen phosphate |
| Me | OMe | 4 | $OP(O)(OH)_2$ | 4-(5-(2,5-difluorophenyl)-3-(methoxy(methyl)carbamoyl)-2-phenyl-2,3-dihydro-1,3,4-thiadiazol-2-yl)butyl dihydrogen phosphate |
| H | OEt | 3 | OH | 5-(2,5-difluorophenyl)-N-ethoxy-2-(3-hydroxypropyl)-2-phenyl-1,3,4-thiadiazole-3(2H)-carboxamide |

-continued

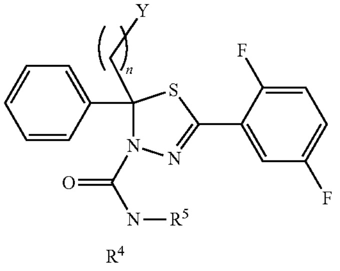

| $R^4$ | $R^5$ | n | Y | Name |
|---|---|---|---|---|
| H | OEt | 3 | $OP(O)(OH)_2$ | 3-(5-(2,5-difluorophenyl)-3-(ethoxycarbamoyl)-2-phenyl-2,3-dihydro-1,3,4-thiadiazol-2-yl)propyl dihydrogen phosphate |
| H | 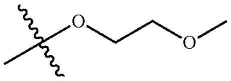 [SMILES: *OCCOC] | 3 | OH | 5-(2,5-difluorophenyl)-2-(3-hydroxypropyl)-N-(2-methoxyethoxy)-2-phenyl-1,3,4-thiadiazole-3(2H)-carboxamide |
| H | 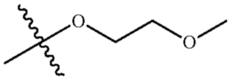 [SMILES: *OCCOC] | 3 | $OP(O)(OH)_2$ | 3-(5-(2,5-difluorophenyl)-3-(2-methoxyethoxycarbamoyl)-2-phenyl-2,3-dihydro-1,3,4-thiadiazol-2-yl)propyl dihydrogen phosphate |
| H | 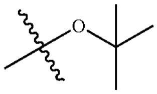 [SMILES: *OC(C)(C)C] | 3 | OH | N-tert-butoxy-5-(2,5-difluorophenyl)-2-(3-hydroxypropyl)-2-phenyl-1,3,4-thiadiazole-3(2H)-carboxamide |
| H | 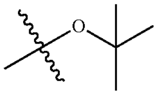 [SMILES: *OC(C)(C)C] | 3 | $OP(O)(OH)_2$ | 3-(3-(tert-butoxycarbamoyl)-5-(2,5-difluorophenyl)-2-phenyl-2,3-dihydro-1,3,4-thiadiazol-2-yl)propyl dihydrogen phosphate |
| H | 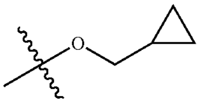 [SMILES: *OCC1CC1] | 3 | OH | N-(cyclopropylmethoxy)-5-(2,5-difluorophenyl)-2-(3-hydroxypropyl)-2-phenyl-1,3,4-thiadiazole-3(2H)-carboxamide |
| H | 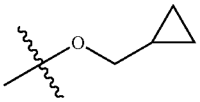 [SMILES: *OCC1CC1] | 3 | $OP(O)(OH)_2$ | 3-(3-(cyclopropylmethoxycarbamoyl)-5-(2,5-difluorophenyl)-2-phenyl-2,3-dihydro-1,3,4-thiadiazol-2-yl)propyl dihydrogen phosphate |
| Me | OEt | 3 | OH | 5-(2,5-difluorophenyl)-N-ethoxy-2-(3-hydroxypropyl)-N-methyl-2-phenyl-1,3,4-thiadiazole-3(2H)-carboxamide |
| Me | OEt | 3 | $OP(O)(OH)_2$ | 3-(5-(2,5-difluorophenyl)-3-(ethoxy(methyl)carbamoyl)-2-phenyl-2,3-dihydro-1,3,4-thiadiazol-2-yl)propyl dihydrogen phosphate |
| Me | 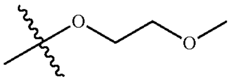 [SMILES: *OCCOC] | 3 | OH | 5-(2,5-difluorophenyl)-2-(3-hydroxypropyl)-N-(2-methoxyethoxy)-N-methyl-2-phenyl-1,3,4-thiadiazole-3(2H)-carboxamide |
| Me | 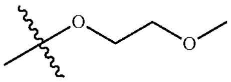 [SMILES: *OCCOC] | 3 | $OP(O)(OH)_2$ | 3-(5-(2,5-difluorophenyl)-3-((2-methoxyethoxy)(methyl)carbamoyl)-2-phenyl-2,3-dihydro-1,3,4-thiadiazol-2-yl)propyl dihydrogen phosphate |
| Me | 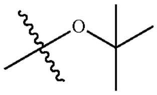 [SMILES: *OC(C)(C)C] | 3 | OH | N-tert-butoxy-5-(2,5-difluorophenyl)-2-(3-hydroxypropyl)-N-methyl-2-phenyl-1,3,4-thiadiazole-3(2H)-carboxamide |

-continued

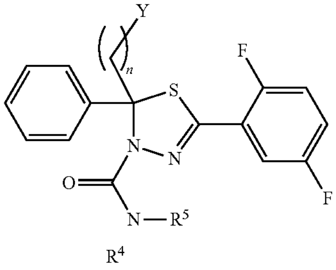

| $R^4$ | $R^5$ | n | Y | Name |
|---|---|---|---|---|
| Me | 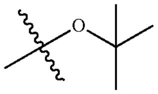 [SMILES: *OC(C)(C)C] | 3 | $OP(O)(OH)_2$ | 3-(3-(tert-butoxy(methyl)carbamoyl)-5-(2,5-difluorophenyl)-2-phenyl-2,3-dihydro-1,3,4-thiadiazol-2-yl)propyl dihydrogen phosphate |
| Me | 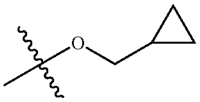 [SMILES: *OCC1CC1] | 3 | OH | N-(cyclopropylmethoxy)-5-(2,5-difluorophenyl)-2-(3-hydroxypropyl)-N-methyl-2-phenyl-1,3,4-thiadiazole-3(2H)-carboxamide |
| Me | 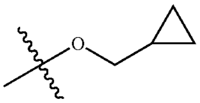 [SMILES: *OCC1CC1] | 3 | $OP(O)(OH)_2$ | 3-(3-((cyclopropylmethoxy)(methyl) carbamoyl)-5-(2,5-difluorophenyl)-2-phenyl-2,3-dihydro-1,3,4-thiadiazol-2-yl)propyl dihydrogen phosphate |
| i-propyl | OH | 3 | OH | 5-(2,5-difluorophenyl)-N-hydroxy-2-(3-hydroxypropyl)-N-isopropyl-2-phenyl-1,3,4-thiadiazole-3(2H)-carboxamide |
| i-propyl | OH | 3 | $OP(O)(OH)_2$ | 3-(5-(2,5-difluorophenyl)-3-(hydroxy(isopropyl)carbamoyl)-2-phenyl-2,3-dihydro-1,3,4-thiadiazol-2-yl)propyl dihydrogen phosphate |
| 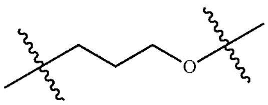 [SMILES: *CCCO*] | | 3 | OH | (5-(2,5-difluorophenyl)-2-(3-hydroxypropyl)-2-phenyl-1,3,4-thiadiazol-3(2H)-yl)(isoxazolidin-2-yl)methanone |
| 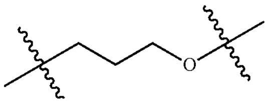 [SMILES: *CCCO*] | | 3 | $OP(O)(OH)_2$ | 3-(5-(2,5-difluorophenyl)-3-(isoxazolidine-2-carbonyl)-2-phenyl-2,3-dihydro-1,3,4-thiadiazol-2-yl)propyl dihydrogen phosphate |
| Phenyl | 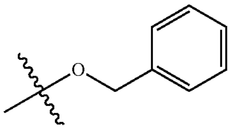 [SMILES: *OCc1ccccc1] | 3 | OH | N-(benzyloxy)-5-(2,5-difluorophenyl)-2-(3-hydroxypropyl)-N,2-diphenyl-1,3,4-thiadiazole-3(2H)-carboxamide |
| Phenyl | 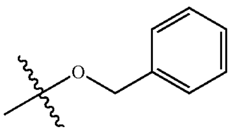 [SMILES: *OCc1ccccc1] | 3 | $OP(O)(OH)_2$ | 3-(3-(benzyloxy(phenyl)carbamoyl)-5-(2,5-difluorophenyl)-2-phenyl-2,3-dihydro-1,3,4-thiadiazol-2-yl)propyl dihydrogen phosphate |

-continued

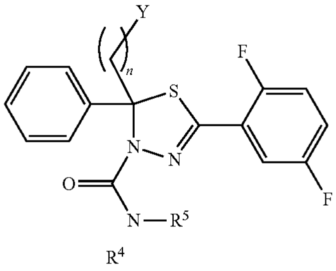

| $R^4$ | $R^5$ | n | Y | Name |
|---|---|---|---|---|
| H | 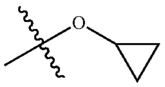 [SMILES: *OC1CC1] | 3 | OH | N-cyclopropoxy-5-(2,5-difluorophenyl)-2-(3-hydroxypropyl)-2-phenyl-1,3,4-thiadiazole-3(2H)-carboxamide |
| H | 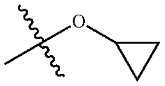 [SMILES: *OC1CC1] | 3 | $OP(O)(OH)_2$ | 3-(3-(cyclopropoxycarbamoyl)-5-(2,5-difluorophenyl)-2-phenyl-2,3-dihydro-1,3,4-thiadiazol-2-yl)propyl dihydrogen phosphate |
| H | 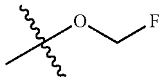 [SMILES: *OCF] | 3 | OH | 5-(2,5-difluorophenyl)-N-(fluoromethoxy)-2-(3-hydroxypropyl)-2-phenyl-1,3,4-thiadiazole-3(2H)-carboxamide |
| H | 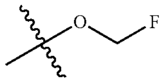 [SMILES: *OCF] | 3 | $OP(O)(OH)_2$ | 3-(5-(2,5-difluorophenyl)-3-(fluoromethoxycarbamoyl)-2-phenyl-2,3-dihydro-1,3,4-thiadiazol-2-yl)propyl dihydrogen phosphate |
| Me | 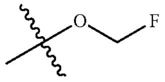 | 3 | OH | 5-(2,5-difluorophenyl)-N-(fluoromethoxy)-2-(3-hydroxypropyl)-N-methyl-2-phenyl-1,3,4-thiadiazole-3(2H)-carboxamide |
| Me | 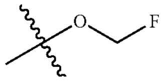 [SMILES: *OCF] | 3 | $OP(O)(OH)_2$ | 3-(5-(2,5-difluorophenyl)-3-((fluoromethoxy)(methyl)carbamoyl)-2-phenyl-2,3-dihydro-1,3,4-thiadiazol-2-yl)propyl dihydrogen phosphate |
| H | 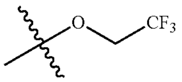 [SMILES: *OCC(F)(F)F] | 3 | OH | 5-(2,5-difluorophenyl)-2-(3-hydroxypropyl)-2-phenyl-N-(2,2,2-trifluoroethoxy)-1,3,4-thiadiazole-3(2H)-carboxamide |
| H | 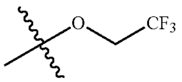 [SMILES: *OCC(F)(F)F] | 3 | $OP(O)(OH)_2$ | 3-(5-(2,5-difluorophenyl)-2-phenyl-3-(2,2,2-trifluoroethoxycarbamoyl)-2,3-dihydro-1,3,4-thiadiazol-2-yl)propyl dihydrogen phosphate |
| Me | 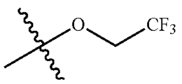 [SMILES: *OCC(F)(F)F] | 3 | OH | 5-(2,5-difluorophenyl)-2-(3-hydroxypropyl)-N-methyl-2-phenyl-N-(2,2,2-trifluoroethoxy)-1,3,4-thiadiazole-3(2H)-carboxamide |
| Me | 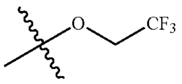 [SMILES: *OCC(F)(F)F] | 3 | $OP(O)(OH)_2$ | 3-(5-(2,5-difluorophenyl)-3-(methyl(2,2,2-trifluoroethoxy)carbamoyl)-2-phenyl-2,3-dihydro-1,3,4-thiadiazol-2-yl)propyl dihydrogen phosphate |

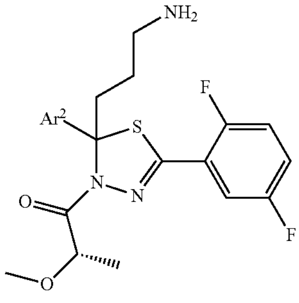

| Ar2 | Name |
|---|---|
| 4-fluorophenyl | (2S)-1-(2-(3-aminopropyl)-5-(2,5-difluorophenyl)-2-(4-fluorophenyl)-1,3,4-thiadiazol-3(2H)-yl)-2-methoxypropan-1-one |
| 4-methylphenyl | (2S)-1-(2-(3-aminopropyl)-5-(2,5-difluorophenyl)-2-p-tolyl-1,3,4-thiadiazol-3(2H)-yl)-2-methoxypropan-1-one |
| 4-chlorophenyl | (2S)-1-(2-(3-aminopropyl)-2-(4-chlorophenyl)-5-(2,5-difluorophenyl)-1,3,4-thiadiazol-3(2H)-yl)-2-methoxypropan-l-one |
| 4-bromophenyl | (2S)-1-(2-(3-aminopropyl)-2-(4-bromophenyl)-5-(2,5-difluorophenyl)-1,3,4-thiadiazol-3(2H)-yl)-2-methoxypropan-1-one |
| 4-t-butylphenyl | (2S)-1-(2-(3-aminopropyl)-2-(4-tert-butylphenyl)-5-(2,5-difluorophenyl)-1,3,4-thiadiazol-3(2H)-yl)-2-methoxypropan-1-one |
| 3,4-dimethylphenyl | (2S)-1-(2-(3-aminopropyl)-5-(2,5-difluorophenyl)-2-(3,4-dimethylphenyl)-1,3,4-thiadiazol-3(2H)-yl)-2-methoxypropan-1-one |
| 3-methylphenyl | (2S)-1-(2-(3-aminopropyl)-5-(2,5-difluorophenyl)-2-m-tolyl-1,3,4-thiadiazol-3(2H)-yl)-2-methoxypropan-1-one |
| 3,5-dimethylphenyl | (2S)-1-(2-(3-aminopropyl)-5-(2,5-difluorophenyl)-2-(3,5-dimethylphenyl)-1,3,4-thiadiazol-3(2H)-yl)-2-methoxypropan-1-one |
| 2-chlorophenyl | (2S)-1-(2-(3-aminopropyl)-2-(2-chlorophenyl)-5-(2,5-difluorophenyl)-1,3,4-thiadiazol-3(2H)-yl)-2-methoxypropan-1-one |
| 2-ethylphenyl | (2S)-1-(2-(3-aminopropyl)-5-(2,5-difluorophenyl)-2-(2-ethylphenyl)-1,3,4-thiadiazol-3(2H)-yl)-2-methoxypropan-1-one |
| 3-nitrophenyl | (2S)-1-(2-(3-aminopropyl)-5-(2,5-difluorophenyl)-2-(3-nitrophenyl)-1,3,4-thiadiazol-3(2H)-yl)-2-methoxypropan-1-one |
| 3-hydroxyphenyl | (2S)-1-(2-(3-aminopropyl)-5-(2,5-difluorophenyl)-2-(3-hydroxyphenyl)-1,3,4-thiadiazol-3(2H)-yl)-2-methoxypropan-1-one |
| 3-aminophenyl | (2S)-1-(2-(3-aminophenyl)-2-(3-aminopropyl)-5-(2,5-difluorophenyl)-1,3,4-thiadiazol-3(2H)-yl)-2-methoxypropan-1-one |

-continued

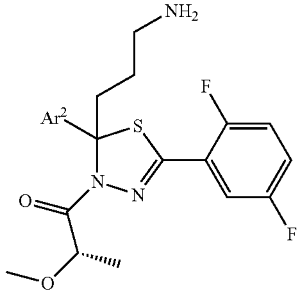

| Ar2 | Name |
|---|---|
| 3-carboxyphenyl | 3-(2-(3-aminopropyl)-5-(2,5-difluorophenyl)-3-((S)-2-methoxypropanoyl)-2,3-dihydro-l,3,4-thiadiazol-2-yl)benzoic acid |
| 3-cyanophenyl | 3-(2-(3-aminopropyl)-5-(2,5-difluorophenyl)-3-((S)-2-methoxypropanoyl)-2,3-dihydro-1,3,4-thiadiazol-2-yl)benzonitrile |
| 3,4-dichlorophenyl | (2S)-1-(2-(3-aminopropyl)-2-(3,4-dichlorophenyl)-5-(2,5-difluorophenyl)-l,3,4-thiadiazol-3(2H)-yl)-2-methoxypropan-1-one |
| 3-chlorophenyl | (2S)-1-(2-(3-aminopropyl)-2-(3-chlorophenyl)-5-(2,5-difluorophenyl)-1,3,4-thiadiazol-3(2H)-yl)-2-methoxypropan-1-one |
| 3-ethylphenyl | (2S)-1-(2-(3-aminopropyl)-5-(2,5-difluorophenyl)-2-(3-ethylphenyl)-1,3,4-thiadiazol-3(2H)-yl)-2-methoxypropan-1-one |
| 3-pyridyl | (2S)-1-(2-(3-aminopropyl)-5-(2,5-difluorophenyl)-2-(pyridin-3-yl)-1,3,4-thiadiazol-3(2H)-yl)-2-methoxypropan-1-one |
| 2-pyridyl | (2S)-1-(2-(3-aminopropyl)-5-(2,5-difluorophenyl)-2-(pyridin-2-yl)-1,3,4-thiadiazol-3(2H)-yl)-2-methoxypropan-1-one |
| 5-methylthiophen-2-yl | (2S)-1-(2-(3-aminopropyl)-5-(2,5-difluorophenyl)-2-(5-methylthiophen-2-yl)-1,3,4-thiadiazol-3(2H)-yl)-2-methoxypropan-1-one |
| 1-methyl-1H-imidazol-2-yl | (2S)-1-(2-(3-aminopropyl)-5-(2,5-difluorophenyl)-2-(1-methyl-1H-imidazol-2-yl)-1,3,4-thiadiazol-3(2H)-yl)-2-methoxypropan-1-one |
| 5-methylthiazol-2-yl | (2S)-1-(2-(3-aminopropyl)-5-(2,5-difluorophenyl)-2-(5-methylthiazol-2-yl)-1,3,4-thiadiazol-3(2H)-yl)-2-methoxypropan-1-one |

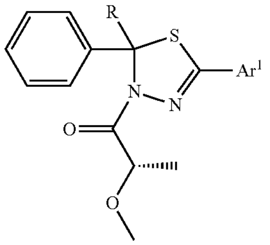

| R | $Ar^1$ | Name |
|---|---|---|
| 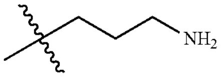 [SMILES: *CCCN] | 2-fluorophenyl | (2S)-1-(2-(3-aminopropyl)-5-(2-fluorophenyl)-2-phenyl-1,3,4-thiadiazol-3(2H)-yl)-2-methoxypropan-1-one |
| 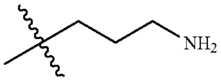 [SMILES: *CCCN] | 2-chlorophenyl | (2S)-1-(2-(3-aminopropyl)-5-(2-chlorophenyl)-2-phenyl-1,3,4-thiadiazol-3(2H)-yl)-2-methoxypropan-1-one |
| 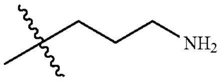 [SMILES: *CCCN] | 2-chloro-5-fluorophenyl | (2S)-1-(2-(3-aminopropyl)-5-(2-chloro-5-fluorophenyl)-2-phenyl-1,3,4-thiadiazol-3(2H)-yl)-2-methoxypropan-1-one |
| 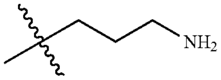 [SMILES: *CCCN] | 2-fluoro-5-chlorophenyl | (2S)-1-(2-(3-aminopropyl)-5-(5-chloro-2-fluorophenyl)-2-phenyl-1,3,4-thiadiazol-3(2H)-yl)-2-methoxypropan-1-one |
| 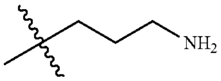 [SMILES: *CCCN] | 2,5-dichlorophenyl | (2S)-1-(2-(3-aminopropyl)-5-(2,5-dichlorophenyl)-2-phenyl-1,3,4-thiadiazol-3(2H)-yl)-2-methoxypropan-1-one |
| 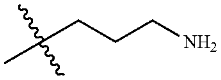 [SMILES: *CCCN] | 5-chloro-2-methylphenyl | (2S)-1-(2-(3-aminopropyl)-5-(5-chloro-2-methylphenyl)-2-phenyl-1,3,4-thiadiazol-3(2H)-yl)-2-methoxypropan-1-one |
| 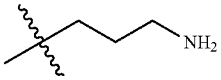 [SMILES: *CCCN] | 2-fluoro-5-trifluoromethyl phenyl | (2S)-1-(2-(3-aminopropyl)-5-(2-fluoro-5-(trifluoromethyl)phenyl)-2-phenyl-1,3,4-thiadiazol-3(2H)-yl)-2-methoxypropan-1-one |
| 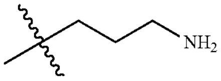 [SMILES: *CCCN] | 2-fluoro-5-methoxyphenyl | (2S)-1-(2-(3-aminopropyl)-5-(2-fluoro-5-methoxyphenyl)-2-phenyl-1,3,4-thiadiazol-3(2H)-yl)-2-methoxypropan-1-one |
| 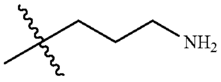 [SMILES: *CCCN] | 2,3-dichlorophenyl | (2S)-1-(2-(3-aminopropyl)-5-(2,3-dichlorophenyl)-2-phenyl-1,3,4-thiadiazol-3(2H)-yl)-2-methoxypropan-1-one |
| 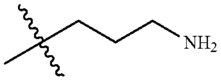 [SMILES: *CCCN] | 3,4-dichlorophenyl | (2S)-1-(2-(3-aminopropyl)-5-(3,4-dichlorophenyl)-2-phenyl-1,3,4-thiadiazol-3(2H)-yl)-2-methoxypropan-1-one |
| 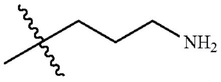 [SMILES: *CCCN] | 3,5-dichlorophenyl | (2S)-1-(2-(3-aminopropyl)-5-(3,5-dichlorophenyl)-2-phenyl-1,3,4-thiadiazol-3(2H)-yl)-2-methoxypropan-1-one |
| 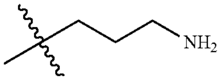 [SMILES: *CCCN] | thiophen-2-yl | (2S)-1-(2-(3-aminopropyl)-2-phenyl-5-(thiophen-2-yl)-1,3,4-thiadiazol-3(2H)-yl)-2-methoxypropan-1-one |
| 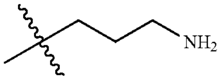 [SMILES: *CCCN] | thiophen-3-yl | (2S)-1-(2-(3-aminopropyl)-2-phenyl-5-(thiophen-3-yl)-1,3,4-thiadiazol-3(2H)-yl)-2-methoxypropan-1-one |

-continued

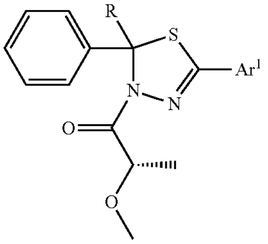

| R | $Ar^1$ | Name |
|---|---|---|
| 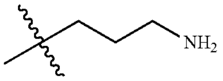 [SMILES: *CCCN] | 5-chloro thiophen-2-yl | (2S)-1-(2-(3-aminopropyl)-5-(5-chlorothiophen-2-yl)-2-phenyl-1,3,4-thiadiazol-3(2H)-yl)-2-methoxypropan-1-one |
| 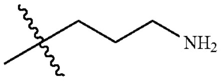 [SMILES: *CCCN] | 2-pyridyl | (2S)-1-(2-(3-aminopropyl)-2-phenyl-5-(pyridin-2-yl)-1,3,4-thiadiazol-3(2H)-yl)-2-methoxypropan-1-one |
| 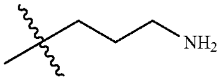 [SMILES: *CCCN] | 3-pyridyl | (2S)-1-(2-(3-aminopropyl)-2-phenyl-5-(pyridin-3-yl)-1,3,4-thiadiazol-3(2H)-yl)-2-methoxypropan-1-one |
| 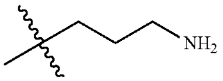 [SMILES: *CCCN] | 3-chloro pyridin-2-yl | (2S)-1-(2-(3-aminopropyl)-5-(3-chloropyridin-2-yl)-2-phenyl-1,3,4-thiadiazol-3(2H)-yl)-2-methoxypropan-1-one |
| 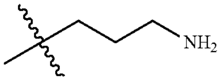 [SMILES: *CCCN] | 4-chloro pyridin-3-yl | (2S)-1-(2-(3-aminopropyl)-5-(4-chloropyridin-3-yl)-2-phenyl-1,3,4-thiadiazol-3(2H)-yl)-2-methoxypropan-1-one |
| 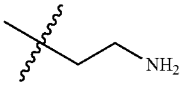 | 2,5-difluorophenyl | (2S)-1-(2-(2-aminoethyl)-5-(2,5-difluorophenyl)-2-phenyl-1,3,4-thiadiazol-3(2H)-yl)-2-methoxypropan-1-one |
| 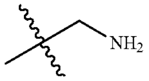 | 2,5-difluorophenyl | (2S)-1-(2-(aminomethyl)-5-(2,5-difluorophenyl)-2-phenyl-1,3,4-thiadiazol-3(2H)-yl)-2-methoxypropan-1-one |
| 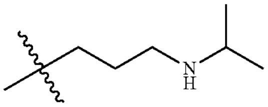 [SMILES: *CCCNC(C)C] | 2,5-difluorophenyl | (2S)-1-(5-(2,5-difluorophenyl)-2-(3-(isopropylamino)propyl)-2-phenyl-1,3,4-thiadiazol-3(2H)-yl)-2-methoxypropan-1-one |
| 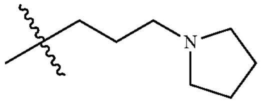 [SMILES: *CCCN1CCCC1] | 2,5-difluorophenyl | (2S)-1-(5-(2,5-difluorophenyl)-2-phenyl-2-(3-(pyrrolidin-1-yl)propyl)-1,3,4-thiadiazol-3(2H)-yl)-2-methoxypropan-1-one |
| 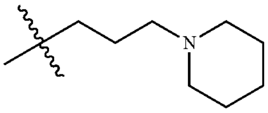 [SMILES: *CCCN1CCCCC1] | 2,5-difluorophenyl | (2S)-1-(5-(2,5-difluorophenyl)-2-phenyl-2-(3-(piperidin-1-yl)propyl)-1,3,4-thiadiazol-3(2H)-yl)-2-methoxypropan-1-one |
| 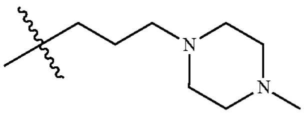 [SMILES: *CCCN1CCN(C)CC1] | 2,5-difluorophenyl | (2S)-1-(5-(2,5-difluorophenyl)-2-(3-(4-methylpiperazin-1-yl)propyl)-2-phenyl-1,3,4-thiadiazol-3(2H)-yl)-2-methoxypropan-1-one |
| 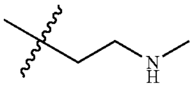 [SMILES: *CCNC] | 2,5-difluorophenyl | (2S)-1-(5-(2,5-difluorophenyl)-2-(2-(methylamino)ethyl)-2-phenyl-1,3,4-thiadiazol-3(2H)-yl)-2-methoxypropan-1-one |

-continued

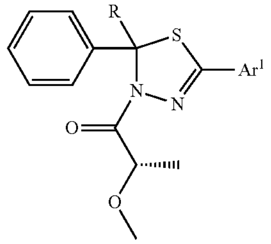

| R | $Ar^1$ | Name |
|---|---|---|
| 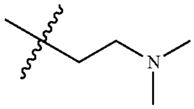 [SMILES: *CCN(C)C] | 2,5-difluorophenyl | (2S)-1-(5-(2,5-difluorophenyl)-2-(2-(dimethylamino)ethyl)-2-phenyl-1,3,4-thiadiazol-3(2H)-yl)-2-methoxypropan-1-one |
| 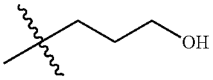 [SMILES: *CCCO] | 2,5-difluorophenyl | (2S)-1-(5-(2,5-difluorophenyl)-2-(3-hydroxypropyl)-2-phenyl-1,3,4-thiadiazol-3(2H)-yl)-2-methoxypropan-1-one |
| 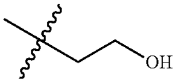 [SMILES: *CCO] | 2,5-difluorophenyl | (2S)-1-(5-(2,5-difluorophenyl)-2-(2-hydroxyethyl)-2-phenyl-1,3,4-thiadiazol-3(2H)-yl)-2-methoxypropan-1-one |
| 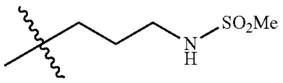 [SMILES: *CCCNS(C)(=O)=O] | 2,5-difluorophenyl | N-(3-(5-(2,5-difluorophenyl)-3-((S)-2-methoxypropanoyl)-2-phenyl-2,3-dihydro-1,3,4-thiadiazol-2-yl)propyl)methanesulfonamide |
| 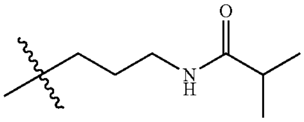 [SMILES: *CCCNC(=O)C(C)C] | 2,5-difluorophenyl | N-(3-(5-(2,5-difluorophenyl)-3-((S)-2-methoxypropanoyl)-2-phenyl-2,3-dihydro-1,3,4-thiadiazol-2-yl)propyl)isobutyramide |
| 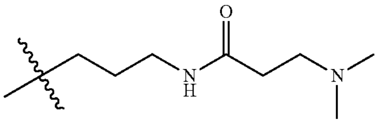 [SMILES: *CCCNC(=O)CCN(C)C] | 2,5-difluorophenyl | N-(3-(5-(2,5-difluorophenyl)-3-((S)-2-methoxypropanoyl)-2-phenyl-2,3-dihydro-1,3,4-thiadiazol-2-yl)propyl)-3-(dimethylamino)propanamide |

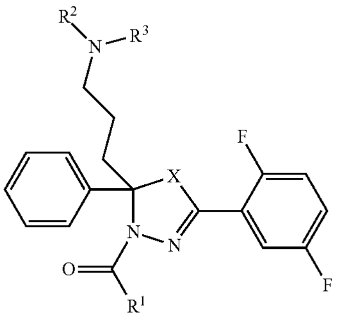

| X | $R^1$ | $NR^2R^3$ | Name |
|---|---|---|---|
| S | (S)-2-methoxyethyl | 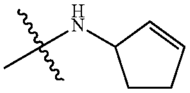 [SMILES: *NC1C=CCC1] | (2S)-1-(2-(3-(cyclopent-2-enylamino)propyl)-5-(2,5-difluorophenyl)-2-phenyl-1,3,4-thiadiazol-3(2H)-yl)-2-methoxypropan-1-one |

-continued

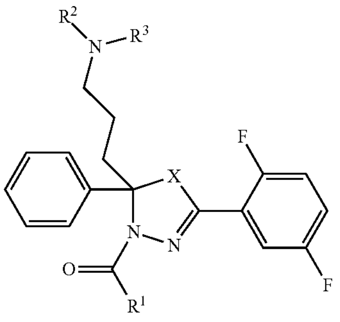

| X | $R^1$ | $NR^2R^3$ | Name |
|---|---|---|---|
| S | (S)-2-methoxyethyl | 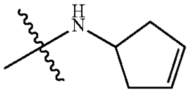 [SMILES: *NC1CC=CC1] | (2S)-1-(2-(3-(cyclopent-3-enylamino)propyl)-5-(2,5-difluorophenyl)-2-phenyl-1,3,4-thiadiazol-3(2H)-yl)-2-methoxypropan-1-one |

-continued

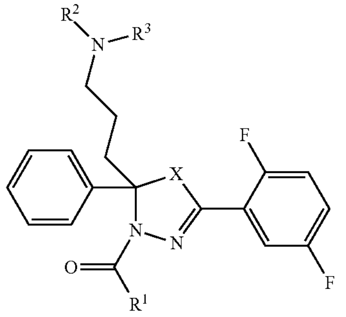

| X | $R^1$ | $NR^2R^3$ | Name |
|---|---|---|---|
| S | (S)-2-methoxyethyl | 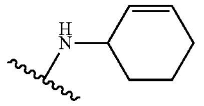 [SMILES: *NC1C=CCCC1] | (2S)-1-(2-(3-(cyclohex-2-enylamino)propyl)-5-(2,5-difluorophenyl)-2-phenyl-1,3,4-thiadiazol-3(2H)-yl)-2-methoxypropan-1-one |
| S | (S)-2-methoxyethyl | 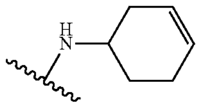 [SMILES: *NC1CC=CCC1] | (2S)-1-(2-(3-(cyclohex-3-enylamino)propyl)-5-(2,5-difluorophenyl)-2-phenyl-1,3,4-thiadiazol-3(2H)-yl)-2-methoxypropan-1-one |
| S | (S)-2-methoxyethyl | 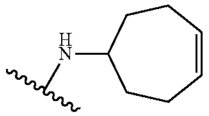 [SMILES: *NC1CCC=CCC1] | (2S)-1-(2-(3-((Z)-cyclohept-4-enylamino)propyl)-5-(2,5-difluorophenyl)-2-phenyl-1,3,4-thiadiazol-3(2H)-yl)-2-methoxypropan-1-one |
| S | i-propyl | 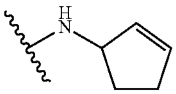 [SMILES: *NC1C=CCC1] | 1-(2-(3-(cyclopent-2-enylamino)propyl)-5-(2,5-difluorophenyl)-2-phenyl-1,3,4-thiadiazol-3(2H)-yl)-2-methylpropan-1-one |
| S | i-propyl | 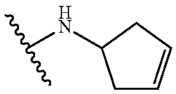 [SMILES: *NC1CC=CC1] | 1-(2-(3-(cyclopent-3-enylamino)propyl)-5-(2,5-difluorophenyl)-2-phenyl-1,3,4-thiadiazol-3(2H)-yl)-2-methylpropan-1-one |
| S | i-propyl | 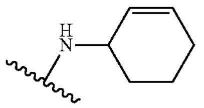 | 1-(2-(3-(cyclohex-2-enylamino)propyl)-5-(2,5-difluorophenyl)-2-phenyl-1,3,4-oxadiazol-3(2H)-yl)-2-methylpropan-1-one |
| S | i-propyl | 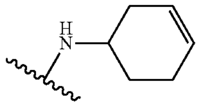 [SMILES: *NC1CC=CCC1] | 1-(2-(3-(cyclohex-3-enylamino)propyl)-5-(2,5-difluorophenyl)-2-phenyl-1,3,4-thiadiazol-3(2H)-yl)-2-methylpropan-1-one |
| S | $NMe_2$ | 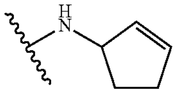 [SMILES: *NC1C=CCC1] | 2-(3-(cyclopent-2-enylamino)propyl)-5-(2,5-difluorophenyl)-N,N-dimethyl-2-phenyl-1,3,4-thiadiazole-3(2H)-carboxamide |
| S | $NMe_2$ | 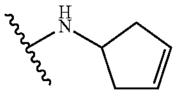 | 2-(3-(cyclopent-3-enylamino)propyl)-5-(2,5-difluorophenyl)-N,N-dimethyl-2-phenyl-1,3,4-thiadiazole-3(2H)-carboxamide |

-continued

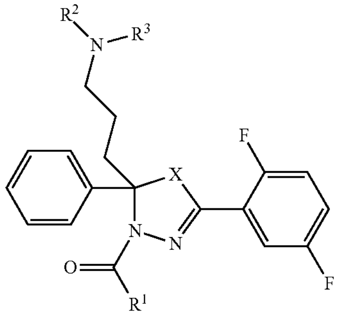

| X | $R^1$ | $NR^2R^3$ | Name |
|---|---|---|---|
| S | $NMe_2$ | 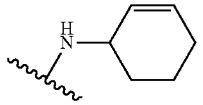 | 2-(3-(cyclohex-2-enylamino)propyl)-5-(2,5-difluorophenyl)-N,N-dimethyl-2-phenyl-1,3,4-thiadiazolc-3(2H)-carboxamide |
| S | $NMe_2$ | 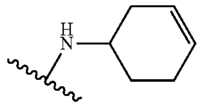 | 2-(3-(cyclohex-3-enylamino)propyl)-5-(2,5-difluorophenyl)-N,N-dimethyl-2-phenyl-1,3,4-thiadiazole-3(2H)-carboxamide |
| S | NHOH | 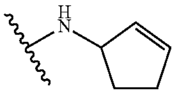 | 2-(3-(cyclopent-2-enylamino)propyl)-5-(2,5-difluorophenyl)-N-hydroxy-2-phenyl-1,3,4-thiadiazole-3(2H)-carboxamide |
| S | NHOH | 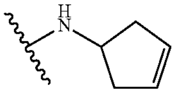 | 2-(3-(cyclopent-3-enylamino)propyl)-5-(2,5-difluorophenyl)-N-hydroxy-2-phenyl-1,3,4-thiadiazole-3(2H)-carboxamide |
| S | NHOH | 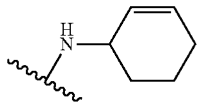 [SMILES: *NC1C=CCCC1] | 2-(3-(cyclohex-2-enylamino)propyl)-5-(2,5-difluorophenyl)-N-hydroxy-2-phenyl-1,3,4-thiadiazole-3(2H)-carboxamide |
| S | NHOH | 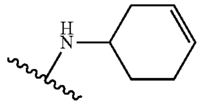 [SMILES: *NC1CC=CCC1] | 2-(3-(cyclohex-3-enylamino)propyl)-5-(2,5-difluorophenyl)-N-hydroxy-2-phenyl-1,3,4-thiadiazole-3(2H)-carboxamide |
| S | NHOH | 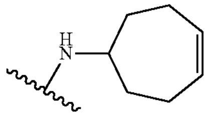 | (Z)-2-(3-(cyclohept-4-enylamino)propyl)-5-(2,5-difluorophenyl)-N-hydroxy-2-phenyl-1,3,4-thiadiazole-3(2H)-carboxamide |
| S | N(Me)OH | 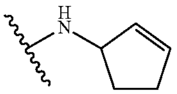 [SMILES: *NC1C=CCC1] | 2-(3-(cyclopent-2-enylamino)propyl)-5-(2,5-difluorophenyl)-N-hydroxy-N-methyl-2-phenyl-1,3,4-thiadiazole-3(2H)-carboxamide |
| S | N(Me)OH | 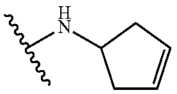 [SMILES: *NC1CC=CC1] | 2-(3-(cyclopent-3-enylamino)propyl)-5-(2,5-difluorophenyl)-N-hydroxy-N-methyl-2-phenyl-1,3,4-thiadiazole-3(2H)-carboxamide |

-continued

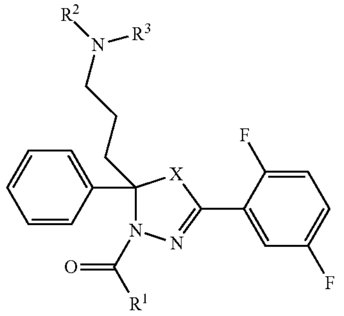

| X | $R^1$ | $NR^2R^3$ | Name |
|---|---|---|---|
| S | N(Me)OH | 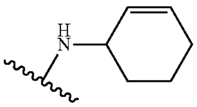 | 2-(3-(cyclohex-2-enylamino)propyl)-5-(2,5-difluorophenyl)-N-hydroxy-N-methyl-2-phenyl-1,3,4-thiadiazole-3(2H)-carboxamide |
| S | N(Me)OH | 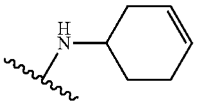 [SMILES: *NC1CC=CCC1] | 2-(3-(cyclohex-3-enylamino)propyl)-5-(2,5-difluorophenyl)-N-hydroxy-N-methyl-2-phenyl-1,3,4-thiadiazole-3(2H)-carboxamide |
| S | N(Me)OH | 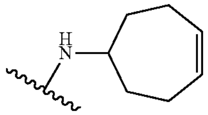 [SMILES: *NC1CCC=CCC1] | (Z)-2-(3-(cyclohept-4-enylamino)propyl)-5-(2,5-difluorophenyl)-N-hydroxy-N-methyl-2-phenyl-1,3,4-thiadiazole-3(2H)-carboxamide |
| S | NHOMe | 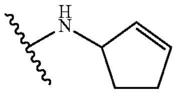 [SMILES: *NC1C=CCC1] | 2-(3-(cyclopent-2-enylamino)propyl)-5-(2,5-difluorophenyl)-N-methoxy-2-phenyl-1,3,4-thiadiazole-3(2H)-carboxamide |
| S | NHOMe | 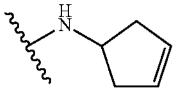 [SMILES: *NC1CC=CC1] | 2-(3-(cyclopent-3-enylamino)propyl)-5-(2,5-difluorophenyl)-N-methoxy-2-phenyl-1,3,4-thiadiazole-3(2H)-carboxamide |
| S | NHOMe | 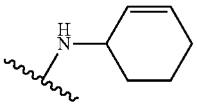 [SMILES: *NC1C=CCCC1] | 2-(3-(cyclohex-2-enylamino)propyl)-5-(2,5-difluorophenyl)-N-methoxy-2-phenyl-1,3,4-thiadiazole-3(2H)-carboxamide |
| S | NHOMe | 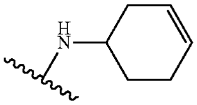 [SMILES: *NC1CC=CCC1] | 2-(3-(cyclohex-3-enylamino)propyl)-5-(2,5-difluorophenyl)-N-methoxy-2-phenyl-1,3,4-thiadiazole-3(2H)-carboxamide |
| S | NHOMe | 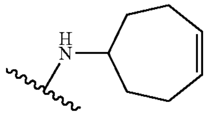 [SMILES: *NC1CCC=CCC1] | (Z)-2-(3-(cyclohept-4-enylamino)propyl)-5-(2,5-difluorophenyl)-N-methoxy-2-phenyl-1,3,4-thiadiazole-3(2H)-carboxamide |
| S | N(Me)OMe | 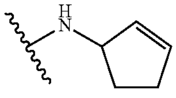 [SMILES: *NC1C=CCC1] | 2-(3-(cyclopent-2-enylamino)propyl)-5-(2,5-difluorophenyl)-N-methoxy-N-methyl-2-phenyl-1,3,4-thiadiazole-3(2H)-carboxamide |

-continued

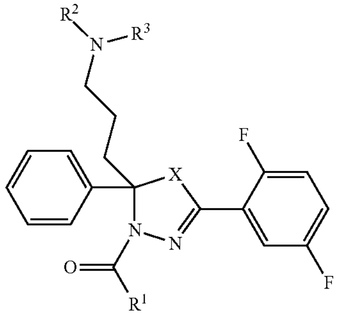

| X | $R^1$ | $NR^2R^3$ | Name |
|---|---|---|---|
| S | N(Me)OMe | 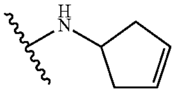 [SMILES: *NC1CC=CC1] | 2-(3-(cyclopent-3-enylamino)propyl)-5-(2,5-difluorophenyl)-N-methoxy-N-methyl-2-phenyl-1,3,4-thiadiazole-3(2H)-carboxamide |
| S | N(Me)OMe | 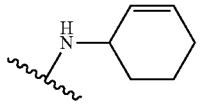 | 2-(3-(cyclohex-2-enylamino)propyl)-5-(2,5-difluorophenyl)-N-methoxy-N-methyl-2-phenyl-1,3,4-thiadiazole-3(2H)-carboxamide |
| S | N(Me)OMe | 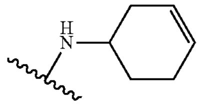 [SMILES: *NC1CC=CCC1] | 2-(3-(cyclohex-3-enylamino)propyl)-5-(2,5-difluorophenyl)-N-methoxy-N-methyl-2-phenyl-1,3,4-thiadiazole-3(2H)-carboxamide |
| S | N(Me)OMe | 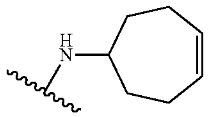 [SMILES: *NC1CCC=CCC1] | (Z)-2-(3-(cyclohept-4-enylamino)propyl)-5-(2,5-difluorophenyl)-N-methoxy-N-methyl-2-phenyl-1,3,4-thiadiazole-3(2H)-carboxamide |
| O | (S)-2-methoxyethyl | 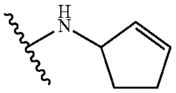 [SMILES: *NC1C=CCC1] | (2S)-1-(2-(3-(cyclopent-2-enylamino)propyl)-5-(2,5-difluorophenyl)-2-phenyl-1,3,4-oxadiazol-3(2H)-yl)-2-methoxypropan-1-one |
| O | (S)-2-methoxyethyl | 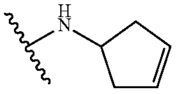 [SMILES: *NC1CC=CC1] | (2S)-1-(2-(3-(cyclopent-3-enylamino)propyl)-5-(2,5-difluorophenyl)-2-phenyl-1,3,4-oxadiazol-3(2H)-yl)-2-methoxypropan-1-one |
| O | (S)-2-methoxyethyl | 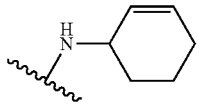 | (2S)-1-(2-(3-(cyclohex-2-enylamino)propyl)-5-(2,5-difluorophenyl)-2-phenyl-1,3,4-oxadiazol-3(2H)-yl)-2-methoxypropan-1-one |
| O | (S)-2-methoxyethyl | 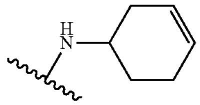 | (2S)-1-(2-(3-(cyclohex-3-enylamino)propyl)-5-(2,5-difluorophenyl)-2-phenyl-1,3,4-oxadiazol-3(2H)-yl)-2-methoxypropan-1-one |
| O | (S)-2-methoxyethyl | 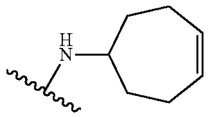 [SMILES: *NC1CCC=CCC1] | (2S)-1-(2-(3-((2)-cyclohept-4-enylamino)propyl)-5-(2,5-difluorophenyl)-2-phenyl-1,3,4-oxadiazol-3(2H)-yl)-2-methoxypropan-1-one |

-continued

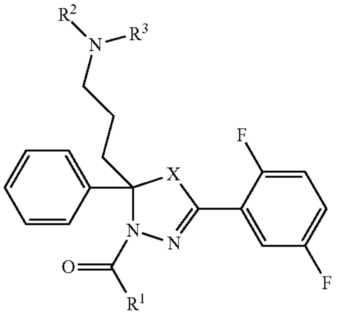

| X | $R^1$ | $NR^2R^3$ | Name |
|---|---|---|---|
| O | i-propyl | 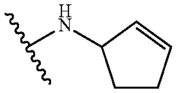 [SMILES: *NC1C=CCC1] | 1-(2-(3-(cyclopent-2-enylamino)propyl)-5-(2,5-difluorophenyl)-2-phenyl-1,3,4-oxadiazol-3(2H)-yl)-2-methylpropan-1-one |
| O | i-propyl | 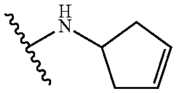 [SMILES: *NC1CC=CC1] | 1-(2-(3-(cyclopent-3-enylamino)propyl)-5-(2,5-difluorophenyl)-2-phenyl-1,3,4-oxadiazol-3(2H)-yl)-2-methylpropan-1-one |
| O | i-propyl | 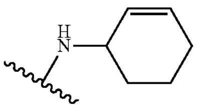 [SMILES: *NC1C=CCCC1] | 1-(2-(3-(cyclohex-2-enylamino)propyl)-5-(2,5-difluorophenyl)-2-phenyl-1,3,4-oxadiazol-3(2H)-yl)-2-methylpropan-1-one |
| O | i-propyl | 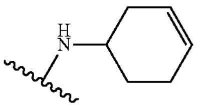 [SMILES: *NC1CC=CCC1] | 1-(2-(3-(cyclohex-3-enylamino)propyl)-5-(2,5-difluorophenyl)-2-phenyl-1,3,4-oxadiazol-3(2H)-yl)-2-methylpropan-1-one |
| O | $NMe_2$ | 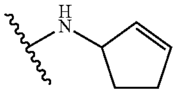 [SMILES: *NC1C=CCC1] | 2-(3-(cyclopent-2-enylamino)propyl)-5-(2,5-difluorophenyl)-N,N-dimethyl-2-phenyl-1,3,4-oxadiazole-3(2H)-carboxamide |
| O | $NMe_2$ | 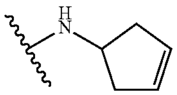 [SMILES: *NC1CC=CC1] | 2-(3-(cyclopent-3-enylamino)propyl)-5-(2,5-difluorophenyl)-N,N-dimethyl-2-phenyl-1,3,4-oxadiazole-3(2H)-carboxamide |
| O | $NMe_2$ | 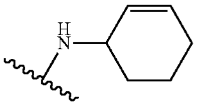 [SMILES: *NC1C=CCCC1] | 2-(3-(cyclohex-2-enylamino)propyl)-5-(2,5-difluorophenyl)-N,N-dimethyl-2-phenyl-1,3,4-oxadiazole-3(2H)-carboxamide |
| O | $NMe_2$ | 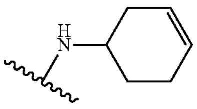 [SMILES: *NC1CC=CCC1] | 2-(3-(cyclohex-3-enylamino)propyl)-5-(2,5-difluorophenyl)-N,N-dimethyl-2-phenyl-1,3,4-oxadiazole-3(2H)-carboxamide |
| O | NHOH | 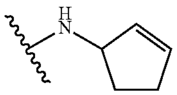 [SMILES: *NC1C=CCC1] | 2-(3-(cyclopent-2-enylamino)propyl)-5-(2,5-difluorophenyl)-N-hydroxy-2-phenyl-1,3,4-oxadiazole-3(2H)-carboxamide |

-continued

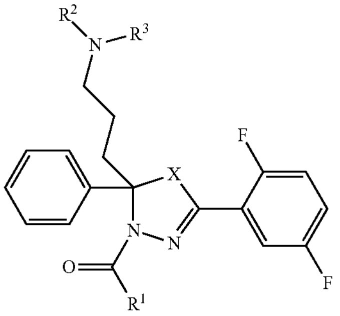

| X | $R^1$ | $NR^2R^3$ | Name |
|---|---|---|---|
| O | NHOH | 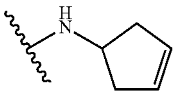 [SMILES: *NC1CC=CC1] | 2-(3-(cyclopent-3-enylamino)propyl)-5-(2,5-difluorophenyl)-N-hydroxy-2-phenyl-1,3,4-oxadiazole-3(2H)-carboxamide |
| O | NHOH | 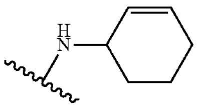 [SMILES: *NC1C=CCCC1] | 2-(3-(cyclohex-2-enylamino)propyl)-5-(2,5-difluorophenyl)-N-hydroxy-2-phenyl-1,3,4-oxadiazole-3(2H)-carboxamide |
| O | NHOH | 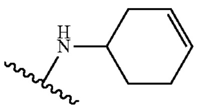 [SMILES: *NC1CC=CCC1] | 2-(3-(cyclohex-3-enylamino)propyl)-5-(2,5-difluorophenyl)-N-hydroxy-2-phenyl-1,3,4-oxadiazole-3(2H)-carboxamide |
| O | N(Me)OH | 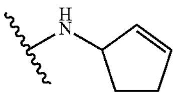 [SMILES: *NC1C=CCC1] | 2-(3-(cyclopent-2-enylamino)propyl)-5-(2,5-difluorophenyl)-N-hydroxy-N-methyl-2-phenyl-1,3,4-oxadiazole-3(2H)-carboxamide |
| O | N(Me)OH | 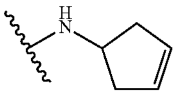 [SMILES: *NC1CC=CC1] | 2-(3-(cyclopent-3-enylamino)propyl)-5-(2,5-difluorophenyl)-N-hydroxy-N-methyl-2-phenyl-1,3,4-oxadiazole-3(2H)-carboxamide |
| O | N(Me)OH | 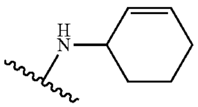 | 2-(3-(cyclohex-2-enylamino)propyl)-5-(2,5-difluorophenyl)-N-hydroxy-N-methyl-2-phenyl-1,3,4-oxadiazole-3(2H)-carboxamide |
| O | N(Me)OH | 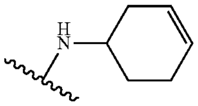 [SMILES: *NC1CC=CCC1] | 2-(3-(cyclohex-3-enylamino)propyl)-5-(2,5-difluorophenyl)-N-hydroxy-N-methyl-2-phenyl-1,3,4-oxadiazole-3(2H)-carboxamide |
| O | NHOMe | 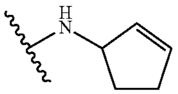 [SMILES: *NC1C=CCC1] | 2-(3-(cyclopent-2-enylamino)propyl)-5-(2,5-difluorophenyl)-N-methoxy-2-phenyl-1,3,4-oxadiazole-3(2H)-carboxamide |
| O | NHOMe | 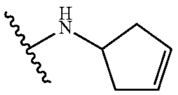 [SMILES: *NC1CC=CC1] | 2-(3-(cyclopent-3-enylamino)propyl)-5-(2,5-difluorophenyl)-N-methoxy-2-phenyl-1,3,4-oxadiazole-3(2H)-carboxamide |

-continued

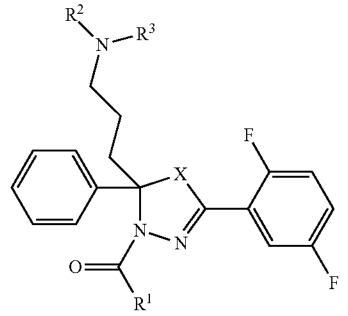

| X | $R^1$ | $NR^2R^3$ | Name |
|---|---|---|---|
| O | NHOMe | 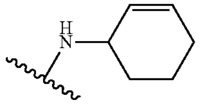 [SMILES: *NC1C=CCCC1] | 2-(3-(cyclohex-2-enylamino)propyl)-5-(2,5-difluorophenyl)-N-methoxy-2-phenyl-1,3,4-oxadiazole-3(2H)-carboxamide |
| O | NHOMe | 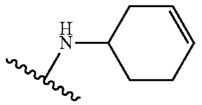 [SMILES: *NC1CC=CCC1] | 2-(3-(cyclohex-3-enylamino)propyl)-5-(2,5-difluorophenyl)-N-methoxy-2-phenyl-1,3,4-oxadiazole-3(2H)-carboxamide |
| O | NHOMe | 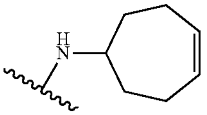 [SMILES: *NC1CCC=CCC1] | (Z)-2-(3-(cyclohept-4-enylamino)propyl)-5-(2,5-difluorophenyl)-N-methoxy-2-phenyl-1,3,4-oxadiazole-3(2H)-carboxamide |
| O | N(Me)OMe | 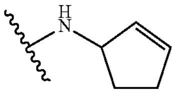 [SMILES: *NC1C=CCC1] | 2-(3-(cyclopent-2-enylamino)propyl)-5-(2,5-difluorophenyl)-N-methoxy-N-methyl-2-phenyl-1,3,4-oxadiazole-3(2H)-carboxamide |
| O | N(Me)OMe | 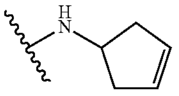 [SMILES: *NC1CC=CC1] | 2-(3-(cyclopent-3-enylamino)propyl)-5-(2,5-difluorophenyl)-N-methoxy-N-methyl-2-phenyl-1,3,4-oxadiazole-3(2H)-carboxamide |
| O | N(Me)OMe | 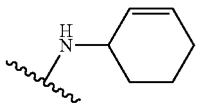 [SMILES: *NC1C=CCCC1] | 2-(3-(cyclohex-2-enylamino)propyl)-5-(2,5-difluorophcnyl)-N-methoxy-N-methyl-2-phenyl-1,3,4-oxadiazole-3(2H)-carboxamide |
| O | N(Me)OMe | 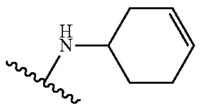 [SMILES: *NC1CC=CCC1] | 2-(3-(cyclohex-3-enylamino)propyl)-5-(2,5-difluorophenyl)-N-methoxy-N-methyl-2-phenyl-1,3,4-oxadiazole-3(2H)-carboxamide |
| O | N(Me)OMe | 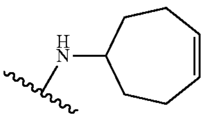 [SMILES: *NC1CCC=CCC1] | (Z)-2-(3-(cyclohept-4-enylamino)propyl)-5-(2,5-difluorophenyl)-N-methoxy-N-methyl-2-phenyl-1,3,4-oxadiazole-3(2H)-carboxamide |

Example 123

The activity of the compounds of the present invention may be determined by the following procedure. The assays were conducted at 30° C. in a Costar 3695 (96-well, polystyrene, ½-area, clear) plate in a final volume of 50 μL. Hydrolysis of ATP was monitored in a system that coupled the product ADP to the oxidation of NADH using pyruvate kinase and lactate dehydrogenase. Assay mixtures contained the following: 20 mM $K^+$Pipes, pH 7.0, 0.01% Triton X-100, 2% DMSO, 25 mM KCl, 2 mM $MgCl_2$, 1 mM DTT, 25 μM ATP, 1 mM phospho(enol)pyruvate, 200 μM NADH, 7.9 U/mL pyruvate kinase, 9 U/mL lactate dehydrogenase, 0.25 μM bovine microtubules, 20 μM paclitaxel and 20 nM Eg5. The concentration of inhibitor was typically varied over the range of 10-200,000 nM. The reaction was monitored kinetically in an absorbance-based plate reader for a period of 10 minutes. Velocities were estimated from linear fits to the progress curves and were expressed as POC (percent of uninhibited control wells). $IC_{50}$'s were estimated from the POC data using a standard 4-parameter logistical model and compared to a control inhibitor run in each plate. In this assay, compounds of the invention exhibited an $IC_{50}$ of less than 50 μM.

Example 124

The ability of the compounds of the present invention to inhibit cellular viability may be determined by the following procedure. Cells from a variety of established tumor cell lines, e.g., HeLa, were plated in Costar 3904 96-well plates, in growth medium for the cell line (for HeLa:DMEM high glucose, L-glutamine, 20 mM Hepes, 10% FBS), at a density that allowed for logarithmic growth over the 72 hour period of the assay (HeLa: 1000 cells/well), and incubated at 37° C., 5% $CO_2$ overnight. The following day, one-tenth volume of a 10× concentration of compounds was added to the wells in an 11-point dilution series. The dilution series was composed of an initial 1:2 dilution in DMSO, followed by a 1:20 dilution in growth medium, for a final DMSO concentration on cells of 0.5%. Control wells were treated with 0.5% DMSO. The typical range of dilution was 2.5 μM to 1 nM, which was expanded to 50 μM to 50 pM depending on the potency of the compound. Once compound was added to the cells, plates were incubated as above. After 72 hour incubation, 20 μL resazurin solution (Cell Titer Blue, Promega G8081) was added to all wells and the plates incubated for an additional 2 hours. Viable cells convert resazurin to resorufin, a fluorescent end product. The plate was read on a fluorescent plate reader at 560 nm excitation/590 nm emission. The fluorescent signal of the control wells was defined as 100% and the percent of control signal for each well of a dilution series for the compound was defined as: (fluorescent signal of treated well) X (average fluorescent signal of the control well)$^{-1}$ X 100. The $EC_{50}$ for inhibition of viability was determined from the inflection point of a standard 4-parameter logistical curve fitted to the values obtained. In this assay, the compounds of the invention exhibited an $EC_{50}$ of less than 50 μM.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words “comprise,” “comprising,” “include,” “including,” and “includes” when used in this specification and in the following claims are intended to specify the presence of stated features, integers, components, or steps, but they do not preclude the presence or addition of one or more other features, integers, components, steps, or groups thereof.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words “comprise,” “comprising,” “include,” “including,” and “includes” when used in this specification and in the following claims are intended to specify the presence of stated features, integers, components, or steps, but they do not preclude the presence or addition of one or more other features, integers, components, steps, or groups thereof.

What is claimed is:

1. A method of treating a disease in a human or animal that can be treated by inhibiting mitosis, wherein said disease is selected from the group consisting of acute myeloid leukemia, chronic myeloid leukemia, acute lymphoblastic leukemia, chronic lymphocytic leukemia, myeloproliferative diseases, multiple myeloma and myelodysplastic syndrome, comprising administering to said human or animal an effective amount of a compound of the Formula:

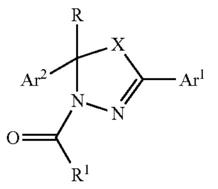

wherein:

X is S,

R is Z—$NR^2R^3$, Z—OH, or Z—OP(═O)($OR^a$)($OR^a$);

$R^1$ is alkyl, alkenyl, alkynyl, aryl, heteroaryl, saturated or partially unsaturated cycloalkyl, —$OR^3$, —$NR^4OR^5$, $CR^b$(═$NOR^c$), C(═O)$R^a$, or —$NR^4R^5$, wherein said alkyl, alkenyl, alkynyl, aryl, heteroaryl, and cycloalkyl are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C═O)$OR^d$, —$NR^bSO_2R^d$, —$SO_2NR^aR^b$, —C(═O)$R^a$, —C(═O)$OR^a$, —OC(═O)$R^a$, —$OCH_2$C(═O)$OR^a$, —$NR^b$C(═O)$OR^d$, —$NR^b$C(═O)$R^a$, —C(═O)$NR^aR^b$, —$NR^aR^b$, —$NR^c$C(═O)$NR^aR^b$, —$NR^c$C(NCN)$NR^aR^b$, —$OR^a$, —OP(═O)$(OR^a)_2$, alkyl, alkenyl, alkynyl, cycloalkyl, aryl, heteroaryl, arylalkyl, and heteroarylalkyl;

$Ar^1$ and $Ar^2$ are phenyl, wherein said phenyl is optionally substituted with one or more groups independently selected from F, Cl, Br, I, cyano, nitro, alkyl, alkenyl, alkynyl, saturated or partially unsaturated cycloalkyl, saturated or partially unsaturated heteorcycloalkyl, trifluoromethyl, difluoromethyl, fluoromethyl, fluoromethoxy, difluoromethoxy, trifluoromethoxy, —$OR^a$, —O(C═O)$OR^d$, —OP(═O)($OR^a$)($OR^a$), —$NR^aR^b$, —$NR^bSO_2R^d$, —$SO_2NR^aR^b$, —$SR^6$, —$SOR^6$, —$SO_2R^6$, —C(═O)$R^a$, —C(═O)$OR^a$, —OC(═O)$R^a$, —$OCH_2$C(═O)$OR^a$, —$NR^b$C(═O)$OR^d$, —$NR^b$C(═O)$R^a$, —C(═O)$NR^aR^b$ and —$NR^c$C(═O)$NR^aR^b$;

$R^2$ is hydrogen, —C(═O)$R^4$, —$SO_2R^6$, alkyl, alkenyl, alkynyl, saturated or partially unsaturated cycloalkyl, wherein said alkyl, alkenyl, alkynyl, and cycloalkyl are optionally substituted with one or more groups independently selected from oxo, halogen, cyano, nitro, trifluoromethyl, difluoromethyl, fluoromethyl, fluoromethoxy, difluoromethoxy, trifluoromethoxy, azido, —O(C═O)$OR^d$, —$NR^bSO_2R^d$, —$SO_2NR^aR^b$, —C(═O)$R^a$, —C(═O)$OR^a$, —OC(═O)$R^a$, —$NR^b$C(═O)$OR^d$, —$NR^b$C(═O)$R^a$, —C(═O)$NR^aR^b$, —$NR^aR^b$, —$NR^c$C(═O)$NR^aR^b$, —$OR^a$, alkyl, alkenyl, alkynyl, cycloalkyl, cycloalkenyl, cycloalkynyl, aryl, heteroaryl, arylalkyl, heteroarylalkyl, heterocycloalkyl and heterocyclylalkyl;

$R^3$ is hydrogen, —C(═O)$R^4$, alkyl, alkenyl, alkynyl, or saturated or partially unsaturated cycloalkyl, wherein said alkyl, alkenyl, alkynyl, and cycloalkyl are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C═O)$OR^d$, —OP(═O)$(OR^a)_2$, —$NR^bSO_2R^d$, —$SO_2NR^aR^b$, —C(═O)$R^a$, —C(═O)$OR^a$, —OC(═O)$R^a$, —$NR^b$C(═O)$OR^d$, —$NR^b$C(═O)$R^a$, —C(═O)$NR^aR^b$, —$NR^aR^b$, —$NR^c$C(═O)$NR^aR^b$, —$OR^a$, alkyl, alkenyl, alkynyl, cycloalkyl, cycloalkenyl, cycloalkynyl, aryl, heteroaryl, arylalkyl, heteroarylalkyl, heterocycloalkyl and heterocyclylalkyl, $R^4$ and $R^5$ are independently H, trifluoromethyl, difluoromethyl, fluoromethyl, alkyl, alkenyl, alkynyl, saturated or partially unsaturated cycloalkyl, aryl or heteroaryl, wherein said alkyl, alkenyl, alkynyl, cycloalkyl, aryl and heteroaryl are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C═O)$OR^d$, —$NR^bSO_2R^d$, —$SO_2NR^aR^b$, —C(═O)$R^a$, —C(═O)$OR^a$, —OC(═O)$R^a$, —$NR^b$C(═O)$OR^d$, —$NR^b$C(═O)$R^a$, —C(═O)$NR^aR^b$, —$NR^aR^b$, —$NR^c$C(═O)$NR^aR^b$, —$NR^c$C(NCN)$NR^aR^b$, —$OR^a$, alkyl, alkenyl, alkynyl, cycloalkyl, aryl, heteroaryl, arylalkyl, heteroarylalkyl, $R^6$ is alkyl, alkenyl, alkynyl, heteroalkyl, heteroalkenyl, heteroalkynyl, saturated or partially unsaturated cycloalkyl, saturated or partially unsaturated heterocycloalkyl, aryl or heteroaryl, wherein said alkyl, alkenyl, alkynyl, heteroalkyl, heteroalkenyl, heteroalkynyl, cycloalkyl, heterocycloalkyl, aryl and heteroaryl are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C═O)$OR^d$, —$NR^bSO_2R^d$, —$SO_2NR^aR^b$, —C(═O)$R^a$, —C(═O)$OR^a$, —OC(═O)$R^a$, —$NR^b$C(═O)$OR^d$, —$NR^b$C(═O)$R^a$, —C(═O)$NR^aR^b$, —$NR^aR^b$, —$NR^c$C(═O)$NR^aR^b$, —$NR^c$C(NCN)$NR^aR^b$, —$OR^a$, alkyl, alkenyl, alkynyl, cycloalkyl, aryl, heteroaryl, arylalkyl, heteroarylalkyl, heterocycloalkyl and heterocyclylalkyl;

$R^a$ is hydrogen, trifluoromethyl, alkyl, alkenyl, alkynyl, saturated or partially unsaturated cycloalkyl, cycloalkylalkyl, aryl, arylalkyl, heteroaryl, heteroarylalkyl, heterocycloalkyl or saturated or partially unsaturated heterocyclylalkyl, wherein said alkyl, alkenyl, alkynyl, cycloalkyl, cycloalkylalkyl, aryl, arylalkyl, heteroaryl, heteroarylalkyl, heterocycloalkyl and heterocyclylalkyl are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C═O)OR$^h$, —NR$^f$SO$_2$R$^h$, —SO$_2$NR$^e$R$^f$, —C(═O)R$^e$, —C(═O)OR$^e$, —OC(═O)R$^e$, —NR$^f$C(═O)OR$^h$, —NR$^f$C(═O)R$^e$, —C(═O)NR$^e$R$^f$, —NR$^e$R$^f$, —NR$^g$C(═O)NR$^e$R$^f$, —NR$^c$C(NCN)NR$^e$R$^f$, —OR$^e$, alkyl, alkenyl, alkynyl, saturated or partially unsaturated cycloalkyl, aryl, heteroaryl, arylalkyl, heteroarylalkyl, saturated or partially unsaturated heterocycloalkyl and heterocyclylalkyl;

R$^b$, R$^c$, R$^f$ and R$^g$ are independently hydrogen or alkyl, or R$^a$ and R$^b$ together with the atom to which they are attached form a 4 to 10 membered saturated or partially unsaturated heterocyclic ring which may include 1 to 3 additional heteroatoms, in addition to the nitrogen atom to which said R$^a$ and R$^b$ are attached, selected from N, O and S;

R$^d$ and R$^h$ are independently trifluoromethyl, alkyl, saturated or partially unsaturated cycloalkyl, aryl, arylalkyl, heteroaryl, heteroarylalkyl, saturated or partially unsaturated heterocycloalkyl or heterocyclylalkyl;

R$^e$ is hydrogen, trifluoromethyl, alkyl, alkenyl, alkynyl, saturated or partially unsaturated cycloalkyl, cycloalkylalkyl, aryl, arylalkyl, heteroaryl, heteroarylalkyl, saturated or partially unsaturated heterocycloalkyl or heterocyclylalkyl; and Z is alkylene having from 1 to 6 carbons, or alkenylene or alkynylene each having from 2 to 6 carbons, wherein said alkylene, alkenylene and alkynylene are optionally substituted with one or more groups independently selected from oxo, halogen, cyano, nitro, trifluoromethyl, difluoromethyl, fluoromethyl, fluoromethoxy, difluoromethoxy, trifluoromethoxy, azido, —O(C═O)OR$^d$, —NR$^b$SO$_2$R$^d$, —SO$_2$NR$^a$R$^b$, —C(═O)R$^a$, —C(═O)OR$^a$, —OC(═O)R$^a$, —NR$^b$C(═O)OR$^d$, —NR$^b$C(═O)R$^a$, —C(═O)NR$^a$R$^b$, —NR$^a$R$^b$, —NR$^c$C(═O)NR$^a$R$^b$, —OR$^a$, alkyl, alkenyl, alkynyl, cycloalkyl, aryl, heteroaryl, arylalkyl, and heteroarylalkyl, or a pharmaceutical composition comprising said compound.

2. The method of claim 1, wherein said compound is selected from:

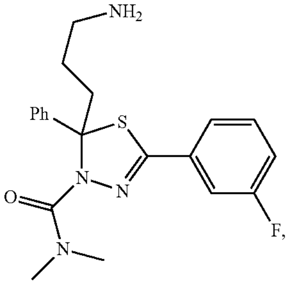

-continued

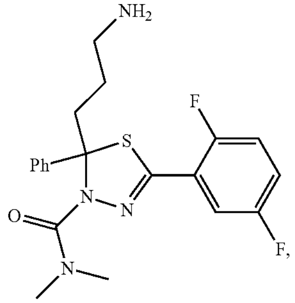

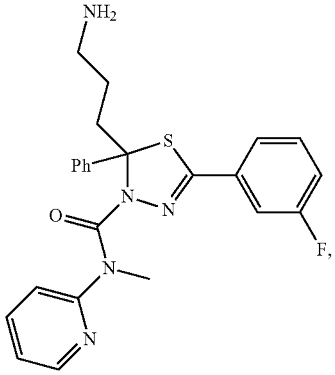

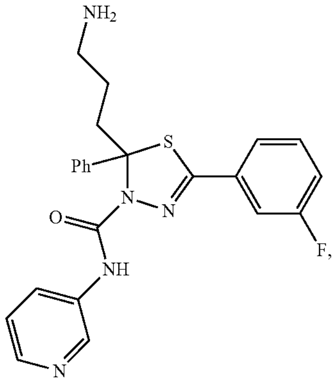

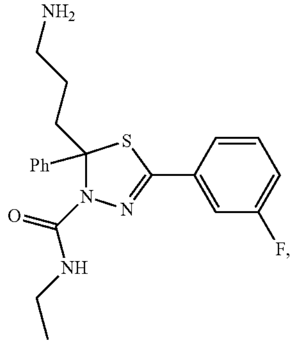

-continued
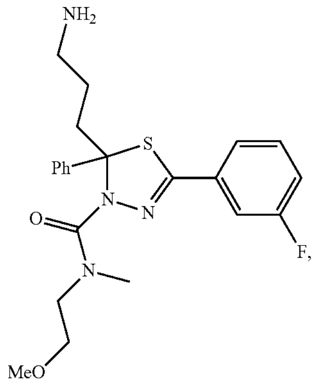
,
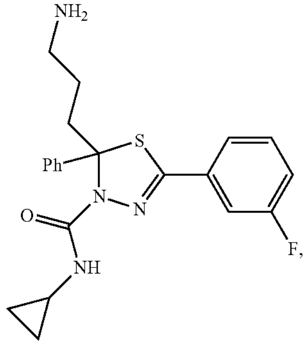
,
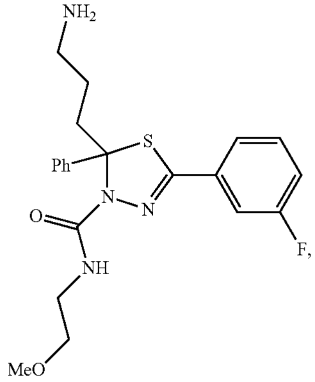
,
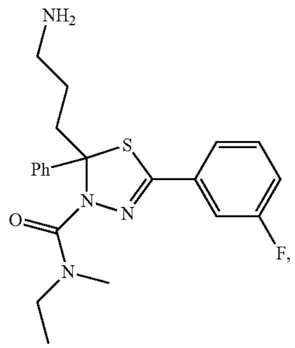
,
-continued
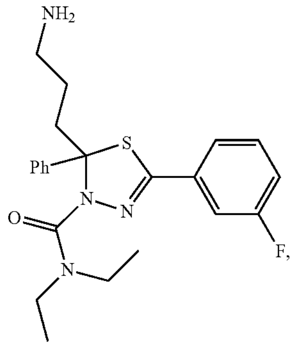
,
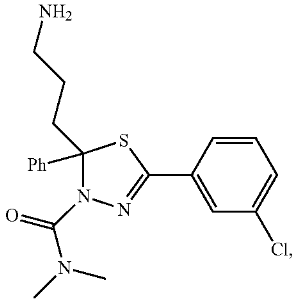
,
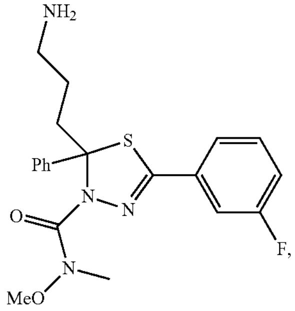
,
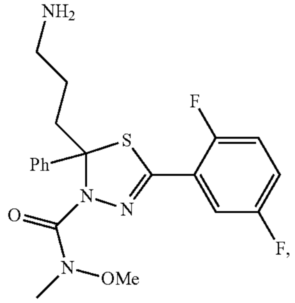
,
(Enantiomer A)
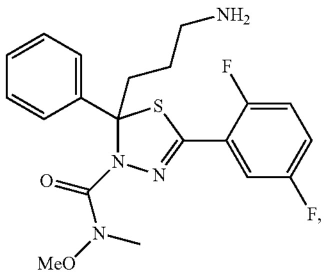
, -continued (Enantiomer B)

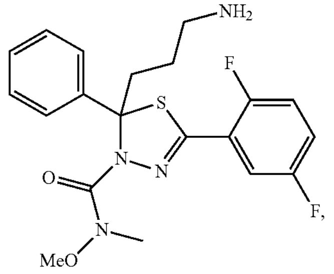

and

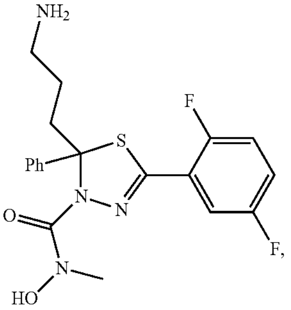

or a pharmaceutically acceptable salt thereof.

3. The method of claim 2, wherein the compound is:

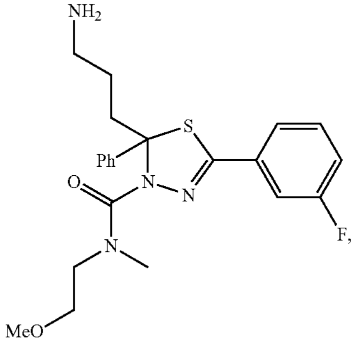 [SMILES: COCCN(C)C(=O)N1N=C(c2cccc(F)c2)SC1(CCCN)c1ccccc1]

or a pharmaceutically acceptable salt thereof.

4. The method of claim 2, wherein the compound is:

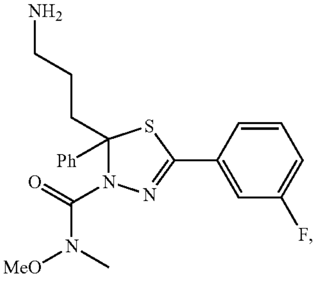 [SMILES: CON(C)C(=O)N1N=C(c2cccc(F)c2)SC1(CCCN)c1ccccc1]

or a pharmaceutically acceptable salt thereof.

5. The method of claim 2, wherein the compound is:

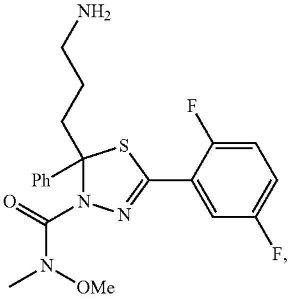 [SMILES: CON(C)C(=O)N1N=C(c2cc(F)ccc2F)SC1(CCCN)c1ccccc1]

or a pharmaceutically acceptable salt thereof.

6. The method of claim 2, wherein the compound is:

(Enantiomer A)

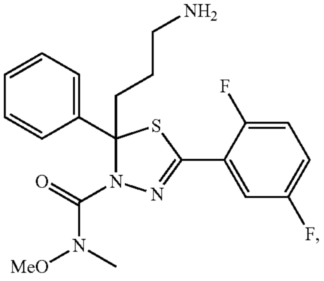

or a pharmaceutically acceptable salt thereof.

7. The method of claim 2, wherein the compound is:

(Enantiomer B)

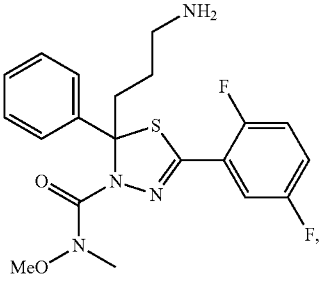

or a pharmaceutically acceptable salt thereof.

8. The method of claim 2, wherein the compound is:

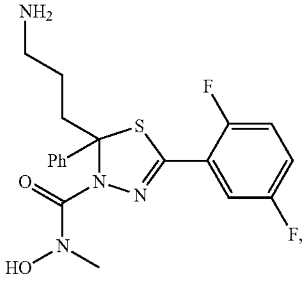 [SMILES: CN(O)C(=O)N1N=C(c2cc(F)ccc2F)SC1(CCCN)c1ccccc1]

or a pharmaceutically acceptable salt thereof.

9. The method of claim 6, wherein the compound is administered in combination with a proteasome inhibitor.

10. The method of claim 9, wherein the proteasome inhibitor is bortezomib.

11. The method of claim 9, wherein the disease is selected from acute myeloid leukemia, chronic myeloid leukemia, acute lymphoblastic leukemia, chronic lymphocytic leukemia and multiple myeloma.

12. The method of claim 11, wherein the disease is selected from acute myeloid leukemia, chronic myeloid leukemia and multiple myeloma.

13. The method of claim 12, wherein the disease is acute myeloid leukemia.

14. The method of claim 12, wherein the disease is chronic myeloid leukemia.

15. The method of claim 12, wherein the disease is multiple myeloma.

16. The method of claim 10, wherein the disease is selected from acute myeloid leukemia, chronic myeloid leukemia and multiple myeloma.

17. The method of claim 16, wherein the disease is acute myeloid leukemia.

18. The method of claim 16, wherein the disease is chronic myeloid leukemia.

19. The method of claim 16, wherein the disease is multiple myeloma.

20. The method of claim 7, wherein the compound is administered in combination with a proteasome inhibitor.

21. The method of claim 20, wherein the proteasome inhibitor is bortezomib.

22. The method of claim 20, wherein the disease is selected from acute myeloid leukemia, chronic myeloid leukemia, acute lymphoblastic leukemia, chronic lymphocytic leukemia and multiple myeloma.

23. The method of claim 22, wherein the disease is selected from acute myeloid leukemia, chronic myeloid leukemia and multiple myeloma.

24. The method of claim 23, wherein the disease is acute myeloid leukemia.

25. The method of claim 23, wherein the disease is chronic myeloid leukemia.

26. The method of claim 23, wherein the disease is multiple myeloma.

27. The method of claim 21, wherein the disease is selected from acute myeloid leukemia, chronic myeloid leukemia and multiple myeloma.

28. The method of claim 27, wherein the disease is acute myeloid leukemia.

29. The method of claim 27, wherein the disease is chronic myeloid leukemia.

30. The method of claim 27, wherein the disease is multiple myeloma.

31. A method of treating a hyperproliferative disorder, wherein said disorder is selected from the group consisting of acute myeloid leukemia, chronic myeloid leukemia, acute lymphoblastic leukemia, chronic lymphocytic leukemia, myeloproliferative diseases, multiple myeloma and myelodysplastic syndrome, in a mammal that comprises administering to said mammal a therapeutically effective amount of a compound of the Formula:

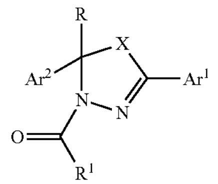

wherein:

X is S,

R is Z—$NR^2R^3$, Z—OH, or Z—OP(=O)($OR^a$)($OR^a$);

$R^1$ is alkyl, alkenyl, alkynyl, aryl, heteroaryl, saturated or partially unsaturated cycloalkyl, —$OR^3$, —$NR^4OR^5$, $CR^b$(=$NOR^c$), C(=O)$R^a$, or —$NR^4R^5$, wherein said alkyl, alkenyl, alkynyl, aryl, heteroaryl, and cycloalkyl are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C=O)$OR^d$, —$NR^bSO_2R^d$, —$SO_2NR^aR^b$, —C(=O)$R^a$, —C(=O)$OR^a$, —OC(=O)$R^a$, —$OCH_2C$(=O)$OR^a$, —$NR^bC$(=O)$OR^d$, —$NR^bC$(=O)$R^a$, —C(=O)$NR^aR^b$, —$NR^aR^b$, —$NR^cC$(=O)$NR^aR^b$, —$NR^cC$(NCN)$NR^aR^b$, —$OR^a$, —OP(=O)$(OR^a)_2$, alkyl, alkenyl, alkynyl, cycloalkyl, aryl, heteroaryl, arylalkyl, and heteroarylalkyl;

$Ar^1$ and $Ar^2$ are phenyl, wherein said phenyl is optionally substituted with one or more groups independently selected from F, Cl, Br, I, cyano, nitro, alkyl, alkenyl, alkynyl, saturated or partially unsaturated cycloalkyl, saturated or partially unsaturated heteorcycloalkyl, trifluoromethyl, difluoromethyl, fluoromethyl, fluoromethoxy, difluoromethoxy, trifluoromethoxy, —$OR^a$, —O(C=O)$OR^d$, —OP(=O)($OR^a$)($OR^a$), —$NR^aR^b$, —$NR^bSO_2R^d$, —$SO_2NR^aR^b$, —$SR^6$, —$SOR^6$, —$SO_2R^6$, —C(=O)$R^a$, —C(=O)$OR^a$, —OC(=O)$R^a$, —$OCH_2C$(=O)$OR^a$, —$NR^bC$(=O)$OR^d$, —$NR^bC$(=O)$R^a$, —C(=O)$NR^aR^b$ and —$NR^cC$(=O)$NR^aR^b$;

$R^2$ is hydrogen, —C(=O)$R^4$, —$SO_2R^6$, alkyl, alkenyl, alkynyl, saturated or partially unsaturated cycloalkyl, wherein said alkyl, alkenyl, alkynyl, and cycloalkyl are optionally substituted with one or more groups independently selected from oxo, halogen, cyano, nitro, trifluoromethyl, difluoromethyl, fluoromethyl, fluoromethoxy, difluoromethoxy, trifluoromethoxy, azido, —O(C=O)$OR^d$, —$NR^bSO_2R^d$, —$SO_2NR^aR^b$, —C(=O)$R^a$, —C(=O)$OR^a$, —OC(=O)$R^a$, —$NR^bC$(=O)$OR^d$, —$NR^bC$(=O)$R^a$, —C(=O)$NR^aR^b$, —$NR^aR^b$, —$NR^cC$(=O)$NR^aR^b$, —$OR^a$, alkyl, alkenyl, alkynyl, cycloalkyl, cycloalkenyl, cycloalkynyl, aryl, heteroaryl, arylalkyl, heteroarylalkyl, heterocycloalkyl and heterocyclylalkyl;

$R^3$ is hydrogen, —C(=O)$R^4$, alkyl, alkenyl, alkynyl, or saturated or partially unsaturated cycloalkyl, wherein said alkyl, alkenyl, alkynyl, and cycloalkyl are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C=O)$OR^d$, —OP(=O)$(OR^a)_2$, —$NR^bSO_2R^d$, —$SO_2NR^aR^b$, —C(=O)$R^a$, —C(=O)$OR^a$, —OC(=O)$R^a$, —$NR^bC$(=O)$OR^d$, —$NR^bC$(=O)$R^a$, —C(=O)$NR^aR^b$, —$NR^aR^b$, —$NR^cC$(=O)$NR^aR^b$, —OR$^a$, alkyl, alkenyl, alkynyl, cycloalkyl, cycloalkenyl, cycloalkynyl, aryl, heteroaryl, arylalkyl, heteroarylalkyl, heterocycloalkyl and heterocyclylalkyl, R$^4$ and R$^5$ are independently H, trifluoromethyl, difluoromethyl, fluoromethyl, alkyl, alkenyl, alkynyl, saturated or partially unsaturated cycloalkyl, aryl or heteroaryl, wherein said alkyl, alkenyl, alkynyl, cycloalkyl, aryl and heteroaryl are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C═O)OR$^d$, —NR$^b$SO$_2$R$^d$, —SO$_2$NR$^a$R$^b$, —C(═O)R$^a$, —C(═O)OR$^a$, —OC(═O)R$^a$, —NR$^b$C(═O)OR$^d$, —NR$^b$C(═O)R$^a$, —C(═O)NR$^a$R$^b$, —NR$^a$R$^b$, —NR$^c$C(═O)NR$^a$R$^b$, —NR$^c$C(NCN)NR$^a$R$^b$, —OR$^a$, alkyl, alkenyl, alkynyl, cycloalkyl, aryl, heteroaryl, arylalkyl, heteroarylalkyl, R$^6$ is alkyl, alkenyl, alkynyl, heteroalkyl, heteroalkenyl, heteroalkynyl, saturated or partially unsaturated cycloalkyl, saturated or partially unsaturated heterocycloalkyl, aryl or heteroaryl, wherein said alkyl, alkenyl, alkynyl, heteroalkyl, heteroalkenyl, heteroalkynyl, cycloalkyl, heterocycloalkyl, aryl and heteroaryl are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C═O)OR$^d$, —NR$^b$SO$_2$R$^d$, —SO$_2$NR$^a$R$^b$, —C(═O)R$^a$, —C(═O)OR$^a$, —OC(═O)R$^a$, —NR$^b$C(═O)OR$^d$, —NR$^b$C(═O)R$^a$, —C(═O)NR$^a$R$^b$, —NR$^a$R$^b$, —NR$^c$C(═O)NR$^a$R$^b$, —NR$^c$C(NCN)NR$^a$R$^b$, —OR$^a$, alkyl, alkenyl, alkynyl, cycloalkyl, aryl, heteroaryl, arylalkyl, heteroarylalkyl, heterocycloalkyl and heterocyclylalkyl;

R$^a$ is hydrogen, trifluoromethyl, alkyl, alkenyl, alkynyl, saturated or partially unsaturated cycloalkyl, cycloalkylalkyl, aryl, arylalkyl, heteroaryl, heteroarylalkyl, heterocycloalkyl or saturated or partially unsaturated heterocyclylalkyl, wherein said alkyl, alkenyl, alkynyl, cycloalkyl, cycloalkylalkyl, aryl, arylalkyl, heteroaryl, heteroarylalkyl, heterocycloalkyl and heterocyclylalkyl are optionally substituted with one or more groups independently selected from oxo (with the proviso that it is not substituted on said aryl or heteroaryl), halogen, cyano, nitro, trifluoromethyl, difluoromethyl, fluoromethyl, fluoromethoxy, difluoromethoxy, trifluoromethoxy, azido, —O(C═O)OR$^h$, —NR$^f$SO$_2$R$^h$, —SO$_2$NR$^e$R$^f$, —C(═O)R$^e$, —C(═O)OR$^e$, —OC(═O)R$^e$, —NR$^f$C(═O)OR$^h$, —NR$^f$C(═O)R$^e$, —C(═O)NR$^e$R$^f$, —NR$^e$R$^f$, —NR$^g$C(═O)NR$^e$R$^f$, —NR$^c$C(NCN)NR$^e$R$^f$, —OR$^e$, alkyl, alkenyl, alkynyl, saturated or partially unsaturated cycloalkyl, aryl, heteroaryl, arylalkyl, heteroarylalkyl, saturated or partially unsaturated heterocycloalkyl and heterocyclylalkyl;

R$^b$, R$^c$, R$^f$ and R$^g$ are independently hydrogen or alkyl, or R$^a$ and R$^b$ together with the atom to which they are attached form a 4 to 10 membered saturated or partially unsaturated heterocyclic ring which may include 1 to 3 additional heteroatoms, in addition to the nitrogen atom to which said R$^a$ and R$^b$ are attached, selected from N, O and S;

R$^d$ and R$^h$ are independently trifluoromethyl, alkyl, saturated or partially unsaturated cycloalkyl, aryl, arylalkyl, heteroaryl, heteroarylalkyl, saturated or partially unsaturated heterocycloalkyl or heterocyclylalkyl;

R$^e$ is hydrogen, trifluoromethyl, alkyl, alkenyl, alkynyl, saturated or partially unsaturated cycloalkyl, cycloalkylalkyl, aryl, arylalkyl, heteroaryl, heteroarylalkyl, saturated or partially unsaturated heterocycloalkyl or heterocyclylalkyl; and Z is alkylene having from 1 to 6 carbons, or alkenylene or alkynylene each having from 2 to 6 carbons, wherein said alkylene, alkenylene and alkynylene are optionally substituted with one or more groups independently selected from oxo, halogen, cyano, nitro, trifluoromethyl, difluoromethyl, fluoromethyl, fluoromethoxy, difluoromethoxy, trifluoromethoxy, azido, —O(C═O)OR$^d$, —NR$^b$SO$_2$R$^d$, —SO$_2$NR$^a$R$^b$, —C(═O)R$^a$, —C(═O)OR$^a$, —OC(═O)R$^a$, —NR$^b$C(═O)OR$^d$, —NR$^b$C(═O)R$^a$, —C(═O)NR$^a$R$^b$, —NR$^a$R$^b$, —NR$^c$C(═O)NR$^a$R$^b$, —OR$^a$, alkyl, alkenyl, alkynyl, cycloalkyl, aryl, heteroaryl, arylalkyl, and heteroarylalkyl, or a pharmaceutically acceptable salt thereof.

32. The method of claim 31, wherein said compound is selected from:

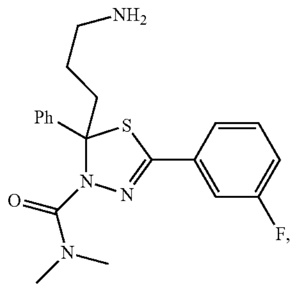

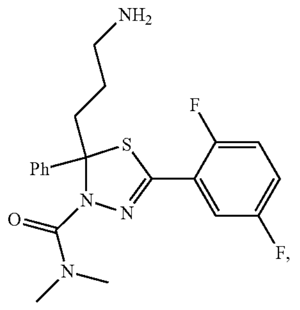

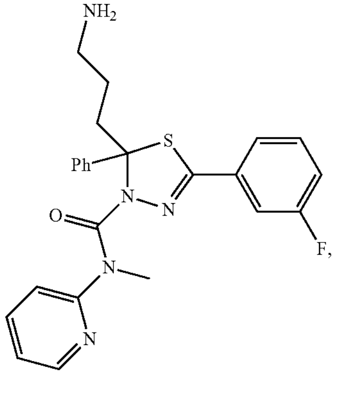

-continued
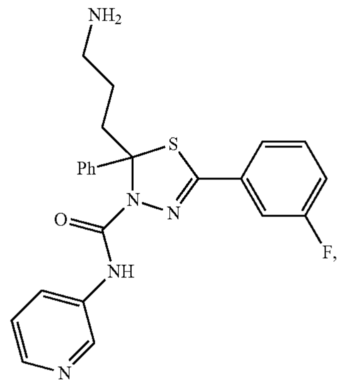
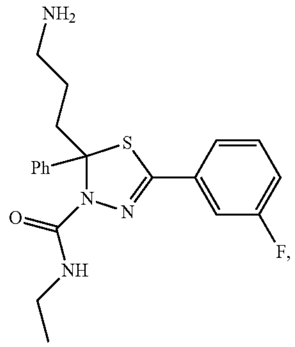
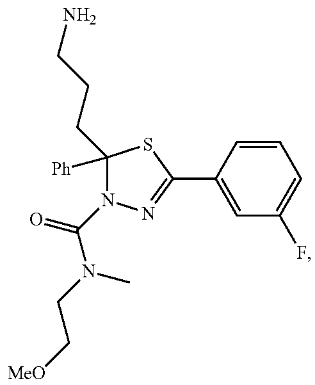
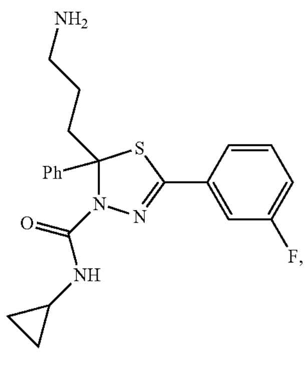
-continued
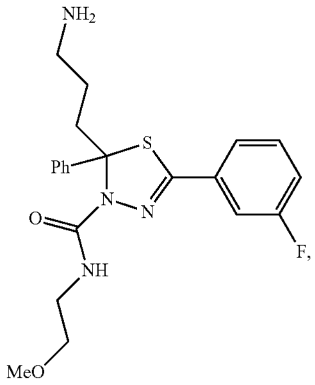
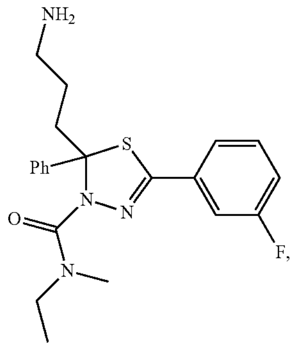
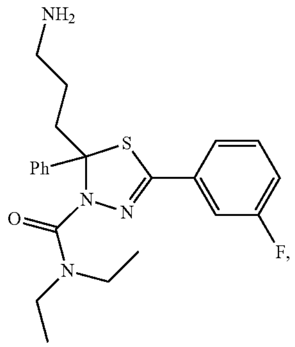
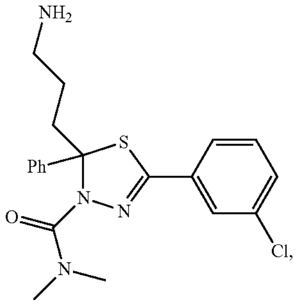
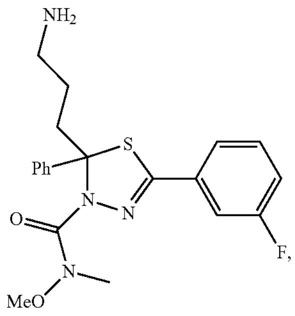

-continued

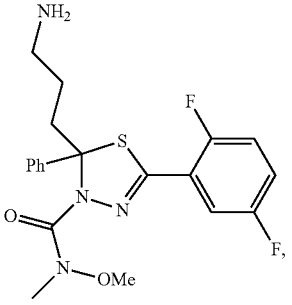

(Enantiomer A)

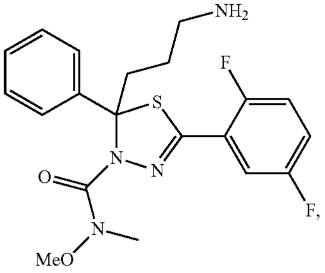

(Enantiomer B)

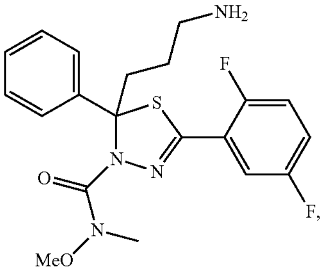

and

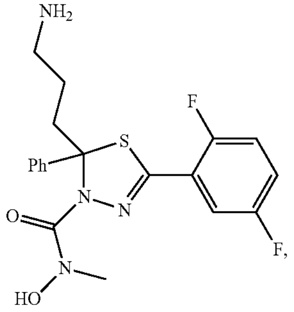

or a pharmaceutically acceptable salt thereof.

33. The method of claim 32, wherein the compound is:

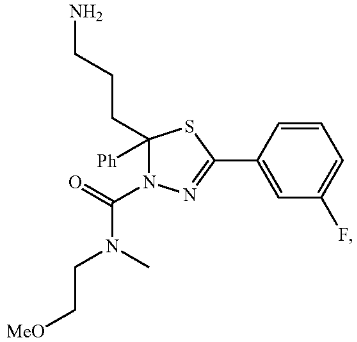 [SMILES: COCCN(C)C(=O)N1N=C(c2cccc(F)c2)SC1(CCCN)c1ccccc1]

or a pharmaceutically acceptable salt thereof.

34. The method of claim 32, wherein the compound is:

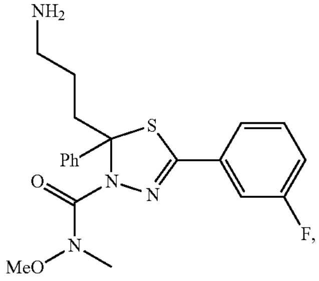

or a pharmaceutically acceptable salt thereof.

35. The method of claim 32, wherein the compound is:

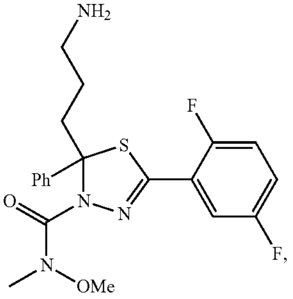 [SMILES: CON(C)C(=O)N1N=C(c2cc(F)ccc2F)SC1(CCCN)c1ccccc1]

or a pharmaceutically acceptable salt thereof.

36. The method of claim 32, wherein the compound is:

(Enantiomer A)

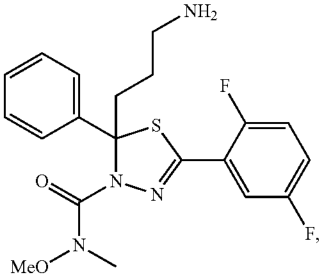

or a pharmaceutically acceptable salt thereof.

37. The method of claim 32, wherein the compound is:

(Enantiomer B)

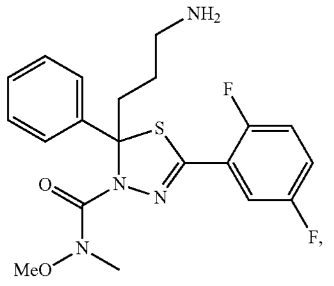

or a pharmaceutically acceptable salt thereof.

38. The method of claim 32, wherein the compound is:

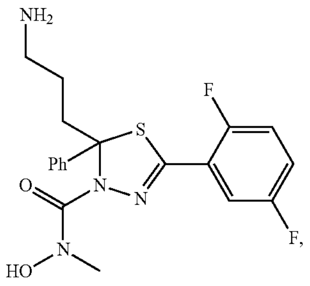 [SMILES: CN(O)C(=O)N1N=C(c2cc(F)ccc2F)SC1(CCCN)c1ccccc1]

or a pharmaceutically acceptable salt thereof.

39. The method of claim 36, wherein the compound is administered in combination with a proteasome inhibitor.

40. The method of claim 39, wherein the proteasome inhibitor is bortezomib.

41. The method of claim 39, wherein the disorder is selected from acute myeloid leukemia, chronic myeloid leukemia, acute lymphoblastic leukemia, chronic lymphocytic leukemia and multiple myeloma.

42. The method of claim 41, wherein the disorder is selected from acute myeloid leukemia, chronic myeloid leukemia and multiple myeloma.

43. The method of claim 42, wherein the disorder is acute myeloid leukemia.

44. The method of claim 42, wherein the disorder is chronic myeloid leukemia.

45. The method of claim 42, wherein the disorder is multiple myeloma.

46. The method of claim 40, wherein the disorder is selected from acute myeloid leukemia, chronic myeloid leukemia and multiple myeloma.

47. The method of claim 46, wherein the disorder is acute myeloid leukemia.

48. The method of claim 46, wherein the disorder is chronic myeloid leukemia.

49. The method of claim 46, wherein the disorder is multiple myeloma.

50. The method of claim 37, wherein the compound is administered in combination with a proteasome inhibitor.

51. The method of claim 50, wherein the proteasome inhibitor is bortezomib.

52. The method of claim 50, wherein the disorder is selected from acute myeloid leukemia, chronic myeloid leukemia, acute lymphoblastic leukemia, chronic lymphocytic leukemia and multiple myeloma.

53. The method of claim 52, wherein the disorder is selected from acute myeloid leukemia, chronic myeloid leukemia and multiple myeloma.

54. The method of claim 53, wherein the disorder is acute myeloid leukemia.

55. The method of claim 53, wherein the disorder is chronic myeloid leukemia.

56. The method of claim 53, wherein the disorder is multiple myeloma.

57. The method of claim 51, wherein the disorder is selected from acute myeloid leukemia, chronic myeloid leukemia and multiple myeloma.

58. The method of claim 57, wherein the disorder is acute myeloid leukemia.

59. The method of claim 57, wherein the disorder is chronic myeloid leukemia.

60. The method of claim 57, wherein the disorder is multiple myeloma.

61. The method of claim 38, wherein the compound is administered in combination with a proteasome inhibitor.

62. The method of claim 61, wherein the proteasome inhibitor is bortezomib.

63. The method of claim 61, wherein the disorder is selected from acute myeloid leukemia, chronic myeloid leukemia, acute lymphoblastic leukemia, chronic lymphocytic leukemia and multiple myeloma.

64. The method of claim 63, wherein the disorder is selected from acute myeloid leukemia, chronic myeloid leukemia and multiple myeloma.

65. The method of claim 64, wherein the disorder is acute myeloid leukemia.

66. The method of claim 64, wherein the disorder is chronic myeloid leukemia.

67. The method of claim 64, wherein the disorder is multiple myeloma.

68. The method of claim 62, wherein the disorder is selected from acute myeloid leukemia, chronic myeloid leukemia and multiple myeloma.

69. The method of claim 68, wherein the disorder is acute myeloid leukemia.

70. The method of claim 68, wherein the disorder is chronic myeloid leukemia.

71. The method of claim 68, wherein the disorder is multiple myeloma.

72. The method of claim 31, wherein the compound is administered in combination with a proteasome inhibitor.

73. The method of claim 72, wherein the proteasome inhibitor is bortezomib.

74. The method of claim 72, wherein the disorder is selected from acute myeloid leukemia, chronic myeloid leukemia, acute lymphoblastic leukemia, chronic lymphocytic leukemia and multiple myeloma.

75. The method of claim 74, wherein the disorder is selected from acute myeloid leukemia, chronic myeloid leukemia and multiple myeloma.

76. The method of claim 75, wherein the disorder is acute myeloid leukemia.

77. The method of claim 75, wherein the disorder is chronic myeloid leukemia.

78. The method of claim 75, wherein the disorder is multiple myeloma.

79. The method of claim 73, wherein the disorder is selected from acute myeloid leukemia, chronic myeloid leukemia and multiple myeloma.

80. The method of claim 79, wherein the disorder is acute myeloid leukemia.

81. The method of claim 79, wherein the disorder is multiple myeloma.

82. The method of claim 81, wherein the disorder is chronic myeloid leukemia.

83. The method of claim 1, wherein the compound is administered in combination with a proteasome inhibitor.

84. The method of claim 83, wherein the proteasome inhibitor is bortezomib.

85. The method of claim 83, wherein the disease is selected from acute myeloid leukemia, chronic myeloid leukemia, acute lymphoblastic leukemia, chronic lymphocytic leukemia and multiple myeloma.

86. The method of claim 85, wherein the disease is selected from acute myeloid leukemia, chronic myeloid leukemia and multiple myeloma.

87. The method of claim 86, wherein the disease is acute myeloid leukemia.

88. The method of claim 86, wherein the disease is chronic myeloid leukemia.

89. The method of claim 86, wherein the disease is multiple myeloma.

90. The method of claim 84, wherein the disease is selected from acute myeloid leukemia, chronic myeloid leukemia and multiple myeloma.

91. The method of claim 90, wherein the disease is acute myeloid leukemia.

92. The method of claim 90, wherein the disease is chronic myeloid leukemia.

93. The method of claim 90, wherein the disease is multiple myeloma.

94. The method of claim 8, wherein the compound is administered in combination with a proteasome inhibitor.

95. The method of claim 94, wherein the proteasome inhibitor is bortezomib.

96. The method of claim 94, wherein the disease is selected from acute myeloid leukemia, chronic myeloid leukemia, acute lymphoblastic leukemia, chronic lymphocytic leukemia and multiple myeloma.

97. The method of claim 96, wherein the disease is selected from acute myeloid leukemia, chronic myeloid leukemia and multiple myeloma.

98. The method of claim 97, wherein the disease is acute myeloid leukemia.

99. The method of claim 97, wherein the disease is chronic myeloid leukemia.

100. The method of claim 97, wherein the disease is multiple myeloma.

101. The method of claim 95, wherein the disease is selected from acute myeloid leukemia, chronic myeloid leukemia and multiple myeloma.

102. The method of claim 101, wherein the disease is acute myeloid leukemia.

103. The method of claim 101, wherein the disease is chronic myeloid leukemia.

104. The method of claim 101, wherein the disease is multiple myeloma.

* * * * *